United States Patent
Anzai et al.

(10) Patent No.: US 9,169,504 B2
(45) Date of Patent: *Oct. 27, 2015

(54) METHOD FOR PRODUCING PYRIPYROPENE

(75) Inventors: Hiroyuki Anzai, Ibaraki-Ken (JP);
Kentaro Yamamoto, Kawasaki (JP);
Kazuhiko Oyama, Higashimurayama (JP); Mariko Tsuchida, Tokyo-To (JP);
Kimihiko Goto, Yokohama (JP);
Masaaki Mitomi, Yokosuka (JP)

(73) Assignee: MEIJI SEIKA PHARMA CO., LTD., Tokyo-To (JP)

( * ) Notice: Subject to any disclaimer, the term of this patent is extended or adjusted under 35 U.S.C. 154(b) by 116 days.

This patent is subject to a terminal disclaimer.

(21) Appl. No.: 13/575,159

(22) PCT Filed: Jan. 19, 2011

(86) PCT No.: PCT/JP2011/050851
§ 371 (c)(1),
(2), (4) Date: Sep. 19, 2012

(87) PCT Pub. No.: WO2011/093185
PCT Pub. Date: Aug. 4, 2011

(65) Prior Publication Data
US 2013/0023017 A1   Jan. 24, 2013

(30) Foreign Application Priority Data
Jan. 26, 2010 (JP) ................. 2010-014727

(51) Int. Cl.
C12P 17/18 (2006.01)
C12N 9/02 (2006.01)
C12N 9/10 (2006.01)
C12N 9/88 (2006.01)
C12N 9/00 (2006.01)
C12N 15/52 (2006.01)

(52) U.S. Cl.
CPC ............. *C12P 17/181* (2013.01); *C12N 9/0071* (2013.01); *C12N 9/1025* (2013.01); *C12N 9/1029* (2013.01); *C12N 9/88* (2013.01); *C12N 9/93* (2013.01); *C12N 15/52* (2013.01); *C12Y 114/13008* (2013.01); *C12Y 114/14001* (2013.01); *C12Y 203/00* (2013.01); *C12Y 203/01* (2013.01); *C12Y 205/01* (2013.01); *C12Y 406/01* (2013.01); *C12Y 602/01* (2013.01)

(58) Field of Classification Search
CPC ........ C12N 15/52; C12N 9/00; C12N 9/1029; C12N 9/1025; C12Y 114/14001; C12P 17/18
USPC ...................................................... 435/119
See application file for complete search history.

(56) References Cited

U.S. PATENT DOCUMENTS

| | | | |
|---|---|---|---|
| 5,597,835 A | 1/1997 | Bok et al. | |
| 5,756,345 A | 5/1998 | Camakaris et al. | |
| 5,807,721 A | 9/1998 | Omura et al. | |
| 8,557,550 B2 * | 10/2013 | Anzai et al. | .......... 435/119 |
| 2006/0135564 A1 | 6/2006 | Kim et al. | |
| 2006/0135664 A1 | 6/2006 | Glassel et al. | |
| 2006/0281780 A1 | 12/2006 | Goto et al. | |
| 2009/0182014 A1 | 7/2009 | Kim et al. | |
| 2010/0160640 A1 | 6/2010 | Goto et al. | |
| 2012/0015410 A1 | 1/2012 | Anzai et al. | |

FOREIGN PATENT DOCUMENTS

| | | |
|---|---|---|
| CN | 1156180 | 8/1997 |
| EP | 2 107 060 | 10/2009 |
| EP | 2 319 923 | 5/2011 |
| JP | 4-360895 | 12/1992 |
| JP | 6-184158 | 7/1994 |
| JP | 8-239385 | 9/1996 |
| JP | 8-259569 | 10/1996 |
| JP | 8-269062 | 10/1996 |
| JP | 8-269063 | 10/1996 |
| JP | 8-269064 | 10/1996 |
| JP | 8-269065 | 10/1996 |
| JP | 8-269066 | 10/1996 |
| JP | 8-291164 | 11/1996 |
| WO | 94/09147 | 4/1994 |
| WO | 2004/060065 | 7/2004 |
| WO | 2006/129714 | 12/2006 |
| WO | 2008/066153 | 6/2008 |
| WO | 2009/022702 | 2/2009 |
| WO | 2009/133098 A2 | 11/2009 |
| WO | 2009/133098 A3 | 11/2009 |
| WO | 2010/010955 | 1/2010 |

OTHER PUBLICATIONS

Narasimhan, Nurani S., et al., "Mechanism of Acylation of Dilithium Salts of β-Keto Esters: An Efficient Synthesis of Anibine", J. Org. Chem., vol. 48, No. 22, 1983, pp. 3945-3947.
Varga, Janos, et al., "Diversity of polyketide synthase gene sequences in *Aspergillus* species", Research in Microbiology, vol. 154, No. 8, Oct. 1, 2003, pp. 593-600.
Office Action issued Jul. 31, 2013 in corresponsing Chinese Application No. 201180007262.5, with English translation.
Extended European Search Report issued Nov. 22, 2013 in corresponding European Application No. 11736899.3.
Tomoda et al., "Biosynthesis of Pyripyropene A", The Journal of Organic Chemistry, American Chemical Society, vol. 61, No. 3, pp. 882-886, Jan. 1, 1996.
Itoh et al., "Reconstitution of a fungal meroterpenoid biosynthesis reveals the involvement of a novel family of terpene cyclases", Nature Chemistry, vol. 2, No. 1, pp. 858-864, Aug. 1, 2010.

(Continued)

*Primary Examiner* — David J Steadman
*Assistant Examiner* — Paul Holland
(74) *Attorney, Agent, or Firm* — Wenderoth, Lind & Ponack, L.L.P.

(57) ABSTRACT

There is provided a method for culturing a microorganism in which a particular polynucleotide or a recombinant vector comprising it/them is introduced with an intermediate compound necessary for biosynthesis of pyripyropene A. The method of the present invention allows for the production of pyripyropene.

5 Claims, 8 Drawing Sheets

(56) References Cited

OTHER PUBLICATIONS

Itoh et al., "Supplementary Information to Reconstitution of a fungal meroterpenoid biosynthesis reveals the involvement of a novel family of terpene cyclases", Nature Chemistry, vol. 2, No. 1, pp. 858-864, Aug. 1, 2010.
"Adenylate-forming enzyme, putative", XP-002715482, retrieved from EBI accession No. UNIPROT: BOXM40, Apr. 8, 2008.
"LovB-like polyketide synthase, putative", XP002715483, retrieved from EBI accession No. UNIPROT: Q4WLD4, Jul. 5, 2005.
"Cytochrome P450", XP002715484, retrieved from EBI accession No. UNIPROT: BOXM33, Apr. 8, 2008.
"Cytochrome P450", XP002715485, retrieved from EBI accession No. UNIPROT: BOXM32, Apr. 8, 2008.
"Integral membrane protein", XP002715486, retrieved from EBI accession No. UNIPROT: BOXM38, Apr. 8, 2008.
"FAD-dependent monooxygenase (PaxM), putative", XP002715487, retrieved from EBI accession No. UNIPROT: BOXM37, Apr. 8, 2008.
"UbiA-like prenyltransferase, putative; EC=2.5.1.-", XP002715488, retrieved from EBI accession No. UNIPROT: Q4WLDO, Jul. 5, 2005.
"Acetyltransferase, putative", XP002715489, retrieved from EBI accession No. UNIPROT: BOXM35, Apr. 8, 2008.
"Toxin biosynthesis protein Tri7-like, putative", XP002715490, retrieved from EBI accession No. UNPROT: BOXM34, Apr. 8, 2008.
Tsujiuchi et al., "Novel microorganism having ability to produce pyripyropenes", Hatsumei Kyokai Kokai Giho—Jiii Journal of Technical Disclosure, Hatsumei Kyokai Japan Institute of Invention and Innovation, vol. 2, No. 500997, pp. 1-7, Jan. 1, 2008.
International Search Report issued Apr. 12, 2011 in International (PCT) Application No. PCT/JP2011/050851, of which the present application is the national stage.
J. Hu et al., "Characterization of two cytochrome P450 monooxygenase genes of the pyripyropene biosynthetic gene cluster from *Penicillium coprobium*", The Journal of Antibiotics, vol. 64, No. 3, 2011, pp. 221-227.
N. Fedorova et al., "Genomic Islands in the Pathogenic Filamentous Fungus *Aspergillus fumigatus*", PLoS Genetics, vol. 4, Issue 4, Apr. 2008, pp. 1-13.
W. Nierman et al., "Genomic sequence of the pathogenic and allergenic filamentous fungus *Aspergillus fumigatus*", Nature, vol. 438, No. 7071, Dec. 22, 2005, pp. 1151-1156.
T. Sunazuka et al., "Total Synthesis of α-Pyrone Meroterpenoids, Novel Bioactive Microbial Metabolites", Chem. Rev. vol. 105, No. 12, 2005, pp. 4559-4580.
International Preliminary Report on Patentability and Written Opinion issued Sep. 27, 2012 in International (PCT) Application No. PCT/JP2011/050852.
International Preliminary Report on Patentability and Written Opinion issued Sep. 27, 2012 in International (PCT) Application No. PCT/JP2011/050851.
Narasimhan, Nurani S., et al., "Mechanism of Acylation of Dilithium Salts γ-Keto Esters: An Efficient Synthesis of Anibine", J. Org. Chem., vol. 48, No. 22, 1983, pp. 3945-3947.

International Search Report issued Oct. 20, 2009 in International (PCT) Application No. PCT/JP2009/063293, with English translation.
Fedorova, Natalie D., et al., "Genomic Islands in the Pathogenic Filamentous Fungus *Aspergillus fumigatus*", PLoS Genetics, vol. 4, No. 4, Apr. 11, 2008, pp. 1-13.
Nierman, William C., et al., "Genomic Sequence of the Pathogenic and Allergenic Filamentous Fungus *Aspergillus fumigatus*", Nature, vol. 438, No. 7071, Dec. 2005, pp. 1151-1156.
Tomoda, Hiroshi, et al., "Biosynthesis of Pyripyropene A", J. Org. Chem., vol. 61, No. 3, 1996, pp. 882-886.
Sunazuka, Toshiaki, et al., "Total Synthesis of α-Pyrone Meroterpenoids, Novel Bioactive Microbial Metabolites", Chem. Rev., vol. 105, No. 12, 2005, pp. 4559-4580.
Tsujiuchi, G., et al., "Pyripyropene-rui Seisanno o Yusuru Shinki Biseibutsu", Hatsumei Kyokai Kokai Giho Kogi Bango, 2008-500997 Go, Feb. 13, 2008, with English translation.
Omura, S., et al., "Pyripyropenes, Highly Potent Inhibitors of Acyl-CoA: Cholesterol Acyltransferase Produced by *Aspergillus fumigatus*", The Journal of Antibiotics, vol. 46, No. 7, Jul. 1993, pp. 1168-1169.
Sunazuka, Toshiaki, et al., "Synthetic Study of α-Pyrone Meroterpenoids, Pyripyropens", Journal of Synthetic Organic Chemistry, Japan, vol. 56, No. 6, 1998, pp. 478-488, with English abstract.
Obata, Rika, et al., "Chemical Modification and Structure-Activity Relationships of Pyripyropenes 3. Synthetic Conversion of Pyridine-Pyrone Moiety", The Journal of Antibiotics, vol. 50, No. 3, Mar. 1997, pp. 229-236.
Wang, Hui-Juan, et al., "Aflavinines and Other Antiisectan Metabolites from the Ascostromata of *Eupenicillium crustaceum* and Related Species", Applied and Environmental Microbiology, vol. 61, No. 12, Dec. 1995, pp. 4429-4435.
Smith, Amos B., et al., "Biomimetic Total Synthesis of the ACAT Inhibitor(+)-Pyripyropene E", Tetrahedron Letters, vol. 37, No. 36, 1996, pp. 6461-6464.
Tomoda, Hiroshi, et al., "Pyripyropenes, Novel ACAT Inhibitors Produced by *Aspergillus fumigates* IV. Structure Elucidation of Pyripyropenes M to R", The Journal of Antibiotics, vol. 49, No. 3, Mar. 1996, pp. 292-298.
Supplementary European Search Report issued Nov. 29, 2011 in corresponding European Application No. 09 80 0469.
Hu, Jie, et al., "Characterization of two cytochrome P450 monooxygenase genes of the pyripyropene biosynthetic gene cluster from *Penicillium coprobium*", The Journal of Antibiotics, vol. 64, No. 3, Jan. 12, 2011, pp. 221-227.
Itoh, Takayuki, et al., "Reconstitution of a fungal meroterpenoid biosynthesis reveals the involvement of a novel family of terpene cyclases", Nature Chemistry, vol. 2, No. 10, published online on Aug. 1, 2010, pp. 858-864.
Cox, Russel J., "Polyketides, proteins and genes in fungi: programmed nano-machines begin to reveal their secrets", Organic and Biomolecular Chemistry, vol. 5, No. 13, Jan. 1, 2007, pp. 2010-2026.
Varga, János, et al., "Diversity of polyketide synthase gene sequences in *Aspergillus* species", Research in Microbiology, vol. 154, No. 8, Oct. 1, 2003, pp. 593-600.

\* cited by examiner

SEQUENCE LISTING

```
<160> NUMBER OF SEQ ID NOS: 298

<210> SEQ ID NO 1
<211> LENGTH: 21
<212> TYPE: DNA
<213> ORGANISM: unknown
<220> FEATURE:
<223> OTHER INFORMATION: Filamentous fungi
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (9)..(9)
<223> OTHER INFORMATION: I

<400> SEQUENCE: 1
gayccnmgnt tyttyaayat g                                       21

<210> SEQ ID NO 2
<211> LENGTH: 20
<212> TYPE: DNA
<213> ORGANISM: unknown
<220> FEATURE:
<223> OTHER INFORMATION: Filamentous fungi
<220> FEATURE:
<221> NAME/KEY: modified_base
<222> LOCATION: (3)..(3)
```

```
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (9)..(9)
<223> OTHER INFORMATION: I

<400> SEQUENCE: 2
gtnccngtnc crtgcatytc                                                  20

<210> SEQ ID NO 3
<211> LENGTH: 500
<212> TYPE: DNA
<213> ORGANISM: unknown
<220> FEATURE:
<223> OTHER INFORMATION: Filamentous fungi

<400> SEQUENCE: 3
cattaccgag tgagggccct ctgggtccaa cctcccaccc gtgtttattt accttgttgc      60
ttcggcgggc ccgccttaac tggccgccgg ggggcttacg cccccgggcc cgcgcccgcc     120
gaagacaccc tcgaactctg tctgaagatt gtagtctgag tataaatata aattatttaa     180
aactttcaac aacggatctc ttggttccgg catcgatgaa gaacgcagcg aaatgcgata     240
cgtaatgtga attgcaaatt cagtgaatca tcgagtcttt gaacgcacat tgcgcccct     300 ggtattccgg ggggcatgcc tgtccgagcg tcattgctgc cctcaagccc ggcttgtgtg     360
ttgggccccg tcctccgatt ccggggggacg ggcccgaaag gcagcggcgg caccgcgtcc    420
ggtcctcgag cgtatggggc tttgtcaccc gctctgtagg cccggccggc gcttgccgat     480
caacccaaat ttttatccag                                                500

<210> SEQ ID NO 4
<211> LENGTH: 28
<212> TYPE: PRT
<213> ORGANISM: Penicillium coprobium PF1169

<400> SEQUENCE: 4

Gln Pro Trp Lys Asp Ser Ile Trp Ala Gly Asp Val Tyr Met Phe Glu
1               5                   10                  15

Gly Asp Asp Ile Val Ala Val Tyr Gly Gly Val Lys
            20                  25

<210> SEQ ID NO 5
<211> LENGTH: 36
<212> TYPE: PRT
<213> ORGANISM: Penicillium coprobium PF1169

<400> SEQUENCE: 5

His Asn Ser Ile Phe Gln Ala Leu Ala Arg Lys Ile Leu Asp Met Ala
1               5                   10                  15

Leu Pro Pro Gly Gly Gly Ala Pro Ala Pro Ala Ala Lys Arg
            20                  25                  30

Pro Ala Pro Ile
        35

<210> SEQ ID NO 6
<211> LENGTH: 70
<212> TYPE: PRT
<213> ORGANISM: Penicillium coprobium PF1169
```

```
<400> SEQUENCE: 6

Gly Arg Phe Leu Ser Ser Asp Gly Arg Cys His Thr Phe Asp Glu Lys
1               5                   10                  15

Ala Asn Gly Tyr Ala Arg Gly Glu Ala Val Gly Cys Leu Ile Leu Lys
                20                  25                  30

Pro Leu Ala Lys Ala Leu His Asp Gln Asn Lys Ile Arg Ala Val Ile
            35                  40                  45

Arg Gly Thr Gly Ser Asn Gln Asp Gly Arg Thr Ala Gly Ile Thr Val
        50                  55                  60

Pro Asn Gly Ala Ala Gln
65                  70

<210> SEQ ID NO 7
<211> LENGTH: 74
<212> TYPE: PRT
<213> ORGANISM: Penicillium coprobium PF1169

<400> SEQUENCE: 7

Arg Ile Ser Tyr Tyr Phe Asp Trp Gln Gly Pro Ser Met Ala Val Asp
1               5                   10                  15

Thr Gly Cys Ser Ser Leu Leu Ala Val His Leu Gly Val Glu Ala
                20                  25                  30

Leu Gln Asn Asp Asp Cys Ser Met Ala Val Ala Val Gly Ser Asn Leu
            35                  40                  45

Ile Leu Ser Pro Asn Ala Tyr Ile Ala Asp Ser Lys Thr Arg Met Leu
        50                  55                  60

Ser Pro Thr Gly Arg Ser Arg Met Trp Asp
65                  70

<210> SEQ ID NO 8
<211> LENGTH: 51
<212> TYPE: PRT
<213> ORGANISM: Penicillium coprobium PF1169

<400> SEQUENCE: 8

Ser Ser Phe Leu Thr Ser Thr Val Gln Gln Ile Val Glu Glu Thr Ile
1               5                   10                  15

Gln Gly Gly Thr Gly Gln Val Val Met Glu Ser Asp Leu Met Gln Thr
                20                  25                  30

Glu Phe Leu Glu Ala Ala Asn Gly His Arg Met Asn Asp Cys Gly Val
            35                  40                  45

Val Thr Ser
        50

<210> SEQ ID NO 9
<211> LENGTH: 79
<212> TYPE: PRT
<213> ORGANISM: Penicillium coprobium PF1169

<400> SEQUENCE: 9

Phe Asn Ala Ala His Arg Val Leu Pro Leu Pro Ser Tyr Lys Trp Asp
1               5                   10                  15

Leu Lys Asn Tyr Trp Ile Pro Tyr Thr Asn Asn Phe Cys Leu Leu Lys
                20                  25                  30

Gly Ala Pro Ala Ala Pro Val Ala Glu Ala Thr Pro Ile Ser Val Phe
            35                  40                  45

Leu Ser Ser Ala Ala Gln Arg Val Leu Glu Thr Ser Gly Asp Asn Ser
        50                  55                  60
```

Ser Ala Phe Ile Val Ile Glu Asn Asp Ile Ala Asp Pro Asp Leu
 65                  70                  75

<210> SEQ ID NO 10
<211> LENGTH: 84
<212> TYPE: PRT
<213> ORGANISM: Penicillium coprobium PF1169

<400> SEQUENCE: 10

Val Ile Arg Gly Thr Gly Ser Asn Gln Asp Gly Arg Thr Ala Gly Ile
 1               5                  10                  15

Thr Val Pro Asn Gly Ala Ala Gln Glu Ser Leu Ile Arg Ser Val Tyr
             20                  25                  30

Ala Gln Ala Asp Leu Asp Pro Ser Gly Thr Asp Phe Val Glu Ala His
         35                  40                  45

Gly Thr Gly Thr Leu Ala Gly Asp Pro Val Glu Thr Gly Ala Ile Ala
     50                  55                  60

Arg Val Phe Gly Thr Asp Arg Pro Pro Gly Asp Pro Val Arg Ile Gly
 65                  70                  75                  80

Ser Ile Lys Thr

<210> SEQ ID NO 11
<211> LENGTH: 81
<212> TYPE: PRT
<213> ORGANISM: Penicillium coprobium PF1169

<400> SEQUENCE: 11

Gln Glu Ala Lys Ala Met Asp Pro Gln Gln Arg Met Leu Leu Glu Cys
 1               5                  10                  15

Thr Tyr Glu Ala Leu Glu Asn Gly Gly Ile Ser Lys Gly Ser Leu Lys
             20                  25                  30

Gly Gln Asn Val Gly Val Phe Val Gly Ser Ala Phe Pro Asp Tyr Glu
         35                  40                  45

Met Tyr Asn Arg Arg Asp Leu Glu Thr Ala Pro Met His Gln Ser Thr
     50                  55                  60

Gly Asn Ala Leu Ala Leu Gln Ser Asn Arg Ile Ser Tyr Tyr Phe Asp
 65                  70                  75                  80

Phe

<210> SEQ ID NO 12
<211> LENGTH: 66
<212> TYPE: PRT
<213> ORGANISM: Penicillium coprobium PF1169

<400> SEQUENCE: 12

Asn His Thr Gly Arg Ala Glu Gln Ser Lys Ile Ala Ile Ile Gly Leu
 1               5                  10                  15

Ser Gly Arg Phe Pro Glu Ala Pro Asp Thr Glu Ala Phe Trp Asp Leu
             20                  25                  30

Leu Lys Lys Gly Leu Asp Val His Arg Glu Val Pro Pro Glu Arg Trp
         35                  40                  45

Asp Val Lys Ala His Val Asp Pro Glu Gly Lys Lys Arg Thr Pro Ala
     50                  55                  60

Lys Leu
 65

<210> SEQ ID NO 13

```
<211> LENGTH: 14
<212> TYPE: PRT
<213> ORGANISM: Penicillium coprobium PF1169

<400> SEQUENCE: 13

Glu Lys Asn Thr Ser Gln Val Glu Tyr Gly Cys Trp Tyr Asn
1               5                   10

<210> SEQ ID NO 14
<211> LENGTH: 71
<212> TYPE: PRT
<213> ORGANISM: Penicillium coprobium PF1169

<400> SEQUENCE: 14

Ala Gly Gly Asn Thr Thr Val Ala Leu Glu Asp Ala Pro Ile Arg Thr
1               5                   10                  15

Arg Ser Gly Ser Asp Pro Arg Ser Leu His Pro Ile Ala Ile Ser Ala
            20                  25                  30

Lys Ser Lys Val Ser Leu Arg Gly Asn Leu Glu Asn Leu Leu Ala Tyr
        35                  40                  45

Leu Asp Thr His Pro Asp Val Ser Leu Ser Asp Leu Ser Tyr Thr Thr
    50                  55                  60

Thr Ala Arg Arg His His His
65                  70

<210> SEQ ID NO 15
<211> LENGTH: 77
<212> TYPE: PRT
<213> ORGANISM: Penicillium coprobium PF1169

<400> SEQUENCE: 15

Ala Thr Asp Thr Glu Lys Phe Trp Asp Leu Leu Ala Ser Gly Val Asp
1               5                   10                  15

Val His Arg Lys Ile Pro Ala Asp Arg Phe Asp Val Glu Thr His Tyr
            20                  25                  30

Asp Pro Asn Gly Lys Arg Met Asn Ala Ser His Thr Pro Tyr Gly Cys
        35                  40                  45

Phe Ile Asp Glu Pro Gly Leu Phe Asp Ala Ala Phe Phe Asn Met Ser
    50                  55                  60

Pro Arg Glu Ala Gln Gln Thr Asp Pro Met Gln Arg Leu
65                  70                  75

<210> SEQ ID NO 16
<211> LENGTH: 39
<212> TYPE: PRT
<213> ORGANISM: Penicillium coprobium PF1169

<400> SEQUENCE: 16

Pro Glu Tyr Ser Gln Pro Leu Cys Thr Ala Ile Gln Ile Ala Leu Val
1               5                   10                  15

Glu Leu Leu Glu Ser Phe Gly Val Val Pro Lys Ala Val Val Gly His
            20                  25                  30

Ser Ser Gly Glu Ile Ala Ala
        35

<210> SEQ ID NO 17
<211> LENGTH: 71
<212> TYPE: PRT
<213> ORGANISM: Penicillium coprobium PF1169

<400> SEQUENCE: 17
```

```
Arg Arg Thr Phe Leu Pro Trp Arg Leu Thr Ser Ser Ala Leu Ser Gly
1               5                   10                  15

Gln Glu Leu Thr Gln Ser Leu Ala Ile Asp Ala Val Pro Ile Arg Ser
            20                  25                  30

Ser Lys Glu Pro Thr Val Gly Phe Val Phe Thr Gly Gln Gly Ala Gln
        35                  40                  45

Trp His Gly Met Gly Lys Glu Leu Leu Ser Thr Tyr Pro Ile Phe Arg
    50                  55                  60

Gln Thr Met Gln Asp Val Asp
65              70
```

<210> SEQ ID NO 18
<211> LENGTH: 75
<212> TYPE: PRT
<213> ORGANISM: Penicillium coprobium PF1169

<400> SEQUENCE: 18

```
Leu Arg Arg Leu Leu His Ala Lys Asn Asp Ser Leu Val Ala Ala Phe
1               5                   10                  15

Phe Gln Lys Thr Tyr Cys Ala Leu Arg Lys Glu Ile Thr Ser Leu Pro
            20                  25                  30

Pro Ser Glu Arg Gln Val Phe Pro Arg Phe Thr Ser Ile Val Asp Leu
        35                  40                  45

Leu Ala Arg Phe Lys Glu Phe Gly Pro Asn Pro Ala Leu Glu Ser Ala
    50                  55                  60

Leu Thr Thr Ile Tyr Gln Leu Gly Cys Phe Ile
65              70                  75
```

<210> SEQ ID NO 19
<211> LENGTH: 81
<212> TYPE: PRT
<213> ORGANISM: Penicillium coprobium PF1169

<400> SEQUENCE: 19

```
Phe Asp Ala Ala Phe Phe Asn Met Ser Pro Arg Glu Ala Gln Gln Thr
1               5                   10                  15

Asp Pro Met Gln Arg Leu Ala Ile Val Thr Ala Tyr Glu Ala Leu Glu
            20                  25                  30

Arg Ala Gly Tyr Val Ala Asn Arg Thr Ala Ala Thr Asn Leu His Arg
        35                  40                  45

Ile Gly Thr Phe Tyr Gly Gln Ala Ser Asp Asp Tyr Arg Glu Val Asn
    50                  55                  60

Thr Ala Gln Glu Ile Ser Thr Tyr Phe Ile Pro Gly Gly Cys Arg Ala
65              70                  75                  80

Phe
```

<210> SEQ ID NO 20
<211> LENGTH: 38
<212> TYPE: PRT
<213> ORGANISM: Penicillium coprobium PF1169

<400> SEQUENCE: 20

```
Asp Thr Ala Cys Ser Ser Ser Leu Val Ala Leu His Tyr Ala Val Gln
1               5                   10                  15

Ser Leu Arg Asn Gly Glu Ser Thr Glu Ala Leu Ile Ala Gly Cys His
            20                  25                  30

Leu Asn Ile Val Pro Asp
```

<210> SEQ ID NO 21
<211> LENGTH: 75
<212> TYPE: PRT
<213> ORGANISM: Penicillium coprobium PF1169

<400> SEQUENCE: 21

Ala Lys His Pro Pro Ala Thr Ser Ile Leu Leu Gln Gly Asn Pro Lys
1               5                   10                  15

Thr Ala Thr Gln Ser Leu Phe Leu Phe Pro Asp Gly Ser Gly Ser Ala
            20                  25                  30

Thr Ser Tyr Ala Thr Ile Pro Gly Ile Ser Pro Asp Val Cys Val Tyr
        35                  40                  45

Gly Leu Asn Cys Pro Tyr Met Arg Thr Pro Glu Lys Leu Lys Phe Ser
    50                  55                  60

Leu Asp Glu Leu Thr Ala Pro Tyr Val Ala Glu
65                  70                  75

<210> SEQ ID NO 22
<211> LENGTH: 38
<212> TYPE: PRT
<213> ORGANISM: Penicillium coprobium PF1169

<400> SEQUENCE: 22

Gly Asn Gly Ser Ala Met Ile Ser Asn Arg Ile Ser Trp Phe Phe Asp
1               5                   10                  15

Leu Lys Gly Pro Ser Leu Ser Leu Asp Thr Ala Cys Ser Ser Ser Leu
            20                  25                  30

Val Ala Leu His Leu Ala
        35

<210> SEQ ID NO 23
<211> LENGTH: 57
<212> TYPE: PRT
<213> ORGANISM: Penicillium coprobium PF1169

<400> SEQUENCE: 23

Ala Ile Arg Asp Glu Val Arg Gln Leu Pro Thr Pro Leu Arg Ala Leu
1               5                   10                  15

Val Pro Ala Phe Glu Asn Val Leu Glu Leu Ala Asn Tyr Thr Asp Leu
            20                  25                  30

Arg Lys Gly Pro Leu Ser Gly Ser Ile Asp Gly Val Leu Leu Cys Val
        35                  40                  45

Val Gln Leu Ser Ser Leu Ile Gly Tyr
    50                  55

<210> SEQ ID NO 24
<211> LENGTH: 74
<212> TYPE: PRT
<213> ORGANISM: Penicillium coprobium PF1169

<400> SEQUENCE: 24

Ala Val Ala Trp Asp Pro Gln Gln Arg Ile Leu Leu Glu Val Val Tyr
1               5                   10                  15

Glu Ala Leu Glu Ser Ala Gly Tyr Phe Arg Ala Gly Ile Lys Pro Glu
            20                  25                  30

Leu Asp Asp Tyr Gly Cys Tyr Ile Gly Ala Val Met Asn Asn Tyr Tyr
        35                  40                  45

```
Asp Asn Met Ser Cys Gln Pro Thr Thr Ala Tyr Ala Thr Val Gly Thr
        50                  55                  60
Ser Arg Cys Phe Leu Ser Gly Cys Val Ser
65                  70
```

<210> SEQ ID NO 25
<211> LENGTH: 52
<212> TYPE: PRT
<213> ORGANISM: Penicillium coprobium PF1169

<400> SEQUENCE: 25

```
Gly Val Ile Val Gly Ser Ala Ala Asn Gln Asn Leu Asn Leu Ser His
1               5                   10                  15
Ile Thr Val Pro His Ser Gly Ser Gln Val Lys Leu Tyr Gln Asn Val
                20                  25                  30
Met Ser Gln Ala Gly Val His Pro His Ser Val Thr Tyr Val Glu Ala
            35                  40                  45
His Gly Thr Gly
        50
```

<210> SEQ ID NO 26
<211> LENGTH: 57
<212> TYPE: PRT
<213> ORGANISM: Penicillium coprobium PF1169

<400> SEQUENCE: 26

```
Trp Arg Ile Thr Val Ala Ile Val Gly Gly Val Asn Ala Leu Cys Gly
1               5                   10                  15
Pro Gly Leu Thr Arg Val Leu Asp Lys Ala Gly Ala Ile Ser Ser Asp
                20                  25                  30
Gly Ser Cys Lys Ser Phe Asp Asp Ala His Gly Tyr Ala Arg Gly
            35                  40                  45
Glu Gly Ala Gly Ala Leu Val Leu Lys
        50                  55
```

<210> SEQ ID NO 27
<211> LENGTH: 78
<212> TYPE: PRT
<213> ORGANISM: Penicillium coprobium PF1169

<400> SEQUENCE: 27

```
Leu Ile Asp Asp Thr Thr Val Trp Ile Glu Ile Gly Pro His Pro Val
1               5                   10                  15
Cys Leu Gly Phe Val Lys Ala Thr Leu Glu Ser Val Ala Val Ala Val
                20                  25                  30
Pro Ser Leu Arg Arg Gly Glu Asn Ala Trp Cys Thr Leu Ala Gln Ser
            35                  40                  45
Leu Thr Thr Leu His Asn Ala Gly Val Pro Val Gly Trp Ser Glu Phe
        50                  55                  60
His Arg Pro Phe Glu Arg Ala Leu Cys Leu Leu Asp Leu Pro
65                  70                  75
```

<210> SEQ ID NO 28
<211> LENGTH: 65
<212> TYPE: PRT
<213> ORGANISM: Penicillium coprobium PF1169

<400> SEQUENCE: 28

```
Val Trp Ile Glu Ile Gly Pro His Pro Val Cys Leu Gly Phe Val Lys
1               5                   10                  15
```

```
Ala Thr Leu Glu Ser Val Ala Val Ala Val Pro Ser Leu Arg Arg Gly
            20                  25                  30

Glu Asn Ala Trp Cys Thr Leu Ala Gln Ser Leu Thr Thr Leu His Asn
        35                  40                  45

Ala Gly Val Pro Val Gly Trp Ser Glu Phe His Arg Pro Phe Glu Arg
    50                  55                  60

Ala
 65

<210> SEQ ID NO 29
<211> LENGTH: 83
<212> TYPE: PRT
<213> ORGANISM: Penicillium coprobium PF1169

<400> SEQUENCE: 29

Thr Ser Asp Asp Tyr Arg Glu Val Asn Ser Gly Gln Asp Ile Asp Thr
 1               5                  10                  15

Tyr Phe Ile Pro Gly Gly Asn Arg Ala Phe Thr Pro Gly Arg Ile Asn
            20                  25                  30

Tyr Tyr Phe Lys Phe Ser Gly Pro Ser Val Ser Val Asp Thr Ala Cys
        35                  40                  45

Ser Ser Ser Leu Ala Ala Ile His Val Ala Cys Asn Ser Leu Trp Arg
    50                  55                  60

Asn Glu Ser Asp Ser Ala Val Ala Gly Gly Val Asn Ile Leu Thr Asn
 65                  70                  75                  80

Pro Asp Asn

<210> SEQ ID NO 30
<211> LENGTH: 54
<212> TYPE: PRT
<213> ORGANISM: Penicillium coprobium PF1169

<400> SEQUENCE: 30

Gly Arg Phe Leu Ser Ser Asp Gly Arg Cys His Thr Phe Asp Glu Lys
 1               5                  10                  15

Ala Asn Gly Tyr Ala Arg Gly Glu Ala Val Gly Cys Leu Ile Leu Lys
            20                  25                  30

Pro Leu Ala Lys Ala Leu His Asp Gln Asn Lys Ile Arg Ala Val Ile
        35                  40                  45

Arg Gly Thr Gly Ser Asn
    50

<210> SEQ ID NO 31
<211> LENGTH: 63
<212> TYPE: PRT
<213> ORGANISM: Penicillium coprobium PF1169

<400> SEQUENCE: 31

Asp Thr Ala Cys Ser Ser Leu Tyr Ala Leu His Ser Ala Cys Leu
 1               5                  10                  15

Ala Leu Asp Ser Arg Asp Cys Asp Gly Ala Val Val Ala Ala Ala Asn
            20                  25                  30

Leu Ile Gln Ser Pro Glu Gln Met Ile Ala Val Lys Ala Gly Ile
        35                  40                  45

Leu Ser Pro Asp Ser Met Cys His Thr Phe Asp Glu Ser Ala Asn
    50                  55                  60
```

```
<210> SEQ ID NO 32
<211> LENGTH: 55
<212> TYPE: PRT
<213> ORGANISM: Penicillium coprobium PF1169

<400> SEQUENCE: 32

Lys Gln Thr Thr Ser Arg Gly Tyr Phe Leu Asp His Leu Glu Asp Phe
1               5                   10                  15

Asp Cys Gln Phe Phe Gly Ile Ser Pro Lys Glu Ala Glu Gln Met Asp
                20                  25                  30

Pro Gln Gln Arg Val Ser Leu Glu Val Ala Ser Glu Ala Leu Glu Asp
        35                  40                  45

Ala Gly Ile Pro Ala Lys Ser
    50                  55

<210> SEQ ID NO 33
<211> LENGTH: 38
<212> TYPE: PRT
<213> ORGANISM: Penicillium coprobium PF1169

<400> SEQUENCE: 33

Pro Val Gly Cys Arg Ala Phe Gly Pro Gly Arg Ile Asn Tyr Phe Phe
1               5                   10                  15

Lys Phe Ser Gly Pro Ser Phe Ser Ile Asp Thr Ala Cys Ser Ser Ser
                20                  25                  30

Leu Ala Thr Ile Gln Val
        35

<210> SEQ ID NO 34
<211> LENGTH: 18
<212> TYPE: PRT
<213> ORGANISM: Penicillium coprobium PF1169

<400> SEQUENCE: 34

Ala Cys Thr Ser Leu Trp Asn Gly Glu Thr Asp Thr Val Val Ala Gly
1               5                   10                  15

Gly Met

<210> SEQ ID NO 35
<211> LENGTH: 12
<212> TYPE: PRT
<213> ORGANISM: Penicillium coprobium PF1169

<400> SEQUENCE: 35

Thr Ala Gln Glu Ile Ser Thr Tyr Phe Ile Pro Gly
1               5                   10

<210> SEQ ID NO 36
<211> LENGTH: 39
<212> TYPE: PRT
<213> ORGANISM: Penicillium coprobium PF1169

<400> SEQUENCE: 36

Pro Glu Tyr Ser Gln Pro Leu Cys Thr Ala Ile Gln Ile Ala Leu Val
1               5                   10                  15

Glu Leu Leu Glu Ser Phe Gly Val Val Pro Lys Ala Val Val Gly His
                20                  25                  30

Ser Ser Gly Glu Ile Ala Ala
        35

<210> SEQ ID NO 37
```

```
<211> LENGTH: 36
<212> TYPE: PRT
<213> ORGANISM: Penicillium coprobium PF1169

<400> SEQUENCE: 37

Ile Ser Gln Pro Ala Cys Thr Ala Leu Gln Ile Ala Leu Val Asp Leu
1               5                   10                  15

Leu Ala Glu Trp Ser Ile Thr Pro Ser Val Val Gly His Ser Ser
            20                  25                  30

Gly Glu Ile Ala
        35

<210> SEQ ID NO 38
<211> LENGTH: 39
<212> TYPE: PRT
<213> ORGANISM: Penicillium coprobium PF1169

<400> SEQUENCE: 38

Pro Glu Tyr Ser Gln Pro Leu Cys Thr Ala Ile Gln Ile Ala Leu Val
1               5                   10                  15

Glu Leu Leu Glu Ser Phe Gly Val Val Pro Lys Ala Val Val Gly His
            20                  25                  30

Ser Ser Gly Glu Ile Ala Ala
        35

<210> SEQ ID NO 39
<211> LENGTH: 76
<212> TYPE: PRT
<213> ORGANISM: Penicillium coprobium PF1169

<400> SEQUENCE: 39

Glu Glu Phe Trp Asp Leu Cys Ser Arg Gly Arg Gly Ala Trp Ser Pro
1               5                   10                  15

Val Pro Lys Asp Arg Phe Asn Ala Gly Ser Phe Tyr His Pro Asn Ala
            20                  25                  30

Asp Arg Pro Gly Ser Phe Asn Ala Ala Gly Ala His Phe Leu Thr Glu
        35                  40                  45

Asp Ile Gly Leu Phe Asp Ala Pro Phe Phe Asn Ile Thr Leu Gln Glu
    50                  55                  60

Ala Gln Thr Met Asp Pro Gln Gln Arg Ile Phe Leu
65                  70                  75

<210> SEQ ID NO 40
<211> LENGTH: 77
<212> TYPE: PRT
<213> ORGANISM: Penicillium coprobium PF1169

<400> SEQUENCE: 40

Ile Asn Glu Pro Arg Asp Arg Pro Gln Phe Phe His Ala His Gly Thr
1               5                   10                  15

Gly Thr Gln Ala Gly Asp Pro Gln Glu Ala Glu Ala Val Ser Thr Ala
            20                  25                  30

Leu Phe Pro Asp Gly Ser Asn Ile Glu Thr Lys Leu Phe Val Gly Ser
        35                  40                  45

Ile Lys Thr Val Ile Gly His Thr Glu Gly Ser Ala Gly Leu Ala Ser
    50                  55                  60

Leu Ile Gly Ser Ser Leu Ala Met Lys His Gly Val Ile
65                  70                  75
```

<210> SEQ ID NO 41
<211> LENGTH: 43
<212> TYPE: PRT
<213> ORGANISM: Penicillium coprobium PF1169

<400> SEQUENCE: 41

Lys Leu Ala Phe Val Phe Thr Gly Gln Gly Gln Trp Ala Gly Met
1               5                   10                  15

Gly Arg Glu Leu Leu Ser Ile Ser Thr Phe Arg Glu Ser Met Ala Arg
            20                  25                  30

Ser Gln Glu Ile Leu Ala Ser Leu Gly Cys Pro
        35                  40

<210> SEQ ID NO 42
<211> LENGTH: 71
<212> TYPE: PRT
<213> ORGANISM: Penicillium coprobium PF1169

<400> SEQUENCE: 42

Lys Ser Phe Leu Asp Asp Leu Ala Phe Thr Val Asn Glu Arg Arg Ser
1               5                   10                  15

Ile Phe Pro Trp Lys Ala Ala Val Val Gly Asp Thr Met Glu Gly Leu
            20                  25                  30

Ala Ala Ser Leu Ala Gln Asn Ile Lys Pro Arg Ser Val Leu Arg Met
        35                  40                  45

Pro Thr Leu Gly Phe Val Phe Thr Gly Gln Gly Gln Trp Pro Gly
    50                  55                  60

Met Gly Lys Glu Leu Leu Gln
65                  70

<210> SEQ ID NO 43
<211> LENGTH: 55
<212> TYPE: PRT
<213> ORGANISM: Penicillium coprobium PF1169

<400> SEQUENCE: 43

Ser Val Ala Cys Ile Asn Ser Pro Phe Asn Cys Thr Leu Ser Gly Pro
1               5                   10                  15

Glu Glu Asp Ile Asp Ala Val Lys Ala Gln Ala Asp Gln Asp Gly Leu
            20                  25                  30

Phe Ala Gln Lys Leu Lys Thr Gly Val Ala Tyr His Ser Thr Ala Met
        35                  40                  45

Ser Ala Ile Ala Asn Asp Tyr
    50                  55

<210> SEQ ID NO 44
<211> LENGTH: 68
<212> TYPE: PRT
<213> ORGANISM: Penicillium coprobium PF1169

<400> SEQUENCE: 44

Met Leu Ala Val Gly Ala Ser Ala Ser Asp Ile Gln Gln Ile Leu Asp
1               5                   10                  15

Ala Met Arg Gly Asn Lys Ala Val Ile Ala Cys Val Asn Ser Glu Ser
            20                  25                  30

Ser Val Thr Leu Ser Gly Asp Leu Asp Val Ile Ala Asn Leu Gln Thr
        35                  40                  45

Ala Leu Asp Lys Glu Gly Ile Phe Thr Arg Lys Leu Lys Val Asp Val
    50                  55                  60

Ala Tyr His Ser
65

<210> SEQ ID NO 45
<211> LENGTH: 38
<212> TYPE: PRT
<213> ORGANISM: Penicillium coprobium PF1169

<400> SEQUENCE: 45

Gly Asn Gly Ser Ala Met Ile Ser Asn Arg Ile Ser Trp Phe Phe Asp
1               5                   10                  15

Leu Lys Gly Pro Ser Leu Ser Leu Asp Thr Ala Cys Ser Ser Ser Leu
            20                  25                  30

Val Ala Leu His Leu Ala
        35

<210> SEQ ID NO 46
<211> LENGTH: 77
<212> TYPE: PRT
<213> ORGANISM: Penicillium coprobium PF1169

<400> SEQUENCE: 46

Gly Pro Ser Met Thr Ile Asp Thr Ala Cys Ser Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Leu Gly Pro Glu Gln Tyr Ile Ala
        35                  40                  45

Glu Ser Lys Leu Lys Met Leu Ser Pro Asn Gly Arg Ser Arg Met Trp
    50                  55                  60

Asp Lys Asp Ala Asp Gly Tyr Ala Arg Gly Asp Gly Ile
65                  70                  75

<210> SEQ ID NO 47
<211> LENGTH: 61
<212> TYPE: PRT
<213> ORGANISM: Penicillium coprobium PF1169

<400> SEQUENCE: 47

Ile Gly Ser Ile Lys Pro Asn Ile Gly His Leu Glu Ala Gly Ala Gly
1               5                   10                  15

Val Met Gly Phe Ile Lys Ala Ile Leu Ser Ile Gln Lys Gly Val Leu
            20                  25                  30

Ala Pro Gln Ala Asn Leu Thr Lys Leu Asn Ser Arg Ile Asp Trp Lys
        35                  40                  45

Thr Ala Gly Val Lys Val Val Gln Glu Ala Thr Pro Trp
    50                  55                  60

<210> SEQ ID NO 48
<211> LENGTH: 37
<212> TYPE: PRT
<213> ORGANISM: Penicillium coprobium PF1169

<400> SEQUENCE: 48

Gly Leu Phe Asp Ala Pro Phe Phe Asn Ile Thr Leu Gln Glu Ala Gln
1               5                   10                  15

Thr Met Asp Pro Gln Gln Arg Ile Phe Leu Glu Cys Val Tyr Glu Ala
            20                  25                  30

Leu Glu Asn Gly Gly
        35

<210> SEQ ID NO 49
<211> LENGTH: 70
<212> TYPE: PRT
<213> ORGANISM: Penicillium coprobium PF1169

<400> SEQUENCE: 49

Gly Arg Phe Leu Ser Ser Asp Gly Arg Cys His Thr Phe Asp Glu Lys
1               5                   10                  15

Ala Asn Gly Tyr Ala Arg Gly Glu Ala Val Gly Cys Leu Ile Leu Lys
            20                  25                  30

Pro Leu Ala Lys Ala Leu His Asp Gln Asn Lys Ile Arg Ala Val Ile
        35                  40                  45

Arg Gly Thr Gly Ser Asn Gln Asp Gly Arg Thr Ala Gly Ile Thr Val
    50                  55                  60

Pro Asn Gly Ala Ala Gln
65                  70

<210> SEQ ID NO 50
<211> LENGTH: 37
<212> TYPE: PRT
<213> ORGANISM: Penicillium coprobium PF1169

<400> SEQUENCE: 50

Ser Phe Asp Ser Arg Ala Glu Gly Tyr Ala Arg Gly Glu Gly Val Gly
1               5                   10                  15

Thr Val Val Val Lys Pro Leu Ser Thr Ala Ile Arg Asp Gly Asp Thr
            20                  25                  30

Ile Arg Ala Val Ile
        35

<210> SEQ ID NO 51
<211> LENGTH: 83
<212> TYPE: PRT
<213> ORGANISM: Penicillium coprobium PF1169

<400> SEQUENCE: 51

Trp Pro Arg Leu Pro Glu Arg Arg Ile Ala Val Val Asn Asn Phe
1               5                   10                  15

Ser Ala Ala Gly Gly Asn Thr Thr Val Ala Leu Glu Asp Ala Pro Ile
            20                  25                  30

Arg Thr Arg Ser Gly Ser Asp Pro Arg Ser Leu His Pro Ile Ala Ile
        35                  40                  45

Ser Ala Lys Ser Lys Val Ser Leu Arg Gly Asn Leu Glu Asn Leu Leu
    50                  55                  60

Ala Tyr Leu Asp Thr His Pro Asp Val Ser Leu Ser Asp Leu Ser Tyr
65                  70                  75                  80

Thr Thr Thr

<210> SEQ ID NO 52
<211> LENGTH: 59
<212> TYPE: PRT
<213> ORGANISM: Penicillium coprobium PF1169

<400> SEQUENCE: 52

Val Tyr Ser Gly Ser Met Thr Asn Asp Tyr Glu Leu Leu Ser Thr Arg
1               5                   10                  15

Asp Ile Tyr Asp Met Pro His Asn Ser Ala Thr Gly Asn Gly Arg Thr
            20                  25                  30

Met Leu Ala Asn Arg Leu Ser Trp Phe Phe Asp Leu Gln Gly Pro Ser
        35                  40                  45

Ile Met Met Asp Thr Ala Cys Ser Ser Ser Leu
    50                  55

<210> SEQ ID NO 53
<211> LENGTH: 67
<212> TYPE: PRT
<213> ORGANISM: Penicillium coprobium PF1169

<400> SEQUENCE: 53

Leu Ser Pro Gln Asn Asn Pro Glu Asp Arg Cys Gln Tyr Phe Glu Ala
1               5                   10                  15

His Gly Thr Gly Thr Gln Ala Gly Asp Pro Gln Glu Ala Ala Ala Ile
            20                  25                  30

Asn Ser Ser Phe Phe Gly Pro Glu Ser Val Pro Asp Ser Thr Asp Arg
        35                  40                  45

Leu Tyr Val Gly Ser Ile Lys Thr Ile Ile Gly His Thr Glu Ala Thr
    50                  55                  60

Ala Gly Leu
65

<210> SEQ ID NO 54
<211> LENGTH: 83
<212> TYPE: PRT
<213> ORGANISM: Penicillium coprobium PF1169

<400> SEQUENCE: 54

Asp Gly Tyr Gly Arg Gly Glu Gly Val Ala Ser Val Val Leu Lys Arg
1               5                   10                  15

Leu Gln Asp Ala Ile Asn Asp Gly Asp Pro Ile Glu Cys Val Ile Arg
            20                  25                  30

Ala Ser Gly Ala Asn Ser Asp Gly Arg Thr Met Gly Ile Thr Met Pro
        35                  40                  45

Asn Pro Lys Ala Gln Gln Ser Leu Ile Leu Ala Thr Tyr Ala Arg Ala
    50                  55                  60

Gly Leu Ser Pro Gln Asn Asn Pro Glu Asp Arg Cys Gln Tyr Phe Glu
65                  70                  75                  80

Ala His Gly

<210> SEQ ID NO 55
<211> LENGTH: 38
<212> TYPE: PRT
<213> ORGANISM: Penicillium coprobium PF1169

<400> SEQUENCE: 55

Met Leu Ala Val Gly Ala Ser Ala Ser Asp Ile Gln Gln Ile Leu Asp
1               5                   10                  15

Ala Met Arg Gly Asn Lys Ala Val Ile Ala Cys Val Asn Ser Glu Ser
            20                  25                  30

Ser Val Thr Leu Ser Gly
        35

<210> SEQ ID NO 56
<211> LENGTH: 29
<212> TYPE: PRT
<213> ORGANISM: Penicillium coprobium PF1169

<400> SEQUENCE: 56

```
Ser Gly Cys Tyr Arg Glu Leu Ala Asp Cys Pro Gly Gln Arg Gly Ile
1               5                  10                 15

Phe Thr Arg Lys Leu Lys Val Asp Val Ala Tyr His Ser
            20                  25
```

<210> SEQ ID NO 57
<211> LENGTH: 38
<212> TYPE: PRT
<213> ORGANISM: Penicillium coprobium PF1169

<400> SEQUENCE: 57

```
Gly Asn Gly Ser Ala Met Ile Ser Asn Arg Ile Ser Trp Phe Phe Asp
1               5                  10                 15

Leu Lys Gly Pro Ser Leu Ser Leu Asp Thr Ala Cys Ser Ser Ser Leu
            20                  25                 30

Val Ala Leu His Leu Ala
            35
```

<210> SEQ ID NO 58
<211> LENGTH: 59
<212> TYPE: PRT
<213> ORGANISM: Penicillium coprobium PF1169

<400> SEQUENCE: 58

```
Ile Ser Glu Cys Val Thr Val Tyr Trp Lys Ala Ile Lys Ser Ala Gln
1               5                  10                 15

Pro Asp Gly Pro Tyr Ala Leu Ala Gly Tyr Ser Tyr Gly Ser Met Leu
            20                  25                 30

Ala Phe Glu Val Ala Lys Leu Leu Ile Lys Asn Gly Asp Lys Val Asp
        35                  40                 45

Phe Leu Gly Cys Phe Asn Leu Pro Pro His Ile
        50                  55
```

<210> SEQ ID NO 59
<211> LENGTH: 72
<212> TYPE: PRT
<213> ORGANISM: Penicillium coprobium PF1169

<400> SEQUENCE: 59

```
Gly Ala Ala Val Gln Leu Val Ile Glu Gly Gly Asn Gln Pro Lys Gly
1               5                  10                 15

Ala Met Met Ala Val Gly Ala Asn Ala Ser Thr Val Gln Pro Leu Leu
            20                  25                 30

Asp Ala Met Lys Asp Lys His Ala Val Val Ala Cys Ile Asn Ser Asp
        35                  40                 45

Ser Ser Ile Thr Val Ser Gly Asp Glu Thr Ala Ile Glu Asp Leu Glu
        50                  55                 60

Ser Val Leu Lys Arg Gln Asp Ile
65                  70
```

<210> SEQ ID NO 60
<211> LENGTH: 79
<212> TYPE: PRT
<213> ORGANISM: Penicillium coprobium PF1169

<400> SEQUENCE: 60

```
Ser Val Pro Ile Glu Glu His Ser Pro Val Thr Gln Leu Gly Thr
1               5                  10                 15

Thr Cys Val Gln Met Ala Leu Thr Lys Tyr Trp Thr Ser Leu Gly Val
```

```
                20                  25                  30
Thr Pro Ser Phe Val Met Gly His Ser Leu Gly Glu Phe Ala Ala Leu
            35                  40                  45
Asn Ala Ala Gly Val Leu Thr Ile Ser Asp Thr Ile Tyr Leu Ala Gly
         50                  55                  60
Arg Arg Ala Gln Leu Leu Thr Glu Gln Ile Lys Val Gly Thr His
 65                  70                  75
```

<210> SEQ ID NO 61
<211> LENGTH: 67
<212> TYPE: PRT
<213> ORGANISM: Penicillium coprobium PF1169

<400> SEQUENCE: 61

```
Phe Ile Glu Asp Ser Ile Ser Lys Glu His Lys Pro Thr Arg Val Pro
 1               5                  10                  15
Ile His Gly Pro Tyr His Ala Ser His Leu Tyr Asn Asp Arg Asp Ile
                20                  25                  30
Asp Arg Ile Met Glu Ser Trp Pro Thr Glu Gln Leu Trp Ala Tyr Val
            35                  40                  45
Pro Gln Ile Pro Val Leu Ser Thr Gln Thr Gly Lys Ala Phe Gln Ala
         50                  55                  60
Asp Ser Leu
 65
```

<210> SEQ ID NO 62
<211> LENGTH: 76
<212> TYPE: PRT
<213> ORGANISM: Penicillium coprobium PF1169

<400> SEQUENCE: 62

```
Gly Pro Ser Met Thr Ile Asp Thr Ala Cys Ser Ser Leu Ile Ala
 1               5                  10                  15
Leu His Gln Ala Val Gln Ser Leu Arg Ser Gly Glu Thr Asp Val Ala
                20                  25                  30
Val Ala Ala Gly Thr Asn Leu Leu Leu Gly Pro Glu Gln Tyr Ile Ala
            35                  40                  45
Glu Ser Lys Leu Lys Met Leu Ser Pro Asn Gly Arg Ser Arg Met Trp
         50                  55                  60
Asp Lys Asp Ala Asp Gly Tyr Ala Arg Gly Asp Gly
 65                  70                  75
```

<210> SEQ ID NO 63
<211> LENGTH: 31
<212> TYPE: PRT
<213> ORGANISM: Penicillium coprobium PF1169

<400> SEQUENCE: 63

```
Leu Phe Leu Phe Pro Asp Gly Ser Gly Ser Ala Thr Ser Tyr Ala Thr
 1               5                  10                  15
Ile Pro Gly Ile Ser Pro Asp Val Cys Val Tyr Gly Leu Asn Cys
                20                  25                  30
```

<210> SEQ ID NO 64
<211> LENGTH: 26
<212> TYPE: PRT
<213> ORGANISM: Penicillium coprobium PF1169

<400> SEQUENCE: 64

```
Ala Lys His Pro Pro Ala Thr Ser Ile Leu Leu Gln Gly Asn Pro Lys
1               5                   10                  15

Thr Ala Thr Gln Ser Phe Ile Phe Val Pro
            20                  25
```

<210> SEQ ID NO 65
<211> LENGTH: 46
<212> TYPE: PRT
<213> ORGANISM: Penicillium coprobium PF1169

<400> SEQUENCE: 65

```
Tyr Gln Ala Thr Gly Cys Ala Ala Ser Leu Gln Ser Asn Arg Ile Ser
1               5                   10                  15

Tyr Phe Phe Asp Leu Arg Gly Pro Ser Ile Thr Ile Asp Thr Ala Cys
            20                  25                  30

Ser Ser Ser Leu Val Ala Leu His Tyr Ala Val Gln Ser Leu
            35                  40                  45
```

<210> SEQ ID NO 66
<211> LENGTH: 66
<212> TYPE: PRT
<213> ORGANISM: Penicillium coprobium PF1169

<400> SEQUENCE: 66

```
Tyr Ser Ala Thr Gly Ser Gly Leu Thr Val Leu Ala Asn Arg Ile Thr
1               5                   10                  15

His Cys Phe Asp Leu Arg Gly Pro Ser His Val Val Asp Thr Ala Cys
            20                  25                  30

Ser Ser Ser Leu Tyr Ala Leu His Ser Ala Cys Leu Ala Leu Asp Ser
            35                  40                  45

Arg Asp Cys Asp Gly Ala Val Val Ala Ala Asn Leu Ile Gln Ser
50                  55                  60

Pro Glu
65
```

<210> SEQ ID NO 67
<211> LENGTH: 76
<212> TYPE: PRT
<213> ORGANISM: Penicillium coprobium PF1169

<400> SEQUENCE: 67

```
Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
            35                  40                  45

Asn Ala Ala Gly Val Leu Thr Ile Ser Asp Thr Ile Tyr Leu Ala Gly
50                  55                  60

Arg Arg Ala Gln Leu Leu Thr Glu Gln Ile Lys Val
65                  70                  75
```

<210> SEQ ID NO 68
<211> LENGTH: 71
<212> TYPE: PRT
<213> ORGANISM: Penicillium coprobium PF1169

<400> SEQUENCE: 68

```
His Leu Asn Leu Met Gly Pro Ser Thr Ala Val Asp Ala Ala Cys Ala
1               5                   10                  15
```

Ser Ser Leu Val Ala Ile His His Gly Val Gln Ala Ile Lys Leu Gly
            20                  25                  30

Glu Ser Arg Val Ala Ile Val Gly Gly Val Asn Ala Leu Cys Gly Pro
        35                  40                  45

Gly Leu Thr Arg Val Leu Asp Lys Ala Gly Ser Ile Ser Ser Asp Gly
    50                  55                  60

Ser Cys Lys Ser Phe Asp Asp
65                  70

<210> SEQ ID NO 69
<211> LENGTH: 84
<212> TYPE: PRT
<213> ORGANISM: Penicillium coprobium PF1169

<400> SEQUENCE: 69

Ser Phe Arg Arg Gln Glu Asp Thr Trp Lys Val Leu Ser Asn Ala Thr
1               5                   10                  15

Ser Thr Leu Tyr Leu Ala Gly Ile Glu Ile Lys Trp Lys Glu Tyr His
            20                  25                  30

Gln Asp Phe Asn Ala Ala His Arg Val Leu Pro Leu Pro Ser Tyr Lys
        35                  40                  45

Trp Asp Leu Lys Asn Tyr Trp Ile Pro Tyr Thr Asn Asn Phe Cys Leu
    50                  55                  60

Leu Lys Gly Ala Pro Ala Ala Pro Val Ala Glu Ala Thr Pro Ile Ser
65                  70                  75                  80

Val Phe Leu Ser

<210> SEQ ID NO 70
<211> LENGTH: 78
<212> TYPE: PRT
<213> ORGANISM: Penicillium coprobium PF1169

<400> SEQUENCE: 70

Lys Thr Ser Cys Phe Val Gly Ser Phe Ser Ala Asp Tyr Thr Asp Leu
1               5                   10                  15

Leu Leu Arg Asp Pro Glu Cys Val Pro Met Tyr Gln Cys Thr Asn Ala
            20                  25                  30

Gly Gln Ser Arg Ala Met Thr Ala Asn Arg Leu Ser Tyr Phe Phe Asp
        35                  40                  45

Leu Lys Gly Pro Ser Val Thr Val Asp Thr Ala Cys Ser Gly Ser Leu
    50                  55                  60

Val Ala Leu His Leu Ala Cys Gln Ser Leu Arg Thr Gly Asp
65                  70                  75

<210> SEQ ID NO 71
<211> LENGTH: 67
<212> TYPE: PRT
<213> ORGANISM: Penicillium coprobium PF1169

<400> SEQUENCE: 71

Tyr Ser Ala Thr Gly Ser Gly Leu Thr Val Leu Ala Asn Arg Ile Thr
1               5                   10                  15

His Cys Phe Asp Leu Arg Gly Pro Ser His Val Asp Thr Ala Cys
            20                  25                  30

Ser Ser Ser Leu Tyr Ala Leu His Ser Ala Cys Phe Gly Pro Leu Asn
        35                  40                  45

Ser Arg Asp Cys Asp Gly Ala Val Val Ala Ala Ala Asn Leu Ile Gln

Ser Pro Glu
65

<210> SEQ ID NO 72
<211> LENGTH: 79
<212> TYPE: PRT
<213> ORGANISM: Penicillium coprobium PF1169

<400> SEQUENCE: 72

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val Leu Thr Ile Ser Asp Thr Ile Tyr Leu Ala Gly
    50                  55                  60

Arg Arg Ala Gln Leu Leu Thr Glu Gln Ile Glu Gly Gly Thr His
65                  70                  75

<210> SEQ ID NO 73
<211> LENGTH: 40
<212> TYPE: PRT
<213> ORGANISM: Penicillium coprobium PF1169

<400> SEQUENCE: 73

Glu Ala Asn Leu His Val Pro Leu Glu Pro Thr Pro Trp Pro Ala Gly
1               5                   10                  15

Arg Pro Glu Arg Ile Ser Val Asn Ser Phe Gly Ile Gly Gly Ser Asn
            20                  25                  30

Ala His Ala Ile Leu Glu Ser Ala
        35                  40

<210> SEQ ID NO 74
<211> LENGTH: 70
<212> TYPE: PRT
<213> ORGANISM: Penicillium coprobium PF1169
<220> FEATURE:
<221> NAME/KEY: misc_feature
<222> LOCATION: (5)..(5)
<223> OTHER INFORMATION: Xaa can be any naturally occurring amino acid

<400> SEQUENCE: 74

Ile Gly His Thr Xaa Gly Ser Ala Gly Leu Ala Ser Leu Ile Gly Ser
1               5                   10                  15

Ser Leu Ala Met Lys His Gly Val Ile Pro Pro Asn Leu His Phe Gly
            20                  25                  30

Gln Leu Ser Glu Lys Val Ala Pro Phe Tyr Thr His Leu Asn Ile Pro
        35                  40                  45

Thr Glu Pro Val Pro Trp Pro Asn Ser Thr Ser Ser Gln Val Lys Arg
    50                  55                  60

Ala Ser Ile Asn Ser Phe
65                  70

<210> SEQ ID NO 75
<211> LENGTH: 45
<212> TYPE: PRT
<213> ORGANISM: Penicillium coprobium PF1169

<400> SEQUENCE: 75

```
Pro Val Cys Ser Gly Met Val Lys Ala Thr Phe Gly Pro Gln Ala Thr
1               5                   10                  15

Thr Val Ala Ser Phe Arg Arg Gln Glu Asp Thr Trp Lys Val Leu Ser
                20                  25                  30

Asn Ala Thr Ser Thr Leu Tyr Leu Ala Gly Ile Glu Ile
                35                  40                  45

<210> SEQ ID NO 76
<211> LENGTH: 19
<212> TYPE: PRT
<213> ORGANISM: Penicillium coprobium PF1169
<220> FEATURE:
<221> NAME/KEY: misc_feature
<222> LOCATION: (13)..(13)
<223> OTHER INFORMATION: Xaa can be any naturally occurring amino acid

<400> SEQUENCE: 76

Leu Leu Gly Leu Arg Leu Lys Trp Lys Glu Tyr His Xaa Asp Phe Asn
1               5                   10                  15

Ala Ala His

<210> SEQ ID NO 77
<211> LENGTH: 69
<212> TYPE: PRT
<213> ORGANISM: Penicillium coprobium PF1169

<400> SEQUENCE: 77

Val Tyr Ser Gly Ser Met Thr Asn Asp Tyr Glu Leu Leu Ser Thr Arg
1               5                   10                  15

Asp Ile Tyr Asp Met Pro His Asn Ser Ala Thr Gly Asn Gly Arg Thr
                20                  25                  30

Met Leu Ala Asn Arg Leu Ser Trp Phe Phe Asp Leu Gln Gly Pro Ser
                35                  40                  45

Ile Met Met Asp Thr Ala Cys Ser Ser Ser Leu Thr Ala Val His Leu
    50                  55                  60

Ala Ala Gln Ser Leu
65

<210> SEQ ID NO 78
<211> LENGTH: 85
<212> TYPE: PRT
<213> ORGANISM: Penicillium coprobium PF1169

<400> SEQUENCE: 78

Asp Ala Gln Phe Phe Gly Thr Lys Pro Val Glu Ala Asn Ser Ile Asp
1               5                   10                  15

Pro Gln Gln Arg Leu Leu Leu Glu Thr Val Tyr Glu Gly Leu Glu Thr
                20                  25                  30

Ser Gly Ile Pro Met Glu Arg Leu Gln Gly Ser Asn Thr Ala Val Tyr
                35                  40                  45

Val Gly Leu Met Thr Asn Asp Tyr Ala Asp Met Leu Gly Arg Asp Met
    50                  55                  60

Gln Asn Phe Pro Thr Tyr Phe Ala Ser Gly Thr Ala Arg Ser Ile Leu
65                  70                  75                  80

Ser Asn Arg Val Ser
                85

<210> SEQ ID NO 79
<211> LENGTH: 28
```

<212> TYPE: PRT
<213> ORGANISM: Penicillium coprobium PF1169

<400> SEQUENCE: 79

Asp Pro Ala Tyr Phe Asp Ser Phe Phe Asn Ile Thr Lys Thr Glu
1               5                   10                  15

Leu Leu Thr Leu Asp Pro Gln Gln Arg Leu Val Leu
            20                  25

<210> SEQ ID NO 80
<211> LENGTH: 51
<212> TYPE: PRT
<213> ORGANISM: Penicillium coprobium PF1169

<400> SEQUENCE: 80

Val Ala Cys Val Asn Ser Pro Ala Ser Thr Thr Leu Ser Gly Asp Val
1               5                   10                  15

Asp Tyr Ile Asn Gln Leu Glu Ala Arg Leu Gln Gln Asp Gly His Phe
            20                  25                  30

Ala Arg Lys Leu Arg Ile Asp Thr Ala Tyr His Ser Pro His Met Glu
        35                  40                  45

Glu Leu Val
    50

<210> SEQ ID NO 81
<211> LENGTH: 24
<212> TYPE: PRT
<213> ORGANISM: Penicillium coprobium PF1169

<400> SEQUENCE: 81

Leu Lys Ser Ile Ser Pro Val Val Thr Gln Leu Gly Thr Thr Cys Val
1               5                   10                  15

Gln Met Ala Leu Thr Lys Tyr Trp
            20

<210> SEQ ID NO 82
<211> LENGTH: 59
<212> TYPE: PRT
<213> ORGANISM: Penicillium coprobium PF1169

<400> SEQUENCE: 82

Gly Cys Phe Tyr Gly Met Thr Ser Asp Asp Tyr Arg Glu Val Asn Ser
1               5                   10                  15

Gly Gln Asp Ile Asp Thr Tyr Phe Ile Pro Gly Gly Asn Arg Ala Phe
            20                  25                  30

Thr Pro Gly Arg Ile Asn Tyr Tyr Phe Lys Phe Ser Gly Pro Ser Val
        35                  40                  45

Ser Val Asp Thr Ala Cys Ser Ser Leu Ala
    50                  55

<210> SEQ ID NO 83
<211> LENGTH: 16
<212> TYPE: PRT
<213> ORGANISM: Penicillium coprobium PF1169

<400> SEQUENCE: 83

Leu Glu Met Ala Gly Phe Ile Pro Asp Ser Ile Pro Leu Arg Arg Arg
1               5                   10                  15

<210> SEQ ID NO 84
<211> LENGTH: 53

<212> TYPE: PRT
<213> ORGANISM: Penicillium coprobium PF1169

<400> SEQUENCE: 84

Ala Ile Val Gly Gly Val Asn Ala Leu Cys Gly Pro Gly Leu Thr Arg
1               5                   10                  15

Val Leu Asp Lys Ala Gly Ala Ile Ser Ser Asp Gly Ser Cys Lys Ser
            20                  25                  30

Phe Asp Asp Ala His Gly Tyr Ala Arg Gly Glu Gly Ala Gly Ala
        35                  40                  45

Leu Val Thr Lys Lys
    50

<210> SEQ ID NO 85
<211> LENGTH: 60
<212> TYPE: PRT
<213> ORGANISM: Penicillium coprobium PF1169

<400> SEQUENCE: 85

Ile Ala Ile Val Gly Ile Gly Gly Arg Phe Pro Gly Glu Ala Thr Asn
1               5                   10                  15

Pro Asn Arg Leu Trp Asp Met Val Ser Asn Gly Arg Ser Ala Leu Thr
            20                  25                  30

Glu Val Pro Lys Asp Arg Phe Asn Ile Asp Ala Phe Tyr His Pro His
        35                  40                  45

Ala Glu Arg Gln Gly Thr Met Asn Val Arg Arg Gly
    50                  55                  60

<210> SEQ ID NO 86
<211> LENGTH: 53
<212> TYPE: PRT
<213> ORGANISM: Penicillium coprobium PF1169

<400> SEQUENCE: 86

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val
    50

<210> SEQ ID NO 87
<211> LENGTH: 18
<212> TYPE: PRT
<213> ORGANISM: Penicillium coprobium PF1169

<400> SEQUENCE: 87

Ser Val Pro Ile Glu Glu His Ser Pro Val Val Thr Gln Leu Gly Thr
1               5                   10                  15

Thr Cys

<210> SEQ ID NO 88
<211> LENGTH: 62
<212> TYPE: PRT
<213> ORGANISM: Penicillium coprobium PF1169

<400> SEQUENCE: 88

Phe Leu Asp Asp Leu Ala Phe Thr Val Asn Glu Arg Arg Ser Ile Phe

```
                1               5                   10                  15
            Pro Trp Lys Ala Ala Val Val Gly Asp Thr Met Glu Gly Leu Ala Ala
                            20                  25                  30

Ser Leu Ala Gln Asn Ile Lys Pro Arg Ser Val Leu Arg Met Pro Thr
                        35                  40                  45

Leu Gly Phe Val Phe Thr Gly Gln Gly Ala Gln Trp Pro Gly
                    50                  55                  60

<210> SEQ ID NO 89
<211> LENGTH: 51
<212> TYPE: PRT
<213> ORGANISM: Penicillium coprobium PF1169

<400> SEQUENCE: 89

Ser Ser Phe Leu Thr Ser Thr Val Gln Gln Ile Val Glu Glu Thr Ile
1               5                   10                  15

Gln Gly Gly Thr Gly Gln Val Val Met Glu Ser Asp Leu Met Gln Thr
            20                  25                  30

Glu Phe Leu Glu Ala Ala Asn Gly His Arg Met Asn Asp Cys Gly Val
        35                  40                  45

Val Thr Ser
    50

<210> SEQ ID NO 90
<211> LENGTH: 77
<212> TYPE: PRT
<213> ORGANISM: Penicillium coprobium PF1169

<400> SEQUENCE: 90

Glu Cys Gly Phe Val Glu Met His Gly Thr Gly Thr Lys Ala Gly Asp
1               5                   10                  15

Pro Val Glu Ala Ala Ala Val His Ala Ala Leu Gly Lys Asn Arg Thr
            20                  25                  30

Leu Arg Asn Pro Leu Tyr Ile Gly Ser Val Lys Ser Asn Ile Gly His
        35                  40                  45

Leu Glu Gly Ala Ser Gly Ile Val Ala Val Ile Lys Ala Ala Met Met
    50                  55                  60

Leu Asp Arg Asp Leu Met Leu Pro Asn Ala Glu Phe Lys
65                  70                  75

<210> SEQ ID NO 91
<211> LENGTH: 78
<212> TYPE: PRT
<213> ORGANISM: Penicillium coprobium PF1169
<220> FEATURE:
<221> NAME/KEY: misc_feature
<222> LOCATION: (4)..(4)
<223> OTHER INFORMATION: Xaa can be any naturally occurring amino acid

<400> SEQUENCE: 91

Phe Phe Lys Xaa Ser Gly Pro Ser Phe Ser Ile Asp Thr Ala Cys Ser
1               5                   10                  15

Ser Ser Leu Ala Thr Ile Gln Val Cys Thr His Leu Phe His Val His
            20                  25                  30

Leu Asn Arg Gln Leu Thr Ile Ala Ala Cys Thr Ser Leu Trp Asn Gly
        35                  40                  45

Glu Thr Asp Thr Val Val Ala Gly Gly Met Asn Ile Leu Thr Asn Ser
    50                  55                  60

Asp Ala Phe Ala Gly Leu Ser His Gly His Phe Leu Thr Lys
```

<210> SEQ ID NO 92
<211> LENGTH: 79
<212> TYPE: PRT
<213> ORGANISM: Penicillium coprobium PF1169

<400> SEQUENCE: 92

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
                20                  25                  30

Thr Pro Ser Phe Val Met Gly His Ser Leu Gly Glu Phe Ala Ala Leu
            35                  40                  45

Asn Ala Ala Gly Val Leu Thr Ile Ser Asp Thr Ile Tyr Leu Ala Gly
        50                  55                  60

Arg Arg Ala Gln Leu Leu Thr Glu Gln Ile Glu Gly Gly Thr His
65                  70                  75

<210> SEQ ID NO 93
<211> LENGTH: 68
<212> TYPE: PRT
<213> ORGANISM: Penicillium coprobium PF1169

<400> SEQUENCE: 93

Leu Ser Ser Asp Gly Arg Cys His Thr Phe Asp Glu Lys Ala Asn Gly
1               5                   10                  15

Tyr Ala Arg Gly Glu Ala Val Gly Cys Leu Ile Leu Lys Pro Leu Ala
                20                  25                  30

Lys Ala Leu His Asp Gln Asn Lys Ile Arg Ala Val Ile Arg Gly Thr
            35                  40                  45

Gly Ser Asn Gln Asp Gly Arg Thr Ala Gly Ile Thr Val Pro Asn Gly
        50                  55                  60

Ala Ala Gln Glu
65

<210> SEQ ID NO 94
<211> LENGTH: 80
<212> TYPE: PRT
<213> ORGANISM: Penicillium coprobium PF1169

<400> SEQUENCE: 94

Ser Pro Leu Phe Gly Leu Ala Arg Ile Ile Ala Ser Glu His Pro Asp
1               5                   10                  15

Leu Gly Ser Leu Ile Asp Ile Glu Glu Pro Ile Ile Pro Leu Ser Thr
                20                  25                  30

Met Arg Tyr Ile Gln Gly Ala Asp Ile Val Arg Ile Ser Asp Gly Ile
            35                  40                  45

Ala Arg Thr Ser Arg Phe Arg Ser Leu Pro Arg Thr Lys Leu Arg Pro
        50                  55                  60

Val Ser Asp Gly Pro Arg Leu Leu Pro Arg Pro Glu Gly Thr Tyr Leu
65                  70                  75                  80

<210> SEQ ID NO 95
<211> LENGTH: 75
<212> TYPE: PRT
<213> ORGANISM: Penicillium coprobium PF1169

<400> SEQUENCE: 95

Asn Arg Ile Ser Tyr Tyr Phe Asp Trp Gln Gly Pro Ser Met Ala Val
1               5                   10                  15

Asp Thr Gly Cys Ser Ser Ser Leu Leu Ala Val His Leu Gly Val Glu
            20                  25                  30

Ala Leu Gln Asn Asp Asp Cys Ser Met Ala Val Ala Val Gly Ser Asn
        35                  40                  45

Leu Ile Leu Ser Pro Asn Ala Tyr Ile Ala Asp Ser Lys Thr Arg Met
50                  55                  60

Leu Ser Pro Thr Gly Arg Ser Arg Met Trp Asp
65                  70                  75

<210> SEQ ID NO 96
<211> LENGTH: 81
<212> TYPE: PRT
<213> ORGANISM: Penicillium coprobium PF1169

<400> SEQUENCE: 96

Val Asp Val Asn Pro Ala Val Leu Lys Asp Ala Pro Leu Pro Trp Asp
1               5                   10                  15

Pro Ser Ser Trp Ala Pro Ile Leu Asp Ala Ala Thr Ser Val Gly Ser
            20                  25                  30

Thr Ile Phe Gln Thr Ala Ala Leu Arg Met Pro Ala Gln Ile Glu Arg
        35                  40                  45

Val Glu Ile Phe Thr Ser Glu Asn Pro Pro Lys Thr Ser Trp Leu Tyr
50                  55                  60

Val Gln Glu Ala Ser Asp Ala Val Pro Thr Ser His Val Ser Val Val
65                  70                  75                  80

Ser

<210> SEQ ID NO 97
<211> LENGTH: 37
<212> TYPE: PRT
<213> ORGANISM: Penicillium coprobium PF1169

<400> SEQUENCE: 97

Pro Leu Phe Gly Leu Ala Arg Ile Ile Ala Ser Glu His Pro Asp Leu
1               5                   10                  15

Gly Ser Leu Ile Asp Ile Glu Glu Pro Ile Ile Pro Leu Ser Thr Met
            20                  25                  30

Arg Tyr Ile Arg Gly
            35

<210> SEQ ID NO 98
<211> LENGTH: 84
<212> TYPE: PRT
<213> ORGANISM: Penicillium coprobium PF1169

<400> SEQUENCE: 98

Ala Val Ile Arg Gly Thr Gly Ser Asn Gln Asp Gly Arg Thr Ala Gly
1               5                   10                  15

Ile Thr Val Pro Asn Gly Ala Ala Gln Glu Ser Leu Ile Arg Ser Val
            20                  25                  30

Tyr Ala Gln Ala Asp Leu Asp Pro Ser Glu Thr Asp Phe Val Glu Ala
        35                  40                  45

His Gly Thr Gly Thr Leu Ala Gly Asp Pro Val Glu Thr Gly Ala Ile
50                  55                  60

Ala Arg Val Phe Gly Thr Asp Arg Pro Pro Gly Asp Pro Val Arg Ile
65                  70                  75                  80

Gly Ser Ile Lys

<210> SEQ ID NO 99
<211> LENGTH: 69
<212> TYPE: PRT
<213> ORGANISM: Penicillium coprobium PF1169

<400> SEQUENCE: 99

Leu Glu Val Val Trp Glu Cys Leu Glu Asn Ser Gly Glu Thr Gln Trp
1               5                   10                  15

Arg Gly Lys Glu Ile Gly Cys Phe Val Gly Val Phe Gly Glu Asp Trp
            20                  25                  30

Leu Glu Met Ser His Lys Asp Pro Gln His Leu Asn Gln Met Phe Pro
        35                  40                  45

Ile Ala Thr Gly Gly Phe Ala Leu Ala Asn Gln Val Ser Tyr Arg Phe
    50                  55                  60

Asp Leu Thr Gly Pro
65

<210> SEQ ID NO 100
<211> LENGTH: 79
<212> TYPE: PRT
<213> ORGANISM: Penicillium coprobium PF1169

<400> SEQUENCE: 100

Gly Gly Ala Thr Asp Thr Glu Lys Phe Trp Asp Leu Leu Ala Ser Gly
1               5                   10                  15

Val Asp Val His Arg Lys Ile Pro Ala Asp Arg Phe Asp Val Glu Thr
            20                  25                  30

His Tyr Asp Pro Asn Gly Lys Arg Met Asn Ala Ser His Thr Pro Tyr
        35                  40                  45

Gly Cys Phe Ile Asp Glu Pro Gly Leu Phe Asp Ala Ala Phe Phe Asn
    50                  55                  60

Met Ser Pro Arg Glu Ala Gln Gln Thr Asp Pro Met Gln Arg Leu
65                  70                  75

<210> SEQ ID NO 101
<211> LENGTH: 52
<212> TYPE: PRT
<213> ORGANISM: Penicillium coprobium PF1169

<400> SEQUENCE: 101

Glu Leu Arg His Gly Lys Asn Ile Asp Lys Pro Glu Tyr Ser Gln Pro
1               5                   10                  15

Leu Cys Thr Ala Ile Gln Ile Ala Leu Val Glu Leu Leu Glu Ser Phe
            20                  25                  30

Gly Val Val Pro Lys Ala Val Val Gly His Ser Ser Gly Glu Ile Ala
        35                  40                  45

Ala Ala Tyr Val
    50

<210> SEQ ID NO 102
<211> LENGTH: 34
<212> TYPE: PRT
<213> ORGANISM: Penicillium coprobium PF1169

<400> SEQUENCE: 102

Val Gly Phe Val Phe Thr Gly Gln Gly Ala Gln Trp His Gly Met Gly
1               5                   10                  15

```
<210> SEQ ID NO 103
<211> LENGTH: 63
<212> TYPE: PRT
<213> ORGANISM: Penicillium coprobium PF1169

<400> SEQUENCE: 103

Phe Asp Ala Ala Phe Phe Asn Met Ser Pro Arg Glu Ala Gln Gln Thr
1               5                   10                  15
Asp Pro Met Gln Arg Leu Ala Ile Val Thr Ala Tyr Glu Ala Leu Glu
            20                  25                  30
Arg Ala Gly Tyr Val Ala Asn Arg Thr Ala Ala Thr Asn Leu His Arg
        35                  40                  45
Ile Gly Thr Phe Tyr Gly Gln Ala Ser Asp Asp Tyr Arg Glu Val
    50                  55                  60

<210> SEQ ID NO 104
<211> LENGTH: 43
<212> TYPE: PRT
<213> ORGANISM: Penicillium coprobium PF1169

<400> SEQUENCE: 104

Ala Val Val Ser Gly Val Ser Ile Leu Glu Asn Pro Val Glu Thr Ile
1               5                   10                  15
Gly Met Ser His His Gly Leu Leu Gly Pro Gln Gly Arg Ser Phe Ser
            20                  25                  30
Phe Asp Ser Arg Ala Glu Gly Tyr Ala Arg Gly
        35                  40

<210> SEQ ID NO 105
<211> LENGTH: 71
<212> TYPE: PRT
<213> ORGANISM: Penicillium coprobium PF1169

<400> SEQUENCE: 105

Lys Ala Ser Leu Ser Leu Gln His Gly Met Ile Ala Pro Asn Leu Leu
1               5                   10                  15
Met Gln His Leu Asn Pro Lys Ile Lys Pro Phe Ala Ala Lys Leu Ser
            20                  25                  30
Val Pro Thr Glu Cys Ile Pro Trp Pro Ala Val Pro Asp Gly Cys Pro
        35                  40                  45
Arg Arg Ala Ser Val Asn Ser Phe Gly Phe Gly Gly Ala Asn Val His
    50                  55                  60
Val Val Leu Glu Ser Tyr Thr
65                  70

<210> SEQ ID NO 106
<211> LENGTH: 28
<212> TYPE: PRT
<213> ORGANISM: Penicillium coprobium PF1169

<400> SEQUENCE: 106

Pro Trp Pro Thr Thr Gly Leu Arg Arg Ala Ser Val Asn Ser Phe Gly
1               5                   10                  15
Tyr Gly Gly Thr Asn Ala His Cys Val Leu Asp Asp
            20                  25
```

(preceding continuation from SEQ ID NO 102:)
```
Lys Glu Leu Leu Ser Thr Tyr Pro Ile Phe Arg Gln Thr Met Gln Asp
            20                  25                  30
Val Asp
```

<210> SEQ ID NO 107
<211> LENGTH: 71
<212> TYPE: PRT
<213> ORGANISM: Penicillium coprobium PF1169

<400> SEQUENCE: 107

Lys Ala Ser Leu Ser Leu Gln His Gly Met Ile Ala Pro Asn Leu Leu
1               5                   10                  15
Met Gln His Leu Asn Pro Lys Ile Lys Pro Phe Ala Ala Lys Leu Ser
            20                  25                  30
Val Pro Thr Glu Cys Ile Pro Trp Pro Ala Val Pro Asp Gly Cys Pro
        35                  40                  45
Arg Arg Ala Ser Val Asn Ser Phe Gly Phe Gly Ala Asn Val His
    50                  55                  60
Val Val Leu Glu Ser Tyr Thr
65                  70

<210> SEQ ID NO 108
<211> LENGTH: 50
<212> TYPE: PRT
<213> ORGANISM: Penicillium coprobium PF1169

<400> SEQUENCE: 108

Asp Arg Leu Phe Leu Gln Met Ser His Glu Trp Glu Ala Ala Leu
1               5                   10                  15
Ala Pro Lys Val Thr Gly Thr Trp Asn Leu His His Ala Thr Ala Gln
            20                  25                  30
His Ser Leu Asp Phe Phe Val Val Phe Gly Ser Ile Ala Gly Val Cys
        35                  40                  45
Gly Asn
    50

<210> SEQ ID NO 109
<211> LENGTH: 82
<212> TYPE: PRT
<213> ORGANISM: Penicillium coprobium PF1169

<400> SEQUENCE: 109

Thr Phe Leu Lys Gly Thr Gly Gly Gln Met Leu Gln Asn Val Val Leu
1               5                   10                  15
Arg Val Pro Val Ala Ile Asn Ala Pro Arg Ser Val Gln Val Val
            20                  25                  30
Gln Gln Asp Gln Val Lys Val Val Ser Arg Leu Ile Pro Ser Glu Ala
        35                  40                  45
Ser Val Leu Asp Asp Ala Ser Trp Val Thr His Thr Thr Ala Tyr
    50                  55                  60
Trp Asp Arg Arg Val Leu Gly Ser Glu Asp Arg Ile Asp Leu Ala Ala
65                  70                  75                  80
Val Lys

<210> SEQ ID NO 110
<211> LENGTH: 30
<212> TYPE: PRT
<213> ORGANISM: Penicillium coprobium PF1169

<400> SEQUENCE: 110

Asp Thr Ala Cys Ser Ser Ser Leu Val Ala Leu His Tyr Ala Val Gln
1               5                   10                  15

Ser Leu Arg Asn Gly Glu Ser Thr Glu Ala Leu Ile Ala Gly
            20                  25                  30

<210> SEQ ID NO 111
<211> LENGTH: 38
<212> TYPE: PRT
<213> ORGANISM: Penicillium coprobium PF1169

<400> SEQUENCE: 111

Gly Thr Gly Asn Gly Ser Ala Met Ile Ser Asn Arg Ile Ser Trp Phe
1               5                   10                  15

Phe Asp Leu Lys Gly Pro Ser Leu Ser Leu Asp Thr Ala Cys Ser Ser
            20                  25                  30

Ser Leu Val Ala Leu His
        35

<210> SEQ ID NO 112
<211> LENGTH: 72
<212> TYPE: PRT
<213> ORGANISM: Penicillium coprobium PF1169

<400> SEQUENCE: 112

Thr Ser Thr Gln Leu Asn Asp Leu Asn Glu Thr Asn Ala Ile Lys Lys
1               5                   10                  15

Val Phe Gly Lys Gln Ala Tyr Asn Ile Pro Ile Ser Ser Thr Lys Ser
            20                  25                  30

Tyr Thr Gly His Leu Ile Gly Ala Ala Gly Thr Met Glu Thr Ile Phe
        35                  40                  45

Cys Ile Lys Thr Met Gln Glu Lys Ile Ala Pro Ala Thr Thr Asn Leu
    50                  55                  60

Lys Glu Arg Asp Ser Asn Cys Asp
65                  70

<210> SEQ ID NO 113
<211> LENGTH: 50
<212> TYPE: PRT
<213> ORGANISM: Penicillium coprobium PF1169

<400> SEQUENCE: 113

Val Ile Val Gly Ser Ala Ala Asn Gln Asn Leu Asn Leu Ser His Ile
1               5                   10                  15

Thr Val Pro His Ser Gly Ser Gln Val Lys Leu Tyr Gln Asn Val Met
            20                  25                  30

Ser Gln Ala Gly Val His Pro His Ser Val Thr Tyr Val Glu Ala His
        35                  40                  45

Gly Thr
    50

<210> SEQ ID NO 114
<211> LENGTH: 48
<212> TYPE: PRT
<213> ORGANISM: Penicillium coprobium PF1169

<400> SEQUENCE: 114

Leu Pro Thr Ala Ile Gln Pro Leu Phe Arg Ala Asn Val Ser Tyr Leu
1               5                   10                  15

Leu Val Gly Gly Leu Gly Gly Ile Gly Lys Glu Val Ala Leu Trp Met
            20                  25                  30

Val Gln Asn Gly Ala Lys Ser Leu Ile Phe Val Asn Arg Ser Gly Leu

```
                 35                  40                  45
```

<210> SEQ ID NO 115
<211> LENGTH: 53
<212> TYPE: PRT
<213> ORGANISM: Penicillium coprobium PF1169

<400> SEQUENCE: 115

```
Val Ala Ile Val Gly Gly Val Asn Ala Leu Cys Gly Pro Gly Leu Thr
1               5                   10                  15

Arg Val Leu Asp Lys Ala Gly Ala Ile Ser Ser Asp Gly Ser Cys Lys
                20                  25                  30

Ser Phe Asp Asp Asp Ala His Gly Tyr Ala Arg Gly Glu Gly Ala Gly
            35                  40                  45

Ala Leu Val Leu Lys
        50
```

<210> SEQ ID NO 116
<211> LENGTH: 28
<212> TYPE: PRT
<213> ORGANISM: Penicillium coprobium PF1169

<400> SEQUENCE: 116

```
Pro Trp Glu Ser Pro Gly Ala Arg Arg Val Ser Val Asn Ser Phe Gly
1               5                   10                  15

Tyr Gly Gly Ser Asn Ala His Val Ile Ile Glu Asp
                20                  25
```

<210> SEQ ID NO 117
<211> LENGTH: 72
<212> TYPE: PRT
<213> ORGANISM: Penicillium coprobium PF1169

<400> SEQUENCE: 117

```
Lys Thr Leu Arg Glu Trp Met Thr Ala Glu Gly Lys Asp His Asn Leu
1               5                   10                  15

Ser Asp Ile Leu Thr Thr Leu Ala Thr Arg Arg Asp His His Asp Tyr
                20                  25                  30

Arg Ala Ala Leu Val Val Asp Asp Asn Arg Asp Ala Glu Leu Ala Leu
            35                  40                  45

Gln Ala Leu Glu His Gly Val Asp Gln Thr Phe Thr Thr Gln Ser Arg
        50                  55                  60

Val Phe Gly Ala Asp Ile Ser Lys
65                  70
```

<210> SEQ ID NO 118
<211> LENGTH: 80
<212> TYPE: PRT
<213> ORGANISM: Penicillium coprobium PF1169

<400> SEQUENCE: 118

```
Ser Asp Asp Tyr Arg Glu Val Asn Ser Gly Gln Asp Ile Asp Thr Tyr
1               5                   10                  15

Phe Ile Pro Gly Gly Asn Arg Ala Phe Thr Pro Gly Arg Ile Asn Tyr
                20                  25                  30

Tyr Phe Lys Phe Ser Gly Pro Ser Val Ser Val Asp Thr Ala Cys Ser
            35                  40                  45

Ser Ser Leu Ala Ala Ile His Val Ala Cys Asn Ser Leu Trp Arg Asn
        50                  55                  60
```

Glu Ser Asp Ser Ala Val Ala Gly Gly Val Asn Ile Leu Thr Asn Pro
 65                  70                  75                  80

<210> SEQ ID NO 119
<211> LENGTH: 56
<212> TYPE: PRT
<213> ORGANISM: Penicillium coprobium PF1169

<400> SEQUENCE: 119

Leu Ser Ser Asp Gly Arg Cys His Thr Phe Asp Glu Lys Ala Asn Gly
1               5                   10                  15

Tyr Ala Arg Gly Glu Ala Val Gly Cys Leu Ile Leu Lys Pro Leu Ala
            20                  25                  30

Lys Ala Leu His Asp Gln Asn Lys Ile Arg Ala Val Ile Arg Gly Thr
        35                  40                  45

Gly Ser Asn Gln Gly Arg Ala Asn
    50                  55

<210> SEQ ID NO 120
<211> LENGTH: 63
<212> TYPE: PRT
<213> ORGANISM: Penicillium coprobium PF1169

<400> SEQUENCE: 120

Asp Thr Ala Cys Ser Ser Ser Leu Tyr Ala Leu His Ser Ala Cys Leu
1               5                   10                  15

Ala Leu Asp Ser Arg Asp Cys Asp Gly Ala Val Val Ala Ala Ala Asn
            20                  25                  30

Leu Ile Gln Ser Pro Glu Gln Gln Met Ile Ala Val Lys Ala Gly Ile
        35                  40                  45

Leu Ser Pro Asp Ser Met Cys His Thr Phe Asp Glu Ser Ala Asn
    50                  55                  60

<210> SEQ ID NO 121
<211> LENGTH: 28
<212> TYPE: PRT
<213> ORGANISM: Penicillium coprobium PF1169

<400> SEQUENCE: 121

Pro Trp Pro Thr Thr Gly Leu Arg Arg Ala Ser Val Asn Ser Phe Gly
1               5                   10                  15

Tyr Gly Gly Thr Asn Ala His Cys Val Leu Asp Asp
            20                  25

<210> SEQ ID NO 122
<211> LENGTH: 62
<212> TYPE: PRT
<213> ORGANISM: Penicillium coprobium PF1169

<400> SEQUENCE: 122

Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

Glu Cys Val Pro Met Tyr Gln Cys Thr Asn Ala Gly Gln Ser Arg Ala
        35                  40                  45

Met Thr Ala Asn Arg Leu Ser Tyr Phe Leu Ile Lys Gly Pro
    50                  55                  60

<210> SEQ ID NO 123

```
<211> LENGTH: 80
<212> TYPE: PRT
<213> ORGANISM: Penicillium coprobium PF1169

<400> SEQUENCE: 123

Arg Trp Glu Pro Tyr Tyr Arg Arg Asp Pro Arg Asn Glu Lys Phe Leu
1               5                   10                  15

Lys Gln Thr Thr Ser Arg Gly Tyr Phe Leu Asp His Leu Glu Asp Phe
            20                  25                  30

Asp Cys Gln Phe Phe Gly Ile Ser Pro Lys Glu Ala Glu Gln Met Asp
        35                  40                  45

Pro Gln Gln Arg Val Ser Leu Glu Val Ala Ser Glu Ala Leu Glu Asp
    50                  55                  60

Ala Gly Ile Pro Ala Lys Ser Leu Ser Gly Ser Asp Thr Ala Val Phe
65                  70                  75                  80

<210> SEQ ID NO 124
<211> LENGTH: 28
<212> TYPE: PRT
<213> ORGANISM: Penicillium coprobium PF1169

<400> SEQUENCE: 124

Pro Gly Arg Ile Asn Tyr Phe Phe Lys Phe Ser Gly Pro Ser Phe Ser
1               5                   10                  15

Ile Asp Thr Ala Cys Ser Ser Ser Leu Ala Thr Ile
            20                  25

<210> SEQ ID NO 125
<211> LENGTH: 64
<212> TYPE: PRT
<213> ORGANISM: Penicillium coprobium PF1169

<400> SEQUENCE: 125

Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

Glu Cys Val Pro Met Tyr Gln Cys Thr Asn Ala Gly Gln Ser Arg Ala
        35                  40                  45

Met Thr Ala Asn Arg Leu Ser Tyr Phe Phe Asp Leu Lys Gly Pro Ser
    50                  55                  60

<210> SEQ ID NO 126
<211> LENGTH: 52
<212> TYPE: PRT
<213> ORGANISM: Penicillium coprobium PF1169

<400> SEQUENCE: 126

Glu Leu Arg His Gly Lys Asn Ile Asp Lys Pro Glu Tyr Ser Gln Pro
1               5                   10                  15

Leu Cys Thr Ala Ile Gln Ile Ala Leu Val Glu Leu Leu Glu Ser Phe
            20                  25                  30

Gly Val Val Pro Lys Ala Val Val Gly His Ser Ser Gly Glu Ile Ala
        35                  40                  45

Ala Ala Tyr Val
    50

<210> SEQ ID NO 127
<211> LENGTH: 38
<212> TYPE: PRT
```

<213> ORGANISM: Penicillium coprobium PF1169

<400> SEQUENCE: 127

```
Gln Pro Leu Cys Thr Ala Ile Gln Ile Ala Leu Val Glu Leu Leu Glu
1               5                   10                  15

Ser Phe Gly Val Val Pro Lys Ala Val Val Gly His Ser Ser Gly Glu
            20                  25                  30

Ile Ala Ala Ala Tyr Val
        35
```

<210> SEQ ID NO 128
<211> LENGTH: 86
<212> TYPE: PRT
<213> ORGANISM: Penicillium coprobium PF1169

<400> SEQUENCE: 128

```
Arg Leu Pro Gly Asp Val Ser Thr Pro Glu Glu Phe Trp Asp Leu Cys
1               5                   10                  15

Ser Arg Gly Arg Gly Ala Trp Ser Pro Val Pro Lys Asp Arg Phe Asn
            20                  25                  30

Ala Gly Ser Phe Tyr His Pro Asn Ala Asp Arg Pro Gly Ser Phe Asn
        35                  40                  45

Ala Ala Gly Ala His Phe Leu Thr Glu Asp Ile Gly Leu Phe Asp Ala
    50                  55                  60

Pro Phe Phe Asn Ile Thr Leu Gln Glu Ala Gln Thr Met Asp Pro Gln
65                  70                  75                  80

Gln Arg Ile Phe Leu Glu
                85
```

<210> SEQ ID NO 129
<211> LENGTH: 69
<212> TYPE: PRT
<213> ORGANISM: Penicillium coprobium PF1169

<400> SEQUENCE: 129

```
Gln Phe Phe His Ala His Gly Thr Gly Thr Gln Ala Gly Asp Pro Gln
1               5                   10                  15

Glu Ala Glu Ala Val Ser Thr Ala Leu Phe Pro Asp Gly Ser Asn Ile
            20                  25                  30

Glu Thr Lys Leu Phe Val Gly Ser Ile Lys Thr Val Ile Gly His Thr
        35                  40                  45

Glu Gly Ser Ala Gly Leu Ala Ser Leu Ile Gly Ser Ser Leu Ala Met
    50                  55                  60

Lys His Gly Val Ile
65
```

<210> SEQ ID NO 130
<211> LENGTH: 64
<212> TYPE: PRT
<213> ORGANISM: Penicillium coprobium PF1169

<400> SEQUENCE: 130

```
Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

Glu Cys Val Pro Met Tyr Gln Cys Thr Asn Ala Gly Gln Ser Arg Ala
        35                  40                  45
```

```
Met Thr Ala Asn Arg Leu Ser Tyr Phe Phe Asp Leu Lys Gly Pro Ser
    50                  55                  60
```

<210> SEQ ID NO 131
<211> LENGTH: 67
<212> TYPE: PRT
<213> ORGANISM: Penicillium coprobium PF1169

<400> SEQUENCE: 131

```
Leu Asp Asp Leu Ala Phe Thr Val Asn Glu Arg Arg Ser Ile Phe Pro
1               5                   10                  15

Trp Lys Ala Ala Val Val Gly Asp Thr Met Glu Gly Leu Ala Ala Ser
            20                  25                  30

Leu Ala Gln Asn Ile Lys Pro Arg Ser Val Leu Arg Met Pro Thr Leu
        35                  40                  45

Gly Phe Val Phe Thr Gly Gln Gly Ala Gln Trp Pro Gly Met Gly Lys
    50                  55                  60

Glu Leu Leu
65
```

<210> SEQ ID NO 132
<211> LENGTH: 21
<212> TYPE: PRT
<213> ORGANISM: Penicillium coprobium PF1169

<400> SEQUENCE: 132

```
Ala His Gly Thr Gly Thr Lys Val Gly Asp Pro Met Glu Val Glu Ala
1               5                   10                  15

Ile Ala Asp Val Phe
            20
```

<210> SEQ ID NO 133
<211> LENGTH: 71
<212> TYPE: PRT
<213> ORGANISM: Penicillium coprobium PF1169

<400> SEQUENCE: 133

```
Lys Gly Gly Met Leu Ala Val Gly Ala Ser Ala Ser Asp Ile Gln Gln
1               5                   10                  15

Ile Leu Asp Ala Met Arg Gly Asn Lys Ala Val Ile Ala Cys Val Asn
            20                  25                  30

Ser Glu Ser Ser Val Thr Leu Ser Gly Asp Leu Asp Val Ile Ala Asn
        35                  40                  45

Leu Gln Thr Ala Leu Asp Lys Glu Gly Ile Phe Thr Arg Lys Leu Lys
    50                  55                  60

Val Asp Val Ala Tyr His Ser
65                  70
```

<210> SEQ ID NO 134
<211> LENGTH: 75
<212> TYPE: PRT
<213> ORGANISM: Penicillium coprobium PF1169

<400> SEQUENCE: 134

```
Leu Glu Asn Leu Glu Thr Ala Leu Ala Arg Asn Ala Pro Ile Tyr Ala
1               5                   10                  15

Glu Val Thr Gly Tyr Ala Asn Tyr Ser Asp Ala Tyr Asp Ile Thr Ala
            20                  25                  30

Pro Ala Asp Asp Leu Met Gly Arg Tyr Met Ser Ile Thr Lys Ala Ile
        35                  40                  45
```

```
Glu Gln Ala Gln Leu Asn Ile Asn Glu Ile Asp Tyr Ile Asn Ala His
    50                  55                  60
Gly Thr Ser Thr Gln Leu Asn Asp Leu Asn Glu
65                  70                  75
```

<210> SEQ ID NO 135
<211> LENGTH: 53
<212> TYPE: PRT
<213> ORGANISM: Penicillium coprobium PF1169

<400> SEQUENCE: 135

```
Met Ala Met Lys Lys Ala Leu Lys Gln Ala Gln Leu Arg Pro Ser Ala
1               5                   10                  15
Val Asp Tyr Val Asn Ala His Ala Thr Ser Thr Ile Val Gly Asp Ala
            20                  25                  30
Ala Glu Asn Ala Ala Ile Lys Ala Leu Leu Leu Gly Ala Asp Gly Lys
        35                  40                  45
Asp Lys Ala Ala Asp
    50
```

<210> SEQ ID NO 136
<211> LENGTH: 38
<212> TYPE: PRT
<213> ORGANISM: Penicillium coprobium PF1169

<400> SEQUENCE: 136

```
Gly Thr Gly Asn Gly Ser Ala Met Ile Ser Asn Arg Ile Ser Trp Phe
1               5                   10                  15
Phe Asp Leu Lys Gly Pro Ser Leu Ser Leu Asp Thr Ala Cys Ser Ser
            20                  25                  30
Ser Leu Val Ala Leu His
        35
```

<210> SEQ ID NO 137
<211> LENGTH: 76
<212> TYPE: PRT
<213> ORGANISM: Penicillium coprobium PF1169

<400> SEQUENCE: 137

```
Gly Pro Ser Met Thr Ile Asp Thr Ala Cys Ser Ser Ser Leu Ile Ala
1               5                   10                  15
Leu His Gln Ala Val Gln Ser Leu Arg Ser Gly Glu Thr Asp Val Ala
            20                  25                  30
Val Ala Ala Gly Thr Asn Leu Leu Leu Gly Pro Glu Gln Tyr Ile Ala
        35                  40                  45
Glu Ser Lys Leu Lys Met Leu Ser Pro Asn Gly Arg Ser Arg Met Trp
    50                  55                  60
Asp Lys Asp Ala Asp Gly Tyr Ala Arg Gly Asp Gly
65                  70                  75
```

<210> SEQ ID NO 138
<211> LENGTH: 85
<212> TYPE: PRT
<213> ORGANISM: Penicillium coprobium PF1169

<400> SEQUENCE: 138

```
Ile Gly Ser Ile Lys Pro Asn Ile Gly His Leu Glu Ala Gly Ala Gly
1               5                   10                  15
Val Met Gly Phe Ile Lys Ala Ile Leu Ser Ile Gln Lys Gly Val Leu
```

```
                20                  25                  30
Ala Pro Gln Ala Asn Leu Thr Lys Leu Asn Ser Arg Ile Asp Trp Lys
            35                  40                  45

Thr Ala Gly Val Lys Val Val Gln Glu Ala Thr Pro Trp Pro Ser Ser
        50                  55                  60

Asp Ser Ile Arg Arg Ala Gly Val Cys Ser Tyr Gly Tyr Gly Gly Thr
65                  70                  75                  80

Val Ser His Ala Val
                85

<210> SEQ ID NO 139
<211> LENGTH: 57
<212> TYPE: PRT
<213> ORGANISM: Penicillium coprobium PF1169

<400> SEQUENCE: 139

Asn Ala Ala Gly Ala His Phe Leu Thr Glu Asp Ile Gly Leu Phe Asp
1               5                   10                  15

Ala Pro Phe Phe Asn Ile Thr Leu Gln Glu Ala Gln Thr Met Asp Pro
            20                  25                  30

Gln Gln Arg Ile Phe Leu Glu Cys Val Tyr Glu Ala Leu Glu Asn Gly
        35                  40                  45

Gly Ile Pro Thr His Glu Ile Thr Gly
    50                  55

<210> SEQ ID NO 140
<211> LENGTH: 68
<212> TYPE: PRT
<213> ORGANISM: Penicillium coprobium PF1169

<400> SEQUENCE: 140

Leu Ser Ser Asp Gly Arg Cys His Thr Phe Asp Glu Lys Ala Asn Gly
1               5                   10                  15

Tyr Ala Arg Gly Glu Ala Val Gly Cys Leu Ile Leu Lys Pro Leu Ala
            20                  25                  30

Lys Ala Leu His Asp Gln Asn Lys Ile Arg Ala Val Ile Arg Gly Thr
        35                  40                  45

Gly Ser Asn Gln Asp Gly Arg Thr Ala Gly Ile Thr Val Pro Asn Gly
    50                  55                  60

Ala Ala Gln Glu
65

<210> SEQ ID NO 141
<211> LENGTH: 37
<212> TYPE: PRT
<213> ORGANISM: Penicillium coprobium PF1169

<400> SEQUENCE: 141

Ser Phe Asp Ser Arg Ala Glu Gly Tyr Ala Arg Gly Glu Gly Val Gly
1               5                   10                  15

Thr Val Val Val Lys Pro Leu Ser Thr Ala Ile Arg Asp Gly Asp Thr
            20                  25                  30

Ile Arg Ala Val Ile
        35

<210> SEQ ID NO 142
<211> LENGTH: 72
<212> TYPE: PRT
<213> ORGANISM: Penicillium coprobium PF1169
```

<400> SEQUENCE: 142

Gly Ile Pro Ile Asp Thr Leu Pro Gly Ser Asn Thr Ala Val Tyr Ser
1               5                   10                  15

Gly Ser Met Thr Asn Asp Tyr Glu Leu Leu Ser Thr Arg Asp Ile Tyr
            20                  25                  30

Asp Met Pro His Asn Ser Ala Thr Gly Asn Gly Arg Thr Met Leu Ala
        35                  40                  45

Asn Arg Leu Ser Trp Phe Phe Asp Leu Gln Gly Pro Ser Ile Met Met
    50                  55                  60

Asp Thr Ala Cys Ser Ser Ser Leu
65                  70

<210> SEQ ID NO 143
<211> LENGTH: 83
<212> TYPE: PRT
<213> ORGANISM: Penicillium coprobium PF1169

<400> SEQUENCE: 143

Ala Gln Gln Ser Leu Ile Leu Ala Thr Tyr Ala Arg Ala Gly Leu Ser
1               5                   10                  15

Pro Gln Asn Asn Pro Glu Asp Arg Cys Gln Tyr Phe Glu Ala His Gly
            20                  25                  30

Thr Gly Thr Gln Ala Gly Asp Pro Gln Glu Ala Ala Ile Asn Ser
        35                  40                  45

Ser Phe Phe Gly Pro Glu Ser Val Pro Asp Ser Thr Asp Arg Leu Tyr
    50                  55                  60

Val Gly Ser Ile Lys Thr Ile Ile Gly His Thr Glu Ala Thr Ala Gly
65                  70                  75                  80

Leu Ala Gly

<210> SEQ ID NO 144
<211> LENGTH: 69
<212> TYPE: PRT
<213> ORGANISM: Penicillium coprobium PF1169

<400> SEQUENCE: 144

Pro Leu Trp Arg Lys Ile Glu Thr Ala Pro Leu Asn Thr Gly Leu Thr
1               5                   10                  15

His Asp Val Glu Lys His Thr Leu Leu Gly Gln Arg Ile Pro Val Ala
            20                  25                  30

Gly Thr Asp Thr Phe Val Tyr Thr Thr Arg Leu Asp Asn Glu Thr Lys
        35                  40                  45

Pro Phe Pro Gly Ser His Pro Leu His Gly Thr Glu Ile Val Pro Ala
    50                  55                  60

Ala Gly Leu Ile Asn
65

<210> SEQ ID NO 145
<211> LENGTH: 64
<212> TYPE: PRT
<213> ORGANISM: Penicillium coprobium PF1169

<400> SEQUENCE: 145

Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

-continued

Glu Cys Val Pro Met Tyr Gln Cys Thr Asn Ala Gly Gln Ser Arg Ala
         35                  40                  45

Met Thr Ala Asn Arg Leu Ser Tyr Phe Phe Asp Leu Lys Gly Pro Ser
    50                  55                  60

<210> SEQ ID NO 146
<211> LENGTH: 81
<212> TYPE: PRT
<213> ORGANISM: Penicillium coprobium PF1169

<400> SEQUENCE: 146

Gly Tyr Gly Arg Gly Glu Gly Val Ala Ser Val Val Leu Lys Arg Leu
1               5                  10                  15

Gln Asp Ala Ile Asn Asp Gly Asp Pro Ile Glu Cys Val Ile Arg Ala
            20                  25                  30

Ser Gly Ala Asn Ser Asp Gly Arg Thr Met Gly Ile Thr Met Pro Asn
         35                  40                  45

Pro Lys Ala Gln Gln Ser Leu Ile Leu Ala Thr Tyr Ala Arg Ala Gly
    50                  55                  60

Leu Ser Pro Gln Asn Asn Pro Glu Asp Arg Cys Gln Tyr Phe Glu Ala
65                  70                  75                  80

His

<210> SEQ ID NO 147
<211> LENGTH: 38
<212> TYPE: PRT
<213> ORGANISM: Penicillium coprobium PF1169

<400> SEQUENCE: 147

Gly Thr Gly Asn Gly Ser Ala Met Ile Ser Asn Arg Ile Ser Trp Phe
1               5                  10                  15

Phe Asp Leu Lys Gly Pro Ser Leu Ser Leu Asp Thr Ala Cys Ser Ser
            20                  25                  30

Ser Leu Val Ala Leu His
         35

<210> SEQ ID NO 148
<211> LENGTH: 53
<212> TYPE: PRT
<213> ORGANISM: Penicillium coprobium PF1169

<400> SEQUENCE: 148

Glu Ala Thr Ser Met Asp Ala Gln Gln Arg Lys Leu Leu Glu Val Thr
1               5                  10                  15

Tyr Glu Ala Leu Glu Asn Ala Gly Val Pro Leu Glu Thr Ile Gln Gly
            20                  25                  30

Ser Asn Thr Gly Val Tyr Val Gly Asn Phe Thr Asn Asp Phe Leu Asn
         35                  40                  45

Met Gln Tyr Lys Asp
    50

<210> SEQ ID NO 149
<211> LENGTH: 82
<212> TYPE: PRT
<213> ORGANISM: Penicillium coprobium PF1169

<400> SEQUENCE: 149

Gly Ser Leu Ile Asp Ile Glu Glu Pro Ile Ile Pro Leu Ser Thr Met
1               5                  10                  15

```
Arg Tyr Ile Gln Gly Ala Asp Ile Val Arg Ile Ser Asp Gly Ile Ala
                20                  25                  30

Arg Thr Ser Arg Phe Arg Ser Leu Pro Arg Thr Lys Leu Arg Pro Val
            35                  40                  45

Ser Asp Gly Pro Arg Leu Leu Pro Arg Pro Glu Gly Thr Tyr Leu Ile
 50                  55                  60

Thr Gly Gly Leu Gly Ile Leu Gly Leu Glu Val Ala Asp Phe Leu Val
 65                  70                  75                  80

Glu Lys
```

<210> SEQ ID NO 150
<211> LENGTH: 65
<212> TYPE: PRT
<213> ORGANISM: Penicillium coprobium PF1169

<400> SEQUENCE: 150

```
Gln Leu Gly Thr Thr Cys Val Gln Met Ala Leu Thr Lys Tyr Trp Thr
 1               5                  10                  15

Ser Leu Gly Val Thr Pro Ser Phe Val Met Gly His Ser Leu Gly Glu
                20                  25                  30

Phe Ala Ala Leu Asn Ala Ala Gly Val Leu Thr Ile Ser Asp Thr Ile
            35                  40                  45

Tyr Leu Ala Gly Arg Arg Ala Gln Leu Leu Thr Glu Gln Ile Lys Val
 50                  55                  60

Gly
 65
```

<210> SEQ ID NO 151
<211> LENGTH: 78
<212> TYPE: PRT
<213> ORGANISM: Penicillium coprobium PF1169
<220> FEATURE:
<221> NAME/KEY: misc_feature
<222> LOCATION: (45)..(45)
<223> OTHER INFORMATION: Xaa can be any naturally occurring amino acid

<400> SEQUENCE: 151

```
Gly Pro Arg Leu Leu Pro Arg Pro Glu Gly Thr Tyr Leu Ile Thr Gly
 1               5                  10                  15

Gly Leu Gly Ile Leu Gly Leu Glu Val Ala Asp Phe Leu Val Glu Lys
                20                  25                  30

Gly Ala Arg Arg Val Leu Leu Ile Ser Arg Arg Ala Xaa Pro Pro Arg
            35                  40                  45

Arg Thr Trp Asp Gln Val Ala Thr Glu Phe Gln Pro Ala Ile Thr Lys
 50                  55                  60

Ile Arg Leu Leu Glu Ser Arg Gly Ala Ser Val Tyr Val Leu
 65                  70                  75
```

<210> SEQ ID NO 152
<211> LENGTH: 76
<212> TYPE: PRT
<213> ORGANISM: Penicillium coprobium PF1169

<400> SEQUENCE: 152

```
Gly Pro Ser Met Thr Ile Asp Thr Ala Cys Ser Ser Ser Leu Ile Ala
 1               5                  10                  15

Leu His Gln Ala Val Gln Ser Leu Arg Ser Gly Glu Thr Asp Val Ala
                20                  25                  30
```

Val Ala Ala Gly Thr Asn Leu Leu Gly Pro Glu Gln Tyr Ile Ala
            35                  40                  45

Glu Ser Lys Leu Lys Met Leu Ser Pro Asn Gly Arg Ser Arg Met Trp
 50                  55                  60

Asp Lys Asp Ala Asp Gly Tyr Ala Arg Gly Asp Gly
 65                  70                  75

<210> SEQ ID NO 153
<211> LENGTH: 38
<212> TYPE: PRT
<213> ORGANISM: Penicillium coprobium PF1169

<400> SEQUENCE: 153

Asn Arg Ile Ser Tyr Phe Phe Asp Leu Arg Gly Pro Ser Ile Thr Ile
 1               5                  10                  15

Asp Thr Ala Cys Ser Ser Ser Leu Val Ala Leu His Tyr Ala Val Gln
                20                  25                  30

Ser Leu Arg Asn Gly Glu
            35

<210> SEQ ID NO 154
<211> LENGTH: 74
<212> TYPE: PRT
<213> ORGANISM: Penicillium coprobium PF1169

<400> SEQUENCE: 154

Gly Ser Gly Leu Thr Val Leu Ala Asn Arg Ile Thr His Cys Phe Asp
 1               5                  10                  15

Leu Arg Gly Pro Ser His Val Val Asp Thr Ala Cys Ser Ser Ser Leu
                20                  25                  30

Tyr Ala Leu His Ser Ala Cys Leu Ala Leu Asp Ser Arg Asp Cys Asp
            35                  40                  45

Gly Ala Val Val Ala Ala Asn Leu Ile Gln Ser Pro Glu Gln Gln
        50                  55                  60

Met Ile Ala Val Lys Ala Gly Ile Leu Ser
 65                  70

<210> SEQ ID NO 155
<211> LENGTH: 57
<212> TYPE: PRT
<213> ORGANISM: Penicillium coprobium PF1169

<400> SEQUENCE: 155

Gln Leu Gly Thr Thr Cys Val Gln Met Ala Leu Thr Lys Tyr Trp Thr
 1               5                  10                  15

Ser Leu Gly Val Thr Pro Ser Phe Val Met Gly His Ser Leu Gly Glu
                20                  25                  30

Phe Ala Ala Leu Asn Ala Ala Gly Val Leu Thr Ile Ser Asp Thr Ile
            35                  40                  45

Tyr Leu Ala Gly Arg Arg Ala Gln Leu
        50                  55

<210> SEQ ID NO 156
<211> LENGTH: 72
<212> TYPE: PRT
<213> ORGANISM: Penicillium coprobium PF1169

<400> SEQUENCE: 156

His Leu Asn Leu Met Gly Pro Ser Thr Ala Val Asp Ala Ala Cys Ala
 1               5                  10                  15

```
Ser Ser Leu Val Ala Ile His His Gly Val Gln Ala Ile Lys Leu Gly
            20                  25                  30

Glu Ser Arg Val Ala Ile Val Gly Val Asn Ala Leu Cys Gly Pro
        35                  40                  45

Gly Leu Thr Arg Val Leu Asp Lys Ala Gly Ser Ile Ser Ser Asp Gly
 50                  55                  60

Ser Cys Lys Ser Phe Asp Asp Asp
 65                  70
```

<210> SEQ ID NO 157
<211> LENGTH: 81
<212> TYPE: PRT
<213> ORGANISM: Penicillium coprobium PF1169

<400> SEQUENCE: 157

```
Leu Lys Gly Thr Gly Gly Gln Met Leu Gln Asn Val Val Leu Arg Val
 1               5                  10                  15

Pro Val Ala Ile Asn Ala Pro Arg Ser Val Gln Val Val Gln Gln
            20                  25                  30

Asp Gln Val Lys Val Ser Arg Leu Ile Pro Ser Glu Ala Ser Val
        35                  40                  45

Leu Asp Asp Asp Ala Ser Trp Val Thr His Thr Thr Ala Tyr Trp Asp
 50                  55                  60

Arg Arg Val Leu Gly Ser Glu Asp Arg Ile Asp Leu Ala Ala Val Lys
 65                  70                  75                  80

Ser
```

<210> SEQ ID NO 158
<211> LENGTH: 82
<212> TYPE: PRT
<213> ORGANISM: Penicillium coprobium PF1169

<400> SEQUENCE: 158

```
Ile Met Gly Thr Lys Thr Ser Cys Phe Val Gly Ser Phe Ser Ala Asp
 1               5                  10                  15

Tyr Thr Asp Leu Leu Arg Asp Pro Glu Cys Val Pro Met Tyr Gln
            20                  25                  30

Cys Thr Asn Ala Gly Gln Ser Arg Ala Met Thr Ala Asn Arg Leu Ser
        35                  40                  45

Tyr Phe Phe Asp Leu Lys Gly Pro Ser Val Thr Val Asp Thr Ala Cys
 50                  55                  60

Ser Gly Ser Leu Val Ala Leu His Leu Ala Cys Gln Ser Leu Arg Thr
 65                  70                  75                  80

Gly Asp
```

<210> SEQ ID NO 159
<211> LENGTH: 75
<212> TYPE: PRT
<213> ORGANISM: Penicillium coprobium PF1169

<400> SEQUENCE: 159

```
Gly Ser Gly Leu Thr Val Leu Ala Asn Arg Ile Thr Cys Phe Asp
 1               5                  10                  15

Leu Arg Gly Pro Ser His Val Val Asp Thr Ala Cys Ser Ser Leu
            20                  25                  30

Tyr Ala Leu His Ser Ala Cys Phe Gly Pro Leu Asn Ser Arg Asp Cys
        35                  40                  45
```

```
Asp Gly Ala Val Val Ala Ala Asn Leu Ile Gln Ser Pro Glu Gln
        50                  55                  60

Gln Met Ile Ala Val Lys Arg Asp Ser Ile Ala
 65                  70                  75

<210> SEQ ID NO 160
<211> LENGTH: 28
<212> TYPE: PRT
<213> ORGANISM: Penicillium coprobium PF1169

<400> SEQUENCE: 160

Pro Trp Pro Thr Thr Gly Leu Arg Arg Ala Ser Val Asn Ser Phe Gly
 1               5                  10                  15

Tyr Gly Gly Thr Asn Ala His Cys Val Leu Asp Asp
            20                  25

<210> SEQ ID NO 161
<211> LENGTH: 64
<212> TYPE: PRT
<213> ORGANISM: Penicillium coprobium PF1169

<400> SEQUENCE: 161

Gln Leu Gly Thr Thr Cys Val Gln Met Ala Leu Thr Lys Tyr Trp Thr
 1               5                  10                  15

Ser Leu Gly Val Thr Pro Ser Phe Val Met Gly His Ser Leu Gly Glu
            20                  25                  30

Phe Ala Ala Leu Asn Ala Ala Gly Val Leu Thr Ile Ser Asp Thr Ile
        35                  40                  45

Tyr Leu Ala Gly Arg Arg Ala Gln Leu Leu Thr Glu Gln Ile Glu Gly
    50                  55                  60

<210> SEQ ID NO 162
<211> LENGTH: 60
<212> TYPE: PRT
<213> ORGANISM: Penicillium coprobium PF1169

<400> SEQUENCE: 162

Ile Ala Pro Asn Ile His Phe Lys Met Pro Asn Pro Gln Ile Pro Phe
 1               5                  10                  15

Asn Glu Ala Asn Leu His Val Pro Leu Glu Pro Thr Pro Trp Pro Ala
            20                  25                  30

Gly Arg Pro Glu Arg Ile Ser Val Asn Ser Phe Gly Ile Gly Gly Ser
        35                  40                  45

Asn Ala His Ala Ile Leu Glu Ser Ala Ser Thr Val
    50                  55                  60

<210> SEQ ID NO 163
<211> LENGTH: 34
<212> TYPE: PRT
<213> ORGANISM: Penicillium coprobium PF1169

<400> SEQUENCE: 163

Gly Leu Val Asn Ile Leu Arg Ser Trp Gly Ile Glu Pro Ser Thr Val
 1               5                  10                  15

Val Gly His Ser Ser Gly Glu Ile Val Ala Ala Tyr Thr Ala Arg Ala
            20                  25                  30

Ile Ser

<210> SEQ ID NO 164
```

-continued

```
<211> LENGTH: 51
<212> TYPE: PRT
<213> ORGANISM: Penicillium coprobium PF1169

<400> SEQUENCE: 164

Pro Trp Pro Ser Glu Gly Leu Arg Arg Ile Ser Val Asn Ser Phe Gly
1               5                   10                  15

Phe Gly Gly Ser Asn Thr His Val Ile Leu Asp Asp Ala Leu His Tyr
            20                  25                  30

Met Gln Gln Arg Gly Leu Thr Gly Asn His Cys Thr Ala Arg Leu Pro
        35                  40                  45

Gly Ile Leu
    50

<210> SEQ ID NO 165
<211> LENGTH: 71
<212> TYPE: PRT
<213> ORGANISM: Penicillium coprobium PF1169
<220> FEATURE:
<221> NAME/KEY: misc_feature
<222> LOCATION: (5)..(5)
<223> OTHER INFORMATION: Xaa can be any naturally occurring amino acid

<400> SEQUENCE: 165

Ile Gly His Thr Xaa Gly Ser Ala Gly Leu Ala Ser Leu Ile Gly Ser
1               5                   10                  15

Ser Leu Ala Met Lys His Gly Val Ile Pro Pro Asn Leu His Phe Gly
            20                  25                  30

Gln Leu Ser Glu Lys Val Ala Pro Phe Tyr Thr His Leu Asn Ile Pro
        35                  40                  45

Thr Glu Pro Val Pro Trp Pro Asn Ser Thr Ser Ser Gln Val Lys Arg
    50                  55                  60

Ala Ser Ile Asn Ser Phe Gly
65                  70

<210> SEQ ID NO 166
<211> LENGTH: 74
<212> TYPE: PRT
<213> ORGANISM: Penicillium coprobium PF1169

<400> SEQUENCE: 166

Gly Ser Asn Thr Ala Val Tyr Ser Gly Ser Met Thr Asn Asp Tyr Glu
1               5                   10                  15

Leu Leu Ser Thr Arg Asp Ile Tyr Asp Met Pro His Asn Ser Ala Thr
            20                  25                  30

Gly Asn Gly Arg Thr Met Leu Ala Asn Arg Leu Ser Trp Phe Phe Asp
        35                  40                  45

Leu Gln Gly Pro Ser Ile Met Met Asp Thr Ala Cys Ser Ser Ser Leu
    50                  55                  60

Thr Ala Val His Leu Ala Ala Gln Ser Leu
65                  70

<210> SEQ ID NO 167
<211> LENGTH: 85
<212> TYPE: PRT
<213> ORGANISM: Penicillium coprobium PF1169

<400> SEQUENCE: 167

Asp Ala Gln Phe Phe Gly Thr Lys Pro Val Glu Ala Asn Ser Ile Asp
1               5                   10                  15
```

```
Pro Gln Gln Arg Leu Leu Leu Glu Thr Val Tyr Glu Gly Leu Glu Thr
                20                  25                  30

Ser Gly Ile Pro Met Glu Arg Leu Gln Gly Ser Asn Thr Ala Val Tyr
        35                  40                  45

Val Gly Leu Met Thr Asn Asp Tyr Ala Asp Met Leu Gly Arg Asp Met
 50                  55                  60

Gln Asn Phe Pro Thr Tyr Phe Ala Ser Gly Thr Ala Arg Ser Ile Leu
 65                  70                  75                  80

Ser Asn Arg Val Ser
                85

<210> SEQ ID NO 168
<211> LENGTH: 60
<212> TYPE: PRT
<213> ORGANISM: Penicillium coprobium PF1169

<400> SEQUENCE: 168

Val Val Ala Cys Val Asn Ser Pro Ala Ser Thr Thr Leu Ser Gly Asp
 1               5                  10                  15

Val Asp Tyr Ile Asn Gln Leu Glu Ala Arg Leu Gln Gln Asp Gly His
                20                  25                  30

Phe Ala Arg Lys Leu Arg Ile Asp Thr Ala Tyr His Ser Pro His Met
        35                  40                  45

Glu Glu Leu Val Gly Val Gly Asp Ala Ile Ser
 50                  55                  60

<210> SEQ ID NO 169
<211> LENGTH: 56
<212> TYPE: PRT
<213> ORGANISM: Penicillium coprobium PF1169

<400> SEQUENCE: 169

Phe Tyr Gly Met Thr Ser Asp Asp Tyr Arg Glu Val Asn Ser Gly Gln
 1               5                  10                  15

Asp Ile Asp Thr Tyr Phe Ile Pro Gly Gly Asn Arg Ala Phe Thr Pro
                20                  25                  30

Gly Arg Ile Asn Tyr Tyr Phe Lys Phe Ser Gly Pro Ser Val Ser Val
        35                  40                  45

Asp Thr Ala Cys Ser Ser Ser Leu
 50                  55

<210> SEQ ID NO 170
<211> LENGTH: 53
<212> TYPE: PRT
<213> ORGANISM: Penicillium coprobium PF1169

<400> SEQUENCE: 170

Val Ala Ile Val Gly Gly Val Asn Ala Leu Cys Gly Pro Gly Leu Thr
 1               5                  10                  15

Arg Val Leu Asp Lys Ala Gly Ala Ile Ser Ser Asp Gly Ser Cys Lys
                20                  25                  30

Ser Phe Asp Asp Asp Ala His Gly Tyr Ala Arg Gly Glu Gly Ala Gly
        35                  40                  45

Ala Leu Val Thr Lys
     50

<210> SEQ ID NO 171
<211> LENGTH: 40
<212> TYPE: PRT
```

-continued

<213> ORGANISM: Penicillium coprobium PF1169

<400> SEQUENCE: 171

Gln Leu Gly Thr Thr Cys Val Gln Met Ala Leu Thr Lys Tyr Trp Thr
1               5                   10                  15

Ser Leu Gly Val Thr Pro Ser Phe Val Met Gly His Ser Leu Gly Glu
            20                  25                  30

Phe Ala Ala Leu Asn Ala Ala Gly
        35                  40

<210> SEQ ID NO 172
<211> LENGTH: 69
<212> TYPE: PRT
<213> ORGANISM: Penicillium coprobium PF1169

<400> SEQUENCE: 172

Arg Glu Trp Met Thr Ala Glu Gly Lys Asp His Asn Leu Ser Asp Ile
1               5                   10                  15

Leu Thr Thr Leu Ala Thr Arg Arg Asp His His Asp Tyr Arg Ala Ala
            20                  25                  30

Leu Val Val Asp Asp Asn Arg Asp Ala Glu Leu Ala Leu Gln Ala Leu
        35                  40                  45

Glu His Gly Val Asp Gln Thr Phe Thr Thr Gln Ser Arg Val Phe Gly
    50                  55                  60

Ala Asp Ile Ser Lys
65

<210> SEQ ID NO 173
<211> LENGTH: 51
<212> TYPE: PRT
<213> ORGANISM: Penicillium coprobium PF1169

<400> SEQUENCE: 173

Pro Trp Pro Ser Glu Gly Leu Arg Arg Ile Ser Val Asn Ser Phe Gly
1               5                   10                  15

Phe Gly Gly Ser Asn Thr His Val Ile Leu Asp Asp Ala Leu His Tyr
            20                  25                  30

Met Gln Gln Arg Gly Leu Thr Gly Asn His Cys Thr Ala Arg Leu Pro
        35                  40                  45

Gly Ile Leu
    50

<210> SEQ ID NO 174
<211> LENGTH: 71
<212> TYPE: PRT
<213> ORGANISM: Penicillium coprobium PF1169

<400> SEQUENCE: 174

Phe Val Glu Met His Gly Thr Gly Thr Lys Ala Gly Asp Pro Val Glu
1               5                   10                  15

Ala Ala Ala Val His Ala Ala Leu Gly Lys Asn Arg Thr Leu Arg Asn
            20                  25                  30

Pro Leu Tyr Ile Gly Ser Val Lys Ser Asn Ile Gly His Leu Glu Gly
        35                  40                  45

Ala Ser Gly Ile Val Ala Val Ile Lys Ala Ala Met Met Leu Asp Arg
    50                  55                  60

Asp Leu Met Leu Pro Asn Ala
65                  70

<210> SEQ ID NO 175
<211> LENGTH: 41
<212> TYPE: PRT
<213> ORGANISM: Penicillium coprobium PF1169

<400> SEQUENCE: 175

Leu Ala Ile Val Gly Met Ala Cys Arg Leu Pro Gly Gln Ile Thr Thr
1               5                   10                  15

Pro Gln Glu Leu Trp Glu Leu Cys Ser Arg Gly Arg Ser Ala Trp Ser
            20                  25                  30

Glu Ile Pro Pro Glu Arg Phe Asn Pro
        35                  40

<210> SEQ ID NO 176
<211> LENGTH: 64
<212> TYPE: PRT
<213> ORGANISM: Penicillium coprobium PF1169

<400> SEQUENCE: 176

Gln Leu Gly Thr Thr Cys Val Gln Met Ala Leu Thr Lys Tyr Trp Thr
1               5                   10                  15

Ser Leu Gly Val Thr Pro Ser Phe Val Met Gly His Ser Leu Gly Glu
            20                  25                  30

Phe Ala Ala Leu Asn Ala Ala Gly Val Leu Thr Ile Ser Asp Thr Ile
        35                  40                  45

Tyr Leu Ala Gly Arg Arg Ala Gln Leu Leu Thr Glu Gln Ile Glu Gly
    50                  55                  60

<210> SEQ ID NO 177
<211> LENGTH: 74
<212> TYPE: PRT
<213> ORGANISM: Penicillium coprobium PF1169

<400> SEQUENCE: 177

Gly Ala Ser Val Tyr Val Leu Ala Leu Asp Ile Thr Lys Pro Asp Ala
1               5                   10                  15

Val Glu Gln Leu Ser Thr Ala Leu Asp Arg Leu Ala Leu Pro Ser Val
            20                  25                  30

Gln Gly Val Val His Ala Ala Gly Val Leu Asp Asn Glu Leu Val Met
        35                  40                  45

Gln Thr Thr Gln Glu Ala Phe Asn Arg Val Leu Ala Pro Lys Ile Ala
    50                  55                  60

Gly Ala Leu Ala Leu His Glu Pro Phe Pro
65                  70

<210> SEQ ID NO 178
<211> LENGTH: 72
<212> TYPE: PRT
<213> ORGANISM: Penicillium coprobium PF1169

<400> SEQUENCE: 178

Gly Leu Val Asn Ile Leu Arg Ser Trp Gly Ile Glu Pro Ser Thr Val
1               5                   10                  15

Val Gly His Ser Ser Gly Glu Ile Val Ala Ala Tyr Thr Ala Arg Ala
            20                  25                  30

Ile Ser Met Arg Thr Ala Ile Ile Leu Ala Tyr Tyr Arg Gly Lys Val
        35                  40                  45

Ala Gln Pro Leu Glu Gly Leu Gly Ala Met Val Ala Val Gly Leu Ser
    50                  55                  60

```
Pro Asp Glu Val Ala Gln Tyr Met
 65                  70
```

<210> SEQ ID NO 179
<211> LENGTH: 70
<212> TYPE: PRT
<213> ORGANISM: Penicillium coprobium PF1169

<400> SEQUENCE: 179

```
Gly Arg Phe Leu Ser Ser Asp Gly Arg Cys His Thr Phe Asp Glu Lys
 1               5                  10                  15

Ala Asn Gly Tyr Ala Arg Gly Glu Ala Val Gly Cys Leu Ile Leu Lys
             20                  25                  30

Pro Leu Ala Lys Ala Leu His Asp Gln Asn Lys Ile Arg Ala Val Ile
         35                  40                  45

Arg Gly Thr Gly Ser Asn Gln Asp Gly Arg Thr Ala Gly Ile Thr Val
     50                  55                  60

Pro Asn Gly Ala Ala Gln
 65                  70
```

<210> SEQ ID NO 180
<211> LENGTH: 51
<212> TYPE: PRT
<213> ORGANISM: Penicillium coprobium PF1169

<400> SEQUENCE: 180

```
Ser Ser Phe Leu Thr Ser Thr Val Gln Gln Ile Val Glu Gly Thr Ile
 1               5                  10                  15

Gln Gly Gly Thr Gly Gln Val Val Met Glu Ser Asp Leu Met Gln Thr
             20                  25                  30

Glu Phe Leu Glu Ala Ala Asn Gly His Arg Met Asn Asp Cys Gly Val
         35                  40                  45

Val Thr Ser
     50
```

<210> SEQ ID NO 181
<211> LENGTH: 64
<212> TYPE: PRT
<213> ORGANISM: Penicillium coprobium PF1169

<400> SEQUENCE: 181

```
Leu Leu Gly Leu Arg Leu Lys Trp Lys Glu Tyr His Gln Asp Phe Asn
 1               5                  10                  15

Ala Ala His Arg Val Leu Pro Leu Pro Ser Tyr Lys Trp Asp Leu Lys
             20                  25                  30

Asn Tyr Trp Ile Pro Tyr Thr Asn Asn Phe Cys Leu Leu Lys Gly Ala
         35                  40                  45

Pro Ala Ala Pro Val Ala Glu Ala Thr Pro Ile Ser Val Phe Leu Ser
     50                  55                  60
```

<210> SEQ ID NO 182
<211> LENGTH: 26
<212> TYPE: PRT
<213> ORGANISM: Penicillium coprobium PF1169

<400> SEQUENCE: 182

```
Ser Phe Arg Arg Gln Glu Asp Thr Trp Lys Val Leu Ser Asn Ala Thr
 1               5                  10                  15

Ser Thr Leu Tyr Leu Ala Gly Ile Glu Ile
```

<210> SEQ ID NO 183
<211> LENGTH: 65
<212> TYPE: PRT
<213> ORGANISM: Penicillium coprobium PF1169

<400> SEQUENCE: 183

Ala Gly Gly Asn Thr Thr Val Ala Leu Glu Asp Ala Pro Ile Arg Thr
1               5                   10                  15
Arg Ser Gly Ser Asp Pro Arg Ser Leu His Pro Ile Ala Ile Ser Ala
                20                  25                  30
Lys Ser Lys Val Ser Leu Arg Gly Asn Leu Glu Asn Leu Leu Ala Tyr
            35                  40                  45
Leu Asp Thr His Pro Asp Val Ser Leu Ser Asp Leu Ser Tyr Thr Thr
50                  55                  60
Thr
65

<210> SEQ ID NO 184
<211> LENGTH: 96
<212> TYPE: PRT
<213> ORGANISM: Penicillium coprobium PF1169

<400> SEQUENCE: 184

Phe Asp Ala Ala Phe Phe Asn Met Ser Pro Arg Glu Ala Gln Gln Thr
1               5                   10                  15
Asp Pro Met Gln Arg Leu Ala Ile Val Thr Ala Tyr Glu Ala Leu Glu
                20                  25                  30
Arg Ala Gly Tyr Val Ala Asn Arg Thr Ala Ala Thr Asn Leu His Arg
            35                  40                  45
Ile Gly Thr Phe Tyr Gly Gln Ala Ser Asp Asp Tyr Arg Glu Val Asn
50                  55                  60
Thr Ala Gln Glu Ile Ser Thr Tyr Phe Ile Pro Gly Gly Cys Arg Ala
65                  70                  75                  80
Phe Gly Pro Gly Arg Ile Asn Tyr Phe Phe Lys Phe Leu Gly Pro Ala
                85                  90                  95

<210> SEQ ID NO 185
<211> LENGTH: 58
<212> TYPE: PRT
<213> ORGANISM: Penicillium coprobium PF1169

<400> SEQUENCE: 185

Phe Leu Gln Ile Ser Gly Pro Ser Phe Ser Ile Asp Thr Ala Cys Ser
1               5                   10                  15
Ser Ser Leu Ala Thr Ile Gln Val Cys Thr His Leu Phe His Val His
                20                  25                  30
Leu Asn Arg Gln Leu Thr Ile Ala Ala Cys Thr Ser Leu Trp Asn Gly
            35                  40                  45
Glu Thr Asp Thr Val Val Ala Gly Gly Met
50                  55

<210> SEQ ID NO 186
<211> LENGTH: 59
<212> TYPE: PRT
<213> ORGANISM: Penicillium coprobium PF1169

<400> SEQUENCE: 186

```
Val Tyr Ser Gly Ser Met Thr Asn Asp Tyr Glu Leu Leu Ser Thr Arg
1               5                   10                  15

Asp Ile Tyr Asp Met Pro His Asn Ser Ala Thr Gly Asn Gly Arg Thr
            20                  25                  30

Met Leu Ala Asn Arg Leu Ser Trp Phe Phe Asp Leu Gln Gly Pro Ser
        35                  40                  45

Ile Met Met Asp Thr Ala Cys Ser Ser Ser Leu
    50                  55
```

<210> SEQ ID NO 187
<211> LENGTH: 31
<212> TYPE: PRT
<213> ORGANISM: Penicillium coprobium PF1169

<400> SEQUENCE: 187

```
Leu Phe Leu Phe Pro Asp Gly Ser Gly Ser Ala Thr Ser Tyr Ala Thr
1               5                   10                  15

Ile Pro Gly Ile Ser Pro Asp Val Cys Val Tyr Gly Leu Asn Cys
            20                  25                  30
```

<210> SEQ ID NO 188
<211> LENGTH: 26
<212> TYPE: PRT
<213> ORGANISM: Penicillium coprobium PF1169

<400> SEQUENCE: 188

```
Ala Lys His Pro Pro Ala Thr Ser Ile Leu Leu Gln Gly Asn Pro Lys
1               5                   10                  15

Thr Ala Thr Gln Ser Phe Ile Phe Val Pro
            20                  25
```

<210> SEQ ID NO 189
<211> LENGTH: 38
<212> TYPE: PRT
<213> ORGANISM: Penicillium coprobium PF1169

<400> SEQUENCE: 189

```
Gly Asn Gly Ser Ala Met Ile Ser Asn Arg Ile Ser Trp Phe Phe Asp
1               5                   10                  15

Leu Lys Gly Pro Ser Leu Ser Leu Asp Thr Ala Cys Ser Ser Ser Leu
            20                  25                  30

Val Ala Leu His Leu Ala
        35
```

<210> SEQ ID NO 190
<211> LENGTH: 76
<212> TYPE: PRT
<213> ORGANISM: Penicillium coprobium PF1169

<400> SEQUENCE: 190

```
Ala Ile His His Gly Val Gln Ala Ile Lys Leu Gly Glu Ser Arg Val
1               5                   10                  15

Ala Ile Val Gly Gly Val Asn Ala Leu Cys Gly Pro Gly Leu Thr Arg
            20                  25                  30

Val Leu Asp Lys Ala Gly Ala Ile Ser Ser Asp Gly Ser Cys Lys Ser
        35                  40                  45

Phe Asp Asp Asp Ala His Gly Tyr Ala Arg Gly Glu Gly Ala Gly Ala
    50                  55                  60

Leu Val Leu Lys Ser Leu His Gln Ala Leu Leu Asp
65                  70                  75
```

<210> SEQ ID NO 191
<211> LENGTH: 65
<212> TYPE: PRT
<213> ORGANISM: Penicillium coprobium PF1169

<400> SEQUENCE: 191

Val Trp Ile Glu Ile Gly Pro His Pro Val Cys Leu Gly Phe Val Lys
1               5                   10                  15

Ala Thr Leu Glu Ser Val Ala Val Ala Val Pro Ser Leu Arg Arg Gly
            20                  25                  30

Glu Asn Ala Trp Cys Thr Leu Ala Gln Ser Leu Thr Thr Leu His Asn
        35                  40                  45

Ala Gly Val Pro Val Gly Trp Ser Glu Phe His Arg Pro Phe Glu Arg
    50                  55                  60

Ala
65

<210> SEQ ID NO 192
<211> LENGTH: 53
<212> TYPE: PRT
<213> ORGANISM: Penicillium coprobium PF1169

<400> SEQUENCE: 192

Thr Ser Asp Asp Tyr Arg Glu Val Asn Ser Gly Gln Asp Ile Asp Thr
1               5                   10                  15

Tyr Phe Ile Pro Gly Gly Asn Arg Ala Phe Thr Pro Gly Arg Ile Asn
            20                  25                  30

Tyr Tyr Phe Lys Phe Ser Gly Pro Ser Val Ser Val Asp Thr Ala Cys
        35                  40                  45

Ser Ser Ser Leu Ala
    50

<210> SEQ ID NO 193
<211> LENGTH: 40
<212> TYPE: PRT
<213> ORGANISM: Penicillium coprobium PF1169

<400> SEQUENCE: 193

Val Asp Thr Ala Cys Ser Ser Ser Leu Tyr Ala Leu His Ser Ala Cys
1               5                   10                  15

Phe Gly Pro Leu Asn Ser Arg Asp Cys Asp Gly Ala Val Val Ala Ala
            20                  25                  30

Ala Asn Leu Ile Gln Ser Pro Glu
        35                  40

<210> SEQ ID NO 194
<211> LENGTH: 68
<212> TYPE: PRT
<213> ORGANISM: Penicillium coprobium PF1169

<400> SEQUENCE: 194

Met Leu Ala Val Gly Ala Ser Ala Ser Asp Ile Gln Gln Ile Leu Asp
1               5                   10                  15

Ala Met Arg Gly Asn Lys Ala Val Ile Ala Cys Val Asn Ser Glu Ser
            20                  25                  30

Ser Val Thr Leu Ser Gly Asp Leu Asp Val Ile Ala Asn Leu Gln Thr
        35                  40                  45

Ala Leu Asp Lys Glu Gly Ile Phe Thr Arg Lys Leu Lys Val Asp Val

Ala Tyr His Ser
65

<210> SEQ ID NO 195
<211> LENGTH: 62
<212> TYPE: PRT
<213> ORGANISM: Penicillium coprobium PF1169

<400> SEQUENCE: 195

Phe Leu Asp Asp Leu Ala Phe Thr Val Asn Glu Arg Ser Ile Phe
1               5                   10                  15

Pro Trp Lys Ala Ala Val Val Gly Asp Thr Met Glu Gly Leu Ala Ala
            20                  25                  30

Ser Leu Ala Gln Asn Ile Lys Pro Arg Ser Val Leu Arg Met Pro Thr
        35                  40                  45

Leu Gly Phe Val Phe Thr Gly Gln Gly Ala Gln Trp Pro Gly
    50                  55                  60

<210> SEQ ID NO 196
<211> LENGTH: 76
<212> TYPE: PRT
<213> ORGANISM: Penicillium coprobium PF1169

<400> SEQUENCE: 196

Gly Pro Ser Met Thr Ile Asp Thr Ala Cys Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Leu Gly Pro Glu Gln Tyr Ile Ala
        35                  40                  45

Glu Ser Lys Leu Lys Met Leu Ser Pro Asn Gly Arg Ser Arg Met Trp
    50                  55                  60

Asp Lys Asp Ala Asp Gly Tyr Ala Arg Gly Asp Gly
65                  70                  75

<210> SEQ ID NO 197
<211> LENGTH: 79
<212> TYPE: PRT
<213> ORGANISM: Penicillium coprobium PF1169

<400> SEQUENCE: 197

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val Leu Thr Ile Ser Asp Thr Ile Tyr Leu Ala Gly
    50                  55                  60

Arg Arg Ala Gln Leu Leu Thr Glu Gln Ile Glu Gly Gly Thr His
65                  70                  75

<210> SEQ ID NO 198
<211> LENGTH: 40
<212> TYPE: PRT
<213> ORGANISM: Penicillium coprobium PF1169

<400> SEQUENCE: 198

```
Phe Asn Leu Lys Gly Ile Ser Gln Ser Ile Ala Ser Cys Ala Thr
1               5                   10                  15

Ser Ala Asp Ala Ile Gly Tyr Ala Phe His Leu Ile Ala Ala Gly Lys
            20                  25                  30

Gln Asp Leu Met Leu Ala Gly Gly
            35                  40

<210> SEQ ID NO 199
<211> LENGTH: 70
<212> TYPE: PRT
<213> ORGANISM: Penicillium coprobium PF1169

<400> SEQUENCE: 199

Gly Arg Phe Leu Ser Ser Asp Gly Arg Cys His Thr Phe Asp Glu Lys
1               5                   10                  15

Ala Asn Gly Tyr Ala Arg Gly Glu Ala Val Gly Cys Leu Ile Leu Lys
            20                  25                  30

Pro Leu Ala Lys Ala Leu His Asp Gln Asn Lys Ile Arg Ala Val Ile
            35                  40                  45

Arg Gly Thr Gly Ser Asn Gln Asp Gly Arg Thr Ala Gly Ile Thr Val
        50                  55                  60

Pro Asn Gly Ala Ala Gln
65                  70

<210> SEQ ID NO 200
<211> LENGTH: 284
<212> TYPE: PRT
<213> ORGANISM: Penicillium coprobium PF1169

<400> SEQUENCE: 200

Leu Ser Val Lys Arg Val Gly Ile His Asp Asp Phe Phe Glu Leu Gly
1               5                   10                  15

Gly His Ser Leu Leu Ala Val Lys Leu Val Asn His Leu Lys Lys Val
            20                  25                  30

Phe Gly Thr Glu Leu Ser Val Ala Leu Leu Ala Gln Tyr Ser Thr Val
            35                  40                  45

Glu Ser Leu Gly Glu Ile Ile Arg Glu Asn Lys Glu Ile Lys Pro Ser
        50                  55                  60

Ile Val Ile Glu Leu Arg Ser Gly Thr Tyr Glu Gln Pro Leu Trp Leu
65                  70                  75                  80

Phe His Pro Ile Gly Gly Ser Thr Phe Cys Tyr Met Glu Leu Ser Arg
                85                  90                  95

His Leu Asn Pro Asn Arg Thr Leu Arg Ala Ile Gln Ser Pro Gly Leu
            100                 105                 110

Ile Glu Ala Asp Ala Ala Glu Val Ala Ile Glu Glu Met Ala Thr Leu
            115                 120                 125

Tyr Ile Ala Glu Met Gln Lys Met Gln Pro Gln Gly Pro Tyr Phe Leu
        130                 135                 140

Gly Gly Trp Cys Phe Gly Gly Ala Ile Ala Tyr Glu Ile Ser Arg Gln
145                 150                 155                 160

Leu Arg Gln Met Gly Gln Gln Val Thr Gly Ile Val Met Ile Asp Thr
                165                 170                 175

Arg Ala Pro Ile Pro Glu Asn Val Pro Glu Asp Ala Asp Ala Met
            180                 185                 190

Leu Leu Ser Trp Phe Ala Arg Asp Leu Ala Val Pro Tyr Gly Lys Lys
            195                 200                 205
```

```
Leu Thr Ile Ser Ala Gln Tyr Leu Arg Glu Leu Ser Pro Asp His Met
    210                 215                 220

Phe Asp His Val Leu Lys Glu Ala Lys Ala Ile Asn Val Ile Pro Leu
225                 230                 235                 240

Asp Ala Asn Pro Ser Asp Phe Arg Leu Tyr Phe Asp Thr Tyr Leu Ala
                245                 250                 255

Asn Gly Val Ala Leu Gln Thr Tyr Phe Pro Glu Pro Glu Asp Phe Pro
            260                 265                 270

Ile Leu Leu Val Lys Ala Lys Asp Glu Ser Glu Asp
            275                 280

<210> SEQ ID NO 201
<211> LENGTH: 73
<212> TYPE: PRT
<213> ORGANISM: Penicillium coprobium PF1169

<400> SEQUENCE: 201

Pro Met Asn Lys Asp Lys Val Tyr Trp Ser Ala Ile Ile Arg Thr Leu
1               5                   10                  15

Val Ala Lys Glu Met Arg Val Glu Pro Glu Thr Ile Asp Pro Glu Gln
            20                  25                  30

Lys Phe Thr Thr Tyr Gly Leu Asp Ser Ile Val Ala Leu Ser Val Ser
        35                  40                  45

Gly Asp Leu Glu Asp Leu Thr Lys Leu Glu Leu Glu Pro Thr Leu Leu
    50                  55                  60

Trp Asp Tyr Pro Thr Ile Asn Ala Leu
65                  70

<210> SEQ ID NO 202
<211> LENGTH: 63
<212> TYPE: PRT
<213> ORGANISM: Penicillium coprobium PF1169

<400> SEQUENCE: 202

Gly Ser Leu Ile Asp Ile Glu Glu Pro Ile Ile Pro Leu Ser Thr Met
1               5                   10                  15

Arg Tyr Ile Gln Gly Ala Asp Ile Val Arg Ile Ser Asp Gly Ile Ala
            20                  25                  30

Arg Thr Ser Arg Phe Arg Ser Leu Pro Arg Thr Lys Leu Arg Pro Val
        35                  40                  45

Ser Asp Gly Pro Arg Leu Leu Pro Arg Pro Glu Gly Thr Tyr Leu
    50                  55                  60

<210> SEQ ID NO 203
<211> LENGTH: 69
<212> TYPE: PRT
<213> ORGANISM: Penicillium coprobium PF1169

<400> SEQUENCE: 203

Leu Glu Val Val Trp Glu Cys Leu Glu Asn Ser Gly Glu Thr Gln Trp
1               5                   10                  15

Arg Gly Lys Glu Ile Gly Cys Phe Val Gly Val Phe Gly Glu Asp Trp
            20                  25                  30

Leu Glu Met Ser His Lys Asp Pro Gln His Leu Asn Gln Met Phe Pro
        35                  40                  45

Ile Ala Thr Gly Gly Phe Ala Leu Ala Asn Gln Val Ser Tyr Arg Phe
    50                  55                  60

Asp Leu Thr Gly Pro
65
```

<210> SEQ ID NO 204
<211> LENGTH: 96
<212> TYPE: PRT
<213> ORGANISM: Penicillium coprobium PF1169

<400> SEQUENCE: 204

Phe Asp Ala Ala Phe Phe Asn Met Ser Pro Arg Glu Ala Gln Gln Thr
1               5                   10                  15

Asp Pro Met Gln Arg Leu Ala Ile Val Thr Ala Tyr Glu Ala Leu Glu
            20                  25                  30

Arg Ala Gly Tyr Val Ala Asn Arg Thr Ala Ala Thr Asn Leu His Arg
        35                  40                  45

Ile Gly Thr Phe Tyr Gly Gln Ala Ser Asp Asp Tyr Arg Glu Val Asn
50                  55                  60

Thr Ala Gln Glu Ile Ser Thr Tyr Phe Ile Pro Gly Gly Cys Arg Ala
65                  70                  75                  80

Phe Gly Pro Gly Arg Ile Asn Tyr Phe Phe Lys Phe Leu Gly Pro Ala
                85                  90                  95

<210> SEQ ID NO 205
<211> LENGTH: 58
<212> TYPE: PRT
<213> ORGANISM: Penicillium coprobium PF1169

<400> SEQUENCE: 205

Phe Leu Gln Ile Ser Gly Pro Ser Phe Ser Ile Asp Thr Ala Cys Ser
1               5                   10                  15

Ser Ser Leu Ala Thr Ile Gln Val Cys Thr His Leu Phe His Val His
            20                  25                  30

Leu Asn Arg Gln Leu Thr Ile Ala Ala Cys Thr Ser Leu Trp Asn Gly
        35                  40                  45

Glu Thr Asp Thr Val Val Ala Gly Gly Met
    50                  55

<210> SEQ ID NO 206
<211> LENGTH: 52
<212> TYPE: PRT
<213> ORGANISM: Penicillium coprobium PF1169

<400> SEQUENCE: 206

Glu Leu Arg His Gly Lys Asn Ile Asp Lys Pro Glu Tyr Ser Gln Pro
1               5                   10                  15

Leu Cys Thr Ala Ile Gln Ile Ala Leu Val Glu Leu Leu Glu Ser Phe
            20                  25                  30

Gly Val Val Pro Lys Ala Val Gly His Ser Ser Gly Glu Ile Ala
        35                  40                  45

Ala Ala Tyr Val
    50

<210> SEQ ID NO 207
<211> LENGTH: 59
<212> TYPE: PRT
<213> ORGANISM: Penicillium coprobium PF1169

<400> SEQUENCE: 207

Val Tyr Ser Gly Ser Met Thr Asn Asp Tyr Glu Leu Leu Ser Thr Arg
1               5                   10                  15

```
Asp Ile Tyr Asp Met Pro His Asn Ser Ala Thr Gly Asn Gly Arg Thr
            20                  25                  30

Met Leu Ala Asn Arg Leu Ser Trp Phe Phe Asp Leu Gln Gly Pro Ser
        35                  40                  45

Ile Met Met Asp Thr Ala Cys Ser Ser Ser Leu
    50                  55

<210> SEQ ID NO 208
<211> LENGTH: 28
<212> TYPE: PRT
<213> ORGANISM: Penicillium coprobium PF1169

<400> SEQUENCE: 208

Pro Trp Pro Thr Thr Gly Leu Arg Arg Ala Ser Val Asn Ser Phe Gly
1               5                   10                  15

Tyr Gly Gly Thr Asn Ala His Cys Val Leu Asp Asp
            20                  25

<210> SEQ ID NO 209
<211> LENGTH: 71
<212> TYPE: PRT
<213> ORGANISM: Penicillium coprobium PF1169

<400> SEQUENCE: 209

Lys Ala Ser Leu Ser Leu Gln His Gly Met Ile Ala Pro Asn Leu Leu
1               5                   10                  15

Met Gln His Leu Asn Pro Lys Ile Lys Pro Phe Ala Ala Lys Leu Ser
            20                  25                  30

Val Pro Thr Glu Cys Ile Pro Trp Pro Ala Val Pro Asp Gly Cys Pro
        35                  40                  45

Arg Arg Ala Ser Val Asn Ser Phe Gly Phe Gly Gly Ala Asn Val His
    50                  55                  60

Val Val Leu Glu Ser Tyr Thr
65                  70

<210> SEQ ID NO 210
<211> LENGTH: 80
<212> TYPE: PRT
<213> ORGANISM: Penicillium coprobium PF1169

<400> SEQUENCE: 210

Leu Lys Gly Thr Gly Gly Gln Met Leu Gln Asn Val Val Leu Arg Val
1               5                   10                  15

Pro Val Ala Ile Asn Ala Pro Arg Ser Val Gln Val Val Gln Gln
            20                  25                  30

Asp Gln Val Lys Val Val Ser Arg Leu Ile Pro Ser Glu Ala Ser Val
        35                  40                  45

Leu Asp Asp Asp Ala Ser Trp Val Thr His Thr Thr Ala Tyr Trp Asp
    50                  55                  60

Arg Arg Val Leu Gly Ser Glu Asp Arg Ile Asp Leu Ala Ala Val Lys
65                  70                  75                  80

<210> SEQ ID NO 211
<211> LENGTH: 38
<212> TYPE: PRT
<213> ORGANISM: Penicillium coprobium PF1169

<400> SEQUENCE: 211

Gly Asn Gly Ser Ala Met Ile Ser Asn Arg Ile Ser Trp Phe Phe Asp
1               5                   10                  15
```

-continued

```
Leu Lys Gly Pro Ser Leu Ser Leu Asp Thr Ala Cys Ser Ser Ser Leu
         20                  25                  30

Val Ala Leu His Leu Ala
        35

<210> SEQ ID NO 212
<211> LENGTH: 76
<212> TYPE: PRT
<213> ORGANISM: Penicillium coprobium PF1169

<400> SEQUENCE: 212

Ala Ile His His Gly Val Gln Ala Ile Lys Leu Gly Glu Ser Arg Val
1               5                   10                  15

Ala Ile Val Gly Gly Val Asn Ala Leu Cys Gly Pro Gly Leu Thr Arg
            20                  25                  30

Val Leu Asp Lys Ala Gly Ala Ile Ser Ser Asp Gly Ser Cys Lys Ser
        35                  40                  45

Phe Asp Asp Ala His Gly Tyr Ala Arg Gly Glu Gly Ala Gly Ala
    50                  55                  60

Leu Val Leu Lys Ser Leu His Gln Ala Leu Leu Asp
65                  70                  75

<210> SEQ ID NO 213
<211> LENGTH: 69
<212> TYPE: PRT
<213> ORGANISM: Penicillium coprobium PF1169

<400> SEQUENCE: 213

Arg Glu Trp Met Thr Ala Glu Gly Lys Asp His Asn Leu Ser Asp Ile
1               5                   10                  15

Leu Thr Thr Leu Ala Thr Arg Arg Asp His His Asp Tyr Arg Ala Ala
            20                  25                  30

Leu Val Val Asp Asp Asn Arg Asp Ala Glu Leu Ala Leu Gln Ala Leu
        35                  40                  45

Glu His Gly Val Asp Gln Thr Phe Thr Thr Gln Ser Arg Val Phe Gly
    50                  55                  60

Ala Asp Ile Ser Lys
65

<210> SEQ ID NO 214
<211> LENGTH: 53
<212> TYPE: PRT
<213> ORGANISM: Penicillium coprobium PF1169

<400> SEQUENCE: 214

Thr Ser Asp Asp Tyr Arg Glu Val Asn Ser Gly Gln Asp Ile Asp Thr
1               5                   10                  15

Tyr Phe Ile Pro Gly Gly Asn Arg Ala Phe Thr Pro Gly Arg Ile Asn
            20                  25                  30

Tyr Tyr Phe Lys Phe Ser Gly Pro Ser Val Ser Val Asp Thr Ala Cys
        35                  40                  45

Ser Ser Ser Leu Ala
    50

<210> SEQ ID NO 215
<211> LENGTH: 63
<212> TYPE: PRT
<213> ORGANISM: Penicillium coprobium PF1169
```

<400> SEQUENCE: 215

Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

Glu Cys Val Pro Met Tyr Gln Cys Thr Asn Ala Gly Gln Ser Arg Ala
        35                  40                  45

Met Thr Ala Asn Arg Leu Ser Tyr Phe Phe Asp Leu Lys Gly Pro
    50                  55                  60

<210> SEQ ID NO 216
<211> LENGTH: 68
<212> TYPE: PRT
<213> ORGANISM: Penicillium coprobium PF1169

<400> SEQUENCE: 216

Met Leu Ala Val Gly Ala Ser Ala Ser Asp Ile Gln Gln Ile Leu Asp
1               5                   10                  15

Ala Met Arg Gly Asn Lys Ala Val Ile Ala Cys Val Asn Ser Glu Ser
            20                  25                  30

Ser Val Thr Leu Ser Gly Asp Leu Asp Val Ile Ala Asn Leu Gln Thr
        35                  40                  45

Ala Leu Asp Lys Glu Gly Ile Phe Thr Arg Lys Leu Lys Val Asp Val
    50                  55                  60

Ala Tyr His Ser
65

<210> SEQ ID NO 217
<211> LENGTH: 39
<212> TYPE: PRT
<213> ORGANISM: Penicillium coprobium PF1169

<400> SEQUENCE: 217

Asn Ala Ala Gly Ala His Phe Leu Thr Glu Asp Ile Gly Leu Phe Asp
1               5                   10                  15

Ala Pro Phe Phe Asn Ile Thr Leu Gln Glu Ala Gln Thr Met Asp Pro
            20                  25                  30

Gln Gln Arg Ile Phe Leu Glu
        35

<210> SEQ ID NO 218
<211> LENGTH: 76
<212> TYPE: PRT
<213> ORGANISM: Penicillium coprobium PF1169

<400> SEQUENCE: 218

Gly Pro Ser Met Thr Ile Asp Thr Ala Cys Ser Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Leu Gly Pro Glu Gln Tyr Ile Ala
        35                  40                  45

Glu Ser Lys Leu Lys Met Leu Ser Pro Asn Gly Arg Ser Arg Met Trp
    50                  55                  60

Asp Lys Asp Ala Asp Gly Tyr Ala Arg Gly Asp Gly
65                  70                  75

<210> SEQ ID NO 219

```
<211> LENGTH: 61
<212> TYPE: PRT
<213> ORGANISM: Penicillium coprobium PF1169

<400> SEQUENCE: 219

Gly Leu Val Asn Ile Leu Arg Ser Trp Gly Ile Glu Pro Ser Thr Val
1               5                   10                  15

Val Gly His Ser Ser Gly Glu Ile Val Ala Ala Tyr Thr Ala Arg Ala
            20                  25                  30

Ile Ser Met Arg Thr Ala Ile Leu Ala Tyr Tyr Arg Gly Lys Val
        35                  40                  45

Ala Gln Pro Leu Glu Gly Leu Gly Ala Met Val Ala Val
    50                  55                  60

<210> SEQ ID NO 220
<211> LENGTH: 79
<212> TYPE: PRT
<213> ORGANISM: Penicillium coprobium PF1169

<400> SEQUENCE: 220

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val Leu Thr Ile Ser Asp Thr Ile Tyr Leu Ala Gly
    50                  55                  60

Arg Arg Ala Gln Leu Leu Thr Glu Gln Ile Glu Gly Thr His
65                  70                  75

<210> SEQ ID NO 221
<211> LENGTH: 81
<212> TYPE: PRT
<213> ORGANISM: Penicillium coprobium PF1169

<400> SEQUENCE: 221

Val Tyr Thr Gly Arg Ile Ser Leu Lys Asp Leu Gly Met Arg Cys Leu
1               5                   10                  15

Pro Leu Cys Leu Phe Leu Phe Leu Trp Thr Ile Tyr Phe Asn Thr Ala
            20                  25                  30

Tyr Ser Tyr Gln Asp Ile Lys Asp Cys Lys Leu Asn Val Asn Ser
        35                  40                  45

Ser Tyr Val Leu Ala Gly Ser His Val Arg Gly Met Leu Leu Leu Gln
    50                  55                  60

Ala Ile Ala Val Val Leu Val Ile Pro Trp Ile Leu Tyr Thr Ser Ala
65                  70                  75                  80

Ser

<210> SEQ ID NO 222
<211> LENGTH: 82
<212> TYPE: PRT
<213> ORGANISM: Penicillium coprobium PF1169

<400> SEQUENCE: 222

Arg His Phe Gly Leu Trp Asp Glu Pro Arg Glu Leu Glu Asp Val Glu
1               5                   10                  15

Phe Leu Leu Lys Ala Asp Val Arg Asn Asn Ser Ala Trp Asn His Arg
            20                  25                  30
```

Tyr Met Leu Arg Phe Gly Pro Arg Asp Thr Ser Leu Pro Asp Ala Gly
        35                  40                  45

Met Val Asn Ala Gly Asp Leu Ser Thr Ala Pro Ala Glu Lys Gly Arg
    50                  55                  60

Leu Ser Val Val Asp Glu Asp Met Val Asp Gly Glu Leu Lys Phe Ala
65                  70                  75                  80

Gln Glu

<210> SEQ ID NO 223
<211> LENGTH: 35
<212> TYPE: PRT
<213> ORGANISM: Penicillium coprobium PF1169

<400> SEQUENCE: 223

Ile Met Arg Gly Ala Gly Cys Ala Ile Asn Asp Leu Trp Asp Arg Asn
1               5                   10                  15

Leu Asp Pro His Val Glu Arg Thr Lys Phe Arg Pro Ile Ala Arg Gly
            20                  25                  30

Ala Leu Ser
        35

<210> SEQ ID NO 224
<211> LENGTH: 86
<212> TYPE: PRT
<213> ORGANISM: Penicillium coprobium PF1169

<400> SEQUENCE: 224

Phe Pro Thr Phe Pro Pro Lys Glu Ala Asp Phe Leu Met Glu Met Phe
1               5                   10                  15

Ala Gln Asp Ser Lys Asn Tyr His Val Trp Thr Tyr Arg His Trp Leu
            20                  25                  30

Val Arg His Phe Gly Leu Trp Asp Glu Pro Arg Glu Leu Glu Asp Val
        35                  40                  45

Glu Phe Leu Leu Lys Ala Asp Val Arg Asn Asn Ser Ala Trp Asn His
    50                  55                  60

Arg Tyr Met Leu Arg Phe Gly Pro Arg Asp Thr Ser Leu Pro Asp Ala
65                  70                  75                  80

Gly Met Val Asn Ala Gly
                85

<210> SEQ ID NO 225
<211> LENGTH: 82
<212> TYPE: PRT
<213> ORGANISM: Penicillium coprobium PF1169

<400> SEQUENCE: 225

Asn His Arg Tyr Met Leu Arg Phe Gly Pro Arg Asp Thr Ser Leu Pro
1               5                   10                  15

Asp Ala Gly Met Val Asn Ala Gly Asp Leu Ser Thr Ala Pro Ala Glu
            20                  25                  30

Lys Gly Arg Leu Ser Val Val Asp Glu Asp Met Val Asp Gly Glu Leu
        35                  40                  45

Lys Phe Ala Gln Glu Ala Ile Leu Arg Ala Pro Glu Asn Arg Ser Pro
    50                  55                  60

Trp Trp Tyr Ala Arg Gly Val Leu Arg Ala Ala Gly Arg Gly Leu Gly
65                  70                  75                  80

Glu Trp

<210> SEQ ID NO 226
<211> LENGTH: 45
<212> TYPE: PRT
<213> ORGANISM: Penicillium coprobium PF1169

<400> SEQUENCE: 226

```
Arg Pro Thr Ser Arg Lys Leu Gly Val Tyr Pro Gln Tyr Ile Leu Gly
1               5                   10                  15

Ala Ser Ser Ala Leu Thr Ile Leu Pro Ala Trp Ala Ser Val Tyr Thr
            20                  25                  30

Gly Arg Ile Ser Leu Lys Asp Leu Gly Met Arg Cys Leu
        35                  40                  45
```

<210> SEQ ID NO 227
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 227
tacaggcggc ctaaattgtc                                           20

<210> SEQ ID NO 228
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 228
gaacacagcg caagagatca                                           20

<210> SEQ ID NO 229
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 229
cgcaagactt gaggaacaag                                           20

<210> SEQ ID NO 230
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 230
tgaggtcaac agtggacagg                                           20

<210> SEQ ID NO 231
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 231
cgcttttacg gcaatcatct                                           20

```
<210> SEQ ID NO 232
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 232
tgttcgtcgt ccttgtatgc                                           20

<210> SEQ ID NO 233
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 233
cagacgctgc ataggatcag                                           20

<210> SEQ ID NO 234
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 234
ttactagcct ctggggtgga                                           20

<210> SEQ ID NO 235
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 235
tctcttgcgc tgtgttcact                                           20

<210> SEQ ID NO 236
<211> LENGTH: 19
<212> TYPE: DNA
<213> ORGANISM: Artificial Sequence
<220> FEATURE:
<223> OTHER INFORMATION: a primer sequence for PCR

<400> SEQUENCE: 236
atgcggcctt tttcaacat                                            19

<210> SEQ ID NO 237
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 237
cgacgtaagg agctgtgagc                                           20

<210> SEQ ID NO 238
<211> LENGTH: 18
<212> TYPE: DNA
<213> ORGANISM: Artificial Sequence
<220> FEATURE:
<223> OTHER INFORMATION: a primer sequence for PCR
```

<400> SEQUENCE: 238
acctcgatcc tgctgcaa                                              18

<210> SEQ ID NO 239
<211> LENGTH: 21
<212> TYPE: DNA
<213> ORGANISM: Artificial Sequence
<220> FEATURE:
<223> OTHER INFORMATION: a primer sequence for PCR

<400> SEQUENCE: 239
ggttgtcagg atttgtcaga a                                          21

<210> SEQ ID NO 240
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 240
ttacttcatc cccggtggta                                            20

<210> SEQ ID NO 241
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 241
agagcatagc ccggttgtta                                            20

<210> SEQ ID NO 242
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 242
cccaccttga tttgctcagt                                            20

<210> SEQ ID NO 243
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 243
agagcatagc ccggttgtta                                            20

<210> SEQ ID NO 244
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 244
gccaccttga tttgctcagt                                            20

<210> SEQ ID NO 245
<211> LENGTH: 22

```
<212> TYPE: DNA
<213> ORGANISM: Artificial Sequence
<220> FEATURE:
<223> OTHER INFORMATION: a primer sequence for PCR

<400> SEQUENCE: 245
aagaacacag agattggtgt gg                                              22

<210> SEQ ID NO 246
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 246
ccaggaagac acttggaagg                                                 20

<210> SEQ ID NO 247
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 247
agagcatagc ccggttgtta                                                 20

<210> SEQ ID NO 248
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 248
ccaccttcga tttgctcagt                                                 20

<210> SEQ ID NO 249
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 249
cgcaagactt gaggaacaag                                                 20

<210> SEQ ID NO 250
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 250
tccctctacg cagaagaacc                                                 20

<210> SEQ ID NO 251
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 251
```
agagcatagc ccggttgtta                                              20

<210> SEQ ID NO 252
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 252
ccaccttcga tttgctcagt                                              20

<210> SEQ ID NO 253
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 253
gaggcgctgg tgtagagaat                                              20

<210> SEQ ID NO 254
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 254
tgtctcccgc tttgtctctt                                              20

<210> SEQ ID NO 255
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 255
agacgtggag ttcctcctga                                              20

<210> SEQ ID NO 256
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 256
caaacttcag ttcgccatca                                              20

<210> SEQ ID NO 257
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 257
caactttccc acccaaagaa                                              20

<210> SEQ ID NO 258
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 258
aagcatgtat cggtggttcc                                          20

<210> SEQ ID NO 259
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 259
cgatacatgc ttcgttttgg                                          20

<210> SEQ ID NO 260
<211> LENGTH: 18
<212> TYPE: DNA
<213> ORGANISM: Artificial Sequence
<220> FEATURE:
<223> OTHER INFORMATION: a primer sequence for PCR

<400> SEQUENCE: 260
cagcagccct cagcacac                                            18

<210> SEQ ID NO 261
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 261
ggcgtctatc cgcaatacat                                          20

<210> SEQ ID NO 262
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 262
gagacaccgc atacccagat                                          20

<210> SEQ ID NO 263
<211> LENGTH: 406
<212> TYPE: DNA
<213> ORGANISM: Penicillium coprobium PF1169

<400> SEQUENCE: 263
cccagcccaa gacttgagta gactatattt attctctttg atatccatct cagcatcaag      60
tttttgacgt tgtattacta tcctcgtttg gaattctcct cccaggtctt gcttcattgc     120
ttatagcatt ctaccaaaaa cgtcactgtc atggacgggt ggtcagacat atcatcagcg     180
cctgccggat acaaggatgt tgtttggata gcagatcggg ctctgctagc ccaaggattg     240
ggatggtcaa tcaactacct ggccatgata taccaatcgc gcaaagaccg cacatacggc     300
atggccattt tgccactatg ttgcaacttt gcgtgggaat tcgtctacac tgtcatctat     360
ccttctcaaa atcccttcga gagagctgtc ctcacaacat ggatgg                    406

<210> SEQ ID NO 264

```
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 264
cccagcccaa gacttgagta                                               20

<210> SEQ ID NO 265
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 265
ccatccatgt tgtgaggaca                                               20

<210> SEQ ID NO 266
<211> LENGTH: 39008
<212> TYPE: DNA
<213> ORGANISM: Penicillium coprobium PF1169

<400> SEQUENCE: 266
gccagccaat gtctcgacga gactctcggt gtcaagctgc ttgaggaggc cattgtgaag      60
atcgaagagc gtatcaggtc gcacggcggt agctgcaccg tgaagatggc acccaaggcc     120
gtcaccgagc aggacgatgc gatcctgcag gagcttatgg agaagcgcga acgtgagaac     180
acccaggtca gcggagatga ggactctgaa agtgatgagg tgttcccga  gtaagcgacg     240
ggctacaaat tcgagtcgag gggcatacag cggtcaccag cgctaaaatt caaagctggt     300
atcaccgcta gaggggagtt ggtgaaagat ggatagaaaa aacttgcaca tatcggaaaa     360
aaggctcgat gggccagtgt gctgatgggc aggattacag tcagaactcg cccaggtaag     420
tcgcctggac ttcggggtct ggatatgaca tattcacacc tgtgtatgcg gtattcccat     480
tgcggtcgaa atcctcgttc ccggcatcaa atacactggg tccgcacagg gtgcaagttc     540
tgatgcacat aatgtttgat gcaaccgata cgttcaatgc cagtcatgct tttagatgca     600
attatccctg tagaggccat gtagcaatgt atgtagcaat gtatgtagca atgtatatag     660
caatgtatgt agcaatgtat gtaagatatc ataacaatcg agctcatgaa atggcgggga     720
gagctgaagc ttatctaccg ccgccgatca ttggtgccct caaagccatc gagaacttcc     780
ctttcggcac ttctcttttt ccaccaactt tcattctacg cgatatggga cattgggcaa     840
agatctttac cgccgatcgt ggcaggaccc ggcatcgggt cgaggtggaa cgtcgtcggc     900
gtacgtcatt ttccaaacat gcggaacact actgacaagc gcagtgcta  ccggcctatg     960
cggccgatga gtctgacgcc tcggatgctt caaaggaaat tgcaaaggtt gctcttcggt    1020
tgaaatatca aattgagcag gttgtctcct gtgaagtgga ggagaacgtc ttgaccgacc    1080
caaacagccg tatcatcacg gatgatgtgg ttgcgactgc taagcaggcc ggtggagatg    1140
aatacaaagc atgcattgtt tattgtctcc tggtttgtct gcgatggttc aaaatccaat    1200
catccgtcga gctttgggat tccgatctcc atgagattcg agctgtggct tgcgaggtca    1260
tcgccaagcg catgtaatgc ccctttttca ttccatgttc tcggccattt cctgacccaa    1320
acagtatcga atccgagcag aaccaagaat acgtgctaaa agacatttta ctcaagcgat    1380
actcaatctt cagtgaaggt gtggagactg atcccgccaa tgtcattgaa cgatcggtag    1440
atctccatgc tttaaggatc atcagctgtg ctgcgtacca gaagtgtatc cagtatctct    1500
```

```
ggagaggttg gatctgccag gaagaaggca acccaactaa ctttgtcgaa tacagtgaga   1560
agtcaaaccc caattattgg gttcatttcc atcctgatcg gatgcggact cctctgtatc   1620
agaatgtctg ccaaattttg ttttccttga tttaccttgc gacttatacc gcagttatca   1680
ataccgtgaa tcccaccggt gacctggatg tagctgaagc catactgtat gttatgactc   1740
tcgcgttcat ctgcgacgag gcggtcaaat tctggaaggt tggatggaat tatctcgaat   1800
tctggaatgc gttcaactca acgctctact ctatcctggc agtgtctctt gtcttgcgct   1860
ttattgcctt ggcacactca tcatctacgc acgatgaaac aaggcaggca tacaatgaac   1920
tcagctacaa cttcctcgcc tttgcgggcc ctatgttctg gatgcggatg atgctatatc   1980
ttgactcgtt ccgcttcttc ggtgccatgt tcgtggtcct tcgagtgatg atgaaagaaa   2040
gcttgatatt ctttgctctt ctattcgtgg ttatggctgg tttcttccag ggcttcgtcg   2100
gcatggccca agtggatgct gatatcccca tccaccgaaa tattctccag ggaatgatca   2160
atagtatcat gcaaagccct gagtttgaca cttttcagga atttgcattt ccctttggta   2220
tcatcctcta ttatgtgttc aacttcattg ttatgactgg taagtctgta ttacatttgt   2280
ttggggtgtc gctaaacatt tttagttctg ttgaatattc tcattgcctt gtacaacagc   2340
gcatatgaag atatctctgg caatgccacg gacgagttca tggccatctt cgcgcagaaa   2400
accatgcagt tcgtccgcgc cccagatgaa aatgtcttca tcccacgtac gtgtttactc   2460
aattctgata tagcatacgt atgactaact ttggtctggg taatagcctt caatctcatc   2520
gagattctct gtttgatagc tccattcgaa tggtggcttt cgcgggagac ttacgccaag   2580
gtgaatgaca ttgtaatggc cgtgatatat tctccgctgc ttgtcgttgc agcctgggtt   2640
gagacccgtc aggcgcataa gattcgatgg aatcgccgtc atggcgaaga agacgatgac   2700
tgcgctcagg aatgggagca tgtggccaag gaggtcaatt ttgatcttga cgatacctgg   2760
aaacagcacg taattgagtc cacgccggat atcaaggttg atagttgtac atatgaactc   2820
cgagagctga gggagcaggt taaaatgttg acggggatgg tgaaggaatt gactcaggag   2880
atggaaaaga aggcggatgg agcaagctag gaagtcctgt tgaattgtac agcaagaata   2940
ctacactgag catgggacat cgcaaaggtg atttgctact gcagtttcac caatattaca   3000
ttgcgaaaac tgtatattct cttaatgtct aatagcagca atcagcccag tggcacggag   3060
gaaagtcacc gtcctgtaag gcaaatactt gtgcttcaaa tgaattttga ctatttttca   3120
tgcgataact ggcaaagggc aggggagaa aaaatgatca ttattcaacc caagcaaact   3180
gtccagaaag tgacatgccc actttgcaag taaagaagat atgtgacaat ctaacagtct   3240
caggtagaca ttcgctcttc attaaaatcc atgcgttgct cgccgtagcc caattcgaag   3300
cactgggcaa cccacatcga gaccttaaaa tcgggtgatc atcacacagc aacaggctca   3360
gcaagaatgg aggcaatcgt ctcccttga tgatccagct gtgagagctt cgctcgatgg   3420
tgcttgccaa tacctatccg aggaatgtca tccacaaata caacacctcc atctagggct   3480
ttatagctgg ccagttggct ttgaatcaga cctgccactt gatcggccgt cgtctccggg   3540
gacgtatcat tgcggacgac ataagctcga ggaacctcgc tgctgccatc tgggagcatg   3600
actccgatca cggctgcgtc cttgatactc gggtccttgc gtaggatccc ttcaatctct   3660
gcgggagcga cggagtatct aaatcaagca cgatatgtta gtctatcatc tgctgcatcg   3720
gatgtcatat ggagaggaaa gaaagcgaag gatgtgaagg atgaagccta gaggactggg   3780
taacttgccc tcgaactttg atgagatctt tggtccgtcc gatgacatgg tagtttccgt   3840
```

```
cttccacatg gaacatgtct ccagtccgga accatccttg ctcatctttg gcatcagttc   3900
gtcctttgta tgctagaagg agtcccggtc cacggacata caactctcca ggggagtctg   3960
gtgtcccggc gacatcttcg cccgtgtcgg gattgacaaa gcgcagctca tatctgggca   4020
aaagagtccc tacactgcca aattgtggtt gtatcccgta gcgattctgg aaaaccactc   4080
caacctcaga catgccccac agatttcccg ctatagcgtc cggtgatagc aggctctgga   4140
attgctgcat agagtacccg tctatgggag cacccgaaat accgatatag cgcagagaag   4200
acaagctctc ggctacattc aaggaggacc tattgagaat gtggatcatg gcaggaacca   4260
tgtacgtttc cgtgatgtgg tgctggcgga tgccgtcgag caaagcggtg atttcgaagc   4320
gcgggataat gtacagaggc tggccgtacc gaatggggaa gatgttgccc cagaagtcgc   4380
caaaagaatg gtacagtggc agtgccatca acgaacgac ggggtatggc acttcatagt   4440
agacgctcag atggtgggaa atgatcgtgt ggtgggttcg aattgcggct ttggggagac   4500
cgctggtgcc actggttagg aacatagccg ccggcgtgat cttgctctcc tcgctatctt   4560
cgaaacgaag ccaatccaac tcgccatact ggagcagact ctccaggcgg ataggttggt   4620
ccactgtctg ggtgtcgaga tcctccgtct gctccgcctg gccatgtgca aattggacta   4680
cactttcgat agacttctca tccatcagaa ggacttggtt tgaggacatt ccttgattat   4740
tgcaaacttc caggactctg gtcagcgcac tcggagcagt aataatcaac cgaggctcgg   4800
cgacacgaag cagatgagcc acttcatggg ggcgactagc gacatcaaac cccatataca   4860
ctccgcccgc accaacgatg gcaaagaaaa gagcagagtg tagaacctag gctgatgtta   4920
gcagcatatc attgttatgg ggtagtgtga ttacactgtt ctccagttgc acgagtacac   4980
aatcgcctcg ttccacaccc cgggctttga ggcccgcaat gagtgatcgc accagccgtc   5040
ggaattggat ggcattgaaa gcacgcgaag ggttgcgggc atcaatatag atgggcttag   5100
attggtcaaa ggcaggacca ctaaaagcaa agctgactag gtctgtctcg tgctccatat   5160
cgatgcttat attgtacagt tctcgtgtgc tattgacatg cagaacttga tgcaggattt   5220
gtgctcactt taagtagtag tacatggaat gctcagacct cccatatcac tttgatcgac   5280
actgcacggg acaagtatca tgcagaagac tattgagaag aatgccacgc caccaattcg   5340
tattatacta atctagccta agccaataca tgtaaagagt actatttagg acccacactg   5400
tcattgcaga gctttgaagc agctgcatgc gctaattcac ccacagatac gccactaaga   5460
atcaaaatta ccccgatgtc gacgctcagc tctttcgtaa accattgact cagcccaatg   5520
gcgataagcg agtcaatccc gagctcagga atcagcgtgt cagcagagag cggtgcatcc   5580
tcggccaagt tcaagctggc ccgaattttc tccattagtg gtctcacgac tgcttcggct   5640
ttttcttcca agcttgtcgc tgcagtgaca agatctttgg tcgaccgggt ctcaatcaat   5700
gcaagtattt gatcttgaga cgccgtggcc gtataggagt agaatggcca taacttcggt   5760
atcgggcact cgccatagcc acacttcaaa ctctggtgtc ggagtccccc gattaactca   5820
gcgttggaat tggaatctga gcgcccgcag aggattgcct cggcgagtat ctcgtcgaca   5880
tcccgctggg atacagctac cgggccacac caaagaggct gactgggaga aggactagaa   5940
atgccgtgga tctcgcccag atgtactaga cttgctggtc tgccctgggc tcgacggtgg   6000
cggaccagca gggccatttt ctcggacatc gctgcagtca ttgcctggtc cgcatggcct   6060
aacactcctg caatagatcc gatgagcacc caaaagtcca gagttggggt cttgtagagc   6120
tcatctagct gctgcagccc cttcaagacc ggatgcagat ggttccggag ggaatctatc   6180
gtgagctggg acaaggaaca gtcaggtaga ggcggaggct gaattagaac tcctcccact   6240
```

```
accgggggga acgcataggg aatagtttga tgcaaactgg tggcagaaat gccatcgatc   6300
aggtttctgg cattgattag cttgtgcatt tgaattcatg ggtacgtaag taacttacat   6360
tttcgagacc gctatgcgcg ttccccgtcg agaaacttct tccaaccacc acgcatctga   6420
gtcaagtcta gagccagcaa ggaggatcca ttttgccccg tgtgttgcta gccaaagaca   6480
gatagcatgg gctagttcac tgcctagacc tacaagtatg taggttttt tctctgacag    6540 ctgcacctgg gaaccagcag tcggtatctg ggcgagcacc ggagttgtag agtcccaatc   6600
taccacggca tcctgggagt caaggattgg gtactcggaa atcctgctga ttggtaacga   6660
gtccacagaa tttggtggga gcccctcgcg gccggtgtac gccactaagc aggcggttag   6720
gaaagccttg gctatgagtg acgaatcatc cgcgttgatc ggccctgtcg atgcagaggt   6780
aaggtagaaa tcctgcaaat ggattcgtgt cgcgttgtca ggcaagagcg atagcatgcg   6840
atcatagaca ccctgtccac gacgatgtag aatcgctatg gccgacacat ctgagggaag   6900
tacctgagac aattgccgcg cagtgctatg ctcgtgcaaa agcaacatcg gtctttcttt   6960
gtctgggttg cttttgctag tgctgaagat aaccttacca tcccgccggg tcagcatttg   7020
gtggaaaaca gactgaagga ccccatcagc ctcgtgcact acaagcgtgc ctgattgtgg   7080
gacttgttcg accaggtatc ctgccaacag agcagccgct gtggcgcgga gataagactg   7140
ctcgtgggct tccaacaccg tgtctggcac tgaccacgcc caggagtctg gaacgataac   7200
atgagatgca atgtgggacg acagagcgat cattctcttg ttgctcttaa cgtccagccc   7260
tatgaccagc cgcagaaata tggccctgc aacccgcacg gctgctatac tggaatgtcg   7320
aactcgcaga tgaagggttg ggccataact tgcggttatc ggcggatcag ccatcgaaag   7380
aaggcggaac ccttcacaag tcttgtcggt cgtagcagga aggatttgta caactccctt   7440
gtcgaggtcc acgcagtctg tcacttttg ccgcctggct agatggcgca gcccagtagc   7500
atggtcgtga tattgccgag gaacacggaa catagagccg tcgtattgaa tttcgggctc   7560
gatgttggtg agtccgcacg aatgaggatt ttcttgagct gcactagctt gaacaaagtg   7620
tccaagagct gtcgccaata tttccgttgt aactccaacc ggatctgtga tatgtagcag   7680
ttgtagcaga gaagacgatc gttcagaagc caggaaggtg gaaaggagac cttcaccag    7740 tccggcatca gggtggtcga ccttctcaca ggtcaccact aacattcgct tactgactgt   7800
catcagtctg cacaactcgc tcaaggtagc gtttgtcaga tctcgatcat cgacgaggta   7860
cagaacagtc aatttagata aatcgcgatc ttcaatgaga tctaggtctg gcgcatgagc   7920
aaccttgacg aagtcatcct gtaccaattc aaaaagctct gaggtaagac aatctgcctc   7980
ctcagcgtca ccgccaagca acagcaggtc tccgcggctc tgtggttccg caggactgtc   8040
tggagtgcga cagagaagga gtgaaaagtc cccaaggctt tcactctctt gggacgcatc   8100
gaacgaatcc aagccataga atccgccgtt agacagtagc tcaacccagt ccctcctggt   8160
agtaattggc tcaccagagc agtagccttt cccggtctct gtgcatctca ttggaggacc   8220
gaatagaaga ttcaaatatg tagtgctggg attcgttcgt actagtagga ccaagaatcc   8280
accaggcttg agcaagcgac gaacatgagc caccgcgacc tcttgcagaa ataccgcggc   8340
tgtgatcagc accatatcgt agaattgctc gcggcagccc tgctcgacag gatcctcatt   8400
gatgtccaac gttttgtgcg cacctcgcc aggttgctca aggtcttcct caatcgcttg    8460
taggccagaa acgagagtc cagcataagt aaatgaccga taagtccgac ccatcttctt     8520
cagtccagag tgaacatggc ctccaaattg gccgatctga aggatattca tttgtggaaa   8580
```

```
gcggaaacac gcctggctga cgacagatac gagctcgtct tctagatcca agacttgcaa    8640
gtcctccttc agatattgac tttcctcatc gatggccggc caggcctcta tttgaagacc    8700
agaatcacgc agaacgcgag gtagccgctg gcctaccgca gcaatggccg tgagaccagg    8760
gtcattcaag agtgacgggc tcactccagc tgtgaagtcc tcaatcttct ggtccaagca    8820
ctcggattcc ccgacagggt ctggctcttg gctagcattt gcaatgcatt ggttcatcca    8880
tgcaagcaga cgagccaccat cgaaatccaa tccgcttcgc tccaagtccg tcagtccatt   8940
gcgagcctgc ttgagataca gtagcgcaag ctcctctcgg agagagtgta gctgtagcat    9000
ggtagctggc aacttccgtg atcccttctt cagagtgggc tcaagcggtc cccacgcggt    9060
ctgggaaaga acctgcaagt tgtttggtgc agttccagat ggctggcata tgagagaaac    9120
accttcgagc tggacagcct ttccccatt catggtgaag atgtcaatat caccgcgaat     9180
tcgatctcca ttaacgcagg tcagatagct tgctaccgtc aattccttgc cttgccaatc    9240
tgaagcacat aacaccggat ttatccaggt actgtcaaca tttctcgata agaatggtcc    9300
cgtcagcagc gtctcttcaa gcccaccaat tgcagcaatc attgtttgaa caccaaggtc    9360
caaaatagcc gggtgaagag ccatgggctc atccgaatca tttgagggaa cgggcacact    9420
cccagtggct agatcacgcc ttttgcggag tcccgtcaag gtagagaatg gccagtaca     9480
gtggtagtca gcgcggcgca ggctgtcata gaattcagtg ctgtccacgg gctccaaggc    9540
ctgaggtagc tgtccctgtg ggggtaggag agcacggtca gaatcccctg gatgcatgat    9600
catcttggct gttgcacact gaacgagctc tccggataca acagcttcgc agcagaacca    9660
agcagtaatg gctccatcat gcgagtgaat actacccacg gtgacaagca cttcagtgcc    9720
gatgggatca ttctgaatcg ggagctgagt gtggatggtc aagtccttga cattcaacaa    9780
gcgtaggcct tgtgtctgtg ccattatcat acctgcctcc agtgccatcg atatgtatcc    9840
tgtctcaggg aagacagatc ccgaatcggc acgacggtcg gccaaccagg gcagctcctc    9900
tggtcgtaga tagtttcgcc aacggaactt ttctgctccg gtctctggac tgagagaacc    9960
gagaagtgcg ttaggagatg tagcacgatg gttatggttc gaagacattc gcgactgtgt   10020
ccagtatgtc tgagtatggt cgaagggta gaatggtagc gattctacca acacaggcca    10080
atgatttgga tcaaagagtg agacatagtc tgtgaggcgg acgacatttg ggccgaggtg   10140
tgcccaggaa gatcctaggg ccgttgccca tgtatcgagg ccgggctttc ctcgctcagc   10200
aagagcaagg taaggaattg ccgagtgggc cgagtgcatt ttggagaggg tctgtaggac   10260
aggccctctc agtgtcggat ggggcccgat ctcaatgatg agatctggtg gcccagcgtc   10320
tcgtgccgcg gcctctaggg cttgggaaaa ctgaacagga cgcagcatat tctcaaccca   10380
gtactcccct gtcaattcct gctggtcata cccagtcatg acctcccctg ggtagacact   10440
cgagtaccag cgcgaggcag aagctgacag ggcgacagga tacgcttta ttgcgtcacg    10500
atatggatct gcacaaggct tcatatgcgg agagtgatat gcggtgtcca ctcgaagcat   10560
acgcggagtg aggcccaggc tcttcagcag ccactccagc tcccgcaggc actctgcgtc   10620
gccggataac gtgacgctgg atggcgagtt ggcggcagca acgcttatac gtccggagta   10680
ggcttctaaa gcacagatat tctgcgcctg ctgccatgtc aaattcacgg ccatcatccg   10740
acctgtcgga tcgcgtgact tatcaatggt catccccta aggtacgcga tgcggattgc    10800
atccgaggcc gtcagcacac ccgcagcata ggctgctaca atctcgccgg aagagtgacc   10860
gaccacaatg gtaagctcaa tccctaccgc acggagcatg ttgacttgca tgatttgcaa   10920
cgctgtccgt agggggagag aaaggaggcc ctcgtttacg cgcgaggacg atgccggctg   10980
```

```
tgacaactcg tcgagaagag aaaactgtgg acgaaggtct agtggaagct catccaaagc   11040
ttcctccaga ttcataatcc attttcgaat tgagggactt gcctcaatca gatcaagtcc   11100
catttgtggc cattggactc cttggcccgt gaagatgccc atgacgcgtc tgggccgagt   11160
gttggatctg gagacgacag aggctggttt acccgtgacc cttcgactta tttctgtatt   11220
gatctggtct ttcaactctt gtattgagtg tgccattagc gtcaaccggt ggcgatgagt   11280
ggaacgtcga tcccacaaag agagcgccag accaacgaga ctgactgttg cgtgttcctg   11340
gaggaatgtt gcgtatgatt ccatcacaca agtgagggtc cgctcagacg cagcagaaaa   11400
gacaaagggc agactggagg gtatgttgtt ggacggactg agctccgagc gagtgtagct   11460
ttctaggacg acatgcacat tggcaccccc gaatccaaag gagttcaccg aggctcgacg   11520
aggacagcca tctgggactg caggccacgg gatgcattct gtggggacag aaagcttggc   11580
ggcaaacggt ttaattttg gattgagatg ctgcatcagg agattaggag caatcatccc   11640
gtgttgcagc gagagggatg ccttgatcaa tcccgctagt ccagcagtgg cctctgtatg   11700
tccaattatt gtcttaattg acccaacata cagccgatcg gtcgaatctg gaacggattc   11760
gggcccaaag aagcttgagt tgattgcggc tgcttcctgc ggatctccgg cctgggttcc   11820
cgtgccatga gcctcgaagt actggcaccg atcttccggg ttgttttgag gagagagccc   11880
cgcgcgtgca taggttgcga ggatcaatga ttgttgtgcc tttggattag gcatcgtgat   11940
ccccatagtt cgcccatccg agtttgcccc tgaggcacgg atcacgcatt cgataggatc   12000
tccatcatta atcgcgtcct gcagacgttt tagtacaacc gaagccacac cctcgccacg   12060
tccgtagccg tcggccttgc tgtcccacat tctactccgg ccggtagggg acagcatccg   12120
tgttttagaa tccgcaatat aggcattggg agacaggatc aggttgcttc ctactgccac   12180
tgccatggaa cagtcatcgt tctgcagagc ctcgactccc agatgaacag ccaagagact   12240
cgaagaacat ccggtgtcaa cggccataga aggaccttgc cagtcaaagt agtaagagat   12300
acgattggcc atgattgacg gtgagtttcc cgtaaccaca tacgcgggga acgcctgagg   12360
atccatggcc tggatttgat tgtaatcgtt gcgaagtgta ccgcagaaca ccccggtctt   12420
tgagcgctgc agcgcatcca tccgtaaccc ggccgcatcg agcgattcgt acacggtctc   12480
taggagcaat cgctgttgtg gatccattgc taccgcttca gttggcgaga tattgaagaa   12540
ggccgcatca aaggctttga tgtcctcgtc caagaagtat gactctttga cgtttgttgt   12600
gccatggtgg tctccatctg gatgataaaa ggcatctata ttgaatctgt cggccggaac   12660
tttgcgcgca atatcccgag ggctttgaag aagctcccac agtttcgaag gagaggaagc   12720
gccaccggga aagcggcatc ctgtaccaat aatagcaaca ggctctgttg ctttcattgt   12780
gagattataa gagaggtgta aaacctgaga tcaaaataat ttgcagttgg gtggctgtag   12840
ctctactgag agtacgttca tagatataag caatgcagtg ttgccttact tacttccacg   12900
atcttgtcag catatctatc gaacgaatag caaaactgga cctatagagc aatttccggc   12960
catcgataga tcattggata gctgtcctat ttgggaagta tgatctacaa tttatgcagc   13020
cacaaactat acaaagtggt ccatcgccag atttggcgat gagcagcggt gtggaatagt   13080
gactttgatg aacatgtcag gtcctgcatc tacatgtgca ggtgtccaag gatgctcctt   13140
gcgcgaagaa gtggagtagg gacattcagc tacctcctta tctttccct tcttttaatg   13200 ctcactctgt gcataataat agtggcgaat atcgaagcat cgaaatccaa cgacattgag   13260
acaacatgga taacatggac aacatgaaca acacaccttt aggtttcaac tgggcctggg   13320
```

```
cagtcatcat ctctttcctg gtctgctga cttttttcctt tgtctcgcca cacctctttc   13380
cttcaagatt gacggtgatt aatggtggaa gagcctggga tatctttcgt accaaggcca   13440
aaaagcgatt tcgctcggac gcagcacgtc ttataaagaa cggcttcgag gaggtgagta   13500
tggaaaaact gcatcattta ggataaagtg ctaaacgttc cttcttactc cagtctcctg   13560
atgcctttcg cattatcacg gataacggtc ctttgctggt cttgtcacct caatacgctc   13620
gtgaggttcg cagcgatgat agactcagcc ttgaccattt cattgcctcg gtttgtcttg   13680
cttcatgtcc aacgttttc tagttggcgt cgctaagctt ctactgttta ggaatttcac    13740
cccaacatcc caggtttcga gccgttcaaa ttgatcttgg atccaaagaa cccgttgaac   13800
acgatcctca agtccaatct cacacaagca ctgggtactg acatcgtcct ctccgctctt   13860
atgcagccca ttacatagct aacattgttt acctggatag cttatctgac agaggacttg   13920
tctgcggagg taacagaggc actatctgca acctgtaccg atgaccctgg taagctataa   13980
aacatggttt tccaaaggtt ctggtatcaa tactaacttt ctttcttctc ttaatcaaag   14040
agtggcacga ggtcagcgtt agtcaaacgg ctctcaaaat tatcgcacaa atggcgtcca   14100
aagccttcat tggacaagaa agatgccggg atgccaagtg gcataacatt atcatcacgt   14160
acacgcacaa cgtctatgga gcagcacagg cactccactt ttggcccagt ttcctacgac   14220
ccatagtggc acagtttttg ccagcatgcc gaactttgca ggctcagatt gctgaagcgc   14280
gagagatctt ggagccattg gtagcccaga gacgagccga gagagccacc cgagccgctc   14340
aggagaagcc tcatccgtct ggtggggata tcattgactg gctggaacag ttttatgggg   14400
accaaccgta tgatcccgtg gccgcacagc tactgctctc atttgctgct atccatggaa   14460
cttccaatct cctggcgcaa gcgctcatag atctctgtgg ccaaccggag ctagtacagg   14520
atctccggga agaagctgtg tccgtgctgg gtaaagaggg atggaccagg gccgccttgt   14580
accaactcaa actaatggac agcgccctga agaaagcca gcggttggcg ccaaacagat   14640
tgtgtgagtg ggcccttcct cttgcccccc aatttgacca ttcaactggc cattagagac   14700
taattcaggt gtgcttttac agtatcgatg ggacgcattg cgcaaggcga tatggacctg   14760
tctgatggtc tccgtatcca ccggggcacg accctcatgg tgtctgccca caacatgtgg   14820
gatcctgaaa tctaccctga tccccgaaaa tacgatggct accgattcca taagttgcga   14880
caaacatcag gcaagagggg ccagcaccaa ctcgtatcct cgacgccgga tcacatggga   14940
ttcggatacg gaaagcatgc ttgcccggga cggttttttcg ccgcagccca gatcaaagtt   15000
gcattgtgca atatcctcct caagtatgat attgaataca ggggtggcaa gtccccaggt   15060
gtgtggggtc agggcataca tctgtttccc gatccgacgt ctaggatcca cgtccgtcgt   15120
cggaaagagg agattaactt gtgatactat tgtctaacta tgcggatgtg gttgaatgca   15180
aggactctct ctctctctct gtctgattga tatttgagtt ttctatggtg atcgagcaag   15240
atttttgcaa tgtggagccc atgcatgctc atgaggccta ttgggccgat ctcttcgaga   15300
tcgtgatcga gagcaaattt gagaacctca gaccttgttt atttgaaagt agcagatgaa   15360
caatagaatt gttttttactt ttggaatggt tccacaataa tcctagtcta gatttaagat   15420
accaatattg aagtgttatg tttgcatgta tcttcagctg ctccacccgc gtggagtgat   15480
tattagctta ttagcgcctt ctcattaata cgccctccag ttccagcctc tcaaaagtaa   15540
tatgctggaa tgatagaggt aattggctaa tggcctcaag gcaaccctgc agatagtgaa   15600
gcaaaagcaa taaatattca atattcacac ataatttgac atacgagta ctccgtactc   15660 cgtttaagat cgggcatagt attggatgat gttagaatat atcttggcaa ggtgacatat   15720
```

```
acaatgtact ccgtatgttg tacagtgtca atggctttgt ggagctgaag atgcggtgat    15780 ttctttcct gatgcatcat caagtccgga aaattgatga aaatctacga gtacctcgag     15840
ggatgaactt ccctgcacag atcatgacat acatataaac tattgatcca cttgcattag    15900
cgggagtcta gcaagagcaa gtctatgtat tccctacatg gtcgaggagg taagttcggg    15960
ctgaaaaata cgatgcagca tacactaccc ttacaactag ctgtttaatc agaaaaagca    16020
aatagaaatt agggcacaat ttactcttta ctgccaaccc cccgtcgtaa cccttgctgc    16080
tagcattgat tggctgtcag tcgtacaacg aagaaacgac actgtctgtg attatattct    16140
attccatcac aaacgtagcc cggagtgccc ttcccagagt ccttgtcttg tacaccgtgc    16200
ttgtcttagc attttcatta tgatcgagct caaagatgct tcgatggggg ctgtattgct    16260
gacatgcgtc cttgtgcttg caggcctata tctcattcga ttgacgttat caagcgacca    16320
attggacaag tttcctagca tcaatcctcg gaagccctgg gaaatcgtca atgtcttcgc    16380
ccaaagaaga tttcaacagg atggccctag gtatctggaa gctgggtatg caaaggtgtg    16440
ttccataagc aactgctcca aaaggcgaat aaggctgaaa gttactacag tcccccatct    16500
ttagcgtggt caccgacctg gggccaaaat tagtggtttc gggtgcattc atcgaggaat    16560
tcaaggatga aaagctgttg gaccattatc ggtcaatgat cgaggtttgt acgacgttag    16620
tgattatgaa agagcaagcg cttacttgtg caaggacttc atggcagagg tacctggttt    16680
tgagtcgatg ttcctgggga atctacacaa tacggtactt cgcgatgtga tttctgtcat    16740
cactcgcgaa ctaggtaaat attctttcct tttgactgtc cggttatccg ctgagttcta    16800
attttataga acaactgcta gcacctctct cggatgaagt atcagcggct ctggtagata    16860
cttggacgga ctcaccaggt gggtcaaagc acacttccca atagaaatca ggaggaaata    16920
aaaactaata tcaatataga ctggcatgag gtagcactgc ttccaagcat gctgggcttg    16980
atcgcaaagg tttcatctct cgtcttcgtg ggtgaaccgt tgtgccgcca cccagtctgg    17040
ttggagacag tgatcaactt caccctcatt cgacacaacg caatcttagc cctccaccag    17100
tgccctgctg tacttcggcc cgtccttcac tgggttcttc caccatgcca gaaactccga    17160
cgagagatca gaactgcacg gacactgatc gactctgctc tggaaaaatc aagaaagaat    17220
ccgcagaccg agaaattttc cagcgttgcc tgggttgatg cttttgccaa aggcaacaag    17280
tataatgcag ccatggtgca gttaagactg gcaaatgcgt ccatccactc cagcgccgat    17340
ctcctggtca agattcttat caatctatgc gagcagccag aattgattcg ggacctccgg    17400
gacgagatta tctctgttct tggggagaat ggatggcgat cctcgacact gaaccaatta    17460
aagctccttg atagtgttct gaaggagagc cagcggttgc atccagtcac aaccggtatg    17520
catcgtcggc tgttcaaact gcgtgcccag tgcatatgct gaccatttac tttaggagca    17580
ttttcgcgct ttactcggca agatatcaag ttgaccaatg gcactgagat tccttcagga    17640
acacccatta tggtcactaa tgatgtcgcc ggggatgcca gtatctatga tgatcccgat    17700
gtcttcgatg ggtatcggta cttcagaatg cgtgaaggag ccgataaggc ccgggcacca    17760
ttcacaacga cgggccaaaa tcaccttggg tttgggtacg ggaagtatgc ttgtcctggt    17820
cgattctttg ctgctaccga gattaagata gcgctctgcc atatgttgtt gaagtatgaa    17880
tggaggctag taaaggacag gccgcatggg atagttacaa gcgggttcgc agcattccgt    17940
gacccacgag caagcataga agtccgcaga cgcgcggtgg cggagaaga gctcgaggta     18000 ttgactggaa agaagtgatc tagggaaaat tacgaactca tagtatgagc aaccataccc    18060
```

```
aaaacaaaga gacttaccaa ccccatcatc aaggtagact ggggattttg actatgtcga   18120
tgtaaatcgg tcaacagcct tattaggata tataaattat acgcttctca ggctttaaag   18180
catcacccag cacgataatt tctctggatt attgcaaaac caagaaattc tctgatccac   18240
agctgtatac tccgtactcc gttcatcatc ttacagtcat gcagagggtg aaagggtca    18300
gtgtgtgacg gtatttcggt atctcgcctc gtaatttgac agatccagcg ttaaacccag   18360
cccaagactt gagtagacta tatttattct ctttgatatc catctcagca tcaagttttt   18420
gacgttgtat tactatcctc gtttggaatt ctcctcccag gtcttgcttc attgcttata   18480
gcattctacc aaaaacgtca ctgtcatgga cgggtggtca gacatatcat cagcgcctgc   18540
cggatacaag gatgttgttt ggatagcaga tcgggctctg ctagcccaag gattgggatg   18600
gtcaatcaac tacctggcca tgatatacca atcgcgcaaa gaccgcacat acggcatggc   18660
cattttgcca ctatgttgca actttgcgtg ggaattcgtc tacactgtca tctatccttc   18720
tcaaaatccc ttcgagagag ctgtcctcac aacatggatg gtcctgaacc tctacctcat   18780
gtacactacc atcaaattcg ctcccaacga atggcagcac gccccgctcg tccagcgaat   18840
tcttccagtg atattccctg tggcaatcgc ggcatttacg gcgggcatc tcgccttggc    18900
tgcgacagtg ggagtggcca aggcagtcaa ctggagcgcc tttctgtgct ttgagctatt   18960
gactgccggt gccgtgtgcc agctcatgag tcggggatct agcagagggg cgtcgtatac   19020
aatctggtat gttcttttg ccttgtggat cttgcttggg tttattggct aatgtgaatt    19080
gtggttggca gggtctcaag atttctgggc tcgtatatcg gtagtatctt tatgcatgtt   19140
cgagagaccc actggccgca ggagtttgac tggatcagct accctttcgt ggcgtggcat   19200
ggcatcatgt gcttctcgct ggatatttct tatgtgggct tactgtggta cattcgtcgg   19260
caggagcgcc agggccaatt gaagaaagct atgtgatcga caggaccatg catgatgag    19320
gtccgcacta acctcaactg tactttgtac aggtctgagt gctatatgac gatagtcaca   19380
aaacagagtt ggaggttatt tgcgcacatt gactaaaaat gggagagctg atggatatat   19440
gcaaggggga tcaggtctcg atctgatcgt gccgatcgac aagaacaatg ctttgtctgg   19500
gcgggtccaa ttgtctagcc tagaagtcta aatttcaatt ttcttcggac tttttacata   19560
gtaactactg cctaggactc gggatatgaa gtataatggc gagaaatggc tggctgcagg   19620
ggacatacag gtgataattt gccctcgatc tggcagctag ttacgtcaat atcttgttag   19680
taaacaccag ttgtagatct ttgcgtatat atgaaactca aaagcatttg tgtctactcc   19740
gtaattacct tcccaacccc tccagtgcca ttgaaaccat gaaggtcatc attgtcggag   19800
ggtccatcgc gggtctcgcc ctcgcccatt gcttggacaa ggccaacatt gactatgtca   19860
ttctagaaaa gaagaaagaa attgcccccc aggaaggtgc ttccattggt atcatgccta   19920
atggtggtcg gatcctggaa cagcttgggt tatacgacca gatcgaggag ctgatcgagc   19980
ctttggtgag ggcgcatgta acttaccccg acggcttcaa ctatacaagt cgatacctg    20040
cactcataca gcagcggtgc gtcaatataa gctttctact ttctgatttg aaactaatgc   20100
gagaggtctt aggtttggct atccacttgc attcttggat cgacagaagt tactgcaaat   20160
tctggcaact cagccggtcc aatccagccg agtgaaacta gaccacaagg ttgagagcat   20220
tgaggtctcc ccatgtggcg tcacggtgat aacaagcaac ggacacacct atcagggcga   20280
tcttgtcgtc ggggctgatg gagtgcatag tcgggtacga gcggagatgt ggcgactggc   20340
agatgcctcg caggggaacg tatgtggaaa tggagacaaa ggtaacatta ttcctactgt   20400
tttgtcctat cctcgctttt ttttttcttg gccaagtgtt ttgactttga gctggaaagc   20460
```

```
taatatattg atttatagca tttacgatca actatgcctg catctttgga atttcgtcac   20520
acgtcgatca attggaccct ggcgagcaaa taacctgtta caatgatggg tggagtatcc   20580
ttagtgtgat cggacagaat ggcaggatct actggttcct ctttatcaag ctggaaaaag   20640
aattcgttta tgatggatca cacaaaaccc agctccactt tagccgtgaa gacgcccgag   20700
ctcattgcga gaggctggcg caggagcctc tctggaaaga tgtgacattt ggtcaggtct   20760
gggctcgatg tgaggtcttt caaatgacac ccttggaaga aggggtgctt ggcaaatggc   20820
actggagaaa cattatctgc atcggagaca gcatgcataa ggtcagcagc tcattatcac   20880
tcctggctta ctgactttg taattaattg acattctcat gcagttcgca ccgcatattg   20940
gacagggtgc taattgcgct atcgaggatg cagctcagct cagcaatagt ttgcacactt   21000
ggctgagcga atctggaaag gagcatcaac taaaaaccga tgatttgaca gagattctgg   21060
ctcaatttgc acaaactcgc ctccagaggc taggtccgac ggccatggcc gctcgatctg   21120
ctatgcgtct gcatgcgcgg gaagggctca aaaactggat actgggacgc tacttcttgc   21180
cctacgctgg tgacaagccg gccgactggg cctcccgagg aatcgcaggt gggaatactt   21240
tggacttcgt agagcctccc acgcgggctg gtcctggctg gattcagttc agccagtcgg   21300
gtaaaaggac ttcgtttccc atggcagtgg caggtctgtg cctagtgagc attgtggccc   21360
gaatcatgta tttgaaatta gttgcataga gaggcccacc atatctggag tacttcatac   21420
agagtgtttt atgggacaat ataaacttta gggcaattta gcgctttgat atagatcatc   21480
tgcatactag taaggcaacc ctgaaggtga tcgacacgat ctgcaaaaat caatatcgtg   21540
cttcgttacg gagtattgtt ttctacatgt catagtgcgc gctgcccag tggggctatg   21600 cagaaagtga tttcgatgta ttgctactta cagtgatgtg gtccagcatg tcagccattg   21660
ctctagtgcg tgcgtgtact gaccacatcg cggccattgc catttatcta gggtcctgtc   21720
gcctcaaaag cttgtggtca caaatcgttt gatccttcga gatcatactg aattttttgtt   21780 caatctgtca tcatggctgg ctctcagtct acggcgcagt tggctcgcct tctcattgat   21840
atctcccgat ttgacaaata caactgttta tttgctatat ccctggagg tacgagtag   21900 tgcagaccac ttcaacatta taccaccgcg ctcacaattt catatagtct ggtctatctt   21960
ccttgcagca gcctcacgac acgctgatgg cgaccccgtc cctctggact ttgtattggg   22020
ccgcgcagga ctggccttca tgtacacgta tatgctgagc ggcgcaggaa tggtatggaa   22080
cgactggatc gaccgcgata tcgatgccca ggtggcccgt accaagaatc ggcccctcgc   22140
ctccggtcgc ctttccacca gagctgccct catttggatg cttgtccagt acgcagcctc   22200
ggtctggctg atggaccgca tggtgagcgg gcaggatgtg tacgtctttt tcctcctcg   22260 taccccaaac aattattctg ttgattgaaa actgaccta atcattctcc agatggacat   22320
acatgcttcc tctcacaacc gggattatct tgtatccctt cggcaagcga ccgacaagtc   22380
gcaagctggg cgtctatccg caatacatcc tcggtgcaag cagcgccctt actatcctcc   22440
cagcctgggc ctccgtctac acaggccgta tatctttgaa ggatctgggt atgcggtgtc   22500
tcccgctttg tctcttcctg tttctgtgga ccatctactt caacaccgcc tacagctatc   22560
aggatattaa ggatgactgt aagctgaatg tgaattcgtc gtacgtcctc gcggggagcc   22620
atgtgcgtgg aatgcttctg ttacaggcta ttgctgtggt gctggtgatc ccctggattc   22680
tctacaccag cgcctccact tggctctggg tctcatggct gggggtatgg acggcatctc   22740
tcggcgagca gctttatctc tttgatgtga aggatccgag tagcggtgga aaggttcatc   22800
```

-continued

```
ggcggaattt cgcactgggg atttggaatg tgctggcctg ctttgttgag ctgctatatg    22860
cttcaggctc tctgtgaatg atgttaatac gatgtggtcc ggatgagact tggggagtag    22920
agtctgagag gcttaaaatg ggtaaatggt gcgatgttgg cacagtgtga actattcata    22980
aatctttgct acgaagttgg gcttcacctt tcaattgaga agttgttact ggaattttc     23040 gacactcaaa attcgaagag acttgtatta ttagagggat atagcctatg tcttccaatt    23100
ggtgtagaat cccaactacg agaccgcttc agaacgttgg agcacaagga tagaaagttc    23160
acctattcga aattctctac tgtcgtacat atgctatgta catgttactc ctttgcttgc    23220
gcacctatag cccagcaaaa caagggatcc tttgctaaca ggagctgatc atcacggttc    23280
agagtcagat gcaaatccca cggctccgta ctcgccacat catcctgacc ctttggaagg    23340
ataaagcaca tccccctaa gacaggcaaa tgtagttgga accctcgagg ttgcgctcca    23400
aggctctccc caaagtccag tccgaagatt tcaaaattcc taaagctgct cagagggata    23460
ggaactcccc gaaatccgat atccgcccag tcaggctgcg agtggagatg ggatagagcg    23520
tcttgaatat attctgcgtc aaccgccaaa agactctggc gtatacgagc tgcaatttgt    23580
gtgagatcct ccagacactc ctggcgcaat tccaccgaag gatctgtgcc atcaactagg    23640
gcctcgtttc tcccagcttg aattggcgta tatgtcaata gcaccatgtt cccagatag    23700 tcatcaaagg ctggagtttt gaaattccca cgcatatcca ccgcgattga cagttcggta    23760
gatttaccag ccaattgtcc cgcttgccga agtatcatgg ccaaaagggc gctcacgatg    23820
tcgttactgg acaggaaccc tggactcggc ctaccatcag cctggaaaga cgtttgccct    23880
ttgatcaacg tattgcaagc ctccttcaaa tactcgatct taggaccggg gatttcagt    23940 cgccaggtga caagctcggt ggctctcgcc cggacgaagc ccgaccaatt ctttgcaagt    24000
agtgctgccc agtctccgag gccacagtag tgcttgctaa aatccatcct ggaaagaccg    24060
gagctgcttt ctgggacaag acgctcaatc tccgatcgta actgccgatc tggcgacaca    24120
cttgcagaag acatcgccgt cgggtctctg cagcaatcgg ctagaaggcc caagactcgc    24180
gcagcgcctg caccatccat tgcggaatga tgaaacgtca tggcgagaat gatcccatcg    24240
cgcatgacat ttgcttgaaa tcgtaggatc ggccttcgtg gcaacgaaat atccatgtcg    24300
ataggcaatg gcgccagccg acttatgatt tcctgctcct cagtgcccgt taggaggcat    24360
tttgattgga tttccttgaa tgactcggcc tggtagtgcc gtatccggag tatagggaac    24420
tggacaagcg actctgaggc ttctggttcg atttgccagg tgtacttcgt ttggctggac    24480
tctgtccgcc gagtcacgtc ccctgcgagg aaggggtgta ccttcaatag cagctcgatg    24540
ccattctcga gaacaccaat gctcttctca ggttgcgtgg tctggaaaaa cagcagaaag    24600
gtgacgttca ttccgagggg attgtggtcg agagaagata aagggtaagc agagcggtcg    24660
ccagttcttc gggcatcgca cattccatct tcacatagac cgtggagtct cacaggtccc    24720
tctttgacct gatctctttg actgactggg agacatactt cctgggtgct catgatttct    24780
gggtgttatc ctattgagtt gagttgtgtc ttgatctttt ttttattt ttttggattt      24840 ctgaccttgt ttcgcttata ttggactttg cttttctttg tatattgtat tgcattaccg    24900
tacaacaaag catgggattc tctgtgttct gcatgattgt ggagcgtatt ttcctcgatt    24960
tggtatacaa tcaggtcgat ccctggcgga ttccggatct gatgcatgta tacaggtcat    25020
atatctgctt tcctcggtat ttttgagctg aatatcacta tatatgcttt ggagacgatc    25080
aatcgcaaga gagggttagt gattaaatca gttagtctca tccatagtgg gcattagagc    25140
caataaaaga tggtttccac cttgagatgt gatcgccaca agaagatttt gtaaatagta    25200
```

```
tgtattttcc aggccctgat ttctatctgc atatttgtca gcttgatcta cggagtacat   25260
cttactgctt ttagatactg acagcagcaa aactccgcgt tgaaggacga gctttgacac   25320
aaggtcaggc acttctctag tacacaaatc ctaatcatcc gacgacatac tactccgtat   25380
gctgtacata gagatccatg tccaattctt gagtctgccc ctctttgatc cacagtccag   25440
ctcagccagg cgcaatctgc atgcattggc atggaagcta ggagctgaca ttggctggaa   25500
ctacgccatc tggggcacaa tgcaagctag caactgacc atgtactggg tcagttttga    25560
ttgagtatgc tatacggaag aaagcgacta gtactccgta ggtttgtgta ctacctgcaa   25620
gtggaaagag atacctagat aggtgacatt agtgtccgaa ccaatgacca atggcccta    25680 tgcacccata tcccttacat ctttcagaaa gagaaagcc acaagtatat catgtactcc    25740
gtactccgta caacggaatt acttgatctc tatattacct tcttcctgaa gaccgtttct   25800
cgctattgtc agttacacac acaatggatt ccctattgac gagcccgtta tggctcaaaa   25860
ttgcacatga gctagcactt tacctctctt ttattgtgcc aaccgccttt ctcatcataa   25920
caactcaaaa atcatccatt attcgatggg cctggacacc atgtctgctt tatatcctgt   25980
accaattctc tcttcgggta ccctctctgt cgacaagtca attcttgaag ggcgttgcag   26040
cgggtcaagc aaccgtggct gctttgcaat gccttaatct tcttctgatc acgaagctgg   26100
accaaacgga tctgctacgg gcaaatctat acagtccgtc tgcaggactg ctttctcgcc   26160
ttgctcaatc ctgcgcattg ctggtcaact ccgcggaat cggcacaatc tgggaggtta    26220
gaaacattcc ccagcacgca gcgtttgtcc aaccaaaagg caaggatcaa tcaatgagcc   26280
ggaagcggtt tgtcttgcgg gaaattgcaa tcattgtatg gcagtacctg ctccttgatt   26340
tcatttacga gtcaaccaag ggcacgtcag ccgaggattt gatgcgtctc tttggccctg   26400
gtatggaaat caagtatctc gatgcaacgt tcgaacaatg gatggggcgc ctctccgtgg   26460
gaatattctc ttggcttgta ccttcccgag tctgtcttaa tatcacttcc cgcctgtact   26520
ttctcatctt ggtagtattg ggcatttctt cgcccgagtc ttgtcgaccg ggcttcggca   26580
gagtgcggga tgtatgcacc atccgtggag tctgggggta agtgaactat tccgactgct   26640
ttcattcatt cactaacgcc accacagcaa gttctggcat caatcctttc gttggccact   26700
cacctctgtc ggaaactata tcgcaagaga cgtcctcgga cttgctcatc cctctctttt   26760
ggaacgctac accaatatct tctttacctt tttcacatcc ggcgtattgc accttgtctg   26820
tgatgctatt ctcggcgtcc cgccatctgc gtccggcgcc atgcagttct tctgctcgtt   26880
tccgcttgct attatgattg aggatggggt tcaagaaatc tggcggagag cgacgggcca   26940
aaccaaggac agtgatcgtg cagtaccgtt ctggcagagg ctcgtgggat atctttgggt   27000
ggctgtctgg atgtgtgtca catctccgtt ctacttgtac ccagctgcgc ggcaacatgc   27060
ggagaagaac tggatagtgc cattcagtat agtggaagaa attggccttg gaactgcgca   27120
aaagattttg ctgggttatg gcttgtttgt gtactgggcg gttggtgggg agatttaaat   27180
tcatgtgtcg ggattgttca tcgtggtcaa cactgtttag attgtgatat atattttcac   27240 cgaacaccc agaaacaaaa gatttaagcc ccaattaact accttgaagg gctcatgaga    27300
tttgatcaat gtagcaaccg tcagtatcct aggtcgtgat tccccagcc agagcgagat    27360 aattttccag acatcatctt atctacatgc aaccaaaaac tccctggcat atattaacag   27420
agcaaaacta gaggagcaaa aaagaaatct caggtttggt ttttaggaat agccgaacgc   27480
gggggtcgaa cccgcagcct taagattaag agtcttacgc tctaccgatt gagctagccc   27540
```

```
ggccgggctg ttgaagagag ttgccatata gcgctacata atcctaaagc ggtcagggcc    27600 tgggggggcga acacgctgac ataatgctag cgcgtcgagc ggcgaatcct ctggaaccaa    27660
aattgttagg tggaaggtgg cttcatctac gaatctgggt gtttcctcga ttggatctta    27720
tcattgcttc cctgattcgt atgagtcttt aattttctgg ttgcttgact ctgaccgcgg    27780
tcactagatt gcccaccatg tgcgttacta gaacctttcc ccgattcttt gctgcagcta    27840
acactataca gggcaaagct cgtggacgac catcagatcc atactgcctc gttgcataac    27900
ccgattcctt ggcaattgca tacatacgtc tggccttttcc tgatcatctg gcccgtgttc    27960
tttgcctttt acctctctcc cgagcgctat gataccctaca ttcagggaca ggagtggacc    28020
tttgtgtttg cggggtctat catcacagtc cagtcgctct tctggctgat gaccaagtgg    28080
aacatcgata ttaacaccct attcacaact actcgatcca aatccatcga cactgcccgg    28140
cttatcaaag tggttccgat caccaatgcc ggctctgccg agatctgtaa cctgattaga    28200
gagcacattg gcccgaagaa gacccttccg ttcctcttcc agaagcgccg cttcctcttt    28260 tacccccgaga ctcgctcctt cgcacccctt tcttacgccc tcgacgccga gccgaagccg    28320
gccctcaaga cttttccagca gagcgagggc ttcacgtcga aggccgagat tgagcgcgtc    28380
caaaaccact atggtgacaa taccttcgat attcccgttc ccggtttcat tgagctcttc    28440
caggagcatg ccgtcgcgcc gttcttcgtc ttccagatct ctgtgttgg attgtggatg    28500 ttggatgaat actggtacta ctcgctcttc accctcttca tgctcgtgat gtttgagagt    28560
accgttgtgt ggcagcgcca gaggacattg agcgagttcc gtgggatgag catcaagcct    28620
tacgatgtct gggtataccg tgaacggaaa tggcaggaga tcaccagtga taagcttctt    28680
cccggtgatc tcatgtcggt gaaccgcacc aaggaggaca gcggtgttgc ttgtgatatt    28740
cttctggttg aaggcagtgt cattgtcaac gaggctatgc tttctggcga gagcacccct    28800
cttctgaaag actctatcca gctccgtcct ggcgatgact tgattgagcc agatggattg    28860
gataagctct cgtttgtgca tggaggtacc aaagtcctcc aggttactca ccctaatctg    28920
actggcgacg cgggcttgaa gaacttggcc agcaacgtta ccatgcctcc agacaatggt    28980
gccttgggtg tggttgtgaa gaccggtttc gaaaccagcc agggtagcct cgtccgtact    29040
atgatctact cgactgaacg tgtctctgcc aacaatgttg aagctctgct gttcattctc    29100
ttccttttga ttttcgccat tgccgcttcg tggtacgtgt ggcaagaagg tgtgattcgg    29160
gatcgcaaac gctccaagct tctgctcgac tgcgtcctta ttatcaccag tgttgttcct    29220
cccgaattgc ctatgaaact cagcttggcc gtcaacacta gtcttgctgc tctgagcaag    29280
tatgccattt tctgcactga gccattccgt atccccttg ctggtcgtgt tgatatcgct    29340
tgcttcgata agactggtac cctgaccgga gaggatcttg tcgttgatgg tattgctgga    29400
ctcactttgg gtgaggctgg ttcaaaggtc gaagctgatg gtgctcacac cgagttggcc    29460
aattcttctg ctgctggacc cgacaccact ctcgttctcg ccagtgctca tgccttggtg    29520 aaaattggatg agggtgaagt cgtcggtgac cccatggaga aggctacttt ggaatggctt    29580
ggctggactc tgggcaagaa cgacactttg tcttccaagg gcaacgctcc cgttgtttct    29640
ggtcgcagcg ttgagtctgt tcaaatcaag agaagattcc agttctcctc ggccctgaag    29700
cgtcagagca ctatcgcgac cattacgacc aatgaccgca atgcttccaa gaagaccaag    29760 tctactttg tgggtgtcaa gggtgccccc gagaccatca acactatgct ggtcaacaca    29820
cctcccaact acgaggagac ctacaagcac ttcacccgta acggtgctcg tgtgcttgct    29880
cttgcttaca agtaccttc ttcggagacc gagctttccc agagccgtgt gaacaattat    29940
```

```
gtccgcgaag agatcgaatc cgaactgatt tttgccggtt tccttgtcct gcagtgcccg    30000
ctgaaggacg atgccatcaa gtctgtccaa atgttaaatg aaagcagtca ccgtgttgtc    30060
atgatcaccg gtgataaccc attgactgct gtccacgtcg cacgcaaggt tgaaattgtt    30120
gaccgtgagg ttctcattct tgatgccccc gaacatgaca actctggaac caagattgtc    30180
tggcgtacca ttgacgataa gctcaacctt gaagtcgacc ccactaagcc tcttgatcct    30240
gaaatcttga agactaagga tatttgtatc actggatatg ccttggcaaa gttcaagggc    30300
cagaaggctc tccctgatct gctccgtcac acctgggttt acgctcgtgt ctctcccaag    30360
cagaaggaag agattctcct tggtcttaaa gatgctggat acaccactct gatgtgcggt    30420
gatggaacca acgatgttgg tgctctgaag caggcccacg tcggtgtcgc gcttctgaac    30480
ggctcgcaag aggatctcac caagatcgct gaacactacc ggaacactaa gatgaaggag    30540
ctgtacgaga agcaggtcag catgatgcaa agatttaacc agcccgcccc tccagtacct    30600
gttctgatcg ctcacctgta tccccccggc cctaccaacc cacactacga aaagcgatg    30660 gagagagagt cgcagcgcaa gggtgctgcg atcaccgctc ccggcagcac tcccgaagct    30720
attccgacta tcacatcccc tggcgcacag gccctgcagc aatcgaactt gaaccccag    30780 cagcagaaaa agcagcaggc ccaggcagct gcagctggcc ttgcagacaa gctcacatcg    30840
tctatgatgg aacaggagct ggatgacagc gagcccccca ctatcaagct gggtgatgca    30900
tccgtcgctg ctcccttcac tagcaagttg gccaacgtta ttgctatccc gaatattatc    30960
cgtcaaggtc gttgcaccct ggtcgcgact attcagatgt ataaaatcct cgctttgaac    31020
tgcttgatca gtgcctacag tcttagtgtc atctacctgg atggtatcaa gtttggtgat    31080
ggacaggtca ctatcagcgg tatgctgatg agtgtctgct tcctttcaat ttcccgcgcc    31140
aaggtatgtc gtatttccca tgtcgaccaa atgatttgct aatatgttac tgtgtgaagt    31200
ctgtcgaggg tctgtccaag gaacgcccgc aacccaatat tttcaacgtc tacatcattg    31260
gatctgttct tggacagttt gccatccaca ttgcgactct gatctacctt ccaactatg    31320 tctataagca cgagccgtac gtgatgaaaa cttcccctttt catttgtcct acttcatagc    31380
taacataatc aacaggagag attctgatat tgatctcgag ggcgagtttg agccttccct    31440
tctgaacagt gccatctacc tcctccagct gattcagcaa atctccacct tctcgattaa    31500
ctaccaaggc cgtcccttcc gtgagtcaat ccgcgagaac aagggcatgt actgggcct    31560 cattgccgcg tccggtgtcg cattctcctg cgccactgaa ttcattcccg agctgaatga    31620
gaagttgcgc ctcgtccct tcaccaacga atttaaggtg acattgactg tgctgatgat    31680
cttcgactac ggtggctgtt ggttgattga gaacgtcctc aagcacctgt tcagtgactt    31740
ccgtcccaag gacattgcca ttcgtcgccc tgaccagctc aagcgggagg cggaacggaa    31800
gttgcaagag caagtcgacg ctgaggccca gaaggagctg caaaggaagg tctagaggtt    31860
ggtggtttga agatttgtat ctgtaaacat agagaggagg ttgttgaatt ttagaaatgt    31920
tcaagtggtg tgtgacattt aatacatttta tttttggctt ttattgaagc attcttggaa    31980
actatatgta gaaacaaatt cgtatagttg aatggctcct actctgtact gtccaatcgt    32040
cgtgaggcca ggtattgcct tggtagagaa cagtgtagac tcaaatgtgg cgatcgtccg    32100
atcagcttgt tacgaggtta gggctcgaaa tgatcggccc accataactt cttgtagctc    32160
cttgtttgag aggatgcagt ctacccgtta tgtagaccta attatccagg atggtcgaga    32220
atacttctca atacacaggg ttagacccca gatatatgat atgtcacctc agagagggc    32280
```

```
aaagactggg taattccaaa aaatgtgatt ttgcagaggg tcaaagctat atcggatact    32340
gcttcttttc tctgcctcat agtgaaggaa acactatatt cttcatggta ggcaaagagg    32400
taaaagtgta cgtgccccaa ttcggtagaa ggataggccc tgtttgaaaa ttccacattt    32460
tgaccgatat atctatagaa acatatgaag tagccgcttg gcccttctcc atttgaagct    32520
tcgagctgac gtggacttca aatgcaggat gctttgttcc tttgtactgc catgcaatat    32580
aatgttgcct tgaactcgag attataatgc gaaaacctcg tagagccgat cgcagcccga    32640
gccaacattt ttctataata cataggtaaa cgatctgtga attcagaaag ctcccacatt    32700
gtattataag catgaatcat tcaacgcgag acttcaagct tcatgaaatc cttcaggaac    32760
ccaacagttg aaagaccacc aattccctag atcccactga tttcgattac gacattccgg    32820
attgtagtag ggcatatggc gatgccgggt ttgattgcaa agaatatatt cccatacatt    32880
gcagtaccca cctttgacaa tccaggattc aggtgcgtcg acgccgccgt gattacaact    32940
agtgctggag gcgccgttgt catagaacca tttgcaggag ttaccgtcaa ttgattcggt    33000
gggtagactt cggtctggtc gcaggcattt gaggtccttc gtccagccca cattatgtcc    33060
tttcatttgg atgtagttgc ccttgcagtt cttcttggtg tacatttcca ctgtccatgg    33120
atggacatat ggcgcatcgc tggttgtggt gcttggtttc gtgttggatg ttttggttga    33180
cttgaccgat gtagttttgc tagtggtggt ggccttggtg gttgtggtgc ttgacgcagc    33240
actggccgat atcgttttat tggatgggga caaggcaagt ctctgaatag tcataaattt    33300
tgcaaaagca ttaaccgcat tagtaggcat ggcagtcttt tttgaggtgg tcgctccaat    33360
ggtgcggttg gtagaagtac agaattccga agtgcttcca caataaccat acgaagagca    33420
ctatgaattt attagatgtt gaagagcagg atttagagcc tcttgactca cacattcatt    33480
agctgcacat ggattcaaag aacccagatc agaccagttg ctagggcgct ttgtcccagg    33540
caccgggggg ccacaaacag cattggaaag cgtagctggc atcatgggtt ctccagaact    33600
gaggcatata acagcaccct gcactaaatg gtcacatcca agccattccc aggtttgagc    33660
attgtaggtc tcgatatcag ccaaggcgag agagtgttct tgagcaatcg tggtgcaggt    33720
ttcgcccgcc tggacaacat atttgtgaca aagaccatca ctacctgctt gaggtgcacc    33780
tgatattgct gtcggactgg ccaaaaggac gcctatgaga gtcacgaagt tgcttggtcg    33840
gaagcaccac atcatattga ctgatggaga gtagttgctt tgcttgtctt tattttgcaa    33900
ggcaggtttc atctttatct gttcaaagag gaaaacatgt gccaaactgc caaggataga    33960
tgcacgcatg aatatgacat tgccggggag gggcaaatgt ttgtgaaaga actaggatac    34020
tgtgccaggg ccattagcat agtattgaag caaattatag aatggcactg catcaaaatg    34080
tggaatcctc gaatttttttc tttgtcttct aacgcctagt gcatgtcttt ccaggttgtc    34140
cttgaaggct ttgtctggtc tcccagaaat ggaaggactc aagggtatgt atacagcttc    34200
taaaacgtaa atgattcacc cgagaaagga attcataatc cgaggaaggt cagacacata    34260
aggctgtctc gaaccccctt gaatgcccaa ggaagaaagg aaattcctac ggctgggtca    34320
gactagcaag aaaacgtcac ttgacttctg agatccactc agatagcaga agaacgtgtt    34380
tggtgatttt cgttctttgt aaatgcatag gaccagatga ttcgaggaat cttcttgtta    34440
gcacccttaa tccaaatctt ctgtagacca agcactcggc tattgatact gtttcgagag    34500
tctgtaagat atgacattac tctgatacag atacgtggaa tggaaacatt gcgggctttc    34560
gaatgacatt gggttgacta acgaaggccc cttcacgcag tgacgaggcc ccaaagttca    34620
aggccaacgc gcaaagcggg accaacatcg aactcccat tctcggggag ctgagggccc    34680
```

```
gccttgattt tgacatcttc ccatttgtca aagtcattat tgaacgcctg cgtcatttcc   34740
gaagcattca gaatgcgggc caaccggaag tgacaatcta ggagatcagc acttggcaga   34800
cttcgtacat tgtctgcgtc cttgttgctg aaaaccacct ctatcggaaa aaagaccttg   34860
taatttgaag aaattccttc gaacgtgtga actttgtatt tattgtccac atcctttgaa   34920
atttcggtta gcaaggtaat aaagtaaaat cattccacaa atgggagcgc actcactgtg   34980
ggttcaaagg caagacggaa cgcgccaag tgttcatgta cccagctagt aagggtgaga    35040
ccgttggata agctgttgat ctcttggtgc ctgaaattca tttcccggat cctgggaaaa   35100
cagcgccaga ggacctccca agctcgtgac gcatttggta tgagatcgtt cttgagcccg   35160
tgagtcattg atcttaatga ggatccgaga acttactcgc cggggatccc agactgcata   35220
tgacaaggga attatgtgtg cgctttctgt attcccgagt ttttcaatat cctctgattt   35280
gcctagactg tcccaccgat cgagatccat gtcaccagtg acaacacagc agtaaccgtc   35340
gcgttttagt aaaccttcct tgaactcccc tgtccgggac ataggctggt ccaaagtgga   35400
atttttcttc gcatgggaat cctgccgttc ggttgacgag atagttactg atggggctt    35460 agaccgagaa cgcactattt cgagtgaacg tataagtcag ggctttgtac ttttttgtta   35520
acttactacg ggttcttaga ccagtgtaca ggttgcgaaa gtattgataa attccatcat   35580
cgtcttccag gctgatgata tccttcgcaa tggagctttt gccgcgatct ggaggaaat    35640 tcaaaaagc ttgtaatgat ttttgcagga tgtcttcgcg ttctccacgg ctcttgggtt    35700
tgtaactttc tattcttaag cgtgcggttt caatatcctg cttttgttcg gtttccgatg   35760
cttcagtaga ttgtgaaaac agcgattgtg cgcggggata ggcacgtgct ggaccagaaa   35820
cttcgctctc ttgggtttgc tgtttacgtt tttgagaccg ggtggtgggt cgatctgatt   35880
caggcaattc agaacggcgc ttttaagat tagttttgga tggtggcgac gaggaagttg     35940
gagggatgtt ttggttcggg gcatcggctt gtagtgaagg gggcggtcgc tttgctggtt   36000
tcttttcttt ccccatgatg tctgctagta gtagtatatt tcttgctttc cttttccaat   36060
actgagatgg tagtttcagt ggatgaaaat gagaacaatg gataattca gtggatggaa    36120 atgagaacaa tgtgatgatg ggggagaaaa gtgatgtggg ggtgtcgggg gatagctccg   36180
agatattcct ccggcagaat cgctccaccg aaaaacagtc cgccggacgg gtcatccccc   36240
ttttggagaa aatgtatttg tagttacaga aaggcattag cccacagaac aagaattcat   36300
ccatatttca ttgttttcca tcaagcaatt actcgtccaa tcgtctctcg gagggtgcag   36360
agaataggct ctctctggaa ggccgctgga aaaagtggga aaaggataca ttctgtggcc   36420
acaggcgtgg gacagggttt ccccctgaca ctgggggaga atgtggaaa tgtggggaa     36480 ctctgcggag acggaagaac aaaaggcggt caactgctgc ctccacgtga tgtcacgtgg   36540
agcttagccg tccagcttgg aagataaccc tagaggaata tgagcatatt ctacggagaa   36600
ctactccgta caacatacgg agtactcata caactctgta gcaaccctg atgtgatctg    36660 tatttgaagt gtggacctga taccgactgc tcctcaaacc ccttaaaccc gtatcgagta   36720
ctccgtaata tgtacaccgt tcactgactc acattgatta atcacattag atctctcgtt   36780
ttcatgtacg tggatcatta tgagttcgag cattgaatat aagctaaaac cataccccct   36840
gaccctaagg ggccttctgg aaagaaaaat cttgtctttt gcaaatcaaa atatatatag   36900
agttgtttac ccgaactgtc gggttatgca tcttcaggcc tgtggagctg tgtcatcatt   36960
ttgttactcc cccttatcta ccgcaggatc gccaaaatgc ctagcgagac tgctacaggt   37020
```

```
gactttggtc cagcgccgcc tgggatagac ttgacagaga accaaactgg cgacttgcta   37080
ggagcagtga ttcctgtagc ggtggtcgcg acgactgcgg tgatattgcg gacgattgcg   37140
ccgacgagga tcaaagagat ccgacaaaca gctattgatg actatctcat tgttgcggcg   37200
cttttattct cttggggaac ggcaatatca tgcttcatca gtgagttgac catgaggcca   37260
aagccgatgg gcccagtact cacaacagac tctttaggca ttccatatgg caacggttat   37320
catttgcaat ctgtgacaaa agcagagttt aacactgttt ggaaagtaag gaatccaata   37380
ttaaatgaga tgcctgggat agacgttgac cagacattca gatccttttc gcctatgtca   37440
tgatttacgc tacagccgtt acctgcacca aagcctcgat cgtcttattt tacgccgca   37500
tcttccactt tcgctggtca ctggccatct gcctgtttct ggtcgttgga tattgggttg   37560
ccattattgt cacggttggg atggcctgtc gaccactgcc acatttctgg ttggtctaca   37620
cagatccatc agcccttggt gtctgcattg atattcccac gttctttttc gcaaatggca   37680
ttgctgccat ggcgattgat gtgatcatac tgtgcatgcc gatgccagca atataccagt   37740
ctcagatgca gttgtcgcaa aaggtagcgg tcgtgggtat cctactcttg ggaagtttgt   37800
atgtacctct gcccgggccc tcctacgaga aggactgtag ctaattattc tcagtgtttg   37860
cgtggcaagt atctgccgga tcatcgcact tcagaatatc accgacggga cagatacgac   37920
gtgggctatc gccccagtct ttatttggtc gtccgtggaa ccatttgttg ggattatttg   37980
cgcatgcctc ccaacatttg gcctttctt tcggcaatgg cggtccatcg ctcggacgcg   38040
ctcatcaact gatggcagta ccgatccaag ctctgagcta ccatctgaga caacgacctg   38100
gctccgaaga tcccgaacca aaaaacctgc caaggactca atattcagta tcaatgattt   38160
ttgctgtgtc gatgaggtcc aactaatgaa cgatatcaat gccactcggt cgctggggga   38220
cgaggctgcg agtgaccatc aggacgtgga gggaggctgt atcacagtcc aaaaagatgt   38280
ggaagtgaca tgggccaagt acaagtcagg aaaaaaaat gatctggcct tcaagtatca   38340
taaaggggct tgatcagctt tgcaaatatt tcgacttgac acggactata tttgcgtttt   38400
gtgtatattt aataaaaata gacgccactg gcaatttgta attgataaag gtaagtctta   38460
ttccgtaatc cataccccgt actctataca aagtactctg tgctccgtac ggagtacacg   38520
gaaacaaacg gggatatagt cgtggcacct ttcccgtgtt ggcggacttg cccgtaacgt   38580
aaacactccg cagatccctt ccaacacagt acataatcct gcagcgaaga gcgatctgat   38640
agacgctatg tgccgtcgtg acttgttatg ccaattaacg gtggcagaat tgtggagcaa   38700
tctagcagag gaaagtttcg atgtgcatgc cgagccctaa aaagtcccag tgcggagaat   38760
gtagtaatcg actggacatt ccatgtactt tgcacgctat aacatatttc tatgccatat   38820
accctctgg taatcatgta gatcctcttg cttactgcgt tggctccttt gtatcgtact   38880
ttccgcgtcg cagcattata agaggataga gagaccgcat gagagaatac acaagagaaa   38940
tcactaattc actacctgat cccccaattc actcaacatg tctcacattc acacttccag   39000
attgcaaa                                                            39008
```

<210> SEQ ID NO 267
<211> LENGTH: 556
<212> TYPE: PRT
<213> ORGANISM: Penicillium coprobium PF1169

<400> SEQUENCE: 267

Met Glu His Glu Thr Asp Leu Val Ser Phe Ala Phe Ser Gly Pro Ala
1               5                   10                  15

-continued

```
Phe Asp Gln Ser Lys Pro Ile Tyr Ile Asp Ala Arg Asn Pro Ser Arg
            20                  25                  30

Ala Phe Asn Ala Ile Gln Phe Arg Arg Leu Val Arg Ser Leu Ile Ala
        35                  40                  45

Gly Leu Lys Ala Arg Gly Val Glu Arg Gly Asp Cys Val Leu Val Gln
    50                  55                  60

Leu Glu Asn Ser Val Leu His Ser Ala Leu Phe Phe Ala Ile Val Gly
65                  70                  75                  80

Ala Gly Gly Val Tyr Met Gly Phe Asp Val Ala Ser Arg Pro His Glu
                85                  90                  95

Val Ala His Leu Leu Arg Val Ala Glu Pro Arg Leu Ile Ile Thr Ala
            100                 105                 110

Pro Ser Ala Leu Thr Arg Val Leu Glu Val Cys Asn Asn Gln Gly Met
        115                 120                 125

Ser Ser Asn Gln Val Leu Leu Met Asp Glu Lys Ser Ile Glu Ser Val
    130                 135                 140

Val Gln Phe Ala His Gly Gln Ala Glu Gln Thr Glu Asp Leu Asp Thr
145                 150                 155                 160

Gln Thr Val Asp Gln Pro Ile Arg Leu Glu Ser Leu Leu Gln Tyr Gly
                165                 170                 175

Glu Leu Asp Trp Leu Arg Phe Glu Asp Ser Glu Glu Ser Lys Ile Thr
            180                 185                 190

Pro Ala Ala Met Phe Leu Thr Ser Gly Thr Ser Gly Leu Pro Lys Ala
        195                 200                 205

Ala Ile Arg Thr His His Thr Ile Ile Ser His Leu Ser Val Tyr
    210                 215                 220

Tyr Glu Val Pro Tyr Pro Val Val Arg Leu Met Ala Leu Pro Leu Tyr
225                 230                 235                 240

His Ser Phe Gly Asp Phe Trp Gly Asn Ile Phe Pro Ile Arg Tyr Gly
                245                 250                 255

Gln Pro Leu Tyr Ile Ile Pro Arg Phe Glu Ile Thr Ala Leu Leu Asp
            260                 265                 270

Gly Ile Arg Gln His His Ile Thr Glu Thr Tyr Met Val Pro Ala Met
        275                 280                 285

Ile His Ile Leu Asn Arg Ser Ser Leu Asn Val Ala Glu Ser Leu Ser
    290                 295                 300

Ser Leu Arg Tyr Ile Gly Ile Ser Gly Ala Pro Ile Asp Gly Tyr Ser
305                 310                 315                 320

Met Gln Gln Phe Gln Ser Leu Leu Ser Pro Asp Ala Ile Ala Gly Asn
                325                 330                 335

Leu Trp Gly Met Ser Glu Val Gly Val Val Phe Gln Asn Arg Tyr Gly
            340                 345                 350

Ile Gln Pro Gln Phe Gly Ser Val Gly Thr Leu Leu Pro Arg Tyr Glu
        355                 360                 365

Leu Arg Phe Val Asn Pro Asp Thr Gly Glu Asp Val Ala Gly Thr Pro
    370                 375                 380

Asp Ser Pro Gly Glu Leu Tyr Val Arg Gly Pro Gly Leu Leu Leu Ala
385                 390                 395                 400

Tyr Lys Gly Arg Thr Asp Ala Lys Asp Glu Gln Gly Trp Phe Arg Thr
                405                 410                 415

Gly Asp Met Phe His Val Glu Asp Gly Asn Tyr His Val Ile Gly Arg
            420                 425                 430

Thr Lys Asp Leu Ile Lys Val Arg Gly Gln Val Thr Gln Tyr Ser Val
```

```
                435                 440                 445
Ala Pro Ala Glu Ile Glu Gly Ile Leu Arg Lys Asp Pro Ser Ile Lys
    450                 455                 460

Asp Ala Ala Val Ile Gly Val Met Leu Pro Asp Gly Ser Ser Glu Val
465                 470                 475                 480

Pro Arg Ala Tyr Val Val Arg Asn Asp Thr Ser Pro Glu Thr Thr Ala
                485                 490                 495

Asp Gln Val Ala Gly Leu Ile Gln Ser Gln Leu Ala Ser Tyr Lys Ala
            500                 505                 510

Leu Asp Gly Gly Val Val Phe Val Asp Asp Ile Pro Arg Ile Gly Ile
        515                 520                 525

Gly Lys His His Arg Ala Lys Leu Ser Gln Leu Asp His Gln Arg Glu
    530                 535                 540

Thr Ile Ala Ser Ile Leu Ala Glu Pro Val Ala Val
545                 550                 555

<210> SEQ ID NO 268
<211> LENGTH: 2447
<212> TYPE: PRT
<213> ORGANISM: Penicillium coprobium PF1169

<400> SEQUENCE: 268

Met Lys Ala Thr Glu Pro Val Ala Ile Ile Gly Thr Gly Cys Arg Phe
1               5                   10                  15

Pro Gly Gly Ala Ser Ser Pro Ser Lys Leu Trp Glu Leu Leu Gln Ser
            20                  25                  30

Pro Arg Asp Ile Ala Arg Lys Val Pro Ala Asp Arg Phe Asn Ile Asp
        35                  40                  45

Ala Phe Tyr His Pro Asp Gly Asp His His Gly Thr Thr Asn Val Lys
    50                  55                  60

Glu Ser Tyr Phe Leu Asp Glu Asp Ile Lys Ala Phe Asp Ala Ala Phe
65                  70                  75                  80

Phe Asn Ile Ser Pro Thr Glu Ala Val Ala Met Asp Pro Gln Gln Arg
                85                  90                  95

Leu Leu Leu Glu Thr Val Tyr Glu Ser Leu Asp Ala Ala Gly Leu Arg
            100                 105                 110

Met Asp Ala Leu Gln Arg Ser Lys Thr Gly Val Phe Cys Gly Thr Leu
        115                 120                 125

Arg Asn Asp Tyr Asn Gln Ile Gln Ala Met Asp Pro Gln Ala Phe Pro
    130                 135                 140

Ala Tyr Val Val Thr Gly Asn Ser Pro Ser Ile Met Ala Asn Arg Ile
145                 150                 155                 160

Ser Tyr Tyr Phe Asp Trp Gln Gly Pro Ser Met Ala Val Asp Thr Gly
                165                 170                 175

Cys Ser Ser Ser Leu Leu Ala Val His Leu Gly Val Glu Ala Leu Gln
            180                 185                 190

Asn Asp Asp Cys Ser Met Ala Val Ala Val Gly Ser Asn Leu Ile Leu
        195                 200                 205

Ser Pro Asn Ala Tyr Ile Ala Asp Ser Lys Thr Arg Met Leu Ser Pro
    210                 215                 220

Thr Gly Arg Ser Arg Met Trp Asp Ser Lys Ala Asp Gly Tyr Gly Arg
225                 230                 235                 240

Gly Glu Gly Val Ala Ser Val Val Leu Lys Arg Leu Gln Asp Ala Ile
                245                 250                 255
```

```
Asn Asp Gly Asp Pro Ile Glu Cys Val Ile Arg Ala Ser Gly Ala Asn
                260                 265                 270

Ser Asp Gly Arg Thr Met Gly Ile Thr Met Pro Asn Pro Lys Ala Gln
            275                 280                 285

Gln Ser Leu Ile Leu Ala Thr Tyr Ala Arg Ala Gly Leu Ser Pro Gln
        290                 295                 300

Asn Asn Pro Glu Asp Arg Cys Gln Tyr Phe Glu Ala His Gly Thr Gly
305                 310                 315                 320

Thr Gln Ala Gly Asp Pro Gln Glu Ala Ala Ile Asn Ser Ser Phe
                325                 330                 335

Phe Gly Pro Glu Ser Val Pro Asp Ser Thr Asp Arg Leu Tyr Val Gly
            340                 345                 350

Ser Ile Lys Thr Ile Ile Gly His Thr Glu Ala Thr Ala Gly Leu Ala
        355                 360                 365

Gly Leu Ile Lys Ala Ser Leu Ser Leu Gln His Gly Met Ile Ala Pro
        370                 375                 380

Asn Leu Leu Met Gln His Leu Asn Pro Lys Ile Lys Pro Phe Ala Ala
385                 390                 395                 400

Lys Leu Ser Val Pro Thr Glu Cys Ile Pro Trp Pro Ala Val Pro Asp
            405                 410                 415

Gly Cys Pro Arg Arg Ala Ser Val Asn Ser Phe Gly Phe Gly Gly Ala
            420                 425                 430

Asn Val His Val Val Leu Glu Ser Tyr Thr Arg Ser Glu Leu Ser Pro
            435                 440                 445

Ser Asn Asn Ile Pro Ser Ser Leu Pro Phe Val Phe Ser Ala Ala Ser
450                 455                 460

Glu Arg Thr Leu Thr Cys Val Met Glu Ser Tyr Ala Thr Phe Leu Gln
465                 470                 475                 480

Glu His Ala Thr Val Ser Leu Val Gly Leu Ala Leu Ser Leu Trp Asp
            485                 490                 495

Arg Arg Ser Thr His Arg His Arg Leu Thr Leu Met Ala His Ser Ile
            500                 505                 510

Gln Glu Leu Lys Asp Gln Ile Asn Thr Glu Ile Ser Arg Arg Val Thr
        515                 520                 525

Gly Lys Pro Ala Ser Val Val Ser Arg Ser Asn Thr Arg Pro Arg Arg
        530                 535                 540

Val Met Gly Ile Phe Thr Gly Gln Gly Val Gln Trp Pro Gln Met Gly
545                 550                 555                 560

Leu Asp Leu Ile Glu Ala Ser Pro Ser Ile Arg Lys Trp Ile Met Asn
                565                 570                 575

Leu Glu Glu Ala Leu Asp Glu Leu Pro Leu Asp Leu Arg Pro Gln Phe
            580                 585                 590

Ser Leu Leu Asp Glu Leu Ser Gln Pro Ala Ser Ser Arg Val Asn
        595                 600                 605

Glu Gly Leu Leu Ser Leu Pro Leu Arg Thr Ala Leu Gln Ile Met Gln
        610                 615                 620

Val Asn Met Leu Arg Ala Val Gly Ile Glu Leu Thr Ile Val Val Gly
625                 630                 635                 640

His Ser Ser Gly Glu Ile Val Ala Ala Tyr Ala Ala Gly Val Leu Thr
                645                 650                 655

Ala Ser Asp Ala Ile Arg Ile Ala Tyr Leu Arg Gly Met Thr Ile Asp
                660                 665                 670

Lys Ser Arg Asp Pro Thr Gly Arg Met Met Ala Val Asn Leu Thr Trp
```

-continued

```
            675                 680                 685
Gln Gln Ala Gln Asn Ile Cys Ala Leu Glu Ala Tyr Ser Gly Arg Ile
690                 695                 700

Ser Val Ala Ala Ala Asn Ser Pro Ser Val Thr Leu Ser Gly Asp
705                 710                 715                 720

Ala Glu Cys Leu Arg Glu Leu Glu Trp Leu Leu Lys Ser Leu Gly Leu
                    725                 730                 735

Thr Pro Arg Met Leu Arg Val Asp Thr Ala Tyr His Ser Pro His Met
                740                 745                 750

Lys Pro Cys Ala Asp Pro Tyr Arg Asp Ala Met Lys Ala Tyr Pro Val
                755                 760                 765

Ala Leu Ser Ala Ser Ala Ser Arg Trp Tyr Ser Ser Val Tyr Pro Gly
                770                 775                 780

Glu Val Met Thr Gly Tyr Asp Gln Gln Glu Leu Thr Gly Glu Tyr Trp
785                 790                 795                 800

Val Glu Asn Met Leu Arg Pro Val Gln Phe Ser Gln Ala Leu Glu Ala
                    805                 810                 815

Ala Ala Arg Asp Ala Gly Pro Pro Asp Leu Ile Ile Glu Ile Gly Pro
                820                 825                 830

His Pro Thr Leu Arg Gly Pro Val Leu Gln Thr Leu Ser Lys Met His
                835                 840                 845

Ser Ala His Ser Ala Ile Pro Tyr Leu Ala Leu Ala Glu Arg Gly Lys
850                 855                 860

Pro Gly Leu Asp Thr Trp Ala Thr Ala Leu Gly Ser Ser Trp Ala His
865                 870                 875                 880

Leu Gly Pro Asn Val Val Arg Leu Thr Asp Tyr Val Ser Leu Phe Asp
                    885                 890                 895

Pro Asn His Trp Pro Val Leu Val Glu Ser Leu Pro Phe Tyr Pro Phe
                900                 905                 910

Asp His Thr Gln Thr Tyr Trp Thr Gln Ser Arg Met Ser Ser Asn His
                915                 920                 925

Asn His Arg Ala Thr Ser Pro Asn Ala Leu Leu Gly Ser Leu Ser Pro
                930                 935                 940

Glu Thr Gly Ala Glu Lys Phe Arg Trp Arg Asn Tyr Leu Arg Pro Glu
945                 950                 955                 960

Glu Leu Pro Trp Leu Ala Asp Arg Arg Ala Asp Ser Gly Ser Val Phe
                    965                 970                 975

Pro Glu Thr Gly Tyr Ile Ser Met Ala Leu Glu Ala Gly Met Ile Met
                980                 985                 990

Ala Gln Thr Gln Gly Leu Arg Leu  Leu Asn Val Lys Asp  Leu Thr Ile
                995                 1000                1005

His Thr  Gln Leu Pro Ile Gln  Asn Asp Pro Ile Gly  Thr Glu Val
        1010                1015                1020

Leu Val  Thr Val Gly Ser Ile  His Ser His Asp Gly  Ala Ile Thr
        1025                1030                1035

Ala Trp  Phe Cys Cys Glu Ala  Val Val Ser Gly Glu  Leu Val Gln
        1040                1045                1050

Cys Ala  Thr Ala Lys Met Ile  Met His Pro Gly Asp  Ser Asp Arg
        1055                1060                1065

Ala Leu  Leu Pro Pro Gln Gly  Gln Leu Pro Gln Ala  Leu Glu Pro
        1070                1075                1080

Val Asp  Ser Thr Glu Phe Tyr  Asp Ser Leu Arg Arg  Ala Asp Tyr
        1085                1090                1095
```

-continued

His Cys Thr Gly Pro Phe Ser Thr Leu Thr Gly Leu Arg Lys Arg
1100                1105                1110

Arg Asp Leu Ala Thr Gly Ser Val Pro Val Pro Ser Asn Asp Ser
1115                1120                1125

Asp Glu Pro Met Ala Leu His Pro Ala Ile Leu Asp Leu Gly Val
1130                1135                1140

Gln Thr Met Ile Ala Ala Ile Gly Gly Leu Glu Glu Thr Leu Leu
1145                1150                1155

Thr Gly Pro Phe Leu Ser Arg Asn Val Asp Ser Thr Trp Ile Asn
1160                1165                1170

Pro Val Leu Cys Ala Ser Asp Trp Gln Gly Lys Glu Leu Thr Val
1175                1180                1185

Ala Ser Tyr Leu Thr Cys Val Asn Gly Asp Arg Ile Arg Gly Asp
1190                1195                1200

Ile Asp Ile Phe Thr Met Asn Gly Glu Lys Ala Val Gln Leu Glu
1205                1210                1215

Gly Val Ser Leu Ile Cys Gln Pro Ser Gly Thr Ala Pro Asn Asn
1220                1225                1230

Leu Gln Val Leu Ser Gln Thr Ala Trp Gly Pro Leu Glu Pro Thr
1235                1240                1245

Leu Lys Lys Gly Ser Arg Lys Leu Pro Ala Thr Met Leu Gln Leu
1250                1255                1260

His Ser Leu Arg Glu Glu Leu Ala Leu Leu Tyr Leu Lys Gln Ala
1265                1270                1275

Arg Asn Gly Leu Thr Asp Leu Glu Arg Ser Gly Leu Asp Phe Asp
1280                1285                1290

Gly Ala Arg Leu Leu Ala Trp Met Asn Gln Cys Ile Ala Asn Ala
1295                1300                1305

Ser Gln Glu Pro Asp Pro Val Gly Glu Ser Glu Cys Leu Asp Gln
1310                1315                1320

Lys Ile Glu Asp Phe Thr Ala Gly Val Ser Pro Ser Leu Leu Asn
1325                1330                1335

Asp Pro Gly Leu Thr Ala Ile Ala Ala Val Gly Gln Arg Leu Pro
1340                1345                1350

Arg Val Leu Arg Asp Ser Gly Leu Gln Ile Glu Ala Trp Pro Ala
1355                1360                1365

Ile Asp Glu Glu Ser Gln Tyr Leu Lys Glu Asp Leu Gln Val Leu
1370                1375                1380

Asp Leu Glu Asp Glu Leu Val Ser Val Val Ser Gln Ala Cys Phe
1385                1390                1395

Arg Phe Pro Gln Met Asn Ile Leu Gln Ile Gly Gln Phe Gly Gly
1400                1405                1410

His Val His Ser Gly Leu Lys Lys Met Gly Arg Thr Tyr Arg Ser
1415                1420                1425

Phe Thr Tyr Ala Gly Leu Ser Val Ser Gly Leu Gln Ala Ile Glu
1430                1435                1440

Glu Asp Leu Glu Gln Pro Gly Glu Val Ser His Lys Thr Leu Asp
1445                1450                1455

Ile Asn Glu Asp Pro Val Glu Gln Gly Cys Arg Glu Gln Phe Tyr
1460                1465                1470

Asp Met Val Leu Ile Thr Ala Ala Val Phe Leu Gln Glu Val Ala
1475                1480                1485

-continued

| | | | | | | | | | | |
|---|---|---|---|---|---|---|---|---|---|---|
| Val | Ala | His | Val | Arg | Arg | Leu | Leu | Lys | Pro | Gly | Gly | Phe | Leu | Val |
| 1490 | | | | | 1495 | | | | | 1500 | | | | |

Val Ala His Val Arg Arg Leu Leu Lys Pro Gly Gly Phe Leu Val
1490                1495                1500

Leu Leu Val Arg Thr Asn Pro Ser Thr Thr Tyr Leu Asn Leu Leu
1505                1510                1515

Phe Gly Pro Pro Met Arg Cys Thr Glu Thr Gly Lys Gly Tyr Cys
1520                1525                1530

Ser Gly Glu Pro Ile Thr Thr Arg Arg Asp Trp Val Glu Leu Leu
1535                1540                1545

Ser Asn Gly Gly Phe Tyr Gly Leu Asp Ser Phe Asp Ala Ser Gln
1550                1555                1560

Glu Ser Glu Ser Leu Gly Asp Phe Ser Leu Leu Cys Arg Thr
1565                1570                1575

Pro Asp Ser Pro Ala Glu Pro Gln Ser Arg Gly Asp Leu Leu Leu
1580                1585                1590

Leu Gly Gly Asp Ala Glu Glu Ala Asp Cys Leu Thr Ser Glu Leu
1595                1600                1605

Phe Glu Leu Val Gln Asp Asp Phe Val Lys Val Ala His Ala Pro
1610                1615                1620

Asp Leu Asp Leu Ile Glu Asp Arg Asp Leu Ser Lys Leu Thr Val
1625                1630                1635

Leu Tyr Leu Val Asp Asp Arg Asp Leu Thr Asn Ala Thr Leu Ser
1640                1645                1650

Glu Leu Cys Arg Leu Met Thr Val Ser Lys Arg Met Leu Val Val
1655                1660                1665

Thr Cys Glu Lys Val Asp His Pro Asp Ala Gly Leu Val Lys Gly
1670                1675                1680

Leu Leu Ser Thr Phe Leu Ala Ser Glu Arg Ser Ser Ser Leu Leu
1685                1690                1695

Gln Leu Leu His Ile Thr Asp Pro Val Gly Val Thr Thr Glu Ile
1700                1705                1710

Leu Ala Thr Ala Leu Gly His Phe Val Gln Ala Ser Ala Ala Gln
1715                1720                1725

Glu Asn Pro His Ser Cys Gly Leu Thr Asn Ile Glu Pro Glu Ile
1730                1735                1740

Gln Tyr Asp Gly Ser Met Phe Arg Val Pro Arg Gln Tyr His Asp
1745                1750                1755

His Ala Thr Gly Leu Arg His Leu Ala Arg Arg Gln Lys Val Thr
1760                1765                1770

Asp Cys Val Asp Leu Asp Lys Gly Val Val Gln Ile Leu Pro Ala
1775                1780                1785

Thr Thr Asp Lys Thr Cys Glu Gly Phe Arg Leu Leu Ser Met Ala
1790                1795                1800

Asp Pro Pro Ile Thr Ala Ser Tyr Gly Pro Thr Leu His Leu Arg
1805                1810                1815

Val Arg His Ser Ser Ile Ala Ala Val Arg Val Ala Gly Ala Ile
1820                1825                1830

Phe Leu Arg Leu Val Ile Gly Leu Asp Val Lys Ser Asn Lys Arg
1835                1840                1845

Met Ile Ala Leu Ser Ser His Ile Ala Ser His Val Ile Val Pro
1850                1855                1860

Asp Ser Trp Ala Trp Ser Val Pro Asp Thr Val Leu Glu Ala His
1865                1870                1875

Glu Gln Ser Tyr Leu Arg Ala Thr Ala Ala Ala Leu Leu Ala Gly

-continued

```
              1880            1885            1890
Tyr Leu Val Glu Gln Val Pro Gln Ser Gly Thr Leu Val Val His
        1895            1900            1905
Glu Ala Asp Gly Val Leu Gln Ser Val Phe His Gln Met Leu Thr
        1910            1915            1920
Arg Arg Asp Gly Lys Val Ile Phe Ser Thr Ser Lys Ser Asn Pro
        1925            1930            1935
Asp Lys Glu Arg Pro Met Leu Leu Leu His Glu His Ser Thr Ala
        1940            1945            1950
Arg Gln Leu Ser Gln Val Leu Pro Ser Asp Val Ser Ala Ile Ala
        1955            1960            1965
Ile Leu His Arg Arg Gly Gln Gly Val Tyr Asp Arg Met Leu Ser
        1970            1975            1980
Leu Leu Pro Asp Asn Ala Thr Arg Ile His Leu Gln Asp Phe Tyr
        1985            1990            1995
Leu Thr Ser Ala Ser Thr Gly Pro Ile Asn Ala Asp Asp Ser Ser
        2000            2005            2010
Leu Ile Ala Lys Ala Phe Leu Thr Ala Cys Leu Val Ala Tyr Thr
        2015            2020            2025
Gly Arg Glu Gly Leu Pro Pro Asn Ser Val Asp Ser Leu Pro Ile
        2030            2035            2040
Ser Arg Ile Ser Glu Tyr Pro Ile Leu Asp Ser Gln Asp Ala Val
        2045            2050            2055
Val Asp Trp Asp Ser Thr Thr Pro Val Leu Ala Gln Ile Pro Thr
        2060            2065            2070
Ala Gly Ser Gln Val Gln Leu Ser Glu Lys Lys Thr Tyr Ile Leu
        2075            2080            2085
Val Gly Leu Gly Ser Glu Leu Ala His Ala Ile Cys Leu Trp Leu
        2090            2095            2100
Ala Thr His Gly Ala Lys Trp Ile Leu Leu Ala Gly Ser Arg Leu
        2105            2110            2115
Asp Ser Asp Ala Trp Trp Leu Glu Glu Val Ser Arg Arg Gly Thr
        2120            2125            2130
Arg Ile Ala Val Ser Lys Ile Asn Leu Ile Asp Gly Ile Ser Ala
        2135            2140            2145
Thr Ser Leu His Gln Thr Ile Pro Tyr Ala Phe Pro Pro Val Val
        2150            2155            2160
Gly Gly Val Leu Ile Gln Pro Pro Leu Pro Asp Cys Ser Leu
        2165            2170            2175
Ser Gln Leu Thr Ile Asp Ser Leu Arg Asn His Leu His Pro Val
        2180            2185            2190
Leu Lys Gly Leu Gln Gln Leu Asp Glu Leu Tyr Lys Thr Pro Thr
        2195            2200            2205
Leu Asp Phe Trp Val Leu Ile Gly Ser Ile Ala Gly Val Leu Gly
        2210            2215            2220
His Ala Asp Gln Ala Met Thr Ala Ala Met Ser Glu Lys Met Ala
        2225            2230            2235
Leu Leu Val Arg His Arg Arg Ala Gln Gly Arg Pro Ala Ser Leu
        2240            2245            2250
Val His Leu Gly Glu Ile His Gly Ile Ser Ser Pro Ser Pro Ser
        2255            2260            2265
Gln Pro Leu Trp Cys Gly Pro Val Ala Val Ser Gln Arg Asp Val
        2270            2275            2280
```

```
Asp Glu Ile Leu Ala Glu Ala Ile Leu Cys Gly Arg Ser Asp Ser
    2285                2290                2295

Asn Ser Asn Ala Glu Leu Ile Gly Gly Leu Arg His Gln Ser Leu
    2300                2305                2310

Lys Cys Gly Tyr Gly Glu Cys Pro Ile Pro Lys Leu Trp Pro Phe
    2315                2320                2325

Tyr Ser Tyr Thr Ala Thr Ala Ser Gln Asp Gln Ile Leu Ala Leu
    2330                2335                2340

Ile Glu Thr Arg Ser Thr Lys Asp Leu Val Thr Ala Ala Thr Ser
    2345                2350                2355

Leu Glu Glu Lys Ala Glu Ala Val Val Arg Pro Leu Met Glu Lys
    2360                2365                2370

Ile Arg Ala Ser Leu Asn Leu Ala Glu Asp Ala Pro Leu Ser Ala
    2375                2380                2385

Asp Thr Leu Ile Pro Glu Leu Gly Ile Asp Ser Leu Ile Ala Ile
    2390                2395                2400

Gly Leu Ser Gln Trp Phe Thr Lys Glu Leu Ser Val Asp Ile Gly
    2405                2410                2415

Val Ile Leu Ile Leu Ser Gly Val Ser Val Gly Glu Leu Ala His
    2420                2425                2430

Ala Ala Ala Ser Lys Leu Cys Asn Val Ser Val Gly Lys Pro
    2435                2440                2445

<210> SEQ ID NO 269
<211> LENGTH: 509
<212> TYPE: PRT
<213> ORGANISM: Penicillium coprobium PF1169

<400> SEQUENCE: 269

Met Asp Asn Met Asp Asn Met Asn Asn Thr Pro Leu Gly Phe Asn Trp
1               5                   10                  15

Ala Trp Ala Val Ile Ile Ser Phe Leu Gly Leu Leu Thr Phe Ser Phe
                20                  25                  30

Val Ser Pro His Leu Phe Pro Ser Arg Leu Thr Val Ile Asn Gly Gly
        35                  40                  45

Arg Ala Trp Asp Ile Phe Arg Thr Lys Ala Lys Lys Arg Phe Arg Ser
    50                  55                  60

Asp Ala Ala Arg Leu Ile Lys Asn Gly Phe Glu Glu Ser Pro Asp Ala
65                  70                  75                  80

Phe Arg Ile Ile Thr Asp Asn Gly Pro Leu Leu Val Leu Ser Pro Gln
                85                  90                  95

Tyr Ala Arg Glu Val Arg Ser Asp Asp Arg Leu Ser Leu Asp His Phe
            100                 105                 110

Ile Ala Ser Glu Phe His Pro Asn Ile Pro Gly Phe Glu Pro Phe Lys
        115                 120                 125

Leu Ile Leu Asp Pro Lys Asn Pro Leu Asn Thr Ile Leu Lys Ser Asn
    130                 135                 140

Leu Thr Gln Ala Leu Glu Asp Leu Ser Ala Glu Val Thr Glu Ala Leu
145                 150                 155                 160

Ser Ala Thr Cys Thr Asp Pro Glu Trp His Glu Val Ser Val Ser
                165                 170                 175

Gln Thr Ala Leu Lys Ile Ile Ala Gln Met Ala Ser Lys Ala Phe Ile
            180                 185                 190

Gly Gln Glu Arg Cys Arg Asp Ala Lys Trp His Asn Ile Ile Ile Thr
```

```
             195                 200                 205
Tyr Thr His Asn Val Tyr Gly Ala Ala Gln Ala Leu His Phe Trp Pro
    210                 215                 220

Ser Phe Leu Arg Pro Ile Val Ala Gln Phe Leu Pro Ala Cys Arg Thr
225                 230                 235                 240

Leu Gln Ala Gln Ile Ala Glu Ala Arg Glu Ile Leu Glu Pro Leu Val
                245                 250                 255

Ala Gln Arg Arg Ala Glu Arg Ala Thr Arg Ala Ala Gln Glu Lys Pro
            260                 265                 270

His Pro Ser Gly Gly Asp Ile Ile Asp Trp Leu Glu Gln Phe Tyr Gly
        275                 280                 285

Asp Gln Pro Tyr Asp Pro Val Ala Gln Leu Leu Leu Ser Phe Ala
    290                 295                 300

Ala Ile His Gly Thr Ser Asn Leu Leu Ala Gln Ala Leu Ile Asp Leu
305                 310                 315                 320

Cys Gly Gln Pro Glu Leu Val Gln Asp Leu Arg Glu Glu Ala Val Ser
                325                 330                 335

Val Leu Gly Lys Glu Gly Trp Thr Arg Ala Ala Leu Tyr Gln Leu Lys
            340                 345                 350

Leu Met Asp Ser Ala Leu Lys Glu Ser Gln Arg Leu Ala Pro Asn Arg
        355                 360                 365

Leu Leu Ser Met Gly Arg Ile Ala Gln Gly Asp Met Asp Leu Ser Asp
    370                 375                 380

Gly Leu Arg Ile His Arg Gly Thr Thr Leu Met Val Ser Ala His Asn
385                 390                 395                 400

Met Trp Asp Pro Glu Ile Tyr Pro Asp Pro Arg Lys Tyr Asp Gly Tyr
                405                 410                 415

Arg Phe His Lys Leu Arg Gln Thr Ser Gly Gln Glu Gly Gln His Gln
            420                 425                 430

Leu Val Ser Ser Thr Pro Asp His Met Gly Phe Gly Tyr Gly Lys His
        435                 440                 445

Ala Cys Pro Gly Arg Phe Phe Ala Ala Ala Gln Ile Lys Val Ala Leu
    450                 455                 460

Cys Asn Ile Leu Leu Lys Tyr Asp Ile Glu Tyr Arg Gly Gly Lys Ser
465                 470                 475                 480

Pro Gly Val Trp Gly Gln Gly Ile His Leu Phe Pro Asp Pro Thr Ser
                485                 490                 495

Arg Ile His Val Arg Arg Arg Lys Glu Glu Ile Asn Leu
            500                 505

<210> SEQ ID NO 270
<211> LENGTH: 505
<212> TYPE: PRT
<213> ORGANISM: Penicillium coprobium PF1169

<400> SEQUENCE: 270

Met Ile Glu Leu Lys Asp Ala Ser Met Gly Ala Val Leu Leu Thr Cys
1               5                   10                  15

Val Leu Val Leu Ala Gly Leu Tyr Leu Ile Arg Leu Thr Leu Ser Ser
            20                  25                  30

Asp Gln Leu Asp Lys Phe Pro Ser Ile Asn Pro Arg Lys Pro Trp Glu
        35                  40                  45

Ile Val Asn Val Phe Ala Gln Arg Arg Phe Gln Gln Asp Gly Pro Arg
    50                  55                  60
```

Tyr Leu Glu Ala Gly Tyr Ala Lys Ser Pro Ile Phe Ser Val Val Thr
65                  70                  75                  80

Asp Leu Gly Pro Lys Leu Val Ser Gly Ala Phe Ile Glu Glu Phe
            85                  90                  95

Lys Asp Glu Lys Leu Leu Asp His Tyr Arg Ser Met Ile Glu Asp Phe
            100                 105                 110

Met Ala Glu Val Pro Gly Phe Glu Ser Met Phe Leu Gly Asn Leu His
            115                 120                 125

Asn Thr Val Leu Arg Asp Val Ile Ser Val Ile Thr Arg Glu Leu Glu
            130                 135                 140

Gln Leu Leu Ala Pro Leu Ser Asp Glu Val Ser Ala Ala Leu Val Asp
145                 150                 155                 160

Thr Trp Thr Asp Ser Pro Asp Trp His Glu Val Ala Leu Leu Pro Ser
            165                 170                 175

Met Leu Gly Leu Ile Ala Lys Val Ser Ser Leu Val Phe Val Gly Glu
            180                 185                 190

Pro Leu Cys Arg His Pro Val Trp Leu Glu Thr Val Ile Asn Phe Thr
            195                 200                 205

Leu Ile Arg His Asn Ala Ile Leu Ala Leu His Gln Cys Pro Ala Val
210                 215                 220

Leu Arg Pro Val Leu His Trp Val Leu Pro Pro Cys Gln Lys Leu Arg
225                 230                 235                 240

Arg Glu Ile Arg Thr Ala Arg Thr Leu Ile Asp Ser Ala Leu Glu Lys
            245                 250                 255

Ser Arg Lys Asn Pro Gln Thr Glu Lys Phe Ser Ser Val Ala Trp Val
            260                 265                 270

Asp Ala Phe Ala Lys Gly Asn Lys Tyr Asn Ala Ala Met Val Gln Leu
            275                 280                 285

Arg Leu Ala Asn Ala Ser Ile His Ser Ser Ala Asp Leu Leu Val Lys
            290                 295                 300

Ile Leu Ile Asn Leu Cys Glu Gln Pro Glu Leu Ile Arg Asp Leu Arg
305                 310                 315                 320

Asp Glu Ile Ile Ser Val Leu Gly Glu Asn Gly Trp Arg Ser Ser Thr
            325                 330                 335

Leu Asn Gln Leu Lys Leu Leu Asp Ser Val Leu Lys Glu Ser Gln Arg
            340                 345                 350

Leu His Pro Val Thr Thr Gly Ala Phe Ser Arg Phe Thr Arg Gln Asp
            355                 360                 365

Ile Lys Leu Thr Asn Gly Thr Glu Ile Pro Ser Gly Thr Pro Ile Met
            370                 375                 380

Val Thr Asn Asp Val Ala Gly Asp Ala Ser Ile Tyr Asp Pro Asp
385                 390                 395                 400

Val Phe Asp Gly Tyr Arg Tyr Phe Arg Met Arg Glu Gly Ala Asp Lys
            405                 410                 415

Ala Arg Ala Pro Phe Thr Thr Thr Gly Gln Asn His Leu Gly Phe Gly
            420                 425                 430

Tyr Gly Lys Tyr Ala Cys Pro Gly Arg Phe Phe Ala Ala Thr Glu Ile
            435                 440                 445

Lys Ile Ala Leu Cys His Met Leu Leu Lys Tyr Glu Trp Arg Leu Val
            450                 455                 460

Lys Asp Arg Pro His Gly Ile Val Thr Ser Gly Phe Ala Ala Phe Arg
465                 470                 475                 480

Asp Pro Arg Ala Ser Ile Glu Val Arg Arg Arg Ala Val Ala Gly Glu

```
                    485                 490                 495
Glu Leu Glu Val Leu Thr Gly Lys Lys
                500                 505

<210> SEQ ID NO 271
<211> LENGTH: 241
<212> TYPE: PRT
<213> ORGANISM: Penicillium coprobium PF1169

<400> SEQUENCE: 271

Met Asp Gly Trp Ser Asp Ile Ser Ala Pro Ala Gly Tyr Lys Asp
1               5                   10                  15

Val Val Trp Ile Ala Asp Arg Ala Leu Leu Ala Gln Gly Leu Gly Trp
                20                  25                  30

Ser Ile Asn Tyr Leu Ala Met Ile Tyr Gln Ser Arg Lys Asp Arg Thr
            35                  40                  45

Tyr Gly Met Ala Ile Leu Pro Leu Cys Cys Asn Phe Ala Trp Glu Phe
        50                  55                  60

Val Tyr Thr Val Ile Tyr Pro Ser Gln Asn Pro Phe Glu Arg Ala Val
65                  70                  75                  80

Leu Thr Thr Trp Met Val Leu Asn Leu Tyr Leu Met Tyr Thr Thr Ile
                85                  90                  95

Lys Phe Ala Pro Asn Glu Trp Gln His Ala Pro Leu Val Gln Arg Ile
            100                 105                 110

Leu Pro Val Ile Phe Pro Val Ala Ile Ala Ala Phe Thr Ala Gly His
        115                 120                 125

Leu Ala Leu Ala Ala Thr Val Gly Val Ala Lys Ala Val Asn Trp Ser
    130                 135                 140

Ala Phe Leu Cys Phe Glu Leu Leu Thr Ala Gly Ala Val Cys Gln Leu
145                 150                 155                 160

Met Ser Arg Gly Ser Ser Arg Gly Ala Ser Tyr Thr Ile Trp Val Ser
                165                 170                 175

Arg Phe Leu Gly Ser Tyr Ile Gly Ser Ile Phe Met His Val Arg Glu
            180                 185                 190

Thr His Trp Pro Gln Glu Phe Asp Trp Ile Ser Tyr Pro Phe Val Ala
        195                 200                 205

Trp His Gly Ile Met Cys Phe Ser Leu Asp Ile Ser Tyr Val Gly Leu
    210                 215                 220

Leu Trp Tyr Ile Arg Arg Gln Glu Arg Gln Gly Gln Leu Lys Lys Ala
225                 230                 235                 240

Met

<210> SEQ ID NO 272
<211> LENGTH: 464
<212> TYPE: PRT
<213> ORGANISM: Penicillium coprobium PF1169

<400> SEQUENCE: 272

Met Lys Val Ile Ile Val Gly Gly Ser Ile Ala Gly Leu Ala Leu Ala
1               5                   10                  15

His Cys Leu Asp Lys Ala Asn Ile Asp Tyr Val Ile Leu Glu Lys Lys
                20                  25                  30

Lys Glu Ile Ala Pro Gln Glu Gly Ala Ser Ile Gly Ile Met Pro Asn
            35                  40                  45

Gly Gly Arg Ile Leu Glu Gln Leu Gly Leu Tyr Asp Gln Ile Glu Glu
        50                  55                  60
```

Leu Ile Glu Pro Leu Val Arg Ala His Val Thr Tyr Pro Asp Gly Phe
65                  70                  75                  80

Asn Tyr Thr Ser Arg Tyr Pro Ala Leu Ile Gln Gln Arg Phe Gly Tyr
            85                  90                  95

Pro Leu Ala Phe Leu Asp Arg Gln Lys Leu Leu Gln Ile Leu Ala Thr
                100                 105                 110

Gln Pro Val Gln Ser Ser Arg Val Lys Leu Asp His Lys Val Glu Ser
                115                 120                 125

Ile Glu Val Ser Pro Cys Gly Val Thr Val Ile Thr Ser Asn Gly His
130                 135                 140

Thr Tyr Gln Gly Asp Leu Val Gly Ala Asp Gly Val His Ser Arg
145                 150                 155                 160

Val Arg Ala Glu Met Trp Arg Leu Ala Asp Ala Ser Gln Gly Asn Val
                165                 170                 175

Cys Gly Asn Gly Asp Lys Ala Phe Thr Ile Asn Tyr Ala Cys Ile Phe
                180                 185                 190

Gly Ile Ser Ser His Val Asp Gln Leu Asp Pro Gly Glu Gln Ile Thr
                195                 200                 205

Cys Tyr Asn Asp Gly Trp Ser Ile Leu Ser Val Ile Gly Gln Asn Gly
210                 215                 220

Arg Ile Tyr Trp Phe Leu Phe Ile Lys Leu Glu Lys Glu Phe Val Tyr
225                 230                 235                 240

Asp Gly Ser His Lys Thr Gln Leu His Phe Ser Arg Glu Asp Ala Arg
                245                 250                 255

Ala His Cys Glu Arg Leu Ala Gln Glu Pro Leu Trp Lys Asp Val Thr
                260                 265                 270

Phe Gly Gln Val Trp Ala Arg Cys Glu Val Phe Gln Met Thr Pro Leu
                275                 280                 285

Glu Glu Gly Val Leu Gly Lys Trp His Trp Arg Asn Ile Ile Cys Ile
290                 295                 300

Gly Asp Ser Met His Lys Phe Ala Pro His Ile Gly Gln Gly Ala Asn
305                 310                 315                 320

Cys Ala Ile Glu Asp Ala Ala Gln Leu Ser Asn Ser Leu His Thr Trp
                325                 330                 335

Leu Ser Gly Ser Gly Lys Glu His Gln Leu Lys Thr Asp Asp Leu Thr
                340                 345                 350

Glu Ile Leu Ala Gln Phe Ala Gln Thr Arg Leu Gln Arg Leu Gly Pro
                355                 360                 365

Thr Ala Met Ala Ala Arg Ser Ala Met Arg Leu His Ala Arg Glu Gly
                370                 375                 380

Leu Lys Asn Trp Ile Leu Gly Arg Tyr Phe Leu Pro Tyr Ala Gly Asp
385                 390                 395                 400

Lys Pro Ala Asp Trp Ala Ser Arg Gly Ile Ala Gly Asn Thr Leu
                405                 410                 415

Asp Phe Val Glu Pro Pro Thr Arg Ala Gly Pro Gly Trp Ile Gln Phe
                420                 425                 430

Ser Gln Ser Gly Lys Arg Thr Ser Phe Pro Met Ala Val Ala Gly Leu
                435                 440                 445

Cys Leu Val Ser Ile Val Ala Arg Ile Met Tyr Leu Lys Leu Val Ala
                450                 455                 460

<210> SEQ ID NO 273
<211> LENGTH: 317

<212> TYPE: PRT
<213> ORGANISM: Penicillium coprobium PF1169

<400> SEQUENCE: 273

Met Ala Gly Ser Gln Ser Thr Ala Gln Leu Ala Arg Leu Leu Ile Asp
1               5                   10                  15

Ile Ser Arg Phe Asp Lys Tyr Asn Cys Leu Phe Ala Ile Phe Pro Gly
            20                  25                  30

Val Trp Ser Ile Phe Leu Ala Ala Ser Arg His Ala Asp Gly Asp
        35                  40                  45

Pro Val Pro Leu Asp Phe Val Leu Gly Arg Ala Gly Leu Ala Phe Met
50                  55                  60

Tyr Thr Tyr Met Leu Ser Gly Ala Gly Met Val Trp Asn Asp Trp Ile
65                  70                  75                  80

Asp Arg Asp Ile Asp Ala Gln Val Ala Arg Thr Lys Asn Arg Pro Leu
            85                  90                  95

Ala Ser Gly Arg Leu Ser Thr Arg Ala Ala Leu Ile Trp Met Leu Val
            100                 105                 110

Gln Tyr Ala Ala Ser Val Trp Leu Met Asp Arg Met Val Ser Gly Gln
        115                 120                 125

Asp Val Trp Thr Tyr Met Leu Pro Leu Thr Thr Gly Ile Ile Leu Tyr
130                 135                 140

Pro Phe Gly Lys Arg Pro Thr Ser Arg Lys Leu Gly Val Tyr Pro Gln
145                 150                 155                 160

Tyr Ile Leu Gly Ala Ser Ser Ala Leu Thr Ile Leu Pro Ala Trp Ala
            165                 170                 175

Ser Val Tyr Thr Gly Arg Ile Ser Leu Lys Asp Leu Gly Met Arg Cys
            180                 185                 190

Leu Pro Leu Cys Leu Phe Leu Phe Leu Trp Thr Ile Tyr Phe Asn Thr
        195                 200                 205

Ala Tyr Ser Tyr Gln Asp Ile Lys Asp Asp Cys Lys Leu Asn Val Asn
    210                 215                 220

Ser Ser Tyr Val Leu Ala Gly Ser His Val Arg Gly Met Leu Leu Leu
225                 230                 235                 240

Gln Ala Ile Ala Val Val Leu Val Ile Pro Trp Ile Leu Tyr Thr Ser
            245                 250                 255

Ala Ser Thr Trp Leu Trp Val Ser Trp Leu Gly Val Trp Thr Ala Ser
            260                 265                 270

Leu Gly Glu Gln Leu Tyr Leu Phe Asp Val Lys Asp Pro Ser Ser Gly
        275                 280                 285

Gly Lys Val His Arg Arg Asn Phe Ala Leu Gly Ile Trp Asn Val Leu
    290                 295                 300

Ala Cys Phe Val Glu Leu Leu Tyr Ala Ser Gly Ser Leu
305                 310                 315

<210> SEQ ID NO 274
<211> LENGTH: 522
<212> TYPE: PRT
<213> ORGANISM: Penicillium coprobium PF1169

<400> SEQUENCE: 274

Met Ser Thr Gln Glu Val Cys Leu Pro Val Ser Gln Arg Asp Gln Val
1               5                   10                  15

Lys Glu Gly Pro Val Arg Leu His Gly Leu Cys Glu Asp Gly Met Cys
            20                  25                  30

-continued

```
Asp Ala Arg Arg Thr Gly Asp Arg Ser Ala Tyr Pro Leu Ser Ser Leu
         35                  40                  45

Asp His Asn Pro Leu Gly Met Asn Val Thr Phe Leu Leu Phe Phe Gln
 50                      55                  60

Thr Thr Gln Pro Glu Lys Ser Ile Gly Val Leu Glu Asn Gly Ile Glu
 65                  70                  75                  80

Leu Leu Leu Lys Val His Pro Phe Leu Ala Gly Asp Val Thr Arg Arg
                 85                  90                  95

Thr Glu Ser Ser Gln Thr Lys Tyr Thr Trp Gln Ile Glu Pro Glu Ala
             100                 105                 110

Ser Glu Ser Leu Val Gln Phe Pro Ile Leu Arg Ile Arg His Tyr Gln
             115                 120                 125

Ala Glu Ser Phe Lys Glu Ile Gln Ser Lys Cys Leu Leu Thr Gly Thr
             130                 135                 140

Glu Glu Gln Glu Ile Ile Ser Arg Leu Ala Pro Leu Pro Ile Asp Met
145                 150                 155                 160

Asp Ile Ser Leu Pro Arg Arg Pro Ile Leu Arg Phe Gln Ala Asn Val
                 165                 170                 175

Met Arg Asp Gly Ile Ile Leu Ala Met Thr Phe His His Ser Ala Met
             180                 185                 190

Asp Gly Ala Gly Ala Ala Arg Val Leu Gly Leu Leu Ala Asp Cys Cys
             195                 200                 205

Arg Asp Pro Thr Ala Met Ser Ser Ala Ser Val Ser Pro Asp Arg Gln
             210                 215                 220

Leu Arg Ser Glu Ile Glu Arg Leu Val Pro Glu Ser Ser Ser Gly Leu
225                 230                 235                 240

Ser Arg Met Asp Phe Ser Lys His Tyr Cys Gly Leu Gly Asp Trp Ala
                 245                 250                 255

Ala Leu Leu Ala Lys Asn Trp Ser Gly Phe Val Arg Ala Arg Ala Thr
             260                 265                 270

Glu Leu Val Thr Trp Arg Leu Lys Ile Pro Gly Pro Lys Ile Glu Tyr
             275                 280                 285

Leu Lys Glu Ala Cys Asn Thr Leu Ile Lys Gly Gln Thr Ser Phe Gln
             290                 295                 300

Ala Asp Gly Arg Pro Ser Pro Gly Phe Leu Ser Ser Asn Asp Ile Val
305                 310                 315                 320

Ser Ala Leu Leu Ala Met Ile Leu Arg Gln Ala Gly Gln Leu Ala Gly
                 325                 330                 335

Lys Ser Thr Glu Leu Ser Ile Ala Val Asp Met Arg Gly Asn Phe Lys
             340                 345                 350

Thr Pro Ala Phe Asp Asp Tyr Leu Gly Asn Met Val Leu Leu Thr Tyr
             355                 360                 365

Thr Pro Ile Gln Ala Gly Arg Asn Glu Ala Leu Val Asp Gly Thr Asp
             370                 375                 380

Pro Ser Val Glu Leu Arg Gln Glu Cys Leu Glu Asp Leu Thr Gln Ile
385                 390                 395                 400

Ala Ala Arg Ile Arg Gln Ser Leu Leu Ala Val Asp Ala Glu Tyr Ile
                 405                 410                 415

Gln Asp Ala Leu Ser His Leu His Ser Gln Pro Asp Trp Ala Asp Ile
             420                 425                 430

Gly Phe Arg Gly Val Pro Ile Pro Leu Ser Ser Phe Arg Asn Phe Glu
             435                 440                 445

Ile Phe Gly Leu Asp Phe Gly Glu Ser Leu Gly Ala Gln Pro Arg Gly
```

```
                  450                 455                 460
Phe Gln Leu His Leu Pro Val Leu Gly Gly Met Cys Phe Ile Leu Pro
465                 470                 475                 480

Lys Gly Gln Asp Asp Val Ala Ser Thr Glu Pro Trp Asp Leu His Leu
                485                 490                 495

Thr Leu Asn Arg Asp Asp Gln Leu Leu Leu Ala Lys Asp Pro Leu Phe
            500                 505                 510

Cys Trp Ala Ile Gly Ala Gln Ala Lys Glu
            515                 520

<210> SEQ ID NO 275
<211> LENGTH: 434
<212> TYPE: PRT
<213> ORGANISM: Penicillium coprobium PF1169

<400> SEQUENCE: 275

Met Asp Ser Leu Leu Thr Ser Pro Leu Trp Leu Lys Ile Ala His Glu
1               5                   10                  15

Leu Ala Leu Tyr Leu Ser Phe Ile Val Pro Thr Ala Phe Leu Ile Ile
                20                  25                  30

Thr Thr Gln Lys Ser Ser Ile Ile Arg Trp Ala Trp Thr Pro Cys Leu
            35                  40                  45

Leu Tyr Ile Leu Tyr Gln Phe Ser Leu Arg Val Pro Ser Leu Ser Thr
    50                  55                  60

Ser Gln Phe Leu Lys Gly Val Ala Ala Gly Gln Ala Thr Val Ala Ala
65                  70                  75                  80

Leu Gln Cys Leu Asn Leu Leu Ile Thr Lys Leu Asp Gln Thr Asp
                85                  90                  95

Leu Leu Arg Ala Asn Leu Tyr Ser Pro Ser Ala Gly Leu Leu Ser Arg
            100                 105                 110

Leu Ala Gln Ser Cys Ala Leu Leu Val Asn Phe Arg Gly Ile Gly Thr
        115                 120                 125

Ile Trp Glu Val Arg Asn Ile Pro Gln His Ala Ala Phe Val Gln Pro
    130                 135                 140

Lys Gly Lys Asp Gln Ser Met Ser Arg Lys Arg Phe Val Leu Arg Glu
145                 150                 155                 160

Ile Ala Ile Ile Val Trp Gln Tyr Leu Leu Leu Asp Phe Ile Tyr Glu
                165                 170                 175

Ser Thr Lys Gly Thr Ser Ala Glu Asp Leu Met Arg Leu Phe Gly Pro
            180                 185                 190

Gly Met Glu Ile Lys Tyr Leu Asp Ala Thr Phe Glu Gln Trp Met Gly
        195                 200                 205

Arg Leu Ser Val Gly Ile Phe Ser Trp Leu Val Pro Ser Arg Val Cys
    210                 215                 220

Leu Asn Ile Thr Ser Arg Leu Tyr Phe Leu Ile Leu Val Val Leu Gly
225                 230                 235                 240

Ile Ser Ser Pro Glu Ser Cys Arg Pro Gly Phe Gly Arg Val Arg Asp
                245                 250                 255

Val Cys Thr Ile Arg Gly Val Trp Gly Lys Phe Trp His Gln Ser Phe
            260                 265                 270

Arg Trp Pro Leu Thr Ser Val Gly Asn Tyr Ile Ala Arg Asp Val Leu
        275                 280                 285

Gly Leu Ala His Pro Ser Leu Leu Glu Arg Tyr Thr Asn Ile Phe Phe
    290                 295                 300
```

```
Thr Phe Phe Thr Ser Gly Val Leu His Leu Val Cys Asp Ala Ile Leu
305                 310                 315                 320

Gly Val Pro Pro Ser Ala Ser Gly Ala Met Gln Phe Phe Cys Ser Phe
            325                 330                 335

Pro Leu Ala Ile Met Ile Glu Asp Gly Val Gln Glu Ile Trp Arg Arg
            340                 345                 350

Ala Thr Gly Gln Thr Lys Asp Ser Asp Arg Ala Val Pro Phe Trp Gln
            355                 360                 365

Arg Leu Val Gly Tyr Leu Trp Val Ala Val Trp Met Cys Val Thr Ser
370                 375                 380

Pro Phe Tyr Leu Tyr Pro Ala Ala Arg Gln His Ala Glu Lys Asn Trp
385                 390                 395                 400

Ile Val Pro Phe Ser Ile Val Glu Glu Ile Gly Leu Gly Thr Ala Gln
            405                 410                 415

Lys Ile Leu Leu Gly Tyr Gly Leu Phe Val Tyr Trp Ala Val Gly Gly
            420                 425                 430

Glu Ile

<210> SEQ ID NO 276
<211> LENGTH: 1299
<212> TYPE: PRT
<213> ORGANISM: Penicillium coprobium PF1169

<400> SEQUENCE: 276

Met Leu Tyr Arg Ala Lys Leu Val Asp Asp His Gln Ile His Thr Ala
1               5                   10                  15

Ser Leu His Asn Pro Ile Pro Trp Gln Leu His Thr Tyr Val Trp Pro
            20                  25                  30

Phe Leu Ile Ile Trp Pro Val Phe Phe Ala Phe Tyr Leu Ser Pro Glu
        35                  40                  45

Arg Tyr Asp Thr Tyr Ile Gln Gly Glu Trp Thr Phe Val Phe Ala
    50                  55                  60

Gly Ser Ile Ile Thr Val Gln Ser Leu Phe Trp Leu Met Thr Lys Trp
65                  70                  75                  80

Asn Ile Asp Ile Asn Thr Leu Phe Thr Thr Thr Arg Ser Lys Ser Ile
                85                  90                  95

Asp Thr Ala Arg Leu Ile Lys Val Val Pro Ile Thr Asn Ala Gly Ser
            100                 105                 110

Ala Glu Ile Cys Asn Leu Ile Arg Glu His Ile Gly Pro Lys Lys Thr
        115                 120                 125

Leu Ser Phe Leu Phe Gln Lys Arg Arg Phe Leu Phe Tyr Pro Glu Thr
    130                 135                 140

Arg Ser Phe Ala Pro Leu Ser Tyr Ala Leu Asp Ala Glu Pro Lys Pro
145                 150                 155                 160

Ala Leu Lys Thr Phe Gln Gln Ser Glu Gly Phe Thr Ser Lys Ala Glu
                165                 170                 175

Ile Glu Arg Val Gln Asn His Tyr Gly Asp Asn Thr Phe Asp Ile Pro
            180                 185                 190

Val Pro Gly Phe Ile Glu Leu Phe Gln Glu His Ala Val Ala Pro Phe
        195                 200                 205

Phe Val Phe Gln Ile Phe Cys Val Gly Leu Trp Met Leu Asp Glu Tyr
    210                 215                 220

Trp Tyr Tyr Ser Leu Phe Thr Leu Phe Met Leu Val Met Phe Glu Ser
225                 230                 235                 240
```

```
Thr Val Val Trp Gln Arg Gln Arg Thr Leu Ser Glu Phe Arg Gly Met
            245                 250                 255

Ser Ile Lys Pro Tyr Asp Val Trp Val Tyr Arg Glu Arg Lys Trp Gln
        260                 265                 270

Glu Ile Thr Ser Asp Lys Leu Leu Pro Gly Asp Leu Met Ser Val Asn
            275                 280                 285

Arg Thr Lys Glu Asp Ser Gly Val Ala Cys Asp Ile Leu Leu Val Glu
        290                 295                 300

Gly Ser Val Ile Val Asn Glu Ala Met Leu Ser Gly Glu Ser Thr Pro
305                 310                 315                 320

Leu Leu Lys Asp Ser Ile Gln Leu Arg Pro Gly Asp Asp Leu Ile Glu
                325                 330                 335

Pro Asp Gly Leu Asp Lys Leu Ser Phe Val His Gly Thr Lys Val
            340                 345                 350

Leu Gln Val Thr His Pro Asn Leu Thr Gly Asp Ala Gly Leu Lys Asn
            355                 360                 365

Leu Ala Ser Asn Val Thr Met Pro Pro Asp Asn Gly Ala Leu Gly Val
370                 375                 380

Val Val Lys Thr Gly Phe Glu Thr Ser Gln Gly Ser Leu Val Arg Thr
385                 390                 395                 400

Met Ile Tyr Ser Thr Glu Arg Val Ser Ala Asn Asn Val Glu Ala Leu
                405                 410                 415

Leu Phe Ile Leu Phe Leu Leu Ile Phe Ala Ile Ala Ala Ser Trp Tyr
            420                 425                 430

Val Trp Gln Glu Gly Val Ile Arg Asp Arg Lys Arg Ser Lys Leu Leu
            435                 440                 445

Leu Asp Cys Val Leu Ile Ile Thr Ser Val Val Pro Pro Glu Leu Pro
450                 455                 460

Met Glu Leu Ser Leu Ala Val Asn Thr Ser Leu Ala Ala Leu Ser Lys
465                 470                 475                 480

Tyr Ala Ile Phe Cys Thr Glu Pro Phe Arg Ile Pro Phe Ala Gly Arg
                485                 490                 495

Val Asp Ile Ala Cys Phe Asp Lys Thr Gly Thr Leu Thr Gly Glu Asp
            500                 505                 510

Leu Val Val Asp Gly Ile Ala Gly Leu Thr Leu Gly Glu Ala Gly Ser
            515                 520                 525

Lys Val Glu Ala Asp Gly Ala His Thr Glu Leu Ala Asn Ser Ser Ala
530                 535                 540

Ala Gly Pro Asp Thr Thr Leu Val Leu Ala Ser Ala His Ala Leu Val
545                 550                 555                 560

Lys Leu Asp Glu Gly Glu Val Val Gly Asp Pro Met Glu Lys Ala Thr
                565                 570                 575

Leu Glu Trp Leu Gly Trp Thr Leu Gly Lys Asn Asp Thr Leu Ser Ser
            580                 585                 590

Lys Gly Asn Ala Pro Val Val Ser Gly Arg Ser Val Glu Ser Val Gln
            595                 600                 605

Ile Lys Arg Arg Phe Gln Phe Ser Ser Ala Leu Lys Arg Gln Ser Thr
            610                 615                 620

Ile Ala Thr Ile Thr Asn Asp Arg Asn Ala Ser Lys Lys Thr Lys
625                 630                 635                 640

Ser Thr Phe Val Gly Val Lys Gly Ala Pro Glu Thr Ile Asn Thr Met
                645                 650                 655

Leu Val Asn Thr Pro Pro Asn Tyr Glu Glu Thr Tyr Lys His Phe Thr
```

```
                    660                 665                 670
Arg Asn Gly Ala Arg Val Leu Ala Leu Ala Tyr Lys Tyr Leu Ser Ser
            675                 680                 685
Glu Thr Glu Leu Ser Gln Ser Arg Val Asn Asn Tyr Val Arg Glu Glu
        690                 695                 700
Ile Glu Ser Glu Leu Ile Phe Ala Gly Phe Leu Val Leu Gln Cys Pro
705                 710                 715                 720
Leu Lys Asp Asp Ala Ile Lys Ser Val Gln Met Leu Asn Glu Ser Ser
                725                 730                 735
His Arg Val Val Met Ile Thr Gly Asp Asn Pro Leu Thr Ala Val His
            740                 745                 750
Val Ala Arg Lys Val Glu Ile Val Asp Arg Glu Val Leu Ile Leu Asp
        755                 760                 765
Ala Pro Glu His Asp Asn Ser Gly Thr Lys Ile Val Trp Arg Thr Ile
    770                 775                 780
Asp Asp Lys Leu Asn Leu Glu Val Asp Pro Thr Lys Pro Leu Asp Pro
785                 790                 795                 800
Glu Ile Leu Lys Thr Lys Asp Ile Cys Ile Thr Gly Tyr Ala Leu Ala
                805                 810                 815
Lys Phe Lys Gly Gln Lys Ala Leu Pro Asp Leu Leu Arg His Thr Trp
            820                 825                 830
Val Tyr Ala Arg Val Ser Pro Lys Gln Lys Glu Glu Ile Leu Leu Gly
        835                 840                 845
Leu Lys Asp Ala Gly Tyr Thr Thr Leu Met Cys Gly Asp Gly Thr Asn
    850                 855                 860
Asp Val Gly Ala Leu Lys Gln Ala His Val Gly Val Ala Leu Leu Asn
865                 870                 875                 880
Gly Ser Gln Glu Asp Leu Thr Lys Ile Ala Glu His Tyr Arg Asn Thr
                885                 890                 895
Lys Met Lys Glu Leu Tyr Glu Lys Gln Val Ser Met Met Gln Arg Phe
            900                 905                 910
Asn Gln Pro Ala Pro Val Pro Val Leu Ile Ala His Leu Tyr Pro
        915                 920                 925
Pro Gly Pro Thr Asn Pro His Tyr Glu Lys Ala Met Glu Arg Glu Ser
    930                 935                 940
Gln Arg Lys Gly Ala Ala Ile Thr Ala Pro Gly Ser Thr Pro Glu Ala
945                 950                 955                 960
Ile Pro Thr Ile Thr Ser Pro Gly Ala Gln Ala Leu Gln Gln Ser Asn
                965                 970                 975
Leu Asn Pro Gln Gln Gln Lys Lys Gln Lys Gln Ala Gln Ala Ala Ala
            980                 985                 990
Gly Leu Ala Asp Lys Leu Thr Ser  Ser Met Met Glu Gln  Glu Leu Asp
        995                 1000                1005
Asp Ser  Glu Pro Pro Thr Ile  Lys Leu Gly Asp Ala  Ser Val Ala
    1010                1015                1020
Ala Pro  Phe Thr Ser Lys Leu  Ala Asn Val Ile Ala  Ile Pro Asn
    1025                1030                1035
Ile Ile  Arg Gln Gly Arg Cys  Thr Leu Val Ala Thr  Ile Gln Met
    1040                1045                1050
Tyr Lys  Ile Leu Ala Leu Asn  Cys Leu Ile Ser Ala  Tyr Ser Leu
    1055                1060                1065
Ser Val  Ile Tyr Leu Asp Gly  Ile Lys Phe Gly Asp  Gly Gln Val
    1070                1075                1080
```

Thr Ile Ser Gly Met Leu Met Ser Val Cys Phe Leu Ser Ile Ser
    1085                1090                1095

Arg Ala Lys Ser Val Glu Gly Leu Ser Lys Glu Arg Pro Gln Pro
    1100                1105                1110

Asn Ile Phe Asn Val Tyr Ile Ile Gly Ser Val Leu Gly Gln Phe
    1115                1120                1125

Ala Ile His Ile Ala Thr Leu Ile Tyr Leu Ser Asn Tyr Val Tyr
    1130                1135                1140

Lys His Glu Pro Arg Asp Ser Asp Ile Asp Leu Glu Gly Glu Phe
    1145                1150                1155

Glu Pro Ser Leu Leu Asn Ser Ala Ile Tyr Leu Leu Gln Leu Ile
    1160                1165                1170

Gln Gln Ile Ser Thr Phe Ser Ile Asn Tyr Gln Gly Arg Pro Phe
    1175                1180                1185

Arg Glu Ser Ile Arg Glu Asn Lys Gly Met Tyr Trp Gly Leu Ile
    1190                1195                1200

Ala Ala Ser Gly Val Ala Phe Ser Cys Ala Thr Glu Phe Ile Pro
    1205                1210                1215

Glu Leu Asn Glu Lys Leu Arg Leu Val Pro Phe Thr Asn Glu Phe
    1220                1225                1230

Lys Val Thr Leu Thr Val Leu Met Ile Phe Asp Tyr Gly Gly Cys
    1235                1240                1245

Trp Leu Ile Glu Asn Val Leu Lys His Leu Phe Ser Asp Phe Arg
    1250                1255                1260

Pro Lys Asp Ile Ala Ile Arg Arg Pro Asp Gln Leu Lys Arg Glu
    1265                1270                1275

Ala Glu Arg Lys Leu Gln Glu Gln Val Asp Ala Glu Ala Gln Lys
    1280                1285                1290

Glu Leu Gln Arg Lys Val
    1295

<210> SEQ ID NO 277
<211> LENGTH: 27
<212> TYPE: DNA
<213> ORGANISM: Artificial Sequence
<220> FEATURE:
<223> OTHER INFORMATION: a primer sequence for PCR

<400> SEQUENCE: 277
gcgcggtacc attgagacaa catggat                                      27

<210> SEQ ID NO 278
<211> LENGTH: 26
<212> TYPE: DNA
<213> ORGANISM: Artificial Sequence
<220> FEATURE:
<223> OTHER INFORMATION: a primer sequence for PCR

<400> SEQUENCE: 278
atttaaatag ttagacaata gtatca                                       26

<210> SEQ ID NO 279
<211> LENGTH: 35
<212> TYPE: DNA
<213> ORGANISM: Artificial Sequence
<220> FEATURE:
<223> OTHER INFORMATION: a primer sequence for PCR

<400> SEQUENCE: 279 gcgcgggta ccatgttgtc ttagcatttt catta                                 35

<210> SEQ ID NO 280
<211> LENGTH: 40
<212> TYPE: DNA
<213> ORGANISM: Artificial Sequence
<220> FEATURE:
<223> OTHER INFORMATION: a primer sequence for PCR

<400> SEQUENCE: 280
accacgctaa agatggggga ctttgcatac ccagcttcca                            40

<210> SEQ ID NO 281
<211> LENGTH: 40
<212> TYPE: DNA
<213> ORGANISM: Artificial Sequence
<220> FEATURE:
<223> OTHER INFORMATION: a primer sequence for PCR

<400> SEQUENCE: 281
tggaagctgg gtatgcaaag tcccccatct ttagcgtggt                            40

<210> SEQ ID NO 282
<211> LENGTH: 40
<212> TYPE: DNA
<213> ORGANISM: Artificial Sequence
<220> FEATURE:
<223> OTHER INFORMATION: a primer sequence for PCR

<400> SEQUENCE: 282
ggtacctctg ccatgaagtc ctcgatcatt gaccgataat                            40

<210> SEQ ID NO 283
<211> LENGTH: 40
<212> TYPE: DNA
<213> ORGANISM: Artificial Sequence
<220> FEATURE:
<223> OTHER INFORMATION: a primer sequence for PCR

<400> SEQUENCE: 283
attatcggtc aatgatcgag gacttcatgg cagaggtacc                            40

<210> SEQ ID NO 284
<211> LENGTH: 40
<212> TYPE: DNA
<213> ORGANISM: Artificial Sequence
<220> FEATURE:
<223> OTHER INFORMATION: a primer sequence for PCR

<400> SEQUENCE: 284
gagaggtgct agcagttgtt ctagttcgcg agtgatgaca                            40

<210> SEQ ID NO 285
<211> LENGTH: 40
<212> TYPE: DNA
<213> ORGANISM: Artificial Sequence
<220> FEATURE:
<223> OTHER INFORMATION: a primer sequence for PCR

<400> SEQUENCE: 285
tgtcatcact cgcgaactag aacaactgct agcacctctc                            40

<210> SEQ ID NO 286
<211> LENGTH: 40
<212> TYPE: DNA

```
<213> ORGANISM: Artificial Sequence
<220> FEATURE:
<223> OTHER INFORMATION: a primer sequence for PCR

<400> SEQUENCE: 286
cagtgctacc tcatgccagt ctggtgagtc cgtccaagta                    40

<210> SEQ ID NO 287
<211> LENGTH: 40
<212> TYPE: DNA
<213> ORGANISM: Artificial Sequence
<220> FEATURE:
<223> OTHER INFORMATION: a primer sequence for PCR

<400> SEQUENCE: 287
tacttggacg gactcaccag actggcatga ggtagcactg                    40

<210> SEQ ID NO 288
<211> LENGTH: 40
<212> TYPE: DNA
<213> ORGANISM: Artificial Sequence
<220> FEATURE:
<223> OTHER INFORMATION: a primer sequence for PCR

<400> SEQUENCE: 288
agtaaagcgc gaaaatgctc cggttgtgac tggatgcaac                    40

<210> SEQ ID NO 289
<211> LENGTH: 40
<212> TYPE: DNA
<213> ORGANISM: Artificial Sequence
<220> FEATURE:
<223> OTHER INFORMATION: a primer sequence for PCR

<400> SEQUENCE: 289
gttgcatcca gtcacaaccg gagcattttc gcgctttact                    40

<210> SEQ ID NO 290
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 290
attttcccta gatcacttct                                          20

<210> SEQ ID NO 291
<211> LENGTH: 40
<212> TYPE: DNA
<213> ORGANISM: Artificial Sequence
<220> FEATURE:
<223> OTHER INFORMATION: a primer sequence for PCR

<400> SEQUENCE: 291
ccgaattcga gctcggtacc ttgtcttagc attttcatta                    40

<210> SEQ ID NO 292
<211> LENGTH: 38
<212> TYPE: DNA
<213> ORGANISM: Artificial Sequence
<220> FEATURE:
<223> OTHER INFORMATION: a primer sequence for PCR

<400> SEQUENCE: 292
ctactacaga tccccgggtc gtaattttcc ctagatca                      38
```

<210> SEQ ID NO 293
<211> LENGTH: 28
<212> TYPE: DNA
<213> ORGANISM: Artificial Sequence
<220> FEATURE:
<223> OTHER INFORMATION: a primer sequence for PCR

<400> SEQUENCE: 293
gcggtacctg atccttcgag atcatact                                      28

<210> SEQ ID NO 294
<211> LENGTH: 28
<212> TYPE: DNA
<213> ORGANISM: Artificial Sequence
<220> FEATURE:
<223> OTHER INFORMATION: a primer sequence for PCR

<400> SEQUENCE: 294
atttaaataa gcctctcaga ctctactc                                      28

<210> SEQ ID NO 295
<211> LENGTH: 26
<212> TYPE: DNA
<213> ORGANISM: Artificial Sequence
<220> FEATURE:
<223> OTHER INFORMATION: a primer sequence for PCR

<400> SEQUENCE: 295
atttaaatgt cgtacatatg ctatgt                                        26

<210> SEQ ID NO 296
<211> LENGTH: 26
<212> TYPE: DNA
<213> ORGANISM: Artificial Sequence
<220> FEATURE:
<223> OTHER INFORMATION: a primer sequence for PCR

<400> SEQUENCE: 296
gcggtaccac aactcaactc aatagg                                        26

<210> SEQ ID NO 297
<211> LENGTH: 40
<212> TYPE: DNA
<213> ORGANISM: Artificial Sequence
<220> FEATURE:
<223> OTHER INFORMATION: a primer sequence for PCR

<400> SEQUENCE: 297
ccgaattcga gctcggtacc tcgctattgt cagttacaca                         40

<210> SEQ ID NO 298
<211> LENGTH: 38
<212> TYPE: DNA
<213> ORGANISM: Artificial Sequence
<220> FEATURE:
<223> OTHER INFORMATION: a primer sequence for PCR

<400> SEQUENCE: 298
ctactacaga tccccgggga acaatcccga cacatgaa                           38

METHOD FOR PRODUCING PYRIPYROPENE

CROSS-REFERENCE TO RELATED APPLICATION

This patent application claims priority to Japanese Patent Application No. 14727/2010 that was filed on Jan. 26, 2010, and the entire disclosure is incorporated herein by reference.

BACKGROUND OF THE INVENTION

1. Field of Invention

The present invention relates to a method for producing pyripyropene, more specifically, a method for producing pyripyropene A, E, O or the like.

2. Background Art

Pyripyropene A has, as disclosed in Japanese Patent Laid-Open Publication No. 360895/1992 (Patent Document 1) and Journal of Antibiotics (1993), 46(7), 1168-9 (Non-patent Document 1), an inhibitory activity against ACAT (acyl CoA cholesterol acyltransferase) and application thereof to treatment of diseases caused by cholesterol accumulation or the like is expected.

As a pyripyropene A-producing fungus, *Aspergillus fumigatus* FO-1289 strain has been disclosed in Japanese Patent Laid-Open Publication No. 360895/1992 (Patent Document 1); *Eupenicillium reticulosporum* NRRL-3446 strain has been disclosed in Applied and Environmental Microbiology (1995), 61(12), 4429-35 (Non-patent Document 2); *Penicillium griseofulvum* F1959 strain has been disclosed in WO2004/060065 (Patent Document 2); and *Penicillium coprobium* PF1169 strain has been disclosed in Journal of Technical Disclosure 500997/2008 (Patent Document 3).

Further, as a biosynthetic route of pyripyropene A, a putative biosynthetic route in *Aspergillus fumigatus* FO-1289 strain has been disclosed in Journal of Organic Chemistry (1996), 61, 882-886 (Non-patent Document 3) and Chemical Review (2005), 105, 4559-4580 (Non-patent Document 4). These documents have disclosed that, in *Aspergillus fumigatus* FO-1289 strain, partial structures individually synthesized by polyketide synthase or prenyltransferase are linked to synthesize pyripyropene A by a cyclase.

PRIOR ART REFERENCES

Patent Documents

[Patent Document 1] Japanese Patent Laid-Open Publication No. 360895/1992
[Patent Document 2] WO2004/060065
[Patent Document 3] Journal of Technical Disclosure 500997/2008

Non-Patent Documents

[Non-patent Document 1] Journal of Antibiotics (1993), 46(7), 1168-9.
[Non-patent Document 2] Applied and Environmental Microbiology (1995), 61(12), 4429-35.
[Non-patent Document 3] Journal of Organic Chemistry (1996), 61, 882-886.
[Non-patent Document 4] Chemical Review (2005), 105, 4559-4580.

SUMMARY OF THE INVENTION

The present inventors have now found that pyripyropene A or the like was able to be produced by culturing a microorganism in which a particular polynucleotide or a recombinant vector comprising it/them was introduced with an intermediate compound necessary for the biosynthesis of pyripyropene A. The present invention has been made based on such finding.

Accordingly, an object of the present invention is to provide a method for producing pyripyropene A.

Further, according to one embodiment of the present invention, a method for producing pyripyropene A, characterized by culturing a microorganism in which at least one polynucleotide in (I) to (III) below or a recombinant vector comprising it/them is introduced with pyripyropene E and isolating pyripyropene A via pyripyropene O is provided:

(I) an isolated polynucleotide having at least one nucleotide sequence selected from the nucleotide sequences in (a) to (d) below:
  (a) a nucleotide sequence of SEQ ID NO:266,
  (b) a nucleotide sequence which is capable of hybridizing with a sequence complementary to the nucleotide sequence of SEQ ID NO:266 under stringent conditions, and which encodes a protein substantially equivalent to a protein encoded by the nucleotide sequence of SEQ ID NO:266,
  (c) a nucleotide sequence of a polynucleotide of the nucleotide sequence of SEQ ID NO:266 in which one or more nucleotides are deleted, substituted, inserted or added, and which encodes a protein substantially equivalent to a protein encoded by the nucleotide sequence of SEQ ID NO:266, and
  (d) a nucleotide sequence having at least 90% identity to a polynucleotide of the nucleotide sequence of SEQ ID NO:266, and which encodes a protein substantially equivalent to a protein encoded by the nucleotide sequence of SEQ ID NO: 266;

(II) an isolated polynucleotide having a nucleotide sequence encoding at least one amino acid sequence selected from SEQ ID NOs:267 to 275 or a substantially equivalent amino acid sequence thereto; and (III) an isolated polynucleotide having at least one nucleotide sequence selected from the nucleotide sequences in (1) to (4) below:
  (1) a nucleotide sequence in (a) to (i) below:
    (a) a nucleotide sequence from 3342 to 5158 of a nucleotide sequence shown in SEQ ID NO:266,
    (b) a nucleotide sequence from 5382 to 12777 of a nucleotide sequence shown in SEQ ID NO:266,
    (c) a nucleotide sequence from 13266 to 15144 of a nucleotide sequence shown in SEQ ID NO:266,
    (d) a nucleotide sequence from 16220 to 18018 of a nucleotide sequence shown in SEQ ID NO:266,
    (e) a nucleotide sequence from 18506 to 19296 of a nucleotide sequence shown in SEQ ID NO:266,
    (f) a nucleotide sequence from 19779 to 21389 of a nucleotide sequence shown in SEQ ID NO:266,
    (g) a nucleotide sequence from 21793 to 22877 of a nucleotide sequence shown in SEQ ID NO:266,
    (h) a nucleotide sequence from 23205 to 24773 of a nucleotide sequence shown in SEQ ID NO:266, and
    (i) a nucleotide sequence from 25824 to 27178 of a nucleotide sequence shown in SEQ ID NO:266;
  (2) a nucleotide sequence which is capable of hybridizing with a sequence complementary to the nucleotide sequence in (1) under stringent conditions, and which encodes a protein substantially equivalent to a protein encoded by each nucleotide sequence;
  (3) a nucleotide sequence of a polynucleotide of the nucleotide sequence in (1) in which one or more nucleotides are deleted, substituted, inserted or added, and which encodes a protein substantially equivalent to a protein encoded by each nucleotide sequence; and (4) a nucleotide sequence having at least 90% identity to a polynucleotide of the nucleotide sequence in (1), and which encodes a protein substantially equivalent to a protein encoded by each nucleotide sequence.

Also, according to another embodiment of the present invention, a method for producing pyripyropene A characterized by culturing a microorganism in which at least one polynucleotide in the above-mentioned (I) to (III) or a recombinant vector comprising it/them is introduced with deacetyl pyripyropene E and isolating pyripyropene A via pyripyropene E and pyripyropene O is provided.

Further, according to another embodiment of the present invention, a method for producing 4-hydroxy-6-(pyridin-3-yl)-3-((2E,6E)-3,7,11-trimethyldodeca-2,6,10-trienyl)-2H-pyran-2-one, characterized by culturing a microorganism in which at least one polynucleotide in the above-mentioned (I) to (III) or a recombinant vector comprising it/them is introduced with 4-oxo-6-(3-pyridyl)-α-pyrone and isolating 4-hydroxy-6-(pyridin-3-yl)-3-((2E,6E)-3,7,11-trimethyldodeca-2,6,10-trienyl)-2H-pyran-2-one is provided.

According to another embodiment of the present invention, at least one isolated polynucleotide of the above (I) to (III) is provided.

Further, according to another embodiment of the present invention, a recombinant vector selected from the group consisting of pPP6 (Accession No. of *Aspergillus oryzae* transformed with plasmid pPP6: FERM BP-11218), pPP7 (Accession No. of *Aspergillus oryzae* transformed with plasmid pPP7: FERM BP-11219) and pPP9 (Accession No. of *Aspergillus oryzae* transformed with plasmid pPP9: FERM BP-11220) is provided.

Still further, according to another embodiment of the present invention, a transformant comprising one or more vectors selected from the group consisting of plasmids pPP6, pPP7 and pPP9 is provided.

According to another embodiment of the present invention, use of the above-mentioned recombinant vector for producing pyripyropene A is provided.

According to another embodiment of the present invention, use of the above-mentioned transformant for producing pyripyropene A is provided.

According to the production method of the present invention, pyripyropene A, E, O or the like is able to be produced by gene recombination techniques. Therefore, the production method of the present invention makes a significant contribution to mass production technology of pyripyropene A, E, O or the like.

BRIEF DESCRIPTION OF DRAWINGS

FIG. 2 shows an electrophoresis pattern of PCR products by agarose gel. For the electrophoresis, the PCR products amplified using the following primers were used: M: molecular weight marker (100 bp ladder), lane 1: primers of SEQ ID NOs:253 and 254, lane 2: primers of SEQ ID NOs:257 and 258, lane 3: primers of SEQ ID NOs: 259 and 260, lane 4: primers of SEQ ID NOs:255 and 256, lane 5: primers of SEQ ID NOs:261 and 262.

FIG. 3 shows an electrophoresis pattern of PCR products by agarose gel. For the electrophoresis, the PCR products amplified using the following primers were used: lane 1: molecular weight marker (100 bp ladder), lane 2: primers of SEQ ID NOs:264 and 265 (400 bp amplified fragment).

DETAILED DESCRIPTION OF THE INVENTION

Deposition of Microorganisms

Figure 1:
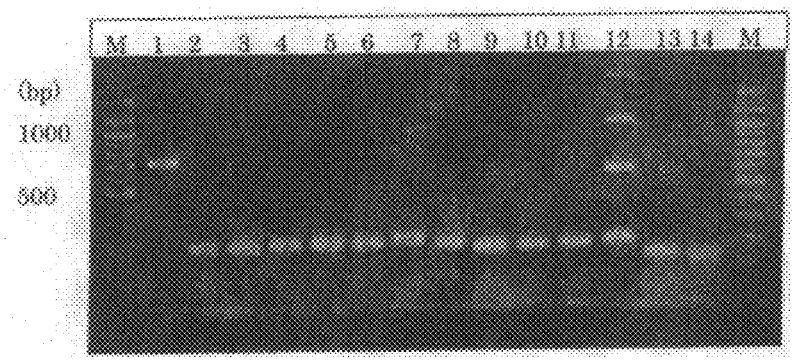
FIG. 1 shows an electrophoresis pattern of PCR products by agarose gel. For the electrophoresis, the PCR products amplified using the following primers were used: M: molecular weight marker (100 bp ladder), lane 1: primers of SEQ ID NOs:1 and 2, lane 2: primers of SEQ ID NOs:239 and 240, lane 3: primers of SEQ ID NOs:237 and 238, lane 4: primers of SEQ ID NOs:241 and 242, lane 5: primers of SEQ ID NOs:247 and 248, lane 6: primers of SEQ ID NOs:251 and 252, lane 7: primers of SEQ ID NOs:245 and 246, lane 8: primers of SEQ ID NOs:243 and 244, lane 9: primers of SEQ ID NOs:249 and 250, lane 10: primers of SEQ ID NOs:235 and 236, lane 11: primers of SEQ ID NOs:233 and 234, lane 12: primers of SEQ ID NOs:227 and 228, lane 13: primers of SEQ ID NOs:229 and 230, lane 14: primers of SEQ ID NOs:231 and 232.

*Escherichia coli* (*Escherichia coli* EPI300™-T1®) transformed with plasmid pCC1-PP1 has been deposited with International Patent Organism Depositary, National Institute of Advanced Industrial Science and Technology (Address: AIST Tsukuba Central 6, 1-1-1 Higashi, Tsukuba, Ibaraki, Japan, 305-8566), under accession No. FERM BP-11133 (converted from domestic deposition under accession No. FERM P-21704) (identification reference by the depositors: *Escherichia coli* EPI300™-T1®/pCC1-PP1) as of Oct. 9, 2008 (original deposition date).

*Aspergillus oryzae* transformed with plasmid pPP2 has been deposited with International Patent Organism Depositary, National Institute of Advanced Industrial Science and Technology (Address: AIST Tsukuba Central 6, 1-1-1 Higashi, Tsukuba, Ibaraki, Japan, 305-8566), under accession No. FERM BP-11137 (identification reference by the depositors: *Aspergillus oryzae* PP2-1) as of Jun. 23, 2009.

*Aspergillus oryzae* transformed with plasmid pPP3 has been deposited with International Patent Organism Depositary, National Institute of Advanced Industrial Science and Technology (Address: AIST Tsukuba Central 6, 1-1-1 Higashi, Tsukuba, Ibaraki, Japan, 305-8566), under accession No. FERM BP-11141 (identification reference by the depositors: *Aspergillus oryzae* PP3-2) as of Jul. 3, 2009.

*Aspergillus oryzae* transformed with plasmid pPP6 has been deposited with International Patent Organism Depositary, National Institute of Advanced Industrial Science and Technology (Address: AIST Tsukuba Central 6, 1-1-1 Higashi, Tsukuba, Ibaraki, Japan, 305-8566), under accession No. FERM BP-11218 (identification reference by the depositors: *Aspergillus oryzae* PP6) as of Dec. 21, 2009.

*Aspergillus oryzae* transformed with plasmid pPP7 has been deposited with International Patent Organism Depositary, National Institute of Advanced Industrial Science and Technology (Address: AIST Tsukuba Central 6, 1-1-1 Higashi, Tsukuba, Ibaraki, Japan, 305-8566), under accession No. FERM BP-11219 (identification reference by the depositors: *Aspergillus oryzae* PP7) as of Dec. 21, 2009.

*Aspergillus oryzae* transformed with plasmid pPP9 has been deposited with International Patent Organism Depositary, National Institute of Advanced Industrial Science and Technology (Address: AIST Tsukuba Central 6, 1-1-1 Higashi, Tsukuba, Ibaraki, Japan, 305-8566), under accession No. FERM BP-11220 (identification reference by the depositors: *Aspergillus oryzae* PP9) as of Dec. 21, 2009.

Method for Producing Pyripyropene

The present invention relates to a method for producing pyripyropene, wherein a secondary metabolism product is obtained by culturing a microorganism in which a gene involved in biosynthesis of pyripyropene A is introduced with an intermediate compound necessary for the biosynthesis of pyripyropene A.

An example of a biosynthetic pathway of pyripyropene A includes the following Scheme 1.

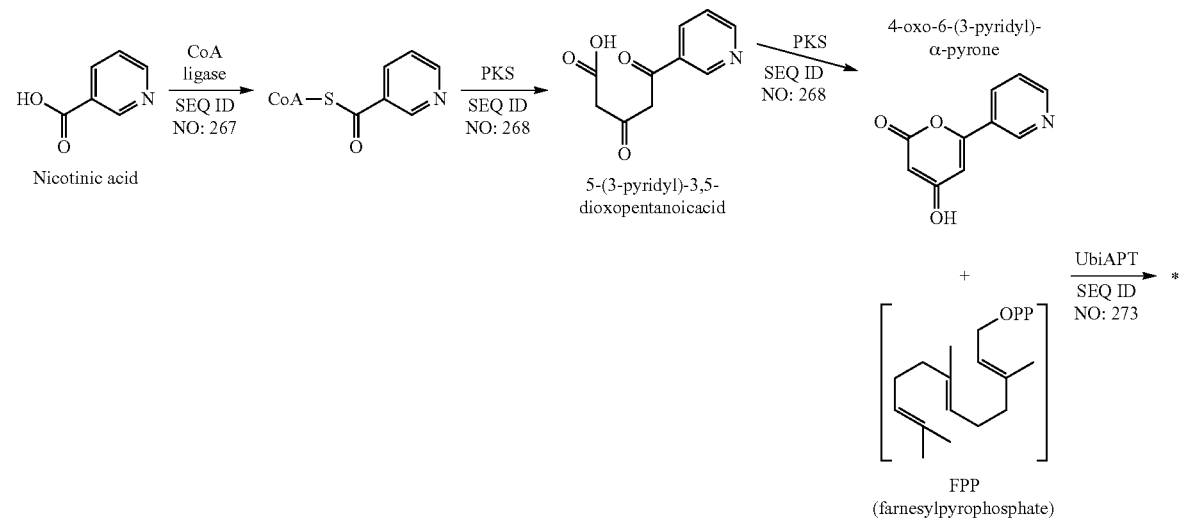

Scheme 1

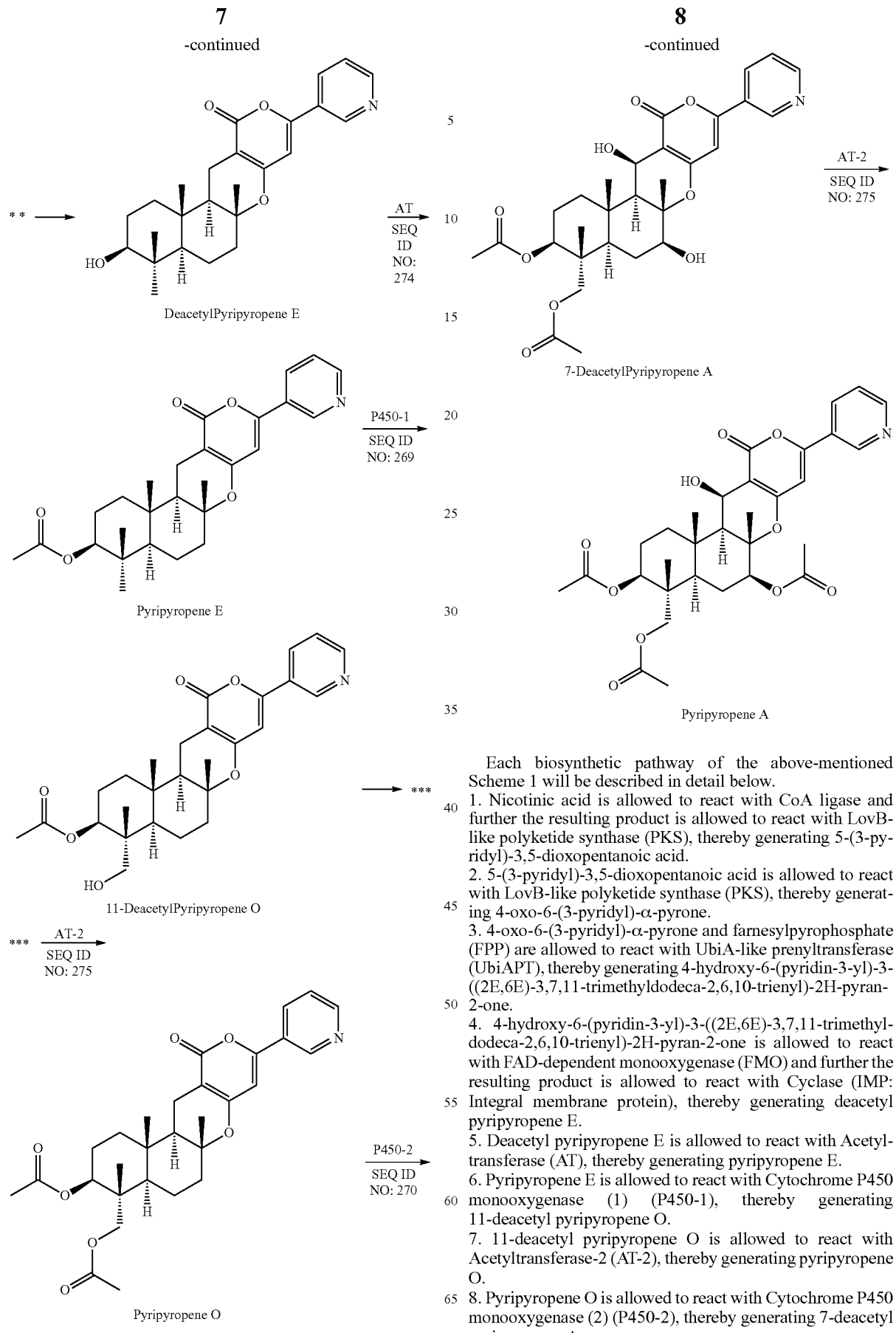

Each biosynthetic pathway of the above-mentioned Scheme 1 will be described in detail below.

1. Nicotinic acid is allowed to react with CoA ligase and further the resulting product is allowed to react with LovB-like polyketide synthase (PKS), thereby generating 5-(3-pyridyl)-3,5-dioxopentanoic acid.

2. 5-(3-pyridyl)-3,5-dioxopentanoic acid is allowed to react with LovB-like polyketide synthase (PKS), thereby generating 4-oxo-6-(3-pyridyl)-α-pyrone.

3. 4-oxo-6-(3-pyridyl)-α-pyrone and farnesylpyrophosphate (FPP) are allowed to react with UbiA-like prenyltransferase (UbiAPT), thereby generating 4-hydroxy-6-(pyridin-3-yl)-3-((2E,6E)-3,7,11-trimethyldodeca-2,6,10-trienyl)-2H-pyran-2-one.

4. 4-hydroxy-6-(pyridin-3-yl)-3-((2E,6E)-3,7,11-trimethyldodeca-2,6,10-trienyl)-2H-pyran-2-one is allowed to react with FAD-dependent monooxygenase (FMO) and further the resulting product is allowed to react with Cyclase (IMP: Integral membrane protein), thereby generating deacetyl pyripyropene E.

5. Deacetyl pyripyropene E is allowed to react with Acetyltransferase (AT), thereby generating pyripyropene E.

6. Pyripyropene E is allowed to react with Cytochrome P450 monooxygenase (1) (P450-1), thereby generating 11-deacetyl pyripyropene O.

7. 11-deacetyl pyripyropene O is allowed to react with Acetyltransferase-2 (AT-2), thereby generating pyripyropene O.

8. Pyripyropene O is allowed to react with Cytochrome P450 monooxygenase (2) (P450-2), thereby generating 7-deacetyl pyripyropene A.

9. 7-deacetyl pyripyropene A is allowed to react with Acetyltransferase-2 (AT-2), thereby generating pyripyropene A.

Deacetyl pyripyropene E is able to be synthesized, for example, by the method in Reference Example 3 below. Pyripyropene E is able to be obtained, for example, by the method described in Japanese Patent Laid-Open Publication No. 239385/1996.

11-deacetyl pyripyropene O is able to be synthesized, for example, by the method described in Reference Example 4 below.

Pyripyropene O is able to be obtained, for example, by the method described in J. Antibiot. 1996, 49, 292.

7-deacetyl pyripyropene A is able to be synthesized, for example, by the method described in Japanese Patent Laid-Open Publication No. 259569/1996.

4-oxo-6-(3-pyridyl)-α-pyrone is able to be synthesized, for example, by the method described in J. Org. Chem. 1983. 48. 3945.

According to a preferred embodiment of the production method of the present invention, which method comprises culturing with pyripyropene E, a method for producing pyripyropene A characterized by culturing a microorganism comprising one or more vectors selected from the group consisting of plasmids pCC1-PP1, pPP2, pPP3, pPP6, pPP7 and pPP9 with pyripyropene E and isolating pyripyropene A via pyripyropene O is provided.

According to a preferred embodiment of the production method of the present invention, which method comprises culturing with pyripyropene E, a method for producing pyripyropene A characterized by culturing a microorganism in which at least one polynucleotide in (IV) and (V) below or a recombinant vector comprising it/them is introduced with pyripyropene E and isolating pyripyropene A via pyripyropene O is provided:

(IV) An isolated polynucleotide having at least one nucleotide sequence selected from the nucleotide sequences encoding at least one amino acid sequence selected from SEQ ID NOs:269, 270 and 275 or a substantially equivalent amino acid sequence thereto; and (V) A polynucleotide having at least one nucleotide sequence selected from the nucleotide sequences in (1) to (4) below:
   (1) a nucleotide sequence in (a) to (c) below:
     (a) a nucleotide sequence from 13266 to 15144 of a nucleotide sequence shown in SEQ ID NO:266,
     (b) a nucleotide sequence from 16220 to 18018 of a nucleotide sequence shown in SEQ ID NO:266, and
     (c) a nucleotide sequence from 25824 to 27178 of a nucleotide sequence shown in SEQ ID NO:266;
   (2) a nucleotide sequence which is capable of hybridizing with a sequence complementary to the nucleotide sequence in (1) under stringent conditions, and which encodes a protein substantially equivalent to a protein encoded by each nucleotide sequence;
   (3) a nucleotide sequence of a polynucleotide of the nucleotide sequence in (1) in which one or more nucleotides are deleted, substituted, inserted or added, and which encodes a protein substantially equivalent to a protein encoded by each nucleotide sequence; and
   (4) a nucleotide sequence having at least 90% identity to a polynucleotide of the nucleotide sequence in (1), and which encodes a protein substantially equivalent to a protein encoded by each nucleotide sequence.

According to a preferred embodiment of the production method of the present invention, which method comprises culturing with pyripyropene E, a method for producing pyripyropene A characterized by culturing a microorganism comprising one or more vectors selected from the group consisting of plasmids pPP2, pPP3 and pPP9 with pyripyropene E and isolating pyripyropene A via pyripyropene O is provided.

According to a more preferred embodiment of the production method of the present invention, which method comprises culturing with pyripyropene E, a method for producing pyripyropene A characterized by culturing a microorganism comprising plasmids pPP2, pPP3 and pPP9 with pyripyropene E and isolating pyripyropene A via pyripyropene O is provided.

According to a preferred embodiment of the production method of the present invention, which method comprises culturing with deacetyl pyripyropene E, a method for producing pyripyropene A characterized by culturing a microorganism in which at least one polynucleotide in the above-mentioned (I) to (III) or a recombinant vector comprising it/them is introduced with deacetyl pyripyropene E and isolating pyripyropene A via pyripyropene E and pyripyropene O is provided.

According to a preferred embodiment of the production method of the present invention, which method comprises culturing with deacetyl pyripyropene E, a method for producing pyripyropene A characterized by culturing a microorganism comprising one or more vectors selected from the group consisting of plasmids pCC1-PP1, pPP2, pPP3, pPP6, pPP7 and pPP9 with deacetyl pyripyropene E and isolating pyripyropene A via pyripyropene E and pyripyropene O is provided.

According to a preferred embodiment of the production method of the present invention, which method comprises culturing with deacetyl pyripyropene E, a method for producing pyripyropene A characterized by culturing a microorganism in which at least one polynucleotide in (VI) and (VII) below or a recombinant vector comprising it/them is introduced with deacetyl pyripyropene E and isolating pyripyropene A via pyripyropene E and pyripyropene O is provided:

(VI) An isolated polynucleotide having at least one nucleotide sequence selected from the polynucleotide sequences encoding at least one amino acid sequence selected from SEQ ID NOs:269, 270, 274 and 275 or a substantially equivalent amino acid sequence thereto; and (VII) An isolated polynucleotide having at least one nucleotide sequence selected from the nucleotide sequences in (1) to (4) below:
   (1) a nucleotide sequence in (a) to (d) below:
     (a) a nucleotide sequence from 13266 to 15144 of a nucleotide sequence shown in SEQ ID NO:266,
     (b) a nucleotide sequence from 16220 to 18018 of a nucleotide sequence shown in SEQ ID NO:266,
     (c) a nucleotide sequence from 23205 to 24773 of a nucleotide sequence shown in SEQ ID NO:266, and
     (d) a nucleotide sequence from 25824 to 27178 of a nucleotide sequence shown in SEQ ID NO:266;
   (2) a nucleotide sequence which is capable of hybridizing with a sequence complementary to the nucleotide sequence in (1) under stringent conditions, and which encodes a protein substantially equivalent to a protein encoded by each nucleotide sequence;
   (3) a nucleotide sequence of a polynucleotide of the nucleotide sequence in (1) in which one or more nucleotides are deleted, substituted, inserted or added, and which encodes a protein substantially equivalent to a protein encoded by each nucleotide sequence; and
   (4) a nucleotide sequence having at least 90% identity to a polynucleotide of the nucleotide sequence in (1), and which encodes a protein substantially equivalent to a protein encoded by each nucleotide sequence.

According to a preferred embodiment of the production method of the present invention, which method comprises culturing with deacetyl pyripyropene E, a method for producing pyripyropene A characterized by culturing a microorganism comprising one or more vectors selected from the group consisting of plasmids pPP2, pPP3, pPP7 and pPP9 with deacetyl pyripyropene E and isolating pyripyropene A via pyripyropene E and pyripyropene O is provided.

According to a more preferred embodiment of the production method of the present invention, which method comprises culturing with deacetyl pyripyropene E, a method for producing pyripyropene A characterized by culturing a microorganism comprising plasmids pPP2, pPP3, pPP7 and pPP9 with deacetyl pyripyropene E and isolating pyripyropene A via pyripyropene E and pyripyropene O is provided.

According to a preferred embodiment of the production method of the present invention, which method comprises culturing with 4-oxo-6-(3-pyridyl)-α-pyrone, a method for producing 4-hydroxy-6-(pyridin-3-yl)-3-((2E,6E)-3,7,11-trimethyldodeca-2,6,10-trienyl)-2H-pyran-2-one characterized by culturing a microorganism in which at least one polynucleotide in the above-mentioned (I) to (III) or a recombinant vector comprising it/them is introduced with 4-oxo-6-(3-pyridyl)-α-pyrone and isolating 4-hydroxy-6-(pyridin-3-yl)-3-((2E,6E)-3,7,11-trimethyldodeca-2,6,10-trienyl)-2H-pyran-2-one is provided. In this case, it is preferred that, as the above-mentioned microorganism, one capable of biosynthesis of farnesylpyrophosphate (FPP) inside the body cell be used. An example of such microorganisms includes microorganisms belonging to the genus *Aspergillus*.

According to a preferred embodiment of the production method of the present invention, which method comprises culturing with 4-oxo-6-(3-pyridyl)-α-pyrone, a method for producing 4-hydroxy-6-(pyridin-3-yl)-3-((2E,6E)-3,7,11-trimethyldodeca-2,6,10-trienyl)-2H-pyran-2-one characterized by culturing a microorganism comprising one or more vectors selected from the group consisting of plasmids pCC1-PP1, pPP2, pPP3, pPP6, pPP7 and pPP9 with 4-oxo-6-(3-pyridyl)-α-pyrone and isolating 4-hydroxy-6-(pyridin-3-yl)-3-((2E,6E)-3,7,11-trimethyldodeca-2,6,10-trienyl)-2H-pyran-2-one is provided.

According to a preferred embodiment of the production method of the present invention, which method comprises culturing with 4-oxo-6-(3-pyridyl)-α-pyrone, a method for producing 4-hydroxy-6-(pyridin-3-yl)-3-((2E,6E)-3,7,11-trimethyldodeca-2,6,10-trienyl)-2H-pyran-2-one, characterized by culturing a microorganism in which at least one polynucleotide in (VIII) and (IX) below or a recombinant vector comprising it/them is introduced with 4-oxo-6-(3-pyridyl)-α-pyrone and isolating 4-hydroxy-6-(pyridin-3-yl)-3-((2E,6E)-3,7,11-trimethyldodeca-2,6,10-trienyl)-2H-pyran-2-one is provided:

(VIII) An isolated polynucleotide having at least one nucleotide sequence selected from the nucleotide sequences encoding the amino acid sequence of SEQ ID NO:273 or a substantially equivalent amino acid sequence thereto;

(IX) A polynucleotide having at least one nucleotide sequence selected from the nucleotide sequences in (1) to (4) below: and (1) a nucleotide sequence from 21793 to 22877 of a nucleotide sequence shown in SEQ ID NO:266;

(2) a nucleotide sequence which is capable of hybridizing with a sequence complementary to the nucleotide sequence in (1) under stringent conditions, and which encodes a protein substantially equivalent to a protein encoded by the nucleotide sequence;

(3) a nucleotide sequence of a polynucleotide of the nucleotide sequence in (1) in which one or more nucleotides are deleted, substituted, inserted or added, and which encodes a protein substantially equivalent to a protein encoded by the nucleotide sequence; and (4) a nucleotide sequence having at least 90% identity to a polynucleotide of the nucleotide sequence in (1), and which encodes a protein substantially equivalent to a protein encoded by the nucleotide sequence.

According to a more preferred embodiment of the production method of the present invention, which method comprises culturing with 4-oxo-6-(3-pyridyl)-α-pyrone, a method for providing 4-hydroxy-6-(pyridin-3-yl)-3-((2E,6E)-3,7,11-trimethyldodeca-2,6,10-trienyl)-2H-pyran-2-one characterized by culturing a microorganism comprising plasmid pPP6 with 4-oxo-6-(3-pyridyl)-α-pyrone and isolating 4-hydroxy-6-(pyridin-3-yl)-3-((2E,6E)-3,7,11-trimethyldodeca-2,6,10-trienyl)-2H-pyran-2-one is provided.

According to a preferred embodiment of the production method of the present invention, which method comprises culturing with deacetyl pyripyropene E, a method for producing pyripyropene E characterized by culturing a microorganism in which at least one polynucleotide in the above-mentioned (I) to (III) or a recombinant vector comprising it/them is introduced with deacetyl pyripyropene E and isolating pyripyropene E is provided.

According to a preferred embodiment of the production method of the present invention, which method comprises culturing with deacetyl pyripyropene E, a method for producing pyripyropene E characterized by culturing a microorganism comprising one or more vectors selected from the group consisting of plasmids pCC1-PP1, pPP2, pPP3, pPP6, pPP7 and pPP9 with deacetyl pyripyropene E and isolating pyripyropene E is provided.

According to a preferred embodiment of the production method of the present invention, which method comprises culturing with deacetyl pyripyropene E, a method for producing pyripyropene E characterized by culturing a microorganism in which at least one polynucleotide in (X) and (XI) below or a recombinant vector comprising it/them is introduced with deacetyl pyripyropene E and isolating pyripyropene E is provided:

(X) an isolated polynucleotide having at least one nucleotide sequence selected from the nucleotide sequences encoding amino acid sequence of SEQ ID NO:274 or a substantially equivalent amino acid sequence thereto; and (XI) an polynucleotide having at least one nucleotide sequence selected from the nucleotide sequences in (1) to (4) below:

(1) a nucleotide sequence from 23205 to 24773 of the nucleotide sequence shown in SEQ ID NO:266, (2) a nucleotide sequence which is capable of hybridizing with a sequence complementary to the nucleotide sequence in (1) under stringent conditions, and which encodes a protein substantially equivalent to a protein encoded by the nucleotide sequence;

(3) a nucleotide sequence of a polynucleotide of the nucleotide sequence in (1) in which one or more nucleotides are deleted, substituted, inserted or added, and which encodes a protein substantially equivalent to a protein encoded by the nucleotide sequence; and (4) a nucleotide sequence having at least 90% identity to a polynucleotide of the nucleotide sequence in (1), and which encodes a protein substantially equivalent to a protein encoded by the nucleotide sequence.

According to a more preferred embodiment of the production method of the present invention, which method comprises culturing with deacetyl pyripyropene E, a method for producing pyripyropene E characterized by culturing a microorganism comprising plasmid pPP7 with deacetyl pyripyropene E and isolating pyripyropene E is provided.

According to a more preferred embodiment of the production method of the present invention, which method comprises culturing with pyripyropene E, a method for producing pyripyropene O characterized by culturing a microorganism in which at least one polynucleotide in the above-mentioned (I) to (III) or a recombinant vector comprising it/them is introduced with pyripyropene E and isolating pyripyropene O is provided.

According to a more preferred embodiment of the production method of the present invention, which method comprises culturing with pyripyropene E, a method for producing pyripyropene O characterized by culturing a microorganism comprising one or more vectors selected from the group consisting of plasmids pCC1-PP1, pPP2, pPP3, pPP6, pPP7 and pPP9 with pyripyropene E and isolating pyripyropene O is provided.

According to a more preferred embodiment of the production method of the present invention, which method comprises culturing with pyripyropene E, a method for producing pyripyropene O characterized by culturing a microorganism in which at least one polynucleotide in (XII) and (XIII) below or a recombinant vector comprising it/them is introduced with pyripyropene E and isolating pyripyropene O is provided:
(XII) an isolated polynucleotide having at least one nucleotide sequence selected from the nucleotide sequences encoding at least one amino acid sequence selected from SEQ ID NOs:269 and 275 or a substantially equivalent amino acid sequence thereto; and
(XIII) a polynucleotide having at least one nucleotide sequence selected from the nucleotide sequences in (1) to (4) below:
  (1) a nucleotide sequence in (a) to (b) below:
    (a) a nucleotide sequence from 13266 to 15144 of a nucleotide sequence shown in SEQ ID NO:266, and
    (b) a nucleotide sequence from 25824 to 27178 of a nucleotide sequence shown in SEQ ID NO:266;
  (2) a nucleotide sequence which is capable of hybridizing with a sequence complementary to the nucleotide sequence in (1) under stringent conditions, and which encodes a protein substantially equivalent to a protein encoded by each nucleotide sequence;
  (3) a nucleotide sequence of a polynucleotide of the nucleotide sequence in (1) in which one or more nucleotides are deleted, substituted, inserted or added, and which encodes a protein substantially equivalent to a protein encoded by each nucleotide sequence; and
  (4) a nucleotide sequence having at least 90% identity to a polynucleotide of the nucleotide sequence in (1), and which encodes a protein substantially equivalent to a protein encoded by each nucleotide sequence.

According to a more preferred embodiment of the production method of the present invention, which method comprises culturing with pyripyropene E, a method for producing pyripyropene O characterized by culturing a microorganism comprising one or more vectors selected from the group consisting of plasmids pPP2 and pPP9 with pyripyropene E and isolating pyripyropene O is provided.

According to a more preferred embodiment of the production method of the present invention, which method comprises culturing with pyripyropene E, a method for producing pyripyropene O characterized by culturing a microorganism comprising plasmids pPP2 and pPP9 with pyripyropene E and isolating pyripyropene O is provided.

According to a more preferred embodiment of the production method of the present invention, which method comprises culturing with pyripyropene E, a method for producing 11-deacetyl pyripyropene O characterized by culturing a microorganism in which at least one polynucleotide in the above-mentioned (I) to (III) or a recombinant vector comprising it/them is introduced with pyripyropene E and isolating 11-deacetyl pyripyropene O is provided.

According to a more preferred embodiment of the production method of the present invention, which method comprises culturing with pyripyropene E, a method for producing 11-deacetyl pyripyropene O characterized by culturing a microorganism comprising one or more vectors selected from the group consisting of plasmids pCC1-PP1, pPP2, pPP3, pPP6, pPP7 and pPP9 with pyripyropene E and isolating 11-deacetyl pyripyropene O is provided.

According to a more preferred embodiment of the production method of the present invention, which method comprises culturing with pyripyropene E, a method for producing 11-deacetyl pyripyropene O characterized by culturing a microorganism in which at least one polynucleotide in (XIV) and (XV) below or a recombinant vector comprising it/them is introduced with pyripyropene E and isolating 11-deacetyl pyripyropene O is provided:
(XIV) an isolated polynucleotide having at least one nucleotide sequence selected from the nucleotide sequences encoding amino acid sequence of SEQ ID NO:269 or a substantially equivalent amino acid sequence thereto; and
(XV) a polynucleotide having at least one nucleotide sequence selected from the nucleotide sequences in (1) to (4) below:
  (1) a nucleotide sequence from 13266 to 15144 of the nucleotide sequence shown in SEQ ID NO:266;
  (2) a nucleotide sequence which is capable of hybridizing with a sequence complementary to the nucleotide sequence in (1) under stringent conditions, and which encodes a protein substantially equivalent to a protein encoded by the nucleotide sequence;
  (3) a nucleotide sequence of a polynucleotide of the nucleotide sequence in (1) in which one or more nucleotides are deleted, substituted, inserted or added, and which encodes a protein substantially equivalent to a protein encoded by the nucleotide sequence; and
  (4) a nucleotide sequence having at least 90% identity to a polynucleotide of the nucleotide sequence in (1), and which encodes a protein substantially equivalent to a protein encoded by the nucleotide sequence.

According to a more preferred embodiment of the production method of the present invention, which method comprises culturing with pyripyropene E, a method for producing 11-deacetyl pyripyropene O characterized by culturing a microorganism comprising plasmid pPP2 with pyripyropene E and isolating 11-deacetyl pyripyropene O is provided.

According to a preferred embodiment of the production method of the present invention, which method comprises culturing with 11-deacetyl pyripyropene O, a method for producing pyripyropene O characterized by culturing a microorganism in which at least one polynucleotide in the above-mentioned (I) to (III) or a recombinant vector comprising it/them is introduced with 11-deacetyl pyripyropene O and isolating pyripyropene O is provided.

According to a preferred embodiment of the production method of the present invention, which method comprises culturing with 11-deacetyl pyripyropene O, a method for producing pyripyropene O characterized by culturing a microorganism comprising one or more vectors selected from the group consisting of plasmids pCC1-PP1, pPP2, pPP3, pPP6, pPP7 and pPP9 with 11-deacetyl pyripyropene O and isolating pyripyropene O is provided.

According to a preferred embodiment of the production method of the present invention, which method comprises culturing with 11-deacetyl pyripyropene O, a method for producing pyripyropene O characterized by culturing a microorganism in which at least one polynucleotide in (XIV) and (XV) below or a recombinant vector comprising it/them is introduced with 11-deacetyl pyripyropene O and isolating pyripyropene O is provided:

(XIV) an isolated polynucleotide having at least one nucleotide sequence selected from the nucleotide sequences encoding amino acid sequence of SEQ ID NO:275 or a substantially equivalent amino acid sequence thereto; and (XV) a polynucleotide having at least one nucleotide sequence selected from the nucleotide sequences in (1) to (4) below:

(1) a nucleotide sequence from 25824 to 27178 of a nucleotide sequence shown in SEQ ID NO:266;

(2) a nucleotide sequence which is capable of hybridizing with a sequence complementary to the nucleotide sequence in (1) under stringent conditions, and which encodes a protein substantially equivalent to a protein encoded by the nucleotide sequence;

(3) a nucleotide sequence of a polynucleotide of the nucleotide sequence in (1) in which one or more nucleotides are deleted, substituted, inserted or added, and which encodes a protein substantially equivalent to a protein encoded by the nucleotide sequence; and (4) a nucleotide sequence having at least 90% identity to a polynucleotide of the nucleotide sequence in (1), and which encodes a protein substantially equivalent to a protein encoded by the nucleotide sequence.

According to a more preferred embodiment of the production method of the present invention, which method comprises culturing with 11-deacetyl pyripyropene O, a method for producing pyripyropene O characterized by culturing a microorganism comprising plasmid pPP9 with 11-deacetyl pyripyropene O and isolating pyripyropene O is provided.

According to a preferred embodiment of the production method of the present invention, which method comprises culturing with pyripyropene O, a method for producing 7-deacetyl pyripyropene A characterized by culturing a microorganism in which at least one polynucleotide in the above-mentioned (I) to (III) or a recombinant vector comprising it/them is introduced with pyripyropene O and isolating 7-deacetyl pyripyropene A is provided.

According to a preferred embodiment of the production method of the present invention, which method comprises culturing with pyripyropene O, a method for producing 7-deacetyl pyripyropene A characterized by culturing a microorganism comprising one or more vectors selected from the group consisting of plasmids pCC1-PP1, pPP2, pPP3, pPP6, pPP7 and pPP9 with pyripyropene O and isolating 7-deacetyl pyripyropene A is provided.

According to a preferred embodiment of the production method of the present invention, which method comprises culturing with pyripyropene O, a method for producing 7-deacetyl pyripyropene A characterized by culturing a microorganism in which at least one polynucleotide in (XIV) and (XV) below or a recombinant vector comprising it/them is introduced with pyripyropene O and isolating 7-deacetyl pyripyropene A is provided:

(XIV) an isolated polynucleotide having at least one nucleotide sequence selected from the nucleotide sequences encoding amino acid sequence of SEQ ID NO:270 or a substantially equivalent amino acid sequence thereto; and (XV) a polynucleotide having at least one nucleotide sequence selected from the nucleotide sequences in (1) to (4) below:

(1) a nucleotide sequence from 16220 to 18018 of a nucleotide sequence shown in SEQ ID NO:266;

(2) a nucleotide sequence which is capable of hybridizing with a sequence complementary to the nucleotide sequence in (1) under stringent conditions, and which encodes a protein substantially equivalent to a protein encoded by the nucleotide sequence;

(3) a nucleotide sequence of a polynucleotide of the nucleotide sequence in (1) in which one or more nucleotides are deleted, substituted, inserted or added, and which encodes a protein substantially equivalent to a protein encoded by the nucleotide sequence; and (4) a nucleotide sequence having at least 90% identity to a polynucleotide of the nucleotide sequence in (1), and which encodes a protein substantially equivalent to a protein encoded by the nucleotide sequence.

According to a preferred embodiment of the production method of the present invention, which method comprises culturing with pyripyropene O, a method for producing 7-deacetyl pyripyropene A characterized by culturing a microorganism comprising plasmid pPP3 with pyripyropene O and isolating 7-deacetyl pyripyropene A is provided.

According to a preferred embodiment of the production method of the present invention, which method comprises culturing with 7-deacetyl pyripyropene A, a method for producing pyripyropene A characterized by culturing a microorganism in which at least one polynucleotide in the above-mentioned (I) to (III) or a recombinant vector comprising it/them is introduced with 7-deacetyl pyripyropene A and isolating pyripyropene A is provided.

According to a preferred embodiment of the production method of the present invention, which method comprises culturing with 7-deacetyl pyripyropene A, a method for producing pyripyropene A characterized by culturing a microorganism comprising one or more vectors selected from the group consisting of plasmids pCC1-PP1, pPP2, pPP3, pPP6, pPP7 and pPP9 with 7-deacetyl pyripyropene A and isolating pyripyropene A is provided.

According to a preferred embodiment of the production method of the present invention, which method comprises culturing with 7-deacetyl pyripyropene A, a method for producing pyripyropene A characterized by culturing a microorganism in which at least one polynucleotide in (XVI) and (XVII) below or a recombinant vector comprising it/them is introduced with 7-deacetyl pyripyropene A and isolating pyripyropene A is provided:

(XVI) an isolated polynucleotide having at least one nucleotide sequence selected from the nucleotide sequences encoding amino acid sequence of SEQ ID NO:275 or a substantially equivalent amino acid sequence thereto; and (XVII) a polynucleotide having at least one nucleotide sequence selected from the nucleotide sequences in (1) to (4) below:

(1) a nucleotide sequence from 25824 to 27178 of a nucleotide sequence shown in SEQ ID NO:266;

(2) a nucleotide sequence which is capable of hybridizing with a sequence complementary to the nucleotide sequence in (1) under stringent conditions, and which encodes a protein substantially equivalent to a protein encoded by the nucleotide sequence;

(3) a nucleotide sequence of a polynucleotide of the nucleotide sequence in (1) in which one or more nucleotides are deleted, substituted, inserted or added, and which encodes a protein substantially equivalent to a protein encoded by the nucleotide sequence; and (4) a nucleotide sequence having at least 90% identity to a polynucleotide of the nucleotide sequence in (1), and which encodes a protein substantially equivalent to a protein encoded by the nucleotide sequence.

According to a preferred embodiment of the production method of the present invention, which method comprises culturing with 7-deacetyl pyripyropene A, a method for producing pyripyropene A characterized by culturing a microorganism comprising plasmid pPP9 with 7-deacetyl pyripyropene A and isolating pyripyropene A is provided.

The microorganism used in the present invention may be introduced with a polynucleotide using the recombinant vector described below. However, the polynucleotide may be introduced into the microorganism, for example, by an electroporation method, a polyethylene glycol method, an *Agrobacterium* method, a lithium method, a calcium chloride method or the like.

The microorganism used in the present invention is not particularly restricted as long as it can be introduced with a polynucleotide or a recombinant vector comprising it/them. Microorganisms belonging to the genus *Aspergillus* are preferred and *Aspergillus oryzae* is particularly preferred.

In the present invention, culturing microorganisms can be carried out, for example, by solid culturing under aerobic conditions, shake culturing, culturing with bubbling under stirring or deep part aerobic culturing, in particular, shake culturing is preferred. As a medium for culturing microorganisms, commonly used components, for example, as carbon sources, glucose, sucrose, starch syrup, dextrin, starch, glycerol, molasses, animal and vegetable oils or the like, can be used. Also, as nitrogen sources, soybean flour, wheat germ, corn steep liquor, cotton seed meal, meat extract, polypeptone, malto extract, yeast extract, ammonium sulfate, sodium nitrate, urea or the like can be used. Besides, as required, addition of sodium, potassium, calcium, magnesium, cobalt, chlorine, phosphoric acid (dipotassium hydrogen phosphate or the like), sulfuric acid (magnesium sulfate or the like) or inorganic salts which can generate other ions is effective. Also, as required, various vitamins such as thiamin (thiamine hydrochloride or the like), amino acids such as glutamic acid (sodium glutamate or the like) or asparagine (DL-asparagine or the like), trace nutrients such as nucleotides or selection agents such as antibiotics can be added. Further, organic substances or inorganic substances which help the growth of a fungus and promote the production of pyripyropene A can be appropriately added.

The pH of the medium is, for example, about pH 5.5 to pH 8. The appropriate temperature for the culturing is 15° C. to 40° C. and, in many cases, the growth takes place around 22° C. to 30° C. The production of 4-hydroxy-6-(pyridin-3-yl)-3-((2E,6E)-3,7,11-trimethyldodeca-2,6,10-trienyl)-2H-pyran-2-one, deacetyl pyripyropene E, pyripyropene E, pyripyropene O and pyripyropene A varies depending on the medium and culturing conditions, or the used host. In any method for culturing, the accumulation usually reaches a peak in 2 days to 10 days. The culturing is terminated at the time when the amount of pyripyropene A in the culture reaches the peak and a desired substance is isolated and purified from the culture.

To isolate 5-(3-pyridyl)-3,5-dioxopentanoic acid, 4-oxo-6-(3-pyridyl)-α-pyrone, deacetyl pyripyropene E, pyripyropene E, pyripyropene O, 7-deacetyl pyripyropene A, pyripyropene A or the like from the culture, it can be extracted and purified by a usual separation means using properties thereof, such as a solvent extraction method, an ion exchange resin method, an adsorption or distribution column chromatography method, a gel filtration method, dialysis, a precipitation method, which may be individually used or appropriately used in combination. The solvent extraction method is particular preferred.

In the present invention, the term "substantially equivalent amino acid sequence" means an amino acid sequence which does not affect an activity of a polypeptide despite the fact that one or more amino acids are altered by substitution, deletion, addition or insertion. Preferably, an amino acid sequence which is altered by amino acid substitution, deletion, addition or insertion has a sequence identity of 70% or more, preferably 80% or more, more preferably 90% or more, still more preferably 95% or more, and still more preferably 98% or more to the amino acid sequence before alteration and the like. Further, the number of the altered amino acid residues is preferably 1 to 40, more preferably 1 to 20, still more preferably 1 to 10, still more preferably 1 to 8, and most preferably 1 to 4.

Further, an example of the alteration which does not affect the activity includes conservative substitution. The term "conservative substitution" means substitution of preferably 1 to 40, more preferably 1 to 20, more preferably 1 to 10, still more preferably 1 to 8, and most preferably 1 to 4 amino acid residues with other chemically similar amino acid residues such that the activity of the polypeptide is not substantially altered. Examples thereof include cases where a certain hydrophobic amino acid residue is substituted with another hydrophobic amino acid residue and cases where a certain polar amino acid residue is substituted with another polar amino acid residue having the same charges. Functionally similar amino acids capable of such a substitution are known in the art for each amino acid. Concretely, examples of nonpolar (hydrophobic) amino acids include alanine, valine, isoleucine, leucine, proline, tryptophan, phenylalanine, methionine and the like. Examples of polar (neutral) amino acids include glycine, serine, threonine, tyrosine, glutamine, asparagine, cysteine and the like. Examples of positively charged (basic) amino acids include arginine, histidine, lysine and the like. Examples of negatively charged (acidic) amino acids include aspartic acid, glutamic acid and the like.

The term, "stringent conditions" in the present invention means conditions where a washing operation of membranes after hybridization is carried out at high temperatures in a solution with low salt concentrations, a person skilled in the art would be able to appropriately determine the condition, for example, the condition includes the condition of washing in a solution with 2×SSC (1×SSC: 15 mM trisodium citrate, 150 mM sodium chloride) and 0.5% SDS at 60° C. for 20 minutes, and the condition of washing in a solution with 0.2×SSC (1×SSC: 15 mM trisodium citrate, 150 mM sodium chloride) and 0.1% SDS at 60° C. for 15 minutes.

Hybridization can be carried out in accordance with a known method. Also, when a commercially-available library is used, it can be carried out in accordance with a method described in the attached instructions.

In the present description, the term "identity" (also referred to as homology) for nucleotide sequences means a degree of match of bases constituting each sequence among the sequences to be compared. At that time, the presence of gap(s) and characteristics of the amino acids are taken into account. Any values of the "identity" shown in the present description may be values calculated using a homology search program known to those skilled in the art. For instance, the value can be readily calculated by using default (initial setting) parameters in FASTA, BLAST or the like.

In the present description, the "identity" for nucleotide sequences is 90% or more, preferably 95% or more, more preferably 98% or more, still more preferably 99% or more.

In the present description, the term, "one or more nucleotides are deleted, substituted, inserted or added in a polynucleotide" means that alteration was made by a known method such as a site specific mutagenesis method, or substitution or the like of a plurality nucleotides in a degree at which they may naturally occur. The number of the altered nucleotides is one or more nucleotides (for example, one to several nucleotides or 1, 2, 3 or 4 nucleotides).

The term "nucleotide sequence which encodes a protein substantially equivalent to the protein encoded by the (each) nucleotide sequence" means a nucleotide sequence encoding a protein which has an activity equivalent to that of "the protein encoded by the (each) nucleotide sequence."

It is preferred that a protein substantially equivalent to a protein encoded by the nucleotide sequence from 3342 to 5158 of the nucleotide sequence shown in SEQ ID NO:266 have CoA ligase activity.

It is preferred that a protein substantially equivalent to a protein encoded by a nucleotide sequence from 5382 to 12777 of the a nucleotide sequence shown in SEQ ID NO:266 have LovB-like polyketide synthase (PKS) activity.

It is preferred that a protein substantially equivalent to a protein encoded by a nucleotide sequence from 13266 to 15144 of a nucleotide sequence shown in SEQ ID NO:266 have Cytochrome P450 monooxygenase (1) (P450-1) activity.

It is preferred that a protein substantially equivalent to a protein encoded by a nucleotide sequence from 16220 to 18018 of a nucleotide sequence shown in SEQ ID NO:266 have Cytochrome P450 monooxygenase (2) (P450-2) activity.

It is preferred that a protein substantially equivalent to a protein encoded by a nucleotide sequence from 18506 to 19296 of a nucleotide sequence shown in SEQ ID NO:266 have Cyclase (IMP: Integral membrane protein) activity.

It is preferred that a protein substantially equivalent to a protein encoded by a nucleotide sequence from 19779 to 21389 of a nucleotide sequence shown in SEQ ID NO:266 have FAD-dependent monooxygenase (FMO) activity.

It is preferred that a protein substantially equivalent to a protein encoded by a nucleotide sequence from 21793 to 22877 of a nucleotide sequence shown in SEQ ID NO:266 have UbiA-like prenyltransferase (UbiAPT) activity.

It is preferred that a protein substantially equivalent to a protein encoded by a nucleotide sequence from 23205 to 24773 of a nucleotide sequence shown in SEQ ID NO:266 have Acetyltransferase (AT) activity.

It is preferred that a protein substantially equivalent to a protein encoded by a nucleotide sequence from 25824 to 27178 of a nucleotide sequence shown in SEQ ID NO:266 have Acetyltransferase-2 (AT-2) activity.

Obtainment of Isolated Polynucleotide

The method for obtaining the isolated polynucleotide of the present invention is not particularly restricted. The polynucleotide can be isolated from *Penicillium coprobium* PF1169 strain or filamentous fungus by the following method. Concretely, based on a homology sequence obtained by the method of Example 9 below or the like, primers capable of specifically amplifying any one or more genes of a polyketide synthase gene, prenyltransferase gene, hydroxylase gene, acetyltransferase gene or adenylate synthetase gene, which are involved in synthesis of pyripyropene A, are synthesized. PCR is carried out for a fosmid genomic library of *Penicillium coprobium* PF1169 strain which is separately prepared and further colony hybridization is carried out, thereby obtaining the isolated polynucleotide used in the present invention.

According to a preferred embodiment of the present invention, there is provided at least one isolated polynucleotide of the above (I) to (III). In particular, there is provided at least one polynucleotide of the following (I) to (III):

(I) an isolated polynucleotide having at least one nucleotide sequence selected from the nucleotide sequences of the following (a) to (d):

(a) a nucleotide sequence of SEQ ID NO:266, (b) a nucleotide sequence which is capable of hybridizing with a sequence complementary to the nucleotide sequence of SEQ ID NO:266 under stringent conditions, and which encodes a protein substantially equivalent to the protein encoded by the nucleotide sequence of SEQ ID NO:266, (c) a nucleotide sequence of SEQ ID NO:266 in which one or more nucleotides are deleted, substituted, inserted or added, and which encodes a protein substantially equivalent to the protein encoded by the nucleotide sequence of SEQ ID NO:266, and (d) a nucleotide sequence which has at least 90% identity to the polynucleotide of the nucleotide sequence of SEQ ID NO:266, and which encodes a protein substantially equivalent to the protein encoded by the nucleotide sequence of SEQ ID NO:266;

(II) an isolated polynucleotide having a nucleotide sequence which encodes at least one amino acid sequence selected from SEQ ID NOs:267 to 275 or amino acid sequence substantially equivalent thereto; and (III) an isolated polynucleotide having at least one nucleotide sequence selected from the nucleotide sequences of the following (1) to (4):

(1) a nucleotide sequence in (a) to (i) below:

(a) a nucleotide sequence from 3342 to 5158 of the nucleotide sequence shown in SEQ ID NO:266, (b) a nucleotide sequence from 5382 to 12777 of the nucleotide sequence shown in SEQ ID NO:266, (c) a nucleotide sequence from 13266 to 15144 of the nucleotide sequence shown in SEQ ID NO:266, (d) a nucleotide sequence from 16220 to 18018 of the nucleotide sequence shown in SEQ ID NO:266, (e) a nucleotide sequence from 18506 to 19296 of the nucleotide sequence shown in SEQ ID NO:266, (f) a nucleotide sequence from 19779 to 21389 of the nucleotide sequence shown in SEQ ID NO:266, (g) a nucleotide sequence from 21793 to 22877 of the nucleotide sequence shown in SEQ ID NO:266, (h) a nucleotide sequence from 23205 to 24773 of the nucleotide sequence shown in SEQ ID NO:266, and (i) a nucleotide sequence from 25824 to 27178 of the nucleotide sequence shown in SEQ ID NO:266;

(2) a nucleotide sequence which is capable of hybridizing with a sequence complementary to the nucleotide sequence of (1) under stringent conditions, and which encodes a protein substantially equivalent to the protein encoded by the each nucleotide sequence;

(3) a nucleotide sequence of a polynucleotide of the nucleotide sequence in (1) in which one or more nucleotides are deleted, substituted, inserted or added, and which encodes a protein substantially equivalent to the protein encoded by each nucleotide sequence; and (4) a nucleotide sequence which has at least 90% identity to the polynucleotide of the nucleotide sequence of (1), and which encodes a protein substantially equivalent to the protein encoded by the each nucleotide sequence.

According to a more preferred embodiment of the present invention, there is provided an isolated polynucleotide selected from the following (a), (b), (c), (d), (e), (f), (g) and (h):

(a) a polynucleotide having the nucleotide sequence of SEQ ID NO:266, (b) a polynucleotide encoding a polypeptide which consists of an amino acid sequence selected from SEQ ID NOs: 269, 270, 273, 274 and 275, (c) a polynucleotide which has an amino acid sequence substantially equivalent to that shown in SEQ ID NO: 269, and, which encodes a polypeptide having hydroxylase activity, (d) a polynucleotide which has an amino acid sequence substantially equivalent to that shown in SEQ ID NO: 270, and which encodes a polypeptide having hydroxylase activity, (e) a polynucleotide which has an amino acid sequence substantially equivalent to that shown in SEQ ID NO: 273, and which encodes a polypeptide having prenyltransferase activity, (f) a polynucleotide which has an amino acid sequence substantially equivalent to that shown in SEQ ID NO: 274, and which encodes a polypeptide having acetylase activity, (g) a polynucleotide which has an amino acid sequence substantially equivalent to that shown in SEQ ID NO: 275, and which encodes a polypeptide having acetylase activity, and (h) an isolated polynucleotide having a nucleotide sequence selected from the following (i), (ii), (iii), (iv) and (v):

(i) a nucleotide sequence from 13266 to 15144 of the nucleotide sequence shown in SEQ ID NO:266, (ii) a nucleotide sequence from 16220 to 18018 of the nucleotide sequence shown in SEQ ID NO:266, (iii) a nucleotide sequence from 21793 to 22877 of the nucleotide sequence shown in SEQ ID NO:266, (iv) a nucleotide sequence from 23205 to 24773 of the nucleotide sequence shown in SEQ ID NO:266, and (v) a nucleotide sequence from 25824 to 27178 of the nucleotide sequence shown in SEQ ID NO:266.

According to a more preferred embodiment of the present invention, there is provided an isolated polynucleotide selected from the following (A), (B) and (C):

(A) a polynucleotide encoding a polypeptide which consists of an amino acid sequence selected from SEQ ID NO: 275, (B) a polynucleotide which has an amino acid sequence substantially equivalent to that shown in SEQ ID NO: 275, and which encodes a polypeptide having acetylase activity, and (C) an isolated polynucleotide having the nucleotide sequence from 25824 to 27178 of the nucleotide sequence shown in SEQ ID NO:266.

According to a still more preferred embodiment of the present invention, there is provided the polynucleotide of said (c), (d), (e), (f) and (g), wherein the amino acid sequences of the polypeptides encoded by the polynucleotide of said (c), (d), (e), (f) and (g) have a sequence identity of 90% or more to the amino acid sequences shown in SEQ ID NOs: 269, 270, 273, 274 and 275, respectively.

According to a still more preferred embodiment of the invention, there is provided the polynucleotide of said (B), wherein the amino acid sequence of the polypeptide encoded by the polynucleotide of said (B) has a sequence identity of 90% or more to the amino acid sequence shown in SEQ ID NO: 275.

Recombinant Vector

The recombinant vector according to the present invention can be prepared by modifying any one or more of the polynucleotides in the above-mentioned (I) to (III) into an appropriate form depending on an object and ligating them to a vector in accordance with a conventional method, for example, gene recombination techniques described in [Sambrook, J. et al., "Molecular cloning: a laboratory manual", (USA), 2nd Edition, Cold Spring Harbor Laboratory, 1989].

The recombinant vector used in the present invention can be appropriately selected from virus, plasmid, fosmid, cosmid vectors or the like. For instance, when a host cell is *Escherichia coli*, examples thereof include λ phage-based bacteriophage and pBR and pUC-based plasmids. In the case of a *Bacillus subtilis*, examples include pUB-based plasmids. In the case of yeast, examples include YEp, YRp, YCp and YIp-based plasmids.

It is preferred that at least one plasmid among the used plasmids contain a selection marker for selecting a transformant. As the selection marker, a gene encoding drug resistance and gene complementing auxotrophy can be used. Concrete preferred examples thereof include, when a host to be used is bacterium, ampicillin resistant genes, kanamycin resistant genes, tetracycline resistant gene and the like; in the case of yeast, tryptophan biosynthetic gene (TRP1), uracil biosynthetic gene (URA3), leucine biosynthetic gene (LEU2) and the like; in the case of a fungus, hygromycin resistant genes, bialaphos resistant genes, bleomycin resistant genes, aureobasidin resistant genes and the like; and in the case of a plant, kanamycin resistant genes, bialaphos resistant genes and the like.

In addition, DNA molecules serving as an expression vector used in the present invention preferably has DNA sequences necessary to express each gene, for example, transcription regulatory signals and translation regulatory signals such as promoters, transcription initiation signals, ribosome binding sites, translation stop signals, terminators. Preferred examples of the promoters include promoters of lactose operon, tryptophan operon and the like in *Escherichia coli*; promoters of alcohol dehydrogenase gene, acid phosphatase gene, galactose metabolizing gene, glyceraldehyde 3-phosphate dehydrogenase gene or the like in yeast; promoters of α-amylase gene, glucoamylase gene, cellobiohydrolase gene, glyceraldehyde 3-phosphate dehydrogenase gene, abp1 gene or the like in fungi; a CaMV 35S RNA promoter, a CaMV 19S RNA promoter or a nopaline synthetase gene promoter in plants.

The recombination vector according to the present invention is preferably a recombination vector selected from the group consisting of plasmids pPP6, pPP7 and pPP9.

Also, according to a preferred embodiment of the present invention, use of a recombination vector selected from the group consisting of plasmids pPP6, pPP7 and pPP9 for producing pyripyropene A is exemplified.

Transformant

A host in which the isolated polynucleotide according to the present invention is introduced may be appropriately selected, depending on the type of the used vector, from actinomycetes, *Escherichia coli*, *Bacillus subtilis*, yeast, filamentous fungus, plant cells or the like.

A method of introducing a recombinant vector into a host may be selected, depending on a host cell under test, from conjugal transfer, transduction by phage, as well as methods of transformation such as a calcium ion method, a lithium ion method, an electroporation method, a PEG method, an *Agrobacterium* method or a particle gun method.

In cases where a plurality of genes is introduced into host cells in the present invention, the genes may be contained in a single DNA molecule or individually in different DNA molecules. Further, when a host cell is a bacterium, each gene can be designed so as to be expressed as polycistronic mRNA and made into one DNA molecule.

The transformant according to the present invention is preferably a transformant comprising one or more vectors selected from the group consisting of plasmids pPP6, pPP7 and pPP9.

According to a preferred embodiment of the present invention, use of a transformant comprising one or more vectors selected from the group consisting of plasmids pPP6, pPP7 and pPP9 for producing pyripyropene A is exemplified.

EXAMPLES

The present invention will be further illustrated in detail by the following examples, which are not intended to restrict the present invention.

Example 1

Preparation of Genomic DNA of *Penicillium coprobium* PF1169 Strain

Sterilized NB medium (500 ml) was placed in an Erlenmeyer flask (1 L). *Penicillium coprobium* PF1169 strain (Journal of Technical Disclosure No. 500997/2008 (Patent Document 3)) precultured in ½ CMMY agar medium at 28° C. for 4 days was added to the above-mentioned medium and subjected to liquid culture at 28° C. for 4 days. Filtration was carried out with Miracloth to obtain 5 g of fungal cells. From these fungal cells, 30 µg of genomic DNA was obtained in accordance with the manual attached to genomic DNA purification kit Genomic-tip 100/G (manufactured by Qiagen K.K.).

Example 2

Degenerate primers for Amplification of Polyketide Synthase (PKS) and Amplified Fragment Thereof Based on an amino acid sequence conserved among various filamentous fungus polyketide synthases, the following primers were designed and synthesized as degenerate primers for amplification:

```
LC1:    GAYCCIMGITTYTTYAAYATG     (SEQ ID NO: 1)

LC2c:   GTICCIGTICCRTGCATYTC      (SEQ ID NO: 2)
```

(wherein R=A/G, Y=C/T, M=A/C, I=inosine).

Using these degenerate primers, the genomic DNA prepared in Example 1 and ExTaq polymerase (manufactured by Takara Bio Inc.) were allowed to react in accordance with the attached manual. An amplified fragment of about 700 bp was detected (FIG. 1). Further then, the above-mentioned amplified fragment was analyzed to specify the sequence of its internal 500 bp (SEQ ID NO:3).

Example 3

Large-scale Sequencing of Genomic DNA and Amino Acid Sequence Homology Search

The genomic DNA of *Penicillium coprobium* PF1169 strain obtained in Example 1 was subjected to large-scale sequencing and homology search for amino acid sequences. Specifically, part of 50 µg of genomic DNA was pretreated and thereafter subjected to Roche 454FLX DNA sequencer to obtain about 250 bp, 103 thousands of fragment sequences (in total, 49 Mb of sequence).

For these sequences, as known sequences among polyketide synthases and prenyltransferases, the following five sequences (sequences derived from polyketide synthases: *Aspergillus* (*A.*) *fumigatus* PKS 2146 a.a. and *Penicillium* (*P.*) *griseofluvum* 6-methylsalycilic acid synthase 1744 a.a.; as well as prenyltransferases: *Aspergillus* (*A.*) *fumigatus* Prenyltransferase, *Aspergillus* (*A.*) *fumigatus* Prenyltransferase (4-hydroxybezoate octaprenyltransferase) and *Penicillium* (*P.*) *marneffei* Prenyltransferase) were selected and search by homology sequence search software blastx was carried out, thereby obtaining 89, 86, 2, 1 and 3 of homology sequences, respectively (see Table 2). Further, from the homology sequences of *A. fumigatus* PKS 2146a.a. and *P. griseofluvum* 6-methylsalycilic acid synthase 1744 a.a., 19 and 23 of contig sequences were respectively obtained (the contig sequences of *A. fumigatus* PKS 2146 a.a.: SEQ ID NOs:179 to 197; the contig sequences of *P. griseofluvum* 6-methylsalycilic acid synthase 1744 a.a.: SEQ ID NOs:198 to 220) (see Table 2).

TABLE 2

| Enzyme Name | Origin | Number of Homology Sequences | SEQ ID NO. |
|---|---|---|---|
| Polyketide Synthases | *A. fumigatus* PKS 2146 a.a. | 89 | 4 to 92 |
| | *P. griseofluvum* 6-methylsalycilic acid synthase 1744 a.a. | 86 | 93 to 178 |
| | *A. fumigatus* PKS 2146 a.a. | 19 (Contig sequences) | 179 to 197 |
| | *P. griseofluvum* 6-methylsalycilic acid synthase 1744 a.a. | 23 (Contig sequences) | 198 to 220 |
| Prenyltransferases | *A. fumigatus* Prenyltransferase | 2 | 221, 222 |
| | *A. fumigatus* Prenyltransferase (4-hydroxybezoate octaprenyltransferase) | 1 | 223 |
| | *P. marneffei* Prenyltransferase | 3 | 224 to 226 |

Example 4

PCR Amplification from Genomic DNA

Figure 2:
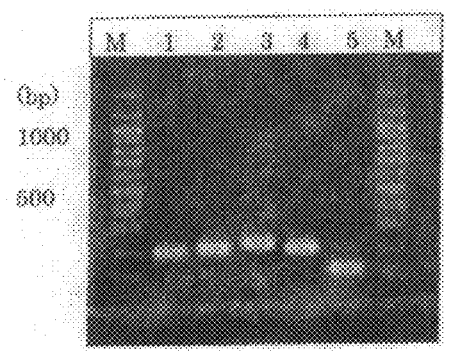
FIG. 2 Similarly to FIG. 1.

From the search results of blastx obtained in Example 3, for polyketide synthases, 13 types of primer pairs shown in SEQ ID NOs:227 to 252 were synthesized. Similarly, for prenyltransferases, 5 types of primer pairs shown in SEQ ID NOs: 253 to 262 were synthesized. When PCR was carried out for the genomic DNA using these primers, amplified fragments with the expected size were seen for all of the primer pairs (see FIG. 1 and FIG. 2).

Example 5

Construction of Phage Genomic Library

A λ phage genomic library of *Penicillium coprobium* PF1169 strain was constructed using λBlueSTAR Xho I Half-site Arms Kit (manufactured by Takara Bio Inc., Cat. No.

69242-3) in accordance with the attached manual. That is, genomic DNA was partially digested using a restriction enzyme, Sau3A1. The DNA fragment with about 20 kb (0.5 µg) was ligated to 0.5 µg of λBlueSTAR DNA attached to the kit. This ligation solution was subjected to in vitro packaging using Lambda INN Packaging kit (manufactured by Nippon Gene Co., Ltd.) based on the manual attached to the kit to obtain 1 ml of a solution. This solution with packaged phages (10 µl) was infected into 100 µl of E. coli ER1647 strain and cultured on a plaque-forming medium at 37° C. overnight, thereby obtaining about 500 clones of plaques. Thus, the genomic library composed of about 50000 clones of phages in which 10 to 20 kb genomic DNA of Penicillium coprobium PF1169 strain were introduced by clone infection was constructed.

Example 6

Screening from Phage Library

For 10000 clones of the phage library prepared in Example 5, the primary screening was carried out by plaque hybridization using, as a probe, the PCR product amplified by LC1-LC2c primer pair prepared above. For labeling and detection of the probe, AlkPhos Direct Labelling and Detection System with CDP-Star (manufactured by GE Healthcare, Cat. No. RPN3690) was used. The above-mentioned hybridization was carried out in accordance with the attached manual.

By the primary screening, 6 clones remained as candidates. Further, as the result of the secondary screening by plaque hybridization, 4 clones were obtained. These positive clones were infected into E. coli BM25.8 strain and the phages were converted to plasmids in accordance with the attached manual, thereby obtaining 4 types of plasmids containing a desired region.

Example 7

Preparation of Fosmid Genome Library

A genomic library of Penicillium coprobium PF1169 strain was constructed in accordance with the manual attached to CopyControl Fosmid Library Production Kit (manufactured by EPICENTRE, Cat. No. CCFOS110). That is, 0.25 µg of DNA fragment of about 40 kb genomic DNA was blunt-ended and then incorporated into fosmid vector pCCFOS (manufactured by Epicentre). This ligation solution was subjected to in vitro packaging using MaxPlax Lambda Packaging Extract attached to the kit based on the manual attached to the kit. This solution with packaged virus (10 µl) was infected into 100 µl of E. coli EPI300™-T1® strain and cultured on a medium containing chloramphenicol at 37° C. overnight and selected, thereby obtaining about 300 clones of colonies. Thus, about 30000 clones of the fosmids in which 40 kb the genomic DNA of Penicillium coprobium PF1169 strain were introduced by infection were obtained. They were aliquoted in a 96 well plate so as to be about 50 clones per well. Thus, the genomic library composed of 96 pools, about 4800 clones was constructed.

Example 8

Fosmid Library Screening

In accordance with the manual attached to the fosmid, plasmid DNAs were individually prepared from 96 pools of the library prepared in Example 7. Using the degenerate primers for polyketide synthase amplification synthesized in Example 2, PCR was carried out for 96 pools of these plasmid DNA samples. As a result, DNA fragments of about 700 bp were amplified from 9 pools. Further, a petri dish containing colonies of about 300 clones or more was prepared from the positive pools and re-screening was carried out by colony hybridization. As a result, using by LC1-LC2c primer pair, 9 types of fosmids were obtained from about 4800 clones.

Example 9

Large-Scale Sequencing of Genomic DNA and Amino Acid Sequence Homology Search

Genomic DNA of Penicillium coprobium PF1169 strain obtained in Example 1 was subjected to large-scale sequencing and homology search for amino acid sequences. Specifically, part of 50 µg of genomic DNA was pretreated and then subjected to Roche 454FLX DNA sequencer to obtain 1405 fragment sequences with an average contig length of 19.621 kb (sequence of a total base length of 27.568160 Mb).

For these sequences, as known sequences among polyketide synthases and prenyltransferases, the following five sequence (sequences derived from polyketide synthases: Penicillium (P.) griseofluvum 6-methylsalycilic acid synthase 1744 a.a. (P22367) and Aspergillus (A.) fumigatus PKS 2146a.a. (Q4WZA8); as well as prenyltransferases: Penicillium (P.) marneffei Prenyltransferase (Q0MRO8), Aspergillus (A.) fumigatus Prenyltransferase (Q4WBI5) and Aspergillus (A.) fumigatus Prenyltransferase (4-hydroxybezoate octaprenyltransferase) (Q4WLD0)) were selected and search by homology sequence search software blastx was carried out, thereby obtaining 22 (P22367), 21 (Q4WZA8), 2 (Q0MRO8), 3 (Q4WBI5) and 3 (Q4WLD0) of the homologous sequences, respectively.

Example 10

Fosmid Library Screening and Sequence Analysis of Cluster Genes

Figure 3:
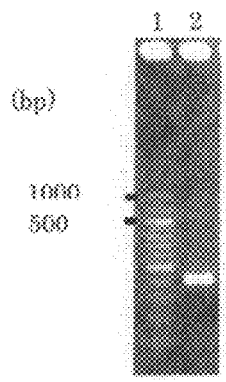
FIG. 3 Similarly to FIG. 1.

In accordance with the manual attached to a fosmid kit (manufactured by EPICENTRE, CopyControl Fosmid Library Production Kit), plasmid DNAs were individually prepared from 96 pools of the library prepared in Example 7. Based on base sequences determined by Roche 454FLX DNA sequencer, homology search for amino acid sequences was carried out to search regions adjacent to polyketide synthase and prenyltransferase. Based on the base sequence of prenyltransferase of the obtained region, a primer pair (No. 27) capable of amplifying 400 bp DNA fragment was synthesized. Using the primers, PCR was carried out for these 48 pools of plasmid DNA samples. As a result, expected DNA fragments of about 400 bp (SEQ ID NO:263) were amplified from 11 pools (see FIG. 3). Further, a petri dish containing colonies of about 300 clones or more was prepared from 6 pools of the positive pools and re-screening was carried out by colony hybridization. As a result, using by 27F+27R primer pair (27F primer: SEQ ID NO:264, 27R primer: SEQ ID NO:265), 4 types of fosmids were obtained from about 4800 clones. One of them was named pCC1-PP1 and the entire sequence of the inserted fragment was determined (SEQ ID NO:266).

The obtained pCC1-PP1 was transformed into Escherichia coli EPI300™-T1® strain (attached to the fosmid kit), thereby obtaining Escherichia coli EPI300™-T1® strain/pCC1-PP1.

When a homology search was carried out between the above-mentioned sequence of SEQ ID NO:266 and each of CoA ligase; LovB-like polyketide synthase (PKS); Cytochrome P450 monooxygenase, Cyclase (IMP: Integral membrane protein), FAD-dependent monooxygenase (FMO), which are hydroxylases; UbiA-like prenyltransferase (UbiAPT); Acetyltransferase (AT), Acetyltransferase-2 (AT-2), which are acetyltransferases; and Cation transporting ATPase (the above-mentioned enzymes are all derived from *Aspergillus fumigatus* Af293 strain), a high homology of 70% or more was seen in any search.

The nucleotides 3342 to 5158 of SEQ ID NO:266 encode CoA ligase and the corresponding polypeptide is shown with the amino acid sequence depicted in SEQ ID NO:267; the nucleotides 5382 to 12777 of SEQ ID NO:266 encode LovB-like polyketide synthase (PKS) and the corresponding polypeptide is shown with the amino acid sequence depicted in SEQ ID NO:268; the nucleotides 13266 to 15144 of SEQ ID NO:266 (hereinafter, a protein encoded by this polynucleotide sequence is referred to as Cytochrome P450 monooxygenase (1) (P450-1)) and the nucleotides 16220 to 18018 (hereinafter, a protein encoded by this polynucleotide sequence is referred to as Cytochrome P450 monooxygenase (2) (P450-2)) encode Cytochrome P450 monooxygenases and the corresponding polypeptides are shown with the amino acid sequences depicted in SEQ ID NOs:269 and 270, respectively; the nucleotides 18506 to 19296 of SEQ ID NO:266 encode Cyclase and the corresponding polypeptide is shown with the amino acid sequence depicted in SEQ ID NO:271; the nucleotides 19779 to 21389 of SEQ ID NO:266 encode FAD-dependent monooxygenase (FMO) and the corresponding polypeptide is shown with the amino acid sequence depicted in SEQ ID NO:272; the nucleotides 21793 to 22877 of SEQ ID NO:266 encode UbiA-like prenyltransferase (UbiAPT) and the corresponding polypeptide is shown with the amino acid sequence depicted in SEQ ID NO:273; the nucleotides 23205 to 24773 of SEQ ID NO:266 encode Acetyltransferase (AT) and the corresponding polypeptide is shown with the amino acid sequence depicted in SEQ ID NO:274; the nucleotides 25824 to 27178 of SEQ ID NO:266 encode Acetyltransferase-2 (AT-2) and the corresponding polypeptide is shown with the amino acid sequence depicted in SEQ ID NO:275; and the nucleotides 27798 to 31855 of SEQ ID NO:266 encode Cation transporting ATPase and the corresponding polypeptide is shown with the amino acid sequence depicted in SEQ ID NO:276.

Example 11

Function Analysis of Gene by Transformation of *Aspergillus Oryzae*

Pyripyropene E used below was able to be produced by a method for culturing a microorganism based on the method described in Japanese Patent Laid-Open Publication No. 239385/1996, WO94/09147 or U.S. Pat. No. 5,597,835, or the total synthesis method described in Tetrahedron Letters, vol. 37, No. 36, 6461-6464, 1996. Also, pyripyropene O used below was able to be produced by a method for culturing a microorganism based on the method described in J. Antibiotics 49, 292-298, 1996 or WO94/09147.

Figure 4:
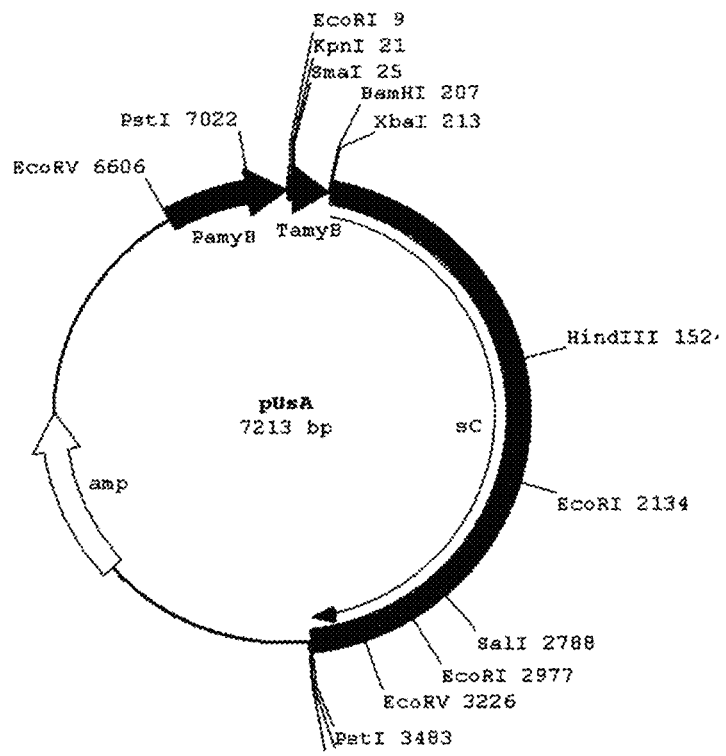
FIG. 4 shows the plasmid map of pUSA.

(1) Preparation of Expression Vector for Introducing into Filamentous Fungus pUSA (FIG. 4) and pHSG399 (Takara Bio Inc.) were individually digested with KpnI and ligated, thereby obtaining pUSA-HSG. This plasmid was digested with SmaI and KpnI in the order mentioned, and subjected to gel purification, thereby obtaining a linear vector DNA having a KpnI cohesive end and SmaI blunt end.

(2) Preparation of Plasmid pPP2

Figure 5:
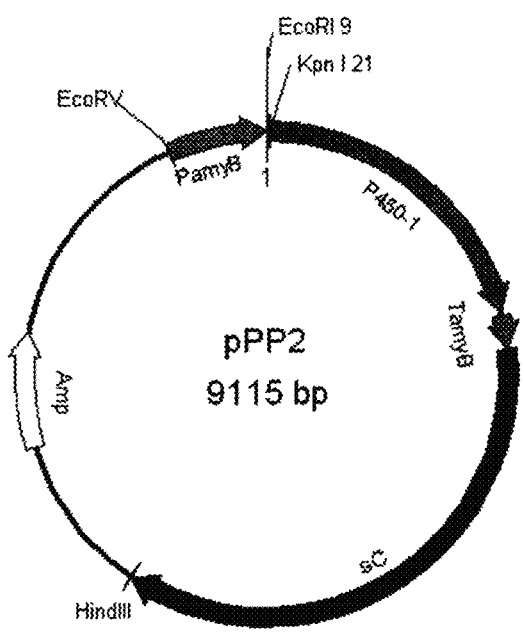
FIG. 5 shows the plasmid map of pPP2.

With fosmid pCC1-PP1 as a template, the polynucleotide of the above-mentioned P450-1 was amplified using a primer pair P450-1 with Kpn F (SEQ ID NO:277)/P450-1 with Swa R (SEQ ID NO:278). A purified DNA fragment was cloned into pCR-Blunt (Invitorogen, Cat. No. K2700-20). The obtained plasmid was digested with KpnI and SwaI. The above-mentioned P450-1 fragment was ligated to the above-described vector pUSA-HSG, thereby obtaining a plasmid pPP2 shown in FIG. 5.

(3) Preparation of Plasmid pPP3

Figure 6:
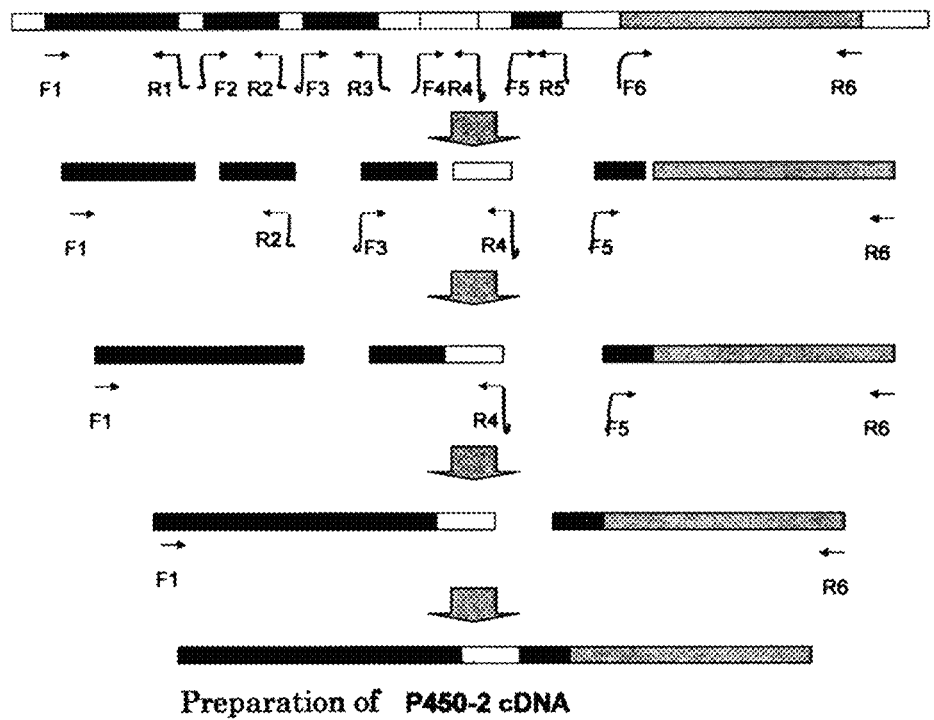
FIG. 6 shows a scheme of P450-2 cDNA amplification.
Figure 7:
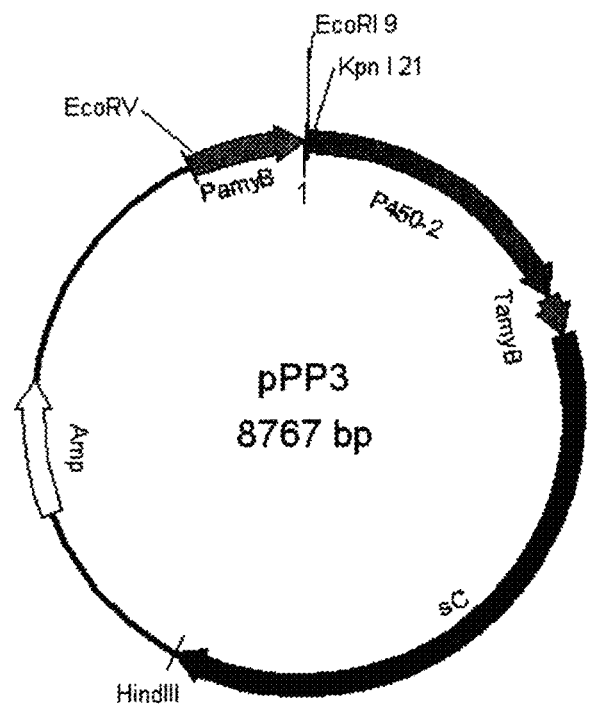
FIG. 7 shows the plasmid map of pPP3.

With fosmid pCC1-PP1 as a template, in accordance with the flow shown in FIG. 6, exons alone were first amplified using primer pairs F1(SEQ ID NO:279)/R1(SEQ ID NO:280), F2(SEQ ID NO:281)/R2(SEQ ID NO:282), F3(SEQ ID NO:283)/R3(SEQ ID NO:284), F4(SEQ ID NO:285)/R4(SEQ ID NO:286), F5(SEQ ID NO:287)/R5 (SEQ ID NO:288) and F6(SEQ ID NO:289)/R6(SEQ ID NO:290), thereby obtaining six fragments. Next, amplification was carried out with these fragments as templates using primer pairs of F1/R2, F3/R4 and F5/R6, thereby obtaining longer fragments. Further, by repeating amplification using primer pairs of F1/R4 and F1/R6, cDNA which did not contain introns of the polynucleotide of the above-mentioned P450-2 was prepared. This cDNA fragment was inserted into pCR-Blunt (Invitorogen, Cat. No. K2700-20) and the obtained plasmid was used as a template for amplification by a primer pair, infusion F of P450-2-cDNA (SEQ ID NO:291)/ infusion R of P450-2-cDNA (SEQ ID NO:292). Based on the manual of the kit, a plasmid pPP3 shown in FIG. 7 was obtained using In-Fusion Advantage PCR Cloning Kit (Clontech).

(4) Preparation of Each Plasmid pPP6, pPP7 and pPP9

Using vector pUSA-HSG for filamentous fungus transformation obtained in the above-mentioned Example 11(1), each of the following plasmids namely pPP6, pPP7, and pPP9 was obtained.

1) Preparation of Plasmid pPP6 (UbiA PT)

Figure 12:
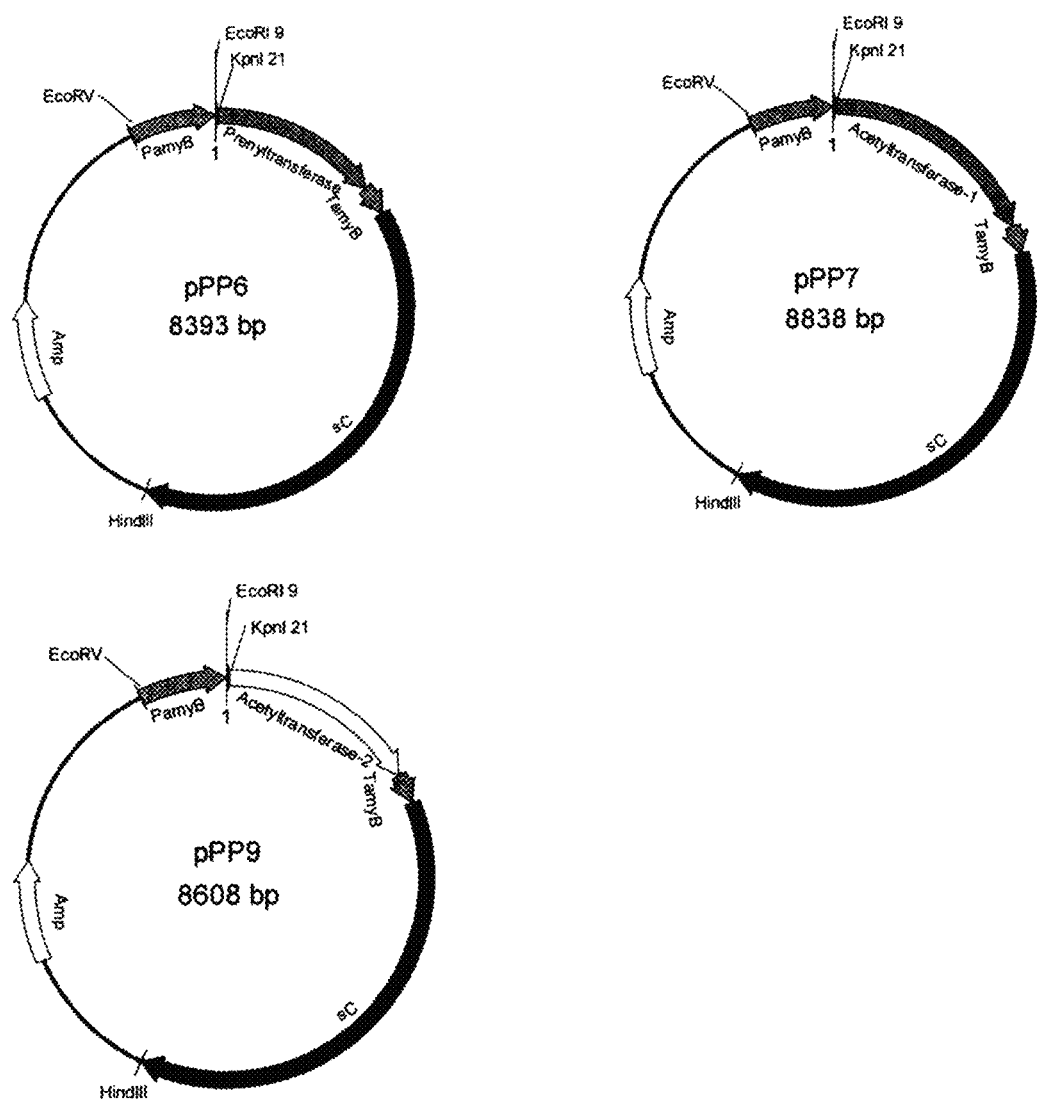
FIG. 12 shows the plasmid map of plasmids pPP6, pPP7 and pPP9.

With fosmid pCC1-PP1 as a template, the polynucleotide of the above-mentioned UbiA PT was each amplified using UbiA PT F with Kpn (SEQ ID NO:293) and UbiA PT R with Swa (SEQ ID NO:294). A purified DNA fragment was cloned into a vector for PCR fragments, pCR-Blunt (Invitorogen, Cat. No. K2700-20). The plasmid obtained was digested with KpnI and SwaI. After each fragment was purified, it was ligated between the KpnI and SmaI sites of the above-described filamentous fungus vector pUSA-HSG, thereby obtaining a plasmid pPP6 shown in FIG. 12.

2) Preparation of Plasmid pPP7 (AT)

With fosmid pCC1-PP1 as a template, the polynucleotide of AT was each amplified using a primer pair AT F with Swa (SEQ ID NO:295) and AT R with Kpn (SEQ ID NO:296). A purified fragment was cloned into a vector for PCR fragments, pCR-Blunt (Invitorogen, Cat. No. K2700-20). The plasmid obtained was digested with KpnI and SwaI. Each fragment was ligated between the KpnI and SmaI sites of the above-described filamentous fungus vector pUSA-HSG, thereby obtaining a plasmid pPP7 shown in FIG. 12.

3) Preparation of Plasmid pPP9 (AT-2)

With fosmid pCC1-PP1 as a template, Toxin fragment was amplified using a primer pair infusion F of Toxin (SEQ ID NO:297) and infusion R of Toxin (SEQ ID NO:298), and inserted between the KpnI and SmaI sites of the above-described filamentous fungus vector pUSA-HSG using In-Fusion Advantage PCR Cloning Kit (manufactured by Clontech, Cat. No. 639619), based on the manual of the kit, thereby obtaining a plasmid pPP9 shown in FIG. 12.

(5) Obtainment of Transformant of Aspergillus Oryzae (*A. oryzae*)

In a CD-Met (containing L-Methionine 40 µg/ml) agar medium, *A. oryzae* (HL-1105 strain) was cultured at 30° C. for one week. From this petri dish, conidia (>10$^8$) were collected and seeded in 100 ml of YPD liquid medium in a 500 ml-flask. After 20-hour culturing (30° C., 180 rpm), fungal cells having a moss ball shape were obtained. The fungal cells were collected with a 3G-1 glass filter, washed with 0.8 M NaCl, and water was removed well. The resultant was suspended with TF solution I (protoplast formation solution) and then shook at 30° C., at 60 rpm for 2 hours. At a 30-minute interval, observation under the microscope was carried out and the presence of protoplasts was checked. Thereafter, the culture medium was filtered and subjected to centrifugation (2000 rpm, 5 minutes) to collect protoplasts, which were then washed with TF solution II. After washing, 0.8 volume of TF solution II and 0.2 volume of TF solution III were added and mixed, thereby obtaining a protoplast suspension.

To 200 µl of this suspension, 10 µg of plasmid DNA (pPP2 or pPP3) was added. The mixture was left to stand on ice 30 minutes and added with TF solution III (1 mL). The resulting mixture was gently mixed and then left to stand at room temperature for 15 minutes. Thereafter, the plasmid DNA was introduced into the above-mentioned protoplasts. To this, TF solution II (8 mL) was added and subjected to centrifugation (at 2000 rpm for 5 minutes). Further, protoplasts were then recovered with 1 to 2 ml being left over. The recovered protoplast solution was dropped to a regeneration medium (lower layer) and a regeneration medium (upper layer) was poured. The resultant was mixed by turning a petri dish and then cultured at 30° C. for 4 to 5 days. Generated clones were isolated in the regeneration medium (lower layer), subcultured and purified, thereby obtaining a transformant (*Aspergillus oryzae* PP2-1 and *Aspergillus oryzae* PP3-2).

Based on the method described in the above-mentioned Example 11 (5), transformants in which each of the plasmid DNAs (pPP6, pPP7 and pPP9) was introduced were obtained (*Aspergillus oryzae* PP6, *Aspergillus oryzae* PP7 and *Aspergillus oryzae* PP9).

The above-mentioned TF solution I (protoplast formation solution) was prepared with the following compositions.

| Name of Compound | Concentration |
| --- | --- |
| Yatalase (manufactured by Takara Bio Inc.) | 20 mg/ml |
| Ammonium sulfate | 0.6M |
| Maleic acid-NaOH | 50 mM |

After the above-mentioned compositions (pH 5.5) were prepared, filter sterilization was carried out.

The above-mentioned TF solution II was prepared with the following compositions.

| Name of Compound | Amount | | |
| --- | --- | --- | --- |
| 1.2M Sorbitol (MW = 182.17) | 43.72 g | | |
| 50 mM CaCl$_2$ | 10 ml | 1M CaCl$_2$ (1/20) |
| 35 mM NaCl | 1.4 ml | 5M NaCl |
| 10 mM Tris-HCl | 2 ml | 1M Tris-HCl (1/100) |

Water was further added to attain a total volume of 200 ml.

After the above-mentioned compositions were prepared, autoclave sterilization was carried out.

The above-mentioned TF solution III was prepared with the following compositions.

| Name of Compound | Amount | |
| --- | --- | --- |
| 60% PEG4000 | 6 g | |
| 50 mM CaCl$_2$ | 500 µl | 1M CaCl$_2$ (1/20) |
| 50 mM Tris-HCl | 500 µl | 1M Tris-HCl (1/100) |

Water was further added to attain a total volume of 10 ml.

After the above-mentioned compositions were prepared, filter sterilization was carried out.

The above-mentioned regeneration medium was prepared with the following compositions.

| Name of Compound | Amount | Concentration | |
| --- | --- | --- | --- |
| Sorbitol (MW = 182.17) | 218.6 g | 1.2M | |
| NaNO$_3$ | 3.0 g | 0.3% (w/v) | |
| KCl | 2.0 g | 0.2% (w/v) | |
| KH$_2$PO$_4$ | 1.0 g | 0.1% (w/v) | |
| MgSO$_4$•7H$_2$O | 2 ml (1M MgSO$_4$) | 0.05% | 2 mM |
| Trace elements solution | 1 ml | | |
| Glucose | 20.0 g | 2% (w/v) | |

Water was further added to attain a total volume of 1 L.

After the above-mentioned compositions (pH 5.5) were prepared, autoclave sterilization was carried out.

In addition, the Trace elements solution used above was prepared with the following composition.

| Name of Compound | Amount |
| --- | --- |
| FeSO$_4$•7H$_2$O | 1.0 g |
| ZnSO$_4$•7H$_2$O | 8.8 g |
| CuSO$_4$•5H$_2$O | 0.4 g |
| Na$_2$B$_4$O$_7$•10H$_2$O | 0.1 g |
| (NH$_4$)$_6$Mo$_7$O$_{24}$•4H$_2$O | 0.05 g |

Water was further added to attain a total volume of 1 L.

After the above-mentioned compositions were prepared, autoclave sterilization was carried out.

(6) Function Analysis and Addition Culture Test of P450-1

To a YPD medium (1% (w/v) Yeast Extract, 2% (w/v) Peptone, 2% (w/v) Dextrose) containing 1% (w/v) maltose, a 1/100 volume of 2 mg/mL dimethyl sulfoxide solution of pyripyropene E was added to provide medium A. From flora of *Aspergillus oryzae* PP2-1 cultured in Czapek Dox agar medium, conidia thereof were collected and suspended in sterilized water. This conidia suspension was adjusted to 10$^4$ spores/mL. Further, 100 µL of this adjusted conidia suspension was added to 10 mL of medium A and cultured with shaking at 25° C. for 96 hours. To this culture solution, 10 mL of acetone was added and the mixture was mixed well. Thereafter, acetone was removed using a centrifugal concentrator. To this, 10 mL of ethyl acetate was added and the resulting mixture was mixed well and then only the ethyl acetate layer was recovered. A dried product obtained by removing ethyl acetate using the centrifugal concentrator was dissolved in 1000 µL of methanol. This was used as a sample and analyzed by LC-MS (Waters, Micromass ZQ, 2996PDA, 2695 Separation module, Column: Waters XTerra C18 (φ4.5×50 mm, 5 µm)) and LC-NMR (manufactured by Burker Daltonik, Avance500).

As the results of the above-mentioned LC-MS measurement, it was confirmed that the obtained compound was single Compound A which increased by a molecular weight of 16 compared with pyripyropene E. Further, as the results of the LC-NMR measurement, it was confirmed that this Compound A was an 11-position hydroxide of pyripyropene E. It was confirmed that the above-mentioned Cytochrome P450 monooxygenase (1) had a hydroxylase activity of the 11-position of pyripyropene E with pyripyropene E as a substrate.

Physicochemical properties of the above-mentioned Compound A are shown below:
1. Mass spectrum: ES-MS 468M/Z $(M+H)^+$
2. Molecular formula: $C_{27}H_{33}NO_6$
3. HPLC: Column: Waters XTerra Column C18 (5 μm, 4.6 mm×50 mm), 40° C., Mobile phase: From 20% aqueous acetonitrile solution to 100% acetonitrile in 10 minutes (linear gradient), Flow rate: 0.8 ml/min, Detection: Retention time 6.696 minutes at UV 323 nm
4. $^1$H-NMR spectrum ($CD_3CN$, 2H, 3.134, 3.157 H-11)

Figure 8:
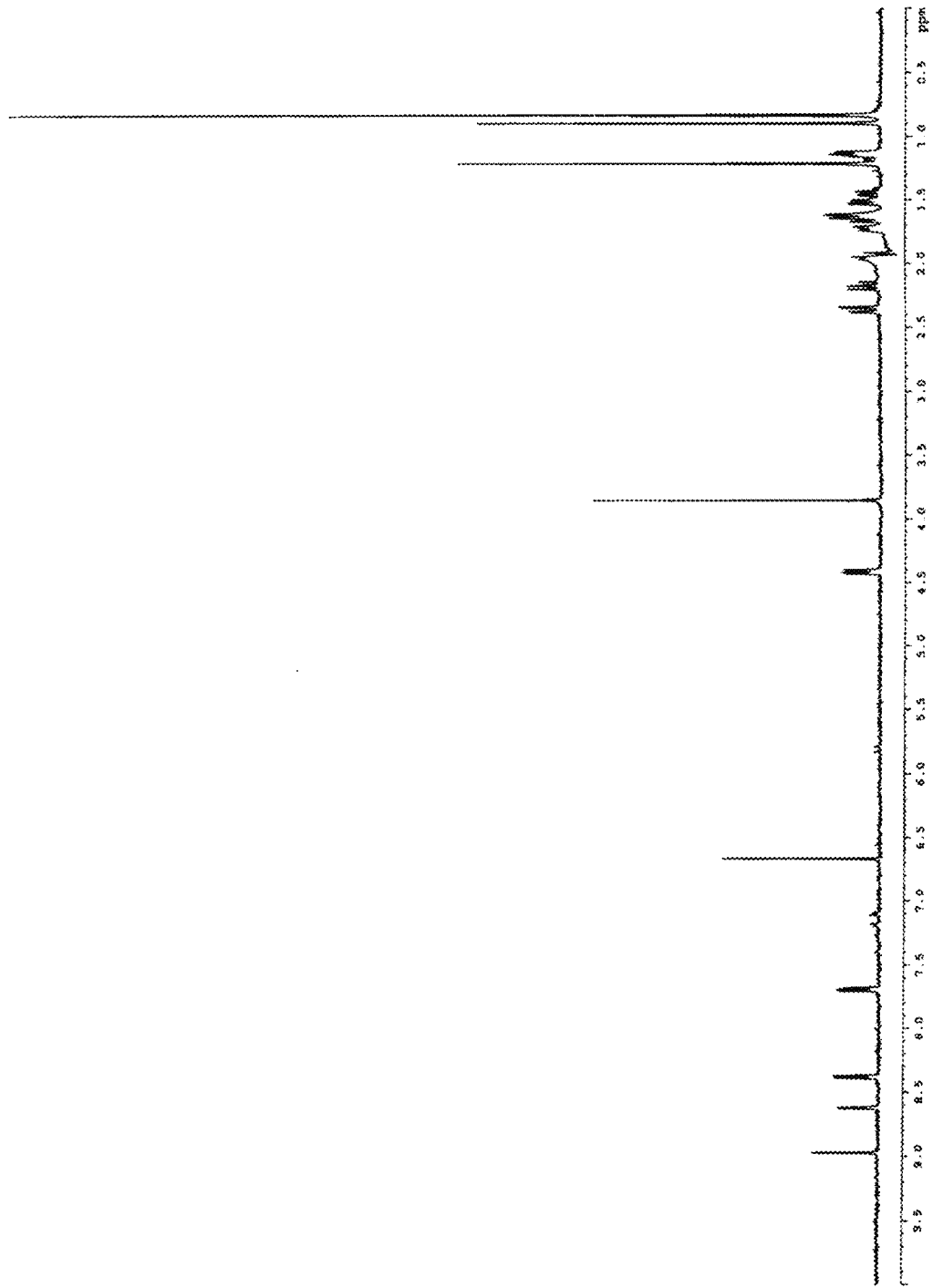
FIG. 8 shows $^1$H-NMR spectrum of pyripyropene E in deuterated acetonitrile.
Figure 9:
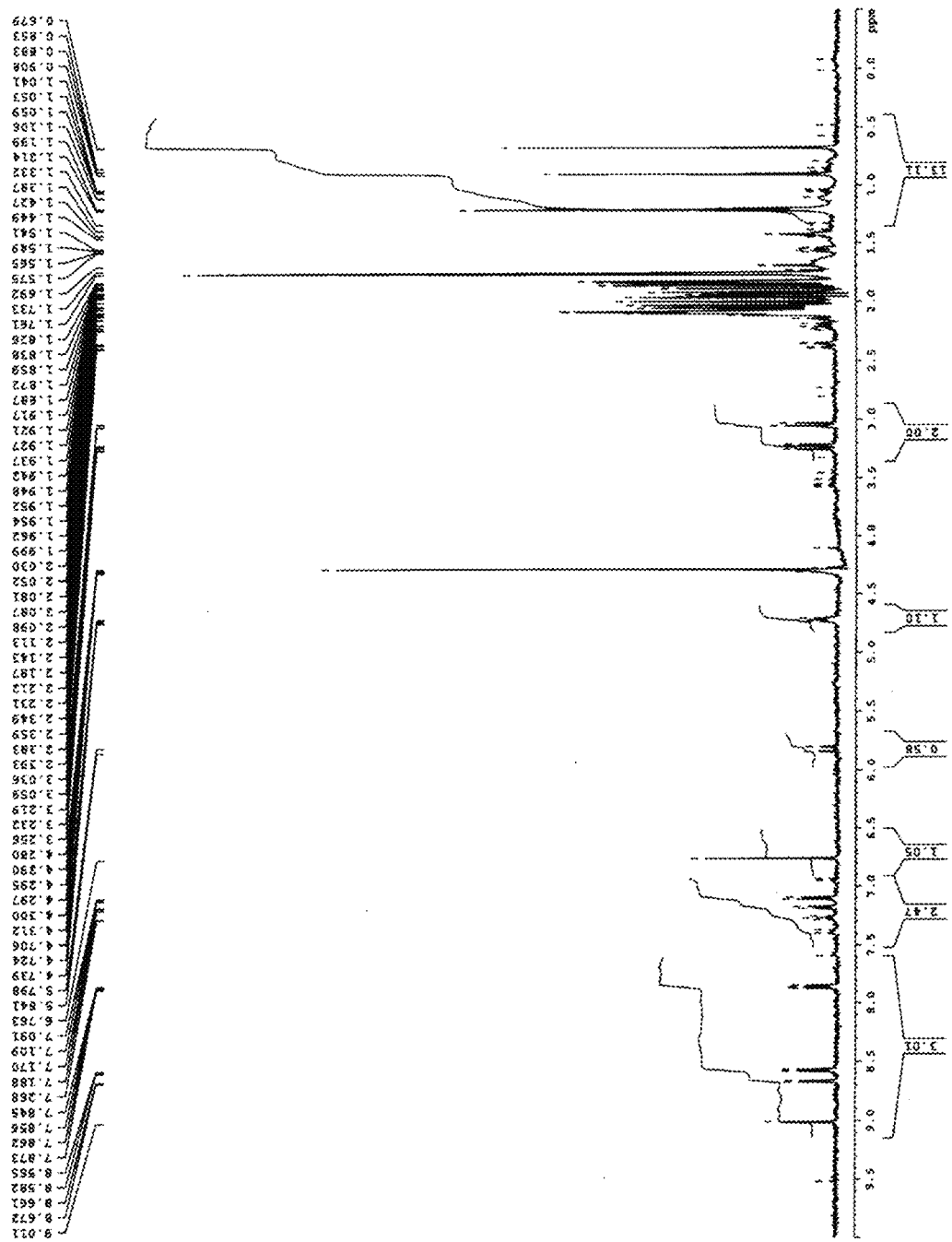
FIG. 9 shows $^1$H-NMR spectrum in deuterated acetonitrile of a product of the culture of *Aspergillus oryzae* transformed with plasmid pPP2.

The charts of the $^1$H-NMR spectrum of pyripyropene E and $^1$H-NMR spectrum according to the above-mentioned 4 are shown in FIG. 8 and FIG. 9, respectively.

(7) Function Analysis and Addition Culture Test of P450-2

To a YPD medium (1% (w/v) Yeast Extract, 2% (w/v) Peptone, 2% (w/v) Dextrose) containing 1% (w/v) maltose, a 1/100 volume of 2 mg/mL dimethyl sulfoxide solution of pyripyropene E was added to provide medium A, and similarly a 1/100 volume of 2 mg/mL dimethyl sulfoxide solution of pyripyropene O was added to provide medium B. From flora of *Aspergillus oryzae* PP3-2 cultured in Czapek Dox agar medium, conidia thereof were collected and suspended in sterilized water. This conidia suspension was adjusted to $10^4$ spores/mL. Further, 500 μL of the adjusted conidia suspension was added to 50 mL of medium A or medium B and cultured with shaking at 25° C. for 96 hours. To this culture solution, 50 mL of acetone was added and the mixture was mixed well. Thereafter, acetone was removed using a centrifugal concentrator. To this, 50 mL of ethyl acetate was added and the resulting mixture was mixed well and then only the ethyl acetate layer was recovered. A dried product obtained by removing ethyl acetate using the centrifugal concentrator was dissolved in 1500 μL of methanol. This was used as a sample and analyzed by LC-MS (manufactured by Waters, Micromass ZQ, 2996PDA, 2695 Separation module, Column: Waters XTerra C18 (φ4.5×50 mm, 5 μm)) and LC-NMR (manufactured by Burker Daltonik, Avance500). As the results of the LC-MS measurement, from a sample obtained from the medium A, Compound B which increased by a molecular weight of 32 compared with pyripyropene E was detected. Also, from a sample obtained from the medium B, Compound C which increased by a molecular weight of 32 compared with pyripyropene O was detected. Further, as the results of the LC-NMR measurement, it was confirmed that Compound C was a 7-position and 13-position hydroxide of pyripyropene O. It was confirmed that the above-mentioned Cytochrome P450 monooxygenase (2) had a hydroxylase activity of the 7-position and 13-position of each of pyripyropene E or pyripyropene O.

Physicochemical properties of the above-mentioned Compound B are shown below:
1. Mass spectrum: ES-MS 484M/Z $(M+H)^+$
2. Molecular formula: $C_{27}H_{33}NO_7$
3. HPLC: Column: Waters XTerra Column C18 (5 μm, 4.6 mm×50 mm), 40° C., Mobile phase: From 20% aqueous acetonitrile solution to 100% acetonitrile in 10 minutes (linear gradient), Flow rate: 0.8 ml/min, Detection: Retention time 5.614 minutes at UV 323 nm Physicochemical properties of the above-mentioned Compound C are shown below:
1. Mass spectrum: ES-MS 542M/Z $(M+H)^+$
2. Molecular formula: $C_{29}H_{35}NO_9$
3. HPLC: Column: Waters XTerra Column C18 (5 μm, 4.6 mm×50 mm), 40° C., Mobile phase: From 20% aqueous acetonitrile solution to 100% acetonitrile in 10 minutes (linear gradient), Flow rate: 0.8 ml/min, Detection: Retention time 5.165 minutes at UV 323 nm
4. $^1$H-NMR spectrum ($CD_3CN$, 1H 4.858 H-13), ($CD_3CN$, 1H 3.65 H-7)

Figure 10:
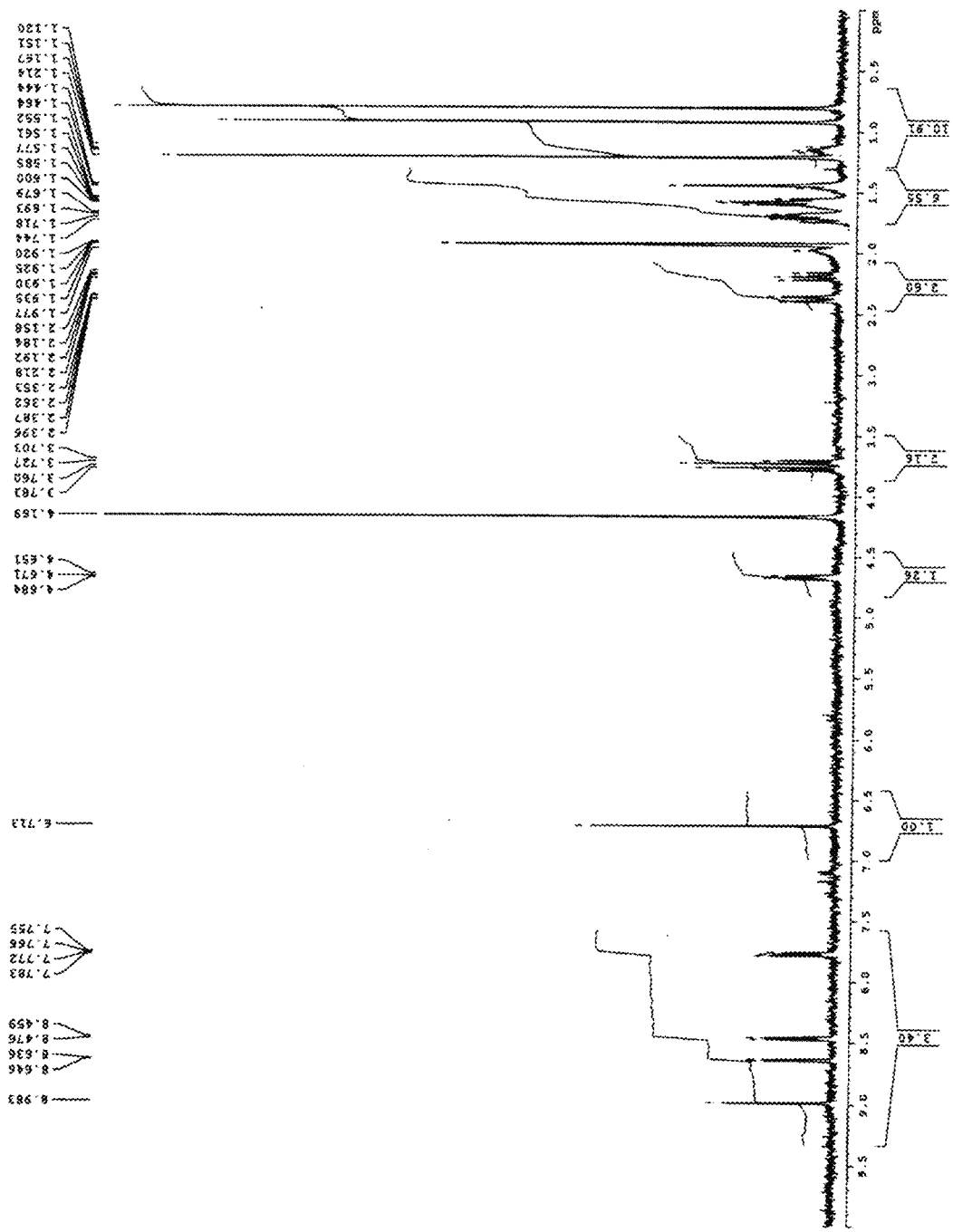
FIG. 10 shows $^1$H-NMR spectrum of pyripyropene O in deuterated acetonitrile.
Figure 11:
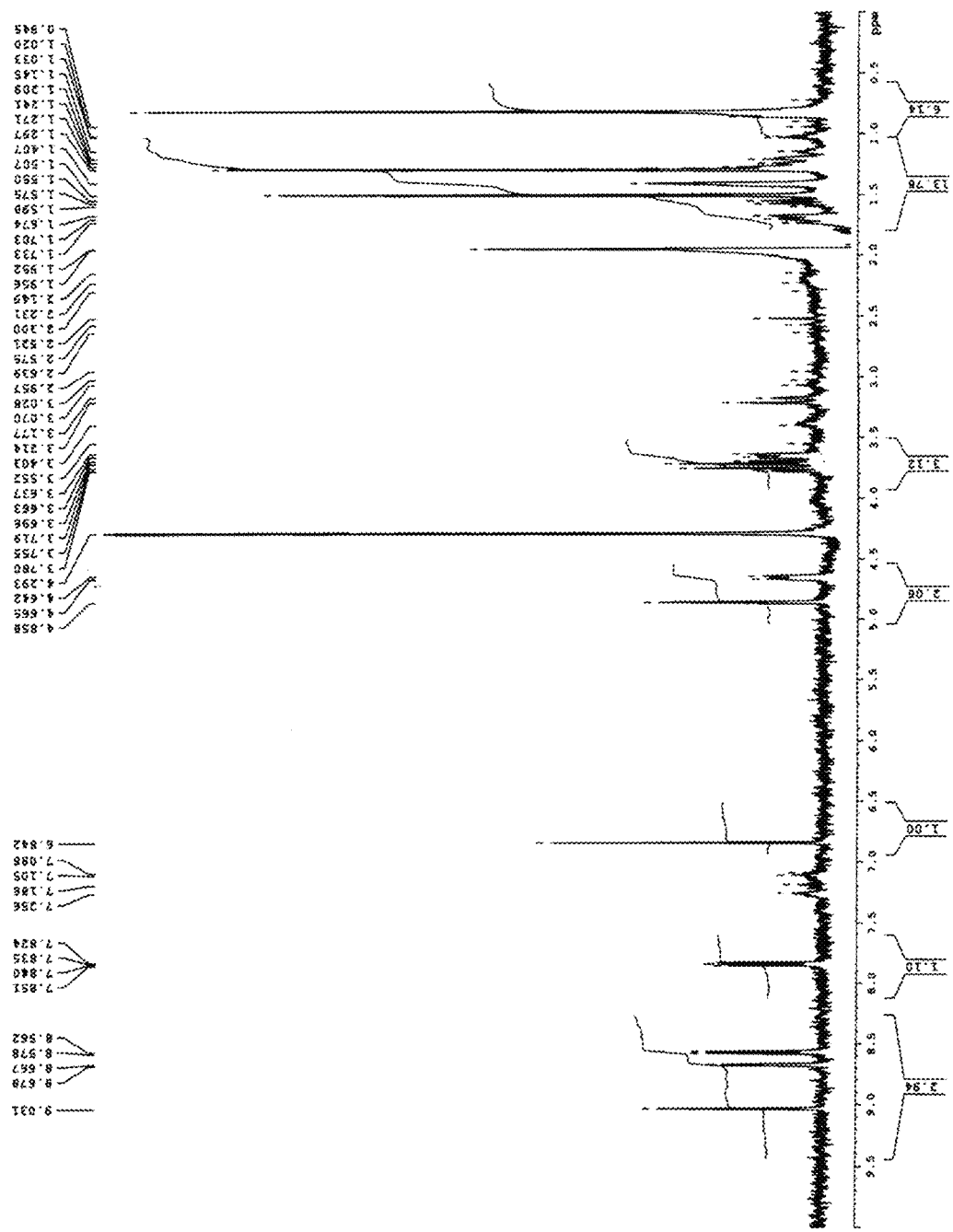
FIG. 11 shows $^1$H-NMR spectrum in deuterated acetonitrile of a product of the culture of *Aspergillus oryzae* transformed with plasmid pPP3.

The charts of the $^1$H-NMR spectrum of pyripyropene O and the above-mentioned Compound C are shown in FIG. 10 and FIG. 11, respectively.

(8) Function Analysis and Addition Culture Test of Prenyltransferase

To a YPD medium (1% (w/v) Yeast Extract, 2% (w/v) Peptone, 2% (w/v) Dextrose) containing 1% (w/v) maltose, a 1/100 volume of 2 mg/mL dimethyl sulfoxide solution of Compound D (4-oxo-6-(3-pyridyl)-α-pyrone, this hereinafter applies) (see Reference Example 1) was added to provide medium C. From flora of *Aspergillus oryzae* PP6 cultured in Czapek Dox agar medium, conidia thereof were collected and suspended in sterilized water. This conidia suspension was adjusted to $10^4$ spores/mL. Further, 200 μL of this was added to 20 mL of medium C and cultured with shaking at 25° C. for 96 hours. To this culture solution, 20 mL of acetone was added and the mixture was mixed well. Thereafter, acetone was removed using a centrifugal concentrator. To this, 20 mL of ethyl acetate was added and the resulting mixture was mixed well and then only the ethyl acetate layer was recovered. A dried product obtained by removing ethyl acetate using the centrifugal concentrator was dissolved in 1000 μL of methanol. This was used as a sample and analyzed by LC-MS (Waters, Micromass ZQ, 2996PDA, 2695 Separation module, Column: Waters XTerra C18 (φ4.5×50 mm, 5 μm)).

As the results of the LC-MS measurement, Compound F (4-hydroxy-6-(pyridin-3-yl)-3-((2E,6E)-3,7,11-trimethyl-dodeca-2,6,10-trienyl)-2H-pyran-2-one, this hereinafter applies) in which a farnesyl group is added to Compound D was detected. It was confirmed that this Compound had the same retention time, molecular ion peaks and UV absorption on LC-MS as the Compound F described in Reference Example 2. From this, it was confirmed that Prenyltransferase had a prenyltransferase activity to add the farnesyl group to Compound D.

(9) Function Analysis and Addition Culture Test of Acetyltransferase-1

To a YPD medium (1% (w/v) Yeast Extract, 2% (w/v) Peptone, 2% (w/v) Dextrose) containing 1% (w/v) maltose, a 1/100 volume of 2 mg/mL dimethyl sulfoxide solution of deacetyl pyripyropene E (see Reference Example 3) was added to provide medium D; a 1/100 volume of 2 mg/mL dimethyl sulfoxide solution of 11-deacetyl pyripyropene O (see Reference Example 4) was added to provide medium E and 2 mg/mL dimethyl sulfoxide solution of 7-deacetyl pyripyropene A (see Reference Example 5) was added to provide medium F. From flora of *Aspergillus oryzae* PP7 cultured in Czapek Dox agar medium, conidia thereof were collected and suspended in sterilized water. This conidia suspension was adjusted to $10^4$ spores/mL. Further, 200 μL of this was added to 20 mL of medium D, medium E or medium F and cultured with shaking at 25° C. for 96 hours. To this culture solution, 20 mL of acetone was added and the mixture was mixed well. Thereafter, acetone was removed using a centrifugal concentrator. To this, 20 mL of ethyl acetate was added and the resulting mixture was mixed well and then only the ethyl acetate layer was recovered. A dried product obtained by removing ethyl acetate using the centrifugal concentrator was dissolved in 1000 μL of methanol. This was used as a sample and analyzed by LC-MS (Waters, Micromass ZQ, 2996PDA, 2695 Separation module, Column: Waters XTerra C18 (φ4.5×50 mm, 5 μm)).

As the results of the LC-MS measurement, a single compound which increased a molecular weight of 42 compared with deacetyl pyripyropene E was detected from the medium D. It was confirmed that the compound had the same retention time, molecular ion peaks and UV absorption as pyripyropene E (see Reference Example 6). Meanwhile, no newly-generated compounds were detected from the medium E and medium F. From this, it was confirmed that Acetyltransferase-1 had an acetyltransferase activity which acetylated specifically the 1-position of deacetyl pyripyropene E.

(10) Function Analysis and Addition Culture Test of Acetyltransferase-2

To a YPD medium (1% (w/v) Yeast Extract, 2% (w/v) Peptone, 2% (w/v) Dextrose) containing 1% (w/v) maltose, a 1/100 volume of 2 mg/mL dimethyl sulfoxide solution of deacetyl pyripyropene E (see Reference Example 3) was added to provide medium D; a 1/100 volume of 2 mg/mL dimethyl sulfoxide solution of 11-deacetyl pyripyropene O (see Reference Example 4) was added to provide medium E and 2 mg/mL dimethyl sulfoxide solution of 7-deacetyl pyripyropene A (see Reference Example 5) was added to provide medium F. From flora of *Aspergillus oryzae* PP9 cultured in Czapek Dox agar medium, conidia thereof were collected and suspended in sterilized water. This conidia suspension was adjusted to $10^4$ spores/mL. Further, 200 μL of this was added to 20 mL of medium D, medium E or medium F and cultured with shaking at 25° C. for 96 hours. To this culture solution, 20 mL of acetone was added and the mixture was mixed well. Thereafter, acetone was removed using a centrifugal concentrator. To this, 20 mL of ethyl acetate was added and the resulting mixture was mixed well and then only the ethyl acetate layer was recovered. A dried product obtained by removing ethyl acetate using the centrifugal concentrator was dissolved in 1000 μL of methanol. This was used as a sample and analyzed by LC-MS (Waters, Micromass ZQ, 2996PDA, 2695 Separation module, Column: Waters XTerra C18 (φ4.5×50 mm, 5 μm)).

As the results of the LC-MS measurement, a single compound which increased a molecular weight of 42 compared with 11-deacetyl pyripyropene O was detected from the medium E. It was confirmed that this compound had the same retention time, molecular ion peaks and UV absorption as pyripyropene O (see Reference Example 7). Further, a single compound which increased a molecular weight of 42 compared with 7-deacetyl pyripyropene A was detected from the medium F. It was confirmed that the compound had the same retention time, molecular ion peaks and UV absorption as pyripyropene A (see Reference Example 8). Meanwhile, no newly-generated compounds were detected from the medium D. From this, it was confirmed that Acetyltransferase-2 have an acetyltransferase activity which acetylated specifically the 11-position of 11-deacetyl pyripyropene O and the 7-position of 7-deacetyl pyripyropene A.

Reference Example 1

Synthesis of Compound D
(4-oxo-6-(3-pyridyl)-α-pyrone)

The above-mentioned Compound D was obtained by the method described in 3. Org. Chem. 1983. 48. 3945.

Reference Example 2

Obtainment and Structural Analysis of Compound F (4-hydroxy-6-(pyridin-3-yl)-3-((2E,6E)-3,7,11-trimethyl-dodeca-2,6,10-trienyl)-2H-pyran-2-one)

A culture broth containing pyripyropenes obtained by the method described in Journal of Technical Disclosure 500997/2008 (Patent Document 3) was extracted with butyl acetate and thereafter filtered using Celite. Celite (2.5 g) used during the filtration was removed and methanol (30 mL) was added. The resultant was stirred at room temperature for 23 hours. Insoluble matter was removed by filtration and methanol was evaporated under reduced pressure, thereby obtaining Compound F (191 mg).

ESI-MS; m/z 394 (M+H)$^+$ $^1$H-NMR (DMSO) δ (ppm) 1.48 (3H, s), 1.51 (3H, s), 1.55 (3H, s), 1.69 (3H, s), 1.85 (2H, t, J=7.5 Hz), 1.91-1.95 (4H, m), 2.01 (2H, dt, 3=6.9, 6.9 Hz), 3.03 (2H, d, J=7.1 Hz), 4.98 (1H, t, J=7.0 Hz), 5.02 (1H, t, 3=6.9 Hz), 5.13 (1H, t, J=7.0 Hz), 6.75 (1H, s), 7.54 (1H, dd, 3=4.8, 8.2 Hz), 8.09 (1H, ddd, J=1.4, 1.9, 8.2 Hz), 8.66 (1H, dd, J=1.4, 4.8 Hz), 8.91 (1H, d, J=1.9 Hz)

Reference Example 3

Synthesis and Structural Analysis of Deacetyl Pyripyropene E

Pyripyropene E (29 mg) was dissolved in methanol-water (19:1, 1 mL) and potassium carbonate (53 mg) was added thereto. The resultant was stirred for 44 hours. Thereafter, the solvent was evaporated under reduced pressure and a mixed solvent of chloroform-methanol (10:1) was added. Insoluble matter was removed by filtration and the solvent was evaporated under reduced pressure, thereby obtaining a crude product. The crude product was purified by preparative thin layer chromatography (Merck silica gel 60F254, 0.5 mm, chloroform:methanol=10:1), thereby obtaining deacetyl pyripyropene E (18 mg).

ESI-MS; m/z 410 (M+H)$^+$ $^1$H-NMR (CDCL$_3$) δ (ppm) 0.82 (3H, s), 0.92 (3H, s), 1.00-1.03 (1H, m), 1.04 (3H, s), 1.12 (1H, dt, 3=4.0, 13.2 Hz), 1.27 (3H, s), 1.41-1.53 (2H, m), 1.59-1.75 (3H, m), 1.80-1.84 (2H, m), 2.15 (1H, dt, J=3.2, 12.4 Hz), 2.18-2.29 (1H, m), 2.54 (1H, dd, J=3.2, 17.6 Hz), 3.25 (1H, dd, 3=4.4, 11.2 Hz), 6.43 (1H, s), 7.39 (1H, dd, J=4.8, 8.0 Hz), 8.11 (1H, d, 3=8.0 Hz), 8.65 (1H, d, 3=4.8 Hz), 8.99 (1H, d, J=1.6 Hz)

Reference Example 4

Synthesis and Structural Analysis of 11-Deacetyl Pyripyropene O

Pyripyropene O (30 mg) was dissolved in methanol-water (19:1, 2 mL) and potassium carbonate (20 mg) was added thereto. The resultant was stirred for 22 hours, and thereafter acetic acid (0.1 mL) was added and the solvent was evaporated under reduced pressure. Ethyl acetate and water were added and then extraction was carried out with ethyl acetate. The ethyl acetate layer was washed with saturated sodium chloride solution and dried with anhydrous sodium sulfate. The solvent was evaporated under reduced pressure, thereby obtaining a crude product of 1,11-dideacetyl pyripyropene O (30 mg).

The crude product of 1,11-dideacetyl pyripyropene O (23 mg) was dissolved in N,N-dimethylformamide (0.4 mL) and triethylamine (8 mg) and acetic acid anhydride (7 mg) were added thereto. After the resulting mixture was stirred at room temperature for 23 hours, water was added and then extraction was carried out with ethyl acetate. The ethyl acetate layer was washed with saturated sodium chloride solution and dried with anhydrous magnesium sulfate. The solvent was evaporated under reduced pressure, thereby obtaining a crude product of 1-deacetyl pyripyropene O (28 mg).

The crude product of 1-deacetyl pyripyropene O (28 mg) was dissolved in toluene and 1,8-diazabicyclo[5,4,0]-7-undecene (20 mg) was added. The mixture was stirred at 70° C. for 20 hours and allowed to cool. Ethyl acetate and water were added and then extraction was carried out with ethyl acetate. The ethyl acetate layer was washed with saturated sodium chloride solution and dried with anhydrous magnesium sulfate. The solvent was evaporated under reduced pressure, thereby obtaining a crude product of 11-deacetyl pyripyropene O (20 mg).

After dissolved in methanol, this was used as a sample and HPLC (manufactured by SHIMADZU, LC-6AD, SPD-M20A PDA, CBM-20A, Column; Waters XTerra C18 (φ4.5× 50 mm, 5 μm, mobile phase 30% aqueous acetonitrile solution to 55% aqueous acetonitrile solution in 25 minutes (linear gradient), flow rate: 1.0 ml/min, retention time 18 to 19 minutes) was repeated to preparative separation, thereby obtaining 11-deacetyl pyripyropene O (4.0 mg).

ESI-MS; m/z 468 (M+H)$^+$ $^1$H-NMR (CDCl$_3$) δ (ppm); 0.68 (3H, s), 0.95 (3H, s), 1.21-2.21 (10H, m), 1.25 (3H, s), 2.05 (3H, s), 2.20 (1H, dd, J=4.63, 17.3 Hz), 2.50 (1H, dd, 3=4.63, 17.3 Hz), 2.94 (1H, d, J=12.5 Hz), 3.33 (1H, d, 3=12.5 Hz), 4.87 (1H, dd, J=4.6, 12.2 Hz), 6.48 (1H, s), 7.57 (1H, dd, J=5.1, 8.1 Hz), 8.29 (1H, d, J=8.3 Hz), 8.68 (1H, d, J=4.6 Hz), 9.04 (1H, s)

Reference Example 5

Synthesis of 7-Deacetyl Pyripyropene A 7-deacetyl pyripyropene A was synthesized by the method described in Japanese Patent Laid-Open Publication No. 259569/1996.

Reference Example 6

Obtainment of Pyripyropene E

Pyripyropene E was obtained by the method described in Japanese Patent Laid-Open Publication No. 239385/1996

Reference Example 7

Obtainment of Pyripyropene O

Pyripyropene O was obtained by the method described in J. Antibiot. 1996, 49, 292.

Reference Example 8

Synthesis of Pyripyropene A

Pyripyropene A was obtained by the method described in WO94/09147.

[Accession Numbers]
FERM BP-11133
FERM BP-11137
FERM BP-11141
FERM BP-11218
FERM BP-11219
FERM BP-11220

---

The invention claimed is:

1. A method for producing pyripyropene A, comprising: culturing a microorganism in the presence of pyripyropene E to produce pyripyropene A and isolating the pyripyropene A, wherein said microorganism is transformed with at least one heterologous polynucleotide in (I) to (III) below or a recombinant vector comprising said heterologous polynucleotide:

(I) a heterologous polynucleotide having at least one nucleotide sequence selected from the nucleotide sequences in (a) to (d) below:
(a) the nucleotide sequence of SEQ ID NO: 266,
(b) a nucleotide sequence which is capable of hybridizing with every nucleotide in the full length complementary sequence in SEQ ID NO: 266 under stringent conditions wherein said stringent conditions comprise washing with 2× saline-sodium citrate (SSC) buffer and 0.5% sodium dodecyl sulfate (SDS) at 60° C. for 20 minutes, and then washing 0.2×SSC and 0.1% SDS at 60° C. for 15 minutes,
(c) the nucleotide sequence of SEQ ID NO: 266 in which one to ten nucleotides are deleted, substituted, inserted or added, and
(d) a nucleotide sequence which has at least 90% identity to the nucleotide sequence of SEQ ID NO: 266;
wherein positions of the nucleotide sequence corresponding to positions 3342 to 5158 in SEQ ID NO: 266 encode a protein having CoA ligase activity, positions of the nucleotide sequence corresponding to positions 5382 to 12777 in SEQ ID NO: 266 encode a protein having LovB-like polyketide synthase activity, positions of the nucleotide sequence corresponding to positions 13266 to 15144 in SEQ ID NO: 266 encode a protein having Cytochrome P450 monooxygenase-1 activity, positions of the nucleotide sequence corresponding to positions 16220 to 18018 in SEQ ID NO: 266 encode a protein having Cytochrome P450 monooxygenase-2 activity, positions of the nucleotide sequence corresponding to positions 18506 to 19296 in SEQ ID NO: 266 encode a protein having Cyclase activity, positions of the nucleotide sequence corresponding to positions 19779 to 21389 in SEQ ID NO: 266 encode a protein having FAD-dependent monooxygenase activity, positions of the nucleotide sequence corresponding to positions 21793 to 22877 in SEQ ID NO: 266 encode a protein having UbiA-like prenyltransferase activity, positions of the nucleotide sequence corresponding to positions 23205 to 24773 in SEQ ID NO: 266 encode a protein having Acetyltransferase activity, and positions of the nucleotide sequence corresponding to positions 25824 to 27178 in SEQ ID NO: 266 encode a protein having Acetyltransferase-2 activity;

(II) a heterologous polynucleotide having a nucleotide sequence encoding the amino acid sequences of SEQ ID NOs: 267-275 or an amino acid sequence having one to ten substituted, deleted, added, or inserted residues in the amino acid sequences of SEQ ID NOs: 267-275 and having the same enzymatic activity as the amino acid sequences set forth in SEQ ID NOs: 267-275, respectively,
wherein SEQ ID NO: 267 is a protein having CoA ligase activity, SEQ ID NO: 268 is a protein having LovB-like polyketide synthase activity, SEQ ID NO: 269 is a protein having Cytochrome P450 monooxygenase-1 activity, SEQ ID NO: 270 is a protein having Cytochrome P450 monooxygenase-2 activity, SEQ ID NO: 271 is a protein having cyclase activity, SEQ ID NO: 272 is a protein having FAD-dependent monooxygenase activity, SEQ ID NO: 273 is a protein having UbiA-like prenyltransferase activity, SEQ ID NO: 274 is a protein having Acetyltransferase activity, and SEQ ID NO: 275 is a protein having Acetyltransferase-2 activity;

(III) a heterologous polynucleotide having at least one nucleotide sequence selected from the group consisting of the nucleotide sequences set forth in (1) to (4) below:
(1) the nucleotide sequences set forth in (a) to (i) below:
(a) a nucleotide sequence comprising positions 3342 to 5158 of the nucleotide sequence set forth in SEQ ID NO: 266,
(b) a nucleotide sequence comprising positions 5382 to 12777 of the nucleotide sequence set forth in SEQ ID NO: 266,
(c) a nucleotide sequence comprising positions 13266 to 15144 of the nucleotide sequence set forth in SEQ ID NO: 266,
(d) a nucleotide sequence comprising positions 16220 to 18018 of the nucleotide sequence set forth in SEQ ID NO: 266,
(e) a nucleotide sequence comprising positions 18506 to 19296 of the nucleotide sequence set forth in SEQ ID NO: 266,
(f) a nucleotide sequence comprising positions 19779 to 21389 of the nucleotide sequence set forth in SEQ ID NO: 266,
(g) a nucleotide sequence comprising positions 21793 to 22877 of the nucleotide sequence set forth in SEQ ID NO: 266,
(h) a nucleotide sequence comprising positions 23205 to 24773 of the nucleotide sequence set forth in SEQ ID NO: 266, and
(i) a nucleotide sequence comprising positions 25824 to 27178 of the nucleotide sequence set forth in SEQ ID NO: 266,
(2) a nucleotide sequence which hybridizes with every nucleotide in the full length complementary sequence in (1) under stringent conditions wherein said stringent conditions comprise washing with 2× saline-sodium citrate (SSC) buffer and 0.5% sodium dodecyl sulfate (SDS) at 60° C. for 20 minutes, and then washing with 0.2×SSC and 0.1% SDS at 60° C. for 15 minutes;
(3) the nucleotide sequence in (1) in which one to ten nucleotides are deleted, substituted, inserted or added, and
(4) a nucleotide sequence with at least 90% sequence identity to the nucleotide sequence in (1),
wherein positions of the nucleotide sequences of (1) to (4) corresponding to positions 3342 to 5158 in SEQ ID NO: 266 encode a protein having CoA ligase activity, positions of the nucleotide sequence corresponding to positions 5382 to 12777 in SEQ ID NO: 266 encode a protein having LovB-like polyketide synthase activity, positions of the nucleotide sequence corresponding to positions 13266 to 15144 in SEQ ID NO: 266 encode a protein having Cytochrome P450 monooxygenase-1 activity, positions of the nucleotide sequence corresponding to positions 16220 to 18018 in SEQ ID NO: 266 encode a protein having Cytochrome P450 monooxygenase-2 activity, positions of the nucleotide sequence corresponding to positions 18506 to 19296 in SEQ ID NO: 266 encode a protein having Cyclase activity, positions of the nucleotide sequence corresponding to positions 19779 to 21389 in SEQ ID NO: 266 encode a protein having FAD-dependent monooxygenase activity, positions of the nucleotide sequence corresponding to positions 21793 to 22877 in SEQ ID NO: 266 encode a protein having UbiA-like prenyltransferase activity, positions of the nucleotide sequence corresponding to positions 23205 to 24773 in SEQ ID NO: 266 encode a protein having Acetyltransferase activity, and positions of the nucleotide sequence corresponding to positions 25824 to 27178 in SEQ ID NO: 266 encode a protein having Acetyltransferase-2 activity.

2. A method for producing pyripyropene A, comprising: culturing a microorganism in the presence of pyripyropene E to produce pyripyropene A and isolating the pyripyropene A, wherein said microorganism is transformed with at least one heterologous polynucleotide in (I) to (II) below or a recombinant vector comprising said heterologous polynucleotide:

(I) a heterologous polynucleotide having a nucleotide sequence encoding polypeptides comprising the amino acid sequences of SEQ ID NOs: 269, 270, and 275 or an amino acid sequence having one to ten substituted, deleted, added, or inserted residues in the amino acid sequences of SEQ ID NOs: 269, 270, and 275 and having the same enzymatic activity as the amino acid sequences set forth in SEQ ID NOs: 269, 270, and 275, respectively;
wherein SEQ ID NO: 269 is a protein having Cytochrome P450 monooxygenase-1 activity, SEQ ID NO: 270 is a protein having Cytochrome P450 monooxygenase-2 activity, and SEQ ID NO: 275 is a protein having Acetyltransferase-2 activity;

(II) a heterologous polynucleotide having a nucleotide sequence selected from the group consisting of the nucleotide sequences in (1) to (4) below:
(1) the nucleotide sequences set forth in (a) to (c) below:
(a) a nucleotide sequence comprising positions 13266 to 15144 of the nucleotide sequence set forth in SEQ ID NO: 266,
(b) a nucleotide sequence comprising positions 16220 to 18018 of the nucleotide sequence set forth in SEQ ID NO: 266, and
(c) a nucleotide sequence comprising positions 25824 to 27178 of the nucleotide sequence set forth in SEQ ID NO: 266,
(2) a nucleotide sequence which is capable of hybridizing with every nucleotide in the full length complementary sequence in (1) under stringent conditions wherein said stringent conditions comprise washing with 2× saline-sodium citrate (SSC) buffer and 0.5% sodium dodecyl sulfate (SDS) at 60° C. for 20 minutes, and then washing with 0.2×SSC and 0.1% SDS at 60° C. for 15 minutes;
(3) the nucleotide sequence in (1) in which one to ten nucleotides are deleted, substituted, inserted or added, and;
(4) a nucleotide sequence comprising at least 90% sequence identity to the nucleotide sequence in (1), wherein positions of the nucleotide sequence corresponding to positions 13266 to 15144 in SEQ ID NO: 266 encode a protein having Cytochrome P450 monooxygenase-1 activity, positions of the nucleotide sequence corresponding to positions 16220 to 18018 in SEQ ID NO: 266 encode a protein having Cytochrome P450 monooxygenase-2 activity, and positions of the nucleotide sequence corresponding to positions 25824 to 27178 in SEQ ID NO: 266 encode a protein having Acetyltransferase-2 activity.

3. A method for producing pyripyropene A, comprising: culturing a microorganism in the presence of deacetyl pyripyropene E to produce pyripyropene A and isolating the pyripyropene A, wherein said microorganism is transformed with at least one heterologous polynucleotide in (I) and (II) below or a recombinant vector comprising said heterologous polynucleotide:

(VI) a heterologous polynucleotide having a nucleotide sequence encoding the amino acid sequences of SEQ ID NOs: 269, 270, 274, and 275,
wherein SEQ ID NO: 269 is a protein having Cytochrome P450 monooxygenase-1 activity, SEQ ID NO: 270 is a protein having Cytochrome P450 monooxygenase-2 activity, SEQ ID NO: 274 is a protein having Acetyltransferase activity, and SEQ ID NO: 275 is a protein having Acetyltransferase-2 activity;

(VII) a heterologous polynucleotide having a nucleotide sequence selected from the group consisting of the nucleotide sequences in (1) to (4) below:
(1) the nucleotide sequences set forth in (a) to (d) below:
(a) a nucleotide sequence comprising positions 13266 to 15144 of the nucleotide sequence set forth in SEQ ID NO: 266,
(b) a nucleotide sequence comprising positions 16220 to 18018 of the nucleotide sequence set forth in SEQ ID NO: 266,
(c) a nucleotide sequence comprising positions 23205 to 24773 of the nucleotide sequence set forth in SEQ ID NO: 266, and
(d) a nucleotide sequence comprising positions 25824 to 27178 of the nucleotide sequence set forth in SEQ ID NO: 266,
(2) a nucleotide sequence which hybridizes with every nucleotide in the full length complementary sequence in (1) under stringent conditions wherein said stringent conditions comprise washing with 2× saline-sodium citrate (SSC) buffer and 0.5% sodium dodecyl sulfate (SDS) at 60° C. for 20 minutes, and then washing with 0.2×SSC and 0.1% SDS at 60° C. for 15 minutes;
(3) the nucleotide sequence in (1) in which one to ten nucleotides are deleted, substituted, inserted, or added, and;
(4) a nucleotide sequence comprising at least 90% sequence identity to the nucleotide sequence in (1)
wherein positions of the nucleotide sequence corresponding to positions 13266 to 15144 in SEQ ID NO: 266 encode a protein having Cytochrome P450 monooxygenase-1 activity, positions of the nucleotide sequence corresponding to positions 16220 to 18018 in SEQ ID NO: 266 encode a protein having Cytochrome P450 monooxygenase-2 activity, positions of the nucleotide sequence corresponding to positions 23205 to 24773 in SEQ ID NO: 266 encode a protein having Acetyltransferase activity, and positions of the nucleotide sequence corresponding to positions 25824 to 27178 in SEQ ID NO: 266 encode a protein having Acetyltransferase-2 activity.

4. A method for producing 4-hydroxy-6-(pyridine-3-yl)-3-((2E,6E)-3,7,11-trimethyldodeca-2,6,10-trienyl)-2H-pyran-2-one comprising: culturing a microorganism in the presence of 4-oxo-6-(3-pyridyl)-α-pyrone and isolating 4-hydroxy-6-(pyridine-3-yl)-3-((2E,6E),3,7,11-trimethyldodeca-2,6,10-trienyl)-2H-pyrane-2-one to produce 4-hydroxy-6-(pyridine-3-yl)-3-((2E,6E)-3,7,11-trimethyl-dodeca-2,6,10-trienyl)-2H-pyrane-2-one and isolating the 4-hydroxy-6-(pyridine-3-yl)-3-((2E,6E)-3,7,11-trimethyl-dodeca-2,6,10-trienyl)-2H-pyrane-2-one, wherein said microorganism is transformed with at least one heterologous polynucleotide in (I) and (II) below or a recombinant vector comprising said heterologous polynucleotide:
(I) a heterologous polynucleotide having a nucleotide sequence encoding the amino acid sequence of SEQ ID NO: 273 or the amino acid sequence of SEQ ID NO: 273 having one to ten substituted, deleted, added, or inserted residues and having the same enzymatic activity as the amino acid sequence of SEQ ID NO: 273,
wherein SEQ ID NO: 273 is a protein having UbiA-like prenyltransferase activity;
(II) a heterologous polynucleotide having a nucleotide sequence selected from the group consisting of the nucleotide sequences in (1) to (4) below:
(1) a nucleotide sequence comprising positions 21793 to 22877 of the nucleotide sequence set forth in SEQ ID NO: 266, (2) a nucleotide sequence which hybridizes with every nucleotide in the full length complementary sequence in (1) under stringent conditions wherein said stringent conditions comprise washing with 2× saline-sodium citrate (SSC) buffer and 0.5% sodium dodecyl sulfate (SDS) at 60° C. for 20 minutes, and then washing with 0.2×SSC and 0.1% SDS at 60° C. for 15 minutes;
(3) the nucleotide sequence in (1) in which one to ten nucleotides are deleted, substituted, inserted, or added, and;
(4) a nucleotide sequence with at least 90% sequence identity to the nucleotide sequence in (1)
wherein positions of the nucleotide sequence corresponding to positions 21793 to 22877 in SEQ ID NO: 266 encode a protein having UbiA-like prenyltransferase activity.

5. A recombinant vector comprising one or more polynucleotides and a promoter that is heterologous to the one or more polynucleotides, wherein the one or more polynucleotides are selected from the following (a), (b), (c), (d), (e), (f), (g) and (h):
(a) a polynucleotide comprising the nucleotide sequence of SEQ ID NO: 266,
(b) a polynucleotide encoding a polypeptide which consists of an amino acid sequence selected from the group consisting of the amino acid sequence of SEQ ID NOs: 269, 270, 273, 274, and 275,
wherein SEQ ID NO: 269 is a protein having Cytochrome P450 monooxygenase-1 activity, SEQ ID NO: 270 is a protein having Cytochrome P450 monooxygenase-2 activity, SEQ ID NO: 273 is a protein having UbiA-like prenyltransferase activity, SEQ ID NO: 274 is a protein having Acetyltransferase activity, and SEQ ID NO: 275 is a protein having Acetyltransferase-2 activity;
(c) a polynucleotide with at least 90% sequence identity to a polynucleotide encoding the amino acid sequence of SEQ ID NO: 269 and having Cytochrome P450 monooxygenase-1 activity,
(d) a polynucleotide with at least 90% sequence identity to a polynucleotide encoding the amino acid sequence of SEQ ID NO: 270 and having Cytochrome P450 monooxygenase-2 activity,
(e) a polynucleotide with at least 90% sequence identity to a polynucleotide encoding the amino acid sequence of SEQ ID NO: 273 and having UbiA-like prenyltransferase activity,
(f) a polynucleotide with at least 90% sequence identity to a polynucleotide encoding the amino acid sequence of SEQ ID NO: 274 and having Acetyltransferase activity,
(g) a polynucleotide with at least 90% sequence identity to a polynucleotide encoding the amino acid sequence of SEQ ID NO: 275 and having Acetyltransferase-2 activity,
(h) a polynucleotide comprising a nucleotide sequence selected from the group consisting of the nucleotide sequences in (i), (ii), (iii), (iv), and (v):
(i) a nucleotide sequence comprising positions 13266 to 15144 of the nucleotide sequence set forth in SEQ ID NO: 266,
(ii) a nucleotide sequence comprising positions 16220 to 18018 of the nucleotide sequence set forth in SEQ ID NO: 266,
(iii) a nucleotide sequence comprising positions 21793 to 22877 of the nucleotide sequence set forth in SEQ ID NO: 266,
(iv) a nucleotide sequence comprising positions 23205 to 24773 of the nucleotide sequence set forth in SEQ ID NO: 266, and
(v) a nucleotide sequence comprising positions 25824 to 27178 of the nucleotide sequence set forth in SEQ ID NO: 266,
wherein positions of the nucleotide sequence corresponding to positions 13266 to 15144 in SEQ ID NO: 266 encode a protein having Cytochrome P450 monooxygenase-1 activity, positions of the nucleotide sequence corresponding to positions 16220 to 18018 in SEQ ID NO: 266 encode a protein having Cytochrome P450 monooxygenase-2 activity, positions of the nucleotide sequence corresponding to positions 21793 to 22877 in SEQ ID NO: 266 encode a protein having UbiA-like prenyltransferase activity, positions of the nucleotide sequence corresponding to positions 23205 to 24773 in SEQ ID NO: 266 encode a protein having Acetyltransferase activity, and positions of the nucleotide sequence corresponding to positions 25824 to 27178 in SEQ ID NO: 266 encode a protein having Acetyltransferase-2 activity.

* * * * *